United States Patent
Puskas

(10) Patent No.: US 7,336,019 B1
(45) Date of Patent: Feb. 26, 2008

(54) APPARATUS, CIRCUITRY, SIGNALS, PROBES AND METHODS FOR CLEANING AND/OR PROCESSING WITH SOUND

(76) Inventor: William L. Puskas, P.O. Box 1676, New London, NH (US) 03257

( * ) Notice: Subject to any disclaimer, the term of this patent is extended or adjusted under 35 U.S.C. 154(b) by 0 days.

(21) Appl. No.: 11/177,750

(22) Filed: Jul. 8, 2005

Related U.S. Application Data

(63) Continuation-in-part of application No. 11/173,468, filed on Jul. 1, 2005.

(51) Int. Cl.
H01L 41/09 (2006.01)
H01L 41/083 (2006.01)

(52) U.S. Cl. ............................ 310/317; 310/337

(58) Field of Classification Search ............ 310/317, 310/334, 335, 316.01, 337, 322
See application file for complete search history.

(56) References Cited

U.S. PATENT DOCUMENTS

| | | | |
|---|---|---|---|
| 2,585,103 A | 2/1952 | Fitzgerald | |
| 2,891,176 A | 6/1959 | Branson | |
| 2,985,003 A | 5/1961 | Gelfand | |
| 3,066,232 A | 11/1962 | Branson | |
| 3,094,314 A | 6/1963 | Kearney et al. | |
| RE25,433 E | 8/1963 | Rich | |
| 3,113,761 A | 12/1963 | Platzman | |
| 3,152,295 A | 10/1964 | Schebler | |
| 3,187,207 A | 6/1965 | Tomes | |
| 3,230,403 A | 1/1966 | Lewis et al. | |
| 3,293,456 A * | 12/1966 | Shoh | 310/316.01 |
| 3,315,102 A | 4/1967 | Quint et al. | |
| 3,318,578 A | 5/1967 | Branson | |
| 3,371,233 A | 2/1968 | Cook | |
| 3,433,462 A | 3/1969 | Cook | |
| 3,614,069 A | 10/1971 | Murry | |
| 3,629,726 A | 12/1971 | Popescu | |
| 3,638,087 A | 1/1972 | Ratcliff | |
| 3,648,188 A | 3/1972 | Ratcliff | |
| 3,651,352 A | 3/1972 | Puskas | |
| 3,690,333 A | 9/1972 | Kierner | |
| 3,727,112 A | 4/1973 | Popescu | |
| 3,735,159 A | 5/1973 | Murry | |
| 3,746,897 A | 7/1973 | Karatjas | |

(Continued)

FOREIGN PATENT DOCUMENTS

EP 0123277 10/1984

(Continued)

OTHER PUBLICATIONS

PCT International Search Report for International Application No. PCT/US06/25804 mailed on Aug. 29, 2007, 12 pages.

Primary Examiner—Darren Schuberg
Assistant Examiner—Derek Rosenau
(74) Attorney, Agent, or Firm—Mark G. Lappin; Foley & Lardner LLP

(57) ABSTRACT

The invention utilizes multiple frequency ultrasound generators driving multiple frequency harmonic transducer arrays at sweeping frequencies into the megasonic range. Generator signals that increase cavitation efficiency and that have successive time periods with predominantly stable cavitation and predominantly transient cavitation further improve the performance of the cleaning, microbiological inactivation, sonochemistry or processing systems. Probes that monitor the ultrasound and feedback the information to the generator provide consistency of process.

21 Claims, 89 Drawing Sheets

U.S. PATENT DOCUMENTS

| | | |
|---|---|---|
| 3,778,758 A | 12/1973 | Carson |
| 3,804,329 A | 4/1974 | Martner |
| 3,842,340 A | 10/1974 | Brandquist |
| 3,893,869 A | 7/1975 | Mayer et al. |
| 3,975,650 A | 8/1976 | Payne |
| 4,044,297 A | 8/1977 | Nobue et al. |
| 4,054,848 A | 10/1977 | Akita |
| 4,069,444 A | 1/1978 | Heim |
| 4,081,706 A | 3/1978 | Edelson |
| 4,109,174 A | 8/1978 | Hodgson |
| 4,118,649 A | 10/1978 | Shwartzman et al. |
| 4,120,699 A | 10/1978 | Kennedy, Jr. et al. |
| 4,141,608 A | 2/1979 | Breining et al. |
| 4,156,157 A | 5/1979 | Mabille |
| 4,175,242 A | 11/1979 | Kleinschmidt |
| 4,275,363 A | 6/1981 | Mishiro et al. |
| 4,326,553 A | 4/1982 | Hall |
| 4,391,672 A | 7/1983 | Lehtinen |
| 4,398,925 A | 8/1983 | Trinh et al. |
| 4,409,999 A | 10/1983 | Pedziwiatr |
| 4,418,297 A | 11/1983 | Marshall |
| 4,431,975 A | 2/1984 | Podlesny |
| 4,527,901 A | 7/1985 | Cook |
| 4,543,130 A | 9/1985 | Shwartzman |
| 4,554,477 A | 11/1985 | Ratcliff |
| 4,559,826 A | 12/1985 | Nelson |
| 4,618,987 A | 10/1986 | Steinke et al. |
| 4,633,119 A | 12/1986 | Thompson |
| 4,736,130 A | 4/1988 | Puskas |
| 4,743,789 A | 5/1988 | Puskas |
| 4,788,992 A | 12/1988 | Swainbank et al. |
| 4,804,007 A | 2/1989 | Bran |
| 4,836,684 A | 6/1989 | Javorik et al. |
| 4,854,337 A | 8/1989 | Bunkenburg et al. |
| 4,864,547 A | 9/1989 | Krsna |
| 4,869,278 A | 9/1989 | Bran |
| 4,979,994 A | 12/1990 | Dussault et al. |
| 4,998,549 A | 3/1991 | Bran |
| 5,037,208 A | 8/1991 | Dussault et al. |
| 5,037,481 A | 8/1991 | Bran |
| 5,090,432 A | 2/1992 | Bran |
| 5,119,840 A | 6/1992 | Shibata |
| 5,143,103 A | 9/1992 | Basso et al. |
| 5,148,823 A | 9/1992 | Bran |
| 5,201,958 A | 4/1993 | Breunsbach et al. |
| 5,218,980 A | 6/1993 | Evans |
| 5,247,954 A | 9/1993 | Grant et al. |
| 5,276,376 A | 1/1994 | Puskas |
| 5,286,657 A | 2/1994 | Bran |
| 5,305,737 A | 4/1994 | Vago |
| 5,355,048 A | 10/1994 | Estes |
| 5,365,960 A | 11/1994 | Bran |
| 5,496,411 A | 3/1996 | Candy |
| 5,523,058 A * | 6/1996 | Umemura et al. .......... 422/128 |
| 5,534,076 A * | 7/1996 | Bran ........................ 134/1 |
| 5,625,249 A * | 4/1997 | Grant ...................... 310/334 |
| 6,016,821 A | 1/2000 | Puskas |
| 6,150,753 A | 11/2000 | DeCastro |
| 6,295,873 B1 | 10/2001 | Condreva |
| 6,309,685 B1 | 10/2001 | Kozari et al. |
| 6,394,111 B1 | 5/2002 | Jacobs et al. |
| 6,447,718 B1 | 9/2002 | Carter et al. |
| 2002/0134402 A1 | 9/2002 | Madanshetty |
| 2003/0146108 A1 | 8/2003 | Nakamura et al. |
| 2004/0182414 A1 | 9/2004 | Puskas |
| 2004/0256952 A1 | 12/2004 | Puskas |
| 2004/0264293 A1 | 12/2004 | Laugharn, Jr. et al. |
| 2005/0006314 A1 | 1/2005 | Talukdar et al. |
| 2005/0017599 A1 | 1/2005 | Puskas et al. |
| 2006/0061225 A1 | 3/2006 | Beck et al. |

FOREIGN PATENT DOCUMENTS

| | | |
|---|---|---|
| GB | 1256188 | 12/1971 |
| GB | 1323196 | 7/1973 |
| GB | 1331100 | 9/1973 |
| GB | 1488252 | 10/1977 |
| GB | 2040150 | 8/1980 |
| GB | 2060220 | 4/1981 |
| GB | 2097890 | 11/1982 |
| GB | 2161037 | 1/1986 |
| GB | 2170663 | 8/1986 |
| JP | 07163954 | 6/1995 |
| WO | WO97/42790 | 11/1997 |

* cited by examiner

FROM FIG. 8A

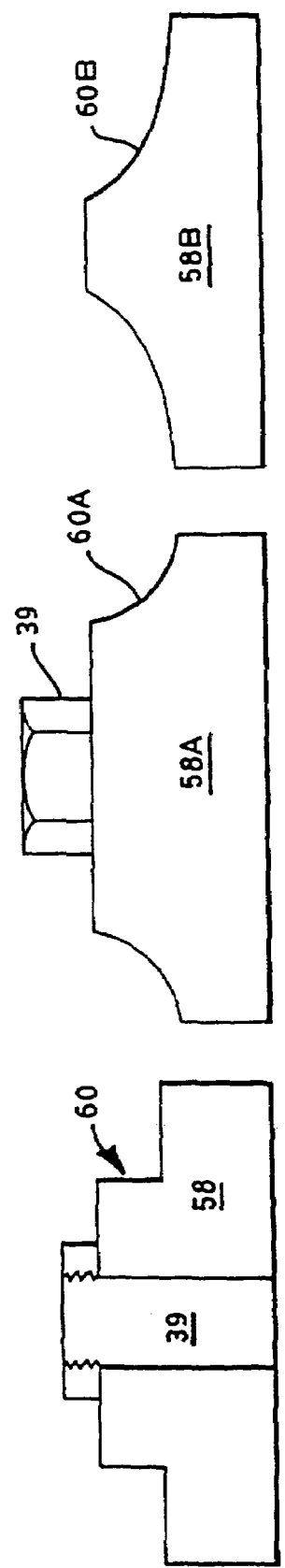

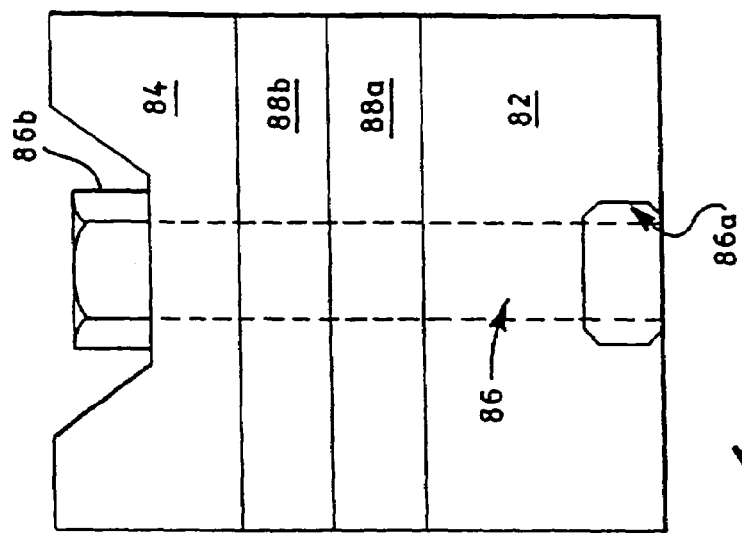
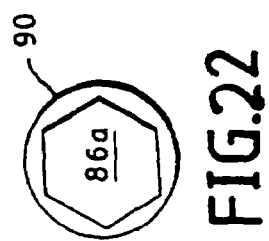
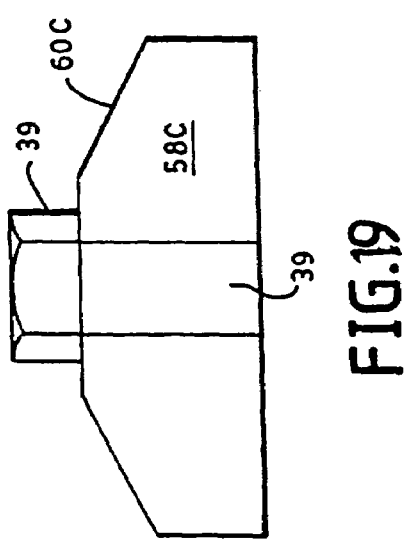
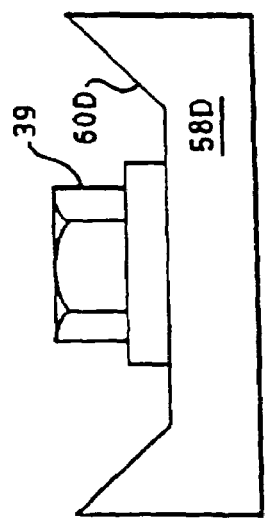

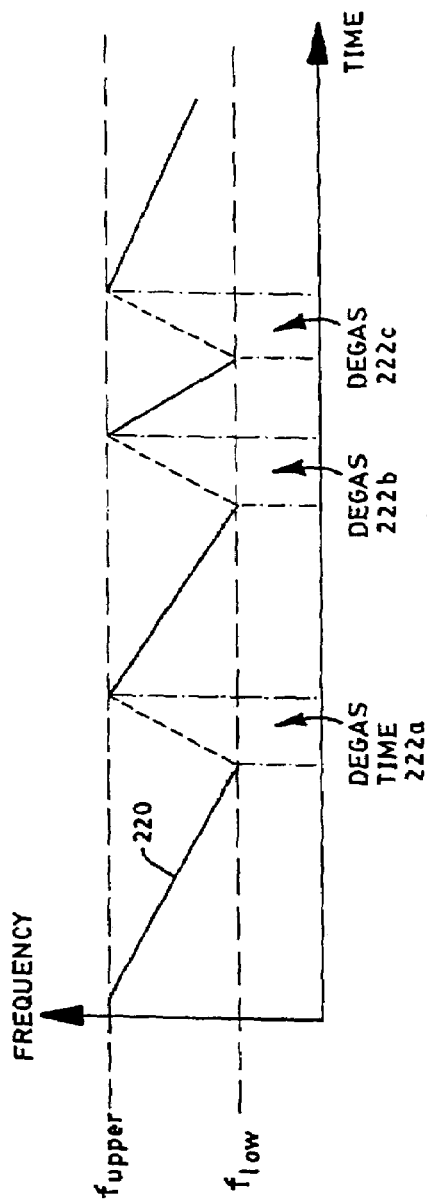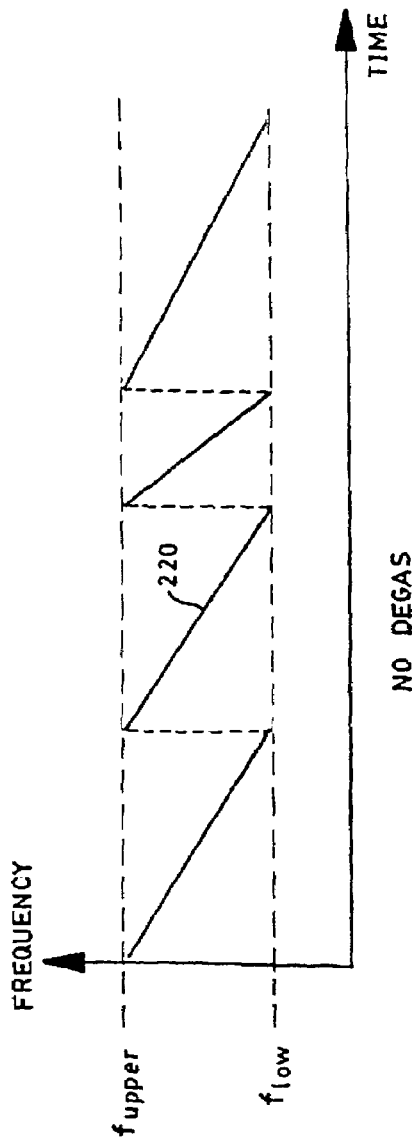

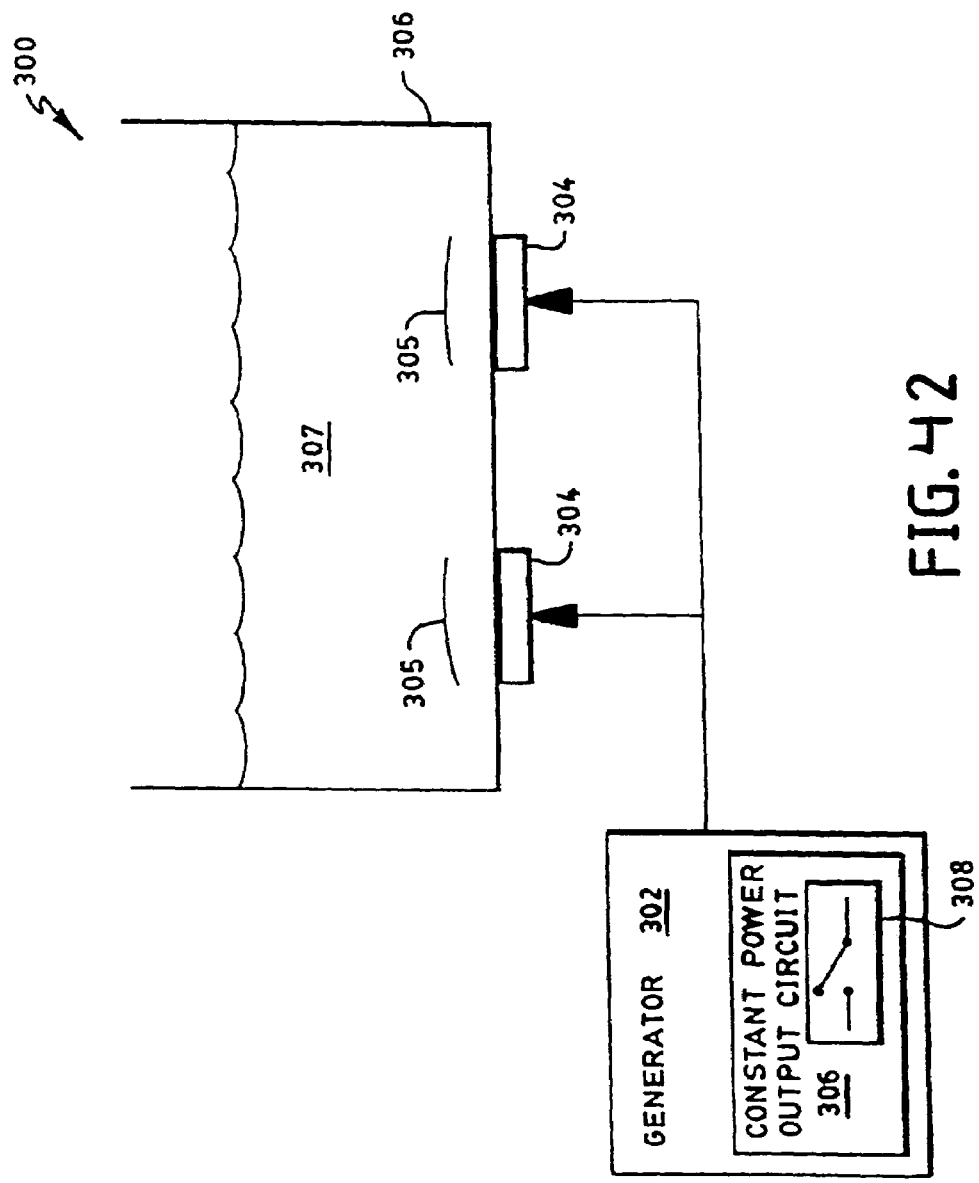

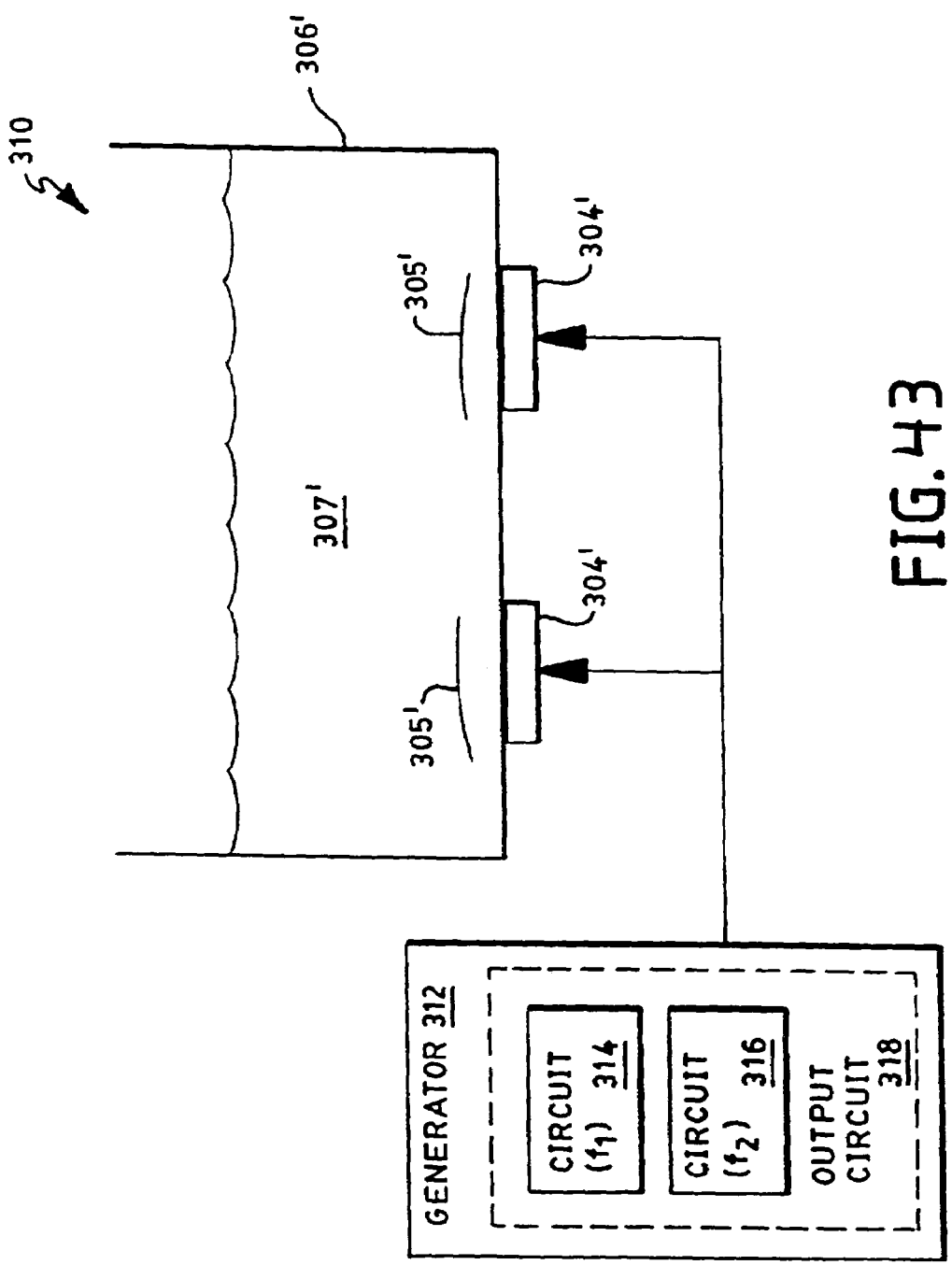

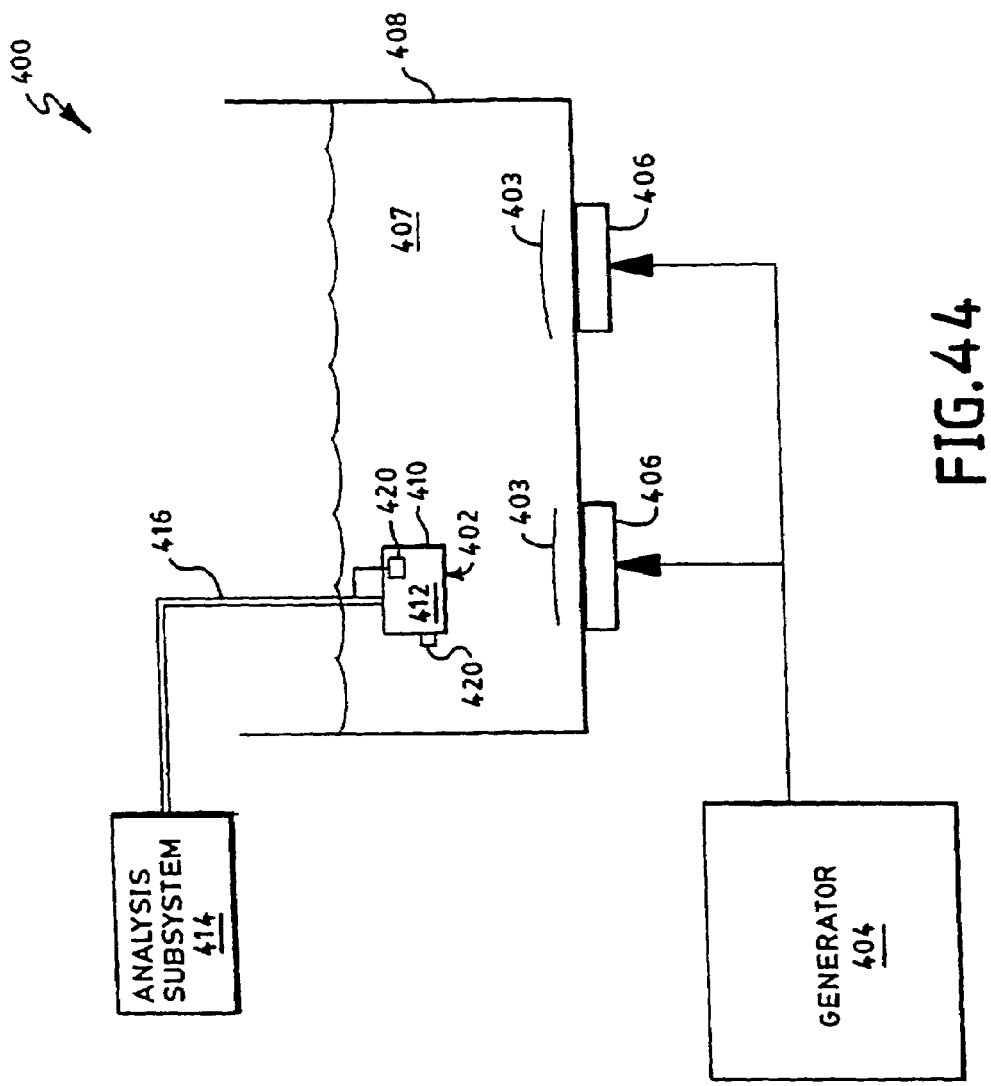

FROM FIG. 56    FIG. 57

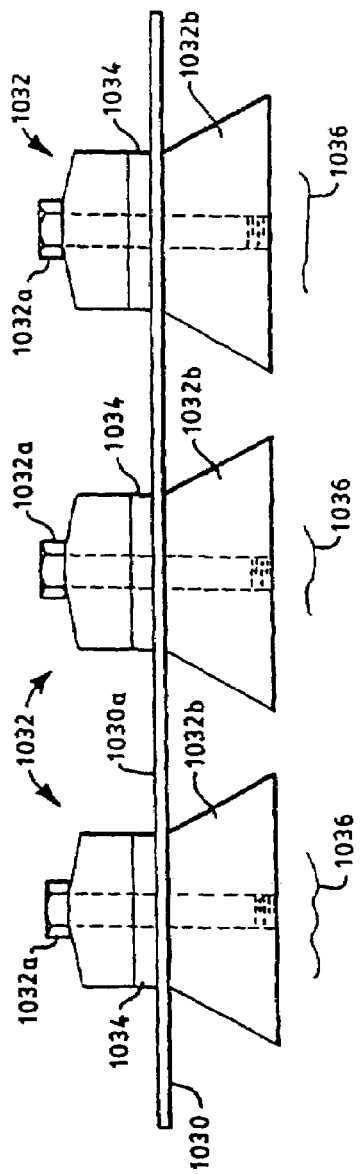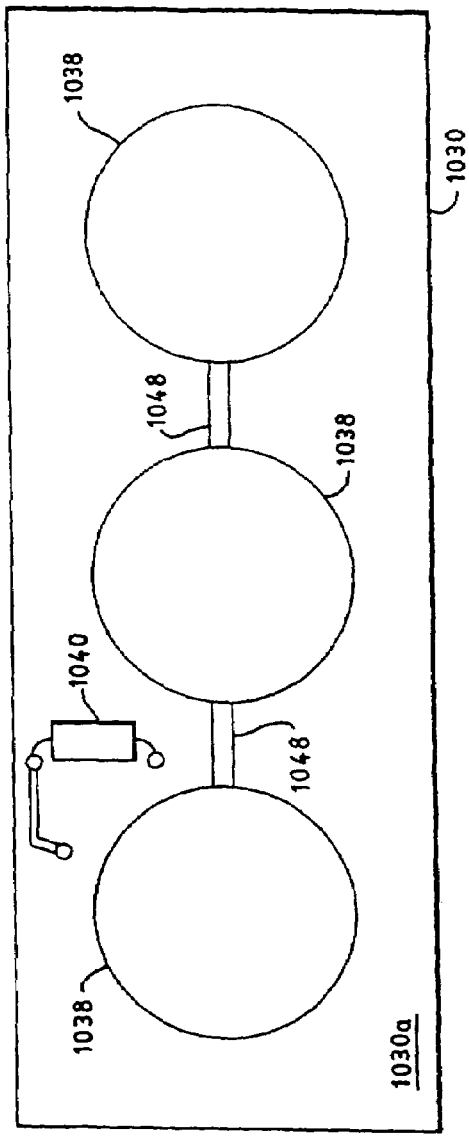
FIG. 64
FIG. 65

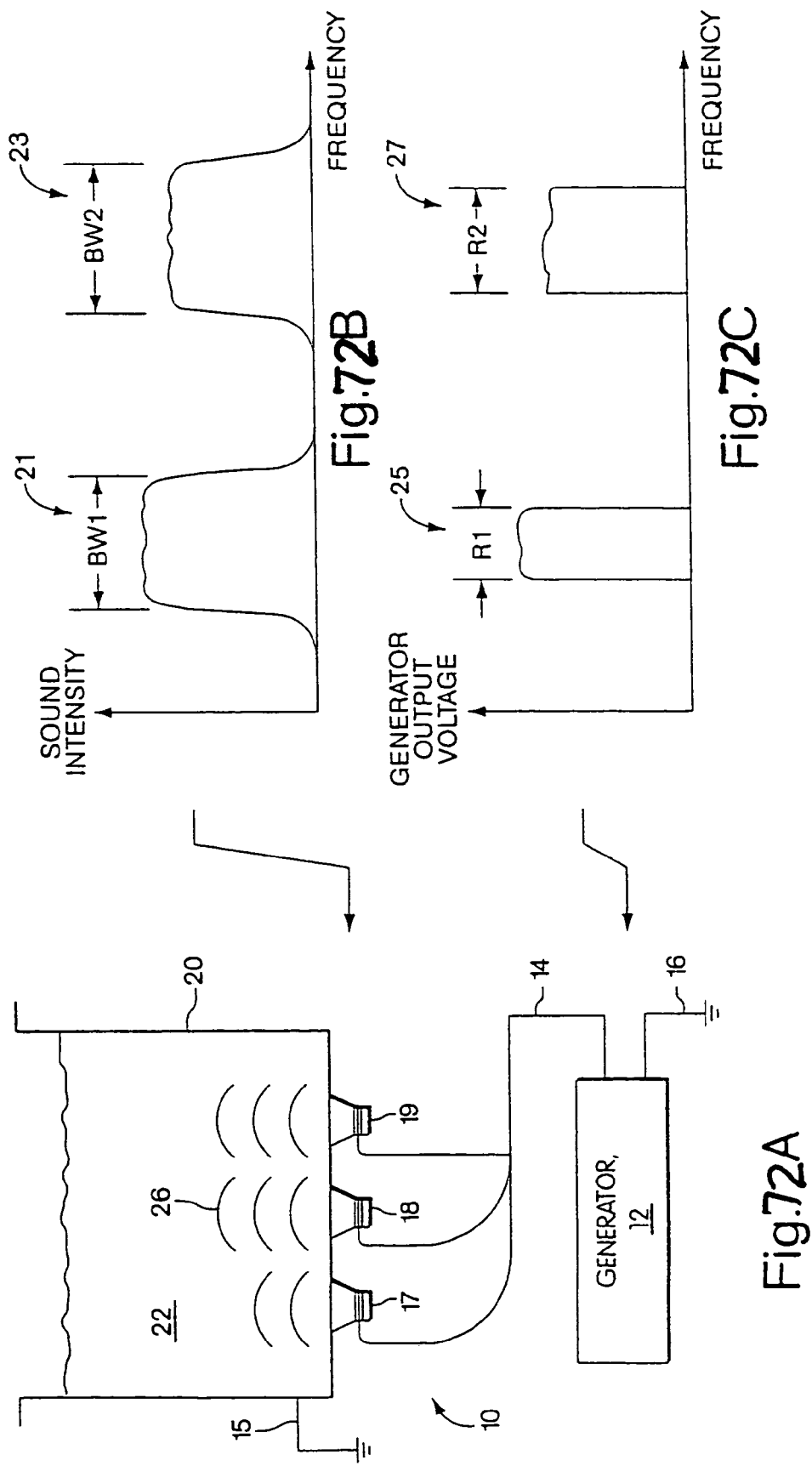

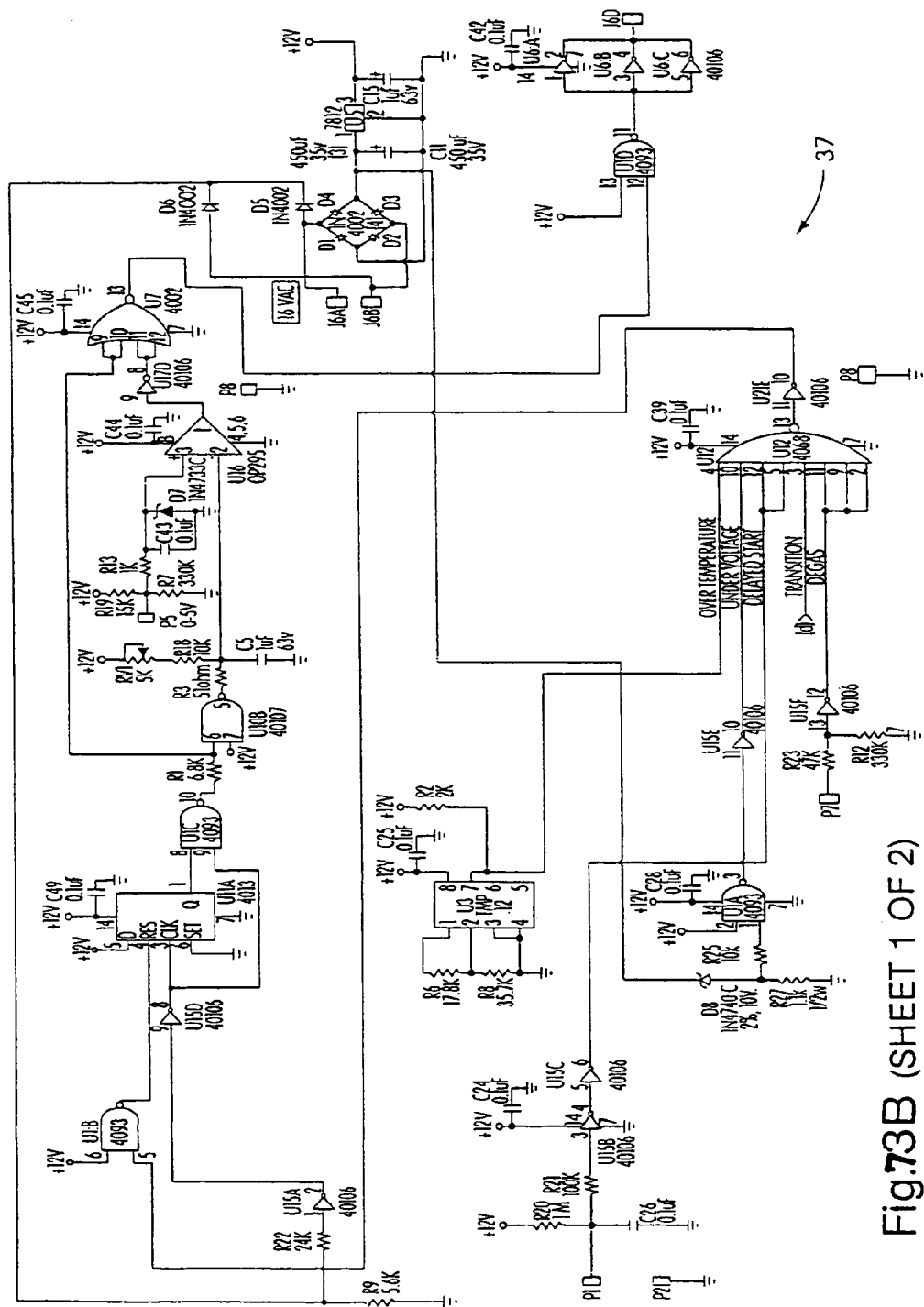
Fig.73B (SHEET 1 OF 2)

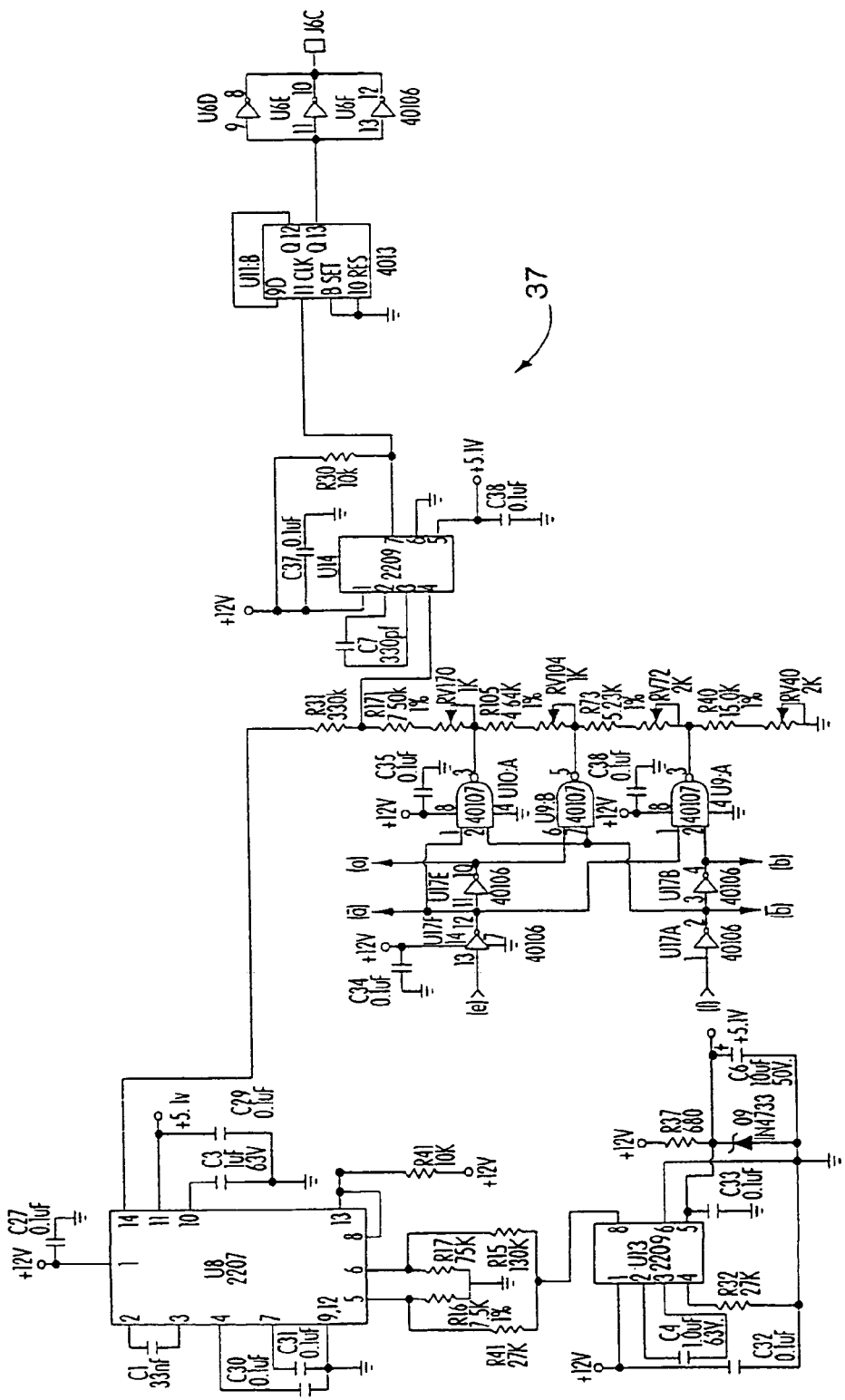
Fig.73B (SHEET 2 OF 2)

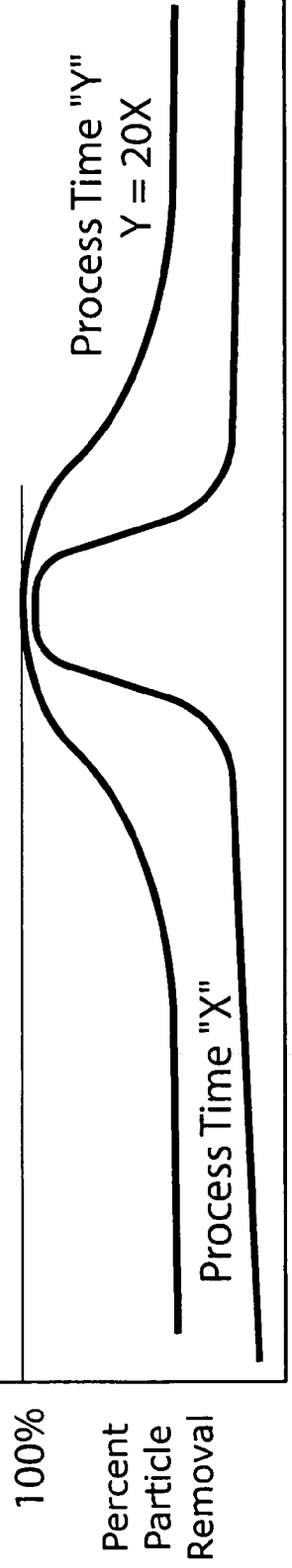
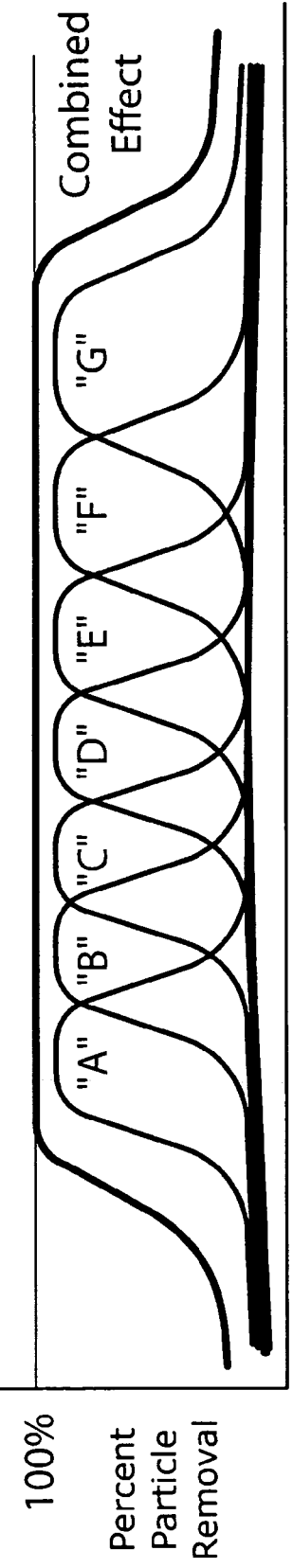
FIG. 96A
FIG. 96B

US 7,336,019 B1

APPARATUS, CIRCUITRY, SIGNALS, PROBES AND METHODS FOR CLEANING AND/OR PROCESSING WITH SOUND

RELATED APPLICATIONS

The subject application is a continuation-in-part of commonly owned and co-pending U.S. patent application Ser. No. 11/173,468 filed Jul. 1, 2005, which is expressly incorporated herein by reference. This application has a priority claim that is detailed below.

Priority claim of U.S. patent application Ser. No. 11/173,468: U.S. patent application Ser. No. 11/173,468 filed Jul. 1, 2005, entitled "Organism Inactivation Method and System", still pending is a continuation-in-part and co-pending U.S. patent application Ser. Nos. 10/855,135 and 11/047,110, each of which is expressly incorporated herein by reference. Each of these applications has a priority claim that is detailed below.

Priority claim of U.S. patent application Ser. No. 10/855,135: U.S. patent application Ser. No. 10/855,135 filed May 27, 2004, entitled "Apparatus, Circuitry, Signals and Methods for Cleaning and/or Processing with Sound", still pending is a continuation-in-part of commonly owned and co-pending U.S. patent application Ser. Nos. 10/178,751 and 10/825,036, each of which is expressly incorporated herein by reference. Each of these applications has a priority claim that is detailed below.

Priority claim of U.S. patent application Ser. No. 10/178,751: U.S. patent application Ser. No. 10/178,751 filed Jun. 24, 2002, entitled "Apparatus, Circuitry and Methods for Cleaning and/or Processing with Sound Waves", (now U.S. Pat. No. 6,822,372, granted Nov. 23, 2004), which is a continuation in part of four U.S. patent application Ser. Nos. 09/370,302, 09/609,036, 09/678,576 and 10/029,751 the priority claim of each is described below.

Priority claim of U.S. patent application Ser. No. 09/370,302: U.S. patent application Ser. No. 09/370,302 filed Aug. 9, 1999, entitled "Probe System for Ultrasonic Processing Tank", still pending, which is a division of U.S. patent application Ser. No. 09/097,374 (now U.S. Pat. No. 6,016,821, granted Jan. 25, 2000); which is a continuation of U.S. patent application Ser. No. 08/718,945 (now U.S. Pat. No. 5,834,871, granted Nov. 10, 1998) and U.S. Provisional Application No. 60/049,717, each of which is expressly incorporated herein by reference.

Priority claim of U.S. patent application Ser. No. 09/609,036: U.S. patent application Ser. No. 09/609,036 was filed Jun. 30, 2000, entitled "Circuitry to Modify the Operation of Ultrasonic Generators" (now U.S. Pat. No. 6,462,461, granted Oct. 8, 2002), which is expressly incorporated herein by reference.

Priority claim of U.S. patent application Ser. No. 09/678,576: U.S. patent application Ser. No. 09/678,576 filed Oct. 3, 2000, entitled "Apparatus and Methods for Cleaning and/or Processing Delicate Parts", (now U.S. Pat. No. 6,433,460, granted Aug. 13, 2002) is a Divisional Application of Continuation-in-Part application Ser. No. 09/066,158, filed Apr. 24, 1998 (now U.S. Pat. No. 6,181,051, granted Jan. 30, 2001), which is a continuation of U.S. patent application Ser. No. 08/718,945 filed on Sep. 24, 1996 (now U.S. Pat. No. 5,834,871, entitled "Apparatus And Methods For Cleaning And/Or Processing Delicate Parts"), and U.S. Provisional Patent Application Ser. No. 60/023,150, filed on Aug. 5, 1996, each of which is expressly incorporated herein by reference.

Priority claim of U.S. patent application Ser. No. 10/029,751: U.S. patent application Ser. No. 10/029,751 filed Oct. 29, 2001, entitled "Multiple Frequency Cleaning System" (now U.S. Pat. No. 6,538,360, granted Mar. 25, 2003) is a divisional application of U.S. patent application Ser. No. 09/504,567 entitled "Multiple Frequency Cleaning System," filed on Feb. 15, 2000 (now U.S. Pat. No. 6,313,565, granted Nov. 6, 2001), the disclosure of which is entirely incorporated herein by reference.

Priority claim of U.S. patent application Ser. No. 10/825,036: U.S. patent application Ser. No. 10/825,036 filed Apr. 15, 2004, entitled "A Multi-Generator System for an Ultrasonic Processing Tank", still pending, is a continuation-in-part of commonly-owned and co-pending U.S. patent application Ser. No. 09/370,302 filed Aug. 9, 1999, entitled "Probe System for Ultrasonic Processing Tank", still pending; which is a division of U.S. patent application Ser. No. 09/097,374 (now U.S. Pat. No. 6,016,821, granted Jan. 25, 2000); which is a continuation of U.S. patent application Ser. No. 08/718,945 (now U.S. Pat. No. 5,834,871, granted Nov. 10, 1998) and U.S. Provisional Application No. 60/049,717, each of which is expressly incorporated herein by reference.

Priority claim of U.S. patent application Ser. No. 11/047,110: U.S. patent application Ser. No. 11/047,110 is a continuation-in-part of U.S. patent application Ser. No. 09/370,302, filed on Aug. 9, 1999, which is a division of U.S. patent application Ser. No. 09/097,374 (now U.S. Pat. No. 6,016,821), filed Jun. 15, 1998, which claims priority of U.S. Provisional Application No. 60/049,717, filed Jun. 16, 1997, the disclosures of which are incorporated herein by reference.

FIELD OF THE INVENTION

The invention relates to systems and methods for cleaning and/or processing parts, processing liquids and inactivating organisms. In particular, the invention relates to ultrasound systems, ultrasound generators, ultrasound transducers, ultrasound signals, ultrasound probes and methods which support or enhance the application of ultrasound energy within liquid.

BACKGROUND OF THE INVENTION

The present invention relates to ultrasound cleaning and processing systems, and more particularly, to systems, generators, transducers, circuitry, probes, signals and methods that clean and/or process by coupling sound waves into a liquid. Prior art ultrasound systems lack performance in certain processes such as organism inactivation, cleaning and sonochemistry; and they lack the ability to remove a wide range of particle types and sizes without doing damage to the part being cleaned or processed. This invention improves the performance of an ultrasound system while eliminating the damage causing mechanisms. It also provides consistent performance by monitoring the process and adjusting the ultrasound to compensate for varying process conditions. It further provides highly reliable operation and improved performance at megasonic frequencies.

A primary parameter of ultrasonic performance is frequency, and in particular multiple frequency ultrasound systems. As used herein, "multiple frequency ultrasound systems" will consist of two types, "concurrent multiple ultrasound frequencies" and "successive multiple ultrasound frequencies".

Concurrent multiple ultrasound frequencies are produced in a liquid filled tank by two or more transducers (or two or more transducer arrays) that couple sound energy into the tank and each of these transducers (or arrays) is driven by a different generator. Typically all the generators are operated at the same time or there is an overlap in the operating times of the generators so that two or more frequencies are simultaneously put into the tank for at least part of the cleaning or processing cycle. The chronological history of concurrent multiple ultrasound frequency equipment starts in 1959 with U.S. Pat. No. 2,891,176 where Branson teaches three transducer arrays driven by three generators, the operation periods of these generators overlap in a way to balance the current in a transformer. In 1974 a tank was designed and built at Branson Cleaning Equipment Company that had an array of 25 kHz transducers on the bottom and a second array of 40 kHz transducers on one side; each of these arrays was simultaneously driven by the appropriate frequency generator. Similar systems were designed and built by others in the 1970's, e.g., Blackstone, but no useful application was found for the technology. In 1981 U.K. Pat. No. 2,097,890A taught three transducer arrays driven by three generators on different phases of a three-phase line. In the mid 1990's Amerimade Technology sold a system consisting of a tank with angled walls and two arrays of transducers on different walls, each array was driven by a different frequency generator, one sweeping around 71.5 kHz and the other sweeping around 104 kHz. At around the same period in time, Zenith sold a two array two generator system operating at 80 kHz and 120 kHz called "crossfire" because the different frequencies intersected at 90 degrees. Unlike the earlier 25 kHz and 40 kHz systems that found no useful application, the personal computer industry now existed and these Amerimade and Zenith systems were sold in large volume to the hard disk drive industry. In U.S. Pat. No. 5,656,095 Honda, et al. teaches high frequency transducers and low frequency transducers on the tank where the high frequency transducers are normally driven and the low frequency transducers are driven for short periods of time to intermittently destroy the high frequency bubbles. In U.S. Pat. Nos. 5,865,199 and 6,019,852 Pedziwatr et al. teaches two arrays of transducers interspersed on the tank and driven by two different frequency generators. In U.S. Pat. No. 5,909,741 Ferrell teaches two arrays of transducers on different angled walls of a plastic container and driven by different frequency generators. In 2004 Crest introduced a three frequency product where the different frequency transducers were spaced in equilateral triangles with each triangle containing the three frequencies and with no frequency next to itself.

These systems have two primary shortcomings; first, the destructive and constructive interference of the different frequency sound waves results in less transient cavitation compared to sweeping single frequency systems with the same total power. Second, the two or more different frequency transducer arrays on a given amount of radiating membrane surface results in lower power at each frequency. In U.S. Pat. Nos. 5,865,199 and 6,019,852 Pedziwatr et al addressed the shortcoming of interference of different frequency sound waves with an interspersed spacing a distance D between adjacent different frequency transducers. D was chosen to enable both sets of transducers to operate simultaneously to transmit the different frequencies. However, workable values of D, for example, 3.2 inches as suggested by Pedziwatr, result in even lower power at each frequency than many prior art systems.

It will be seen that the present invention overcomes the shortcomings of the prior art concurrent ultrasound frequency systems and it results in increased transient cavitation per input watt compared to prior art systems and allows higher power at each frequency than is possible with the Pedziwatr spacing.

Successive ultrasound frequencies are produced when different frequencies are supplied to an ultrasound tank in series, i.e., sweeping frequencies from one frequency range (for example, 38 khz to 42 khz) are followed by sweeping frequencies from a different frequency range (for example, 102 khz to 106 khz). These tanks contain universal transducers that can produce the frequencies in each of the ranges. Successive ultrasound frequencies were supplied in 1998 by Ney Ultrasonics where tanks with four frequency universal transducers were driven by individual, discreet generators operating in frequency ranges around 40 khz, 72 khz, 104 khz and 170 khz. This was the first primitive implementation of supplying different sweeping frequencies in succession to an array of transducers that operated at each of the supplied frequencies, i.e., universal transducers. This equipment used relays to connect the appropriate frequency generator to the array of universal transducers for the period of time required by the process at that frequency. The second frequency required by the process was then supplied to the transducer array by first disconnecting the prior frequency generator and then connecting the generator producing the second sweeping frequency. This frequency switching was done safely by electronic control of the relays and took less than one second of degas time to complete a frequency transition.

One advantage to the use of a single universal transducer array to produce a succession of multiple ultrasound frequencies is the high power density that can be achieved at each frequency. Each frequency utilizes the total membrane surface to supply that frequency as opposed to the necessity of sharing the available real estate among the various frequencies when using discreet frequency transducers. A second advantage for applications requiring transient cavitation is that many cycles of closely spaced frequencies are available to resonate bubbles up to the energy value needed for transient collapse. It can be expect that a process requiring the removal of small particulate contamination, the removal of spores or the high energies required by sonochemistry will be successfully accomplished by this technology.

A third advantage of applying multiple ultrasound frequencies in succession is realized when cleaning delicate parts. For example, components of a computer hard drive, semiconductors, ferrite parts and optical parts can be excited into resonance and fractured by beat frequencies produced by the interaction of two frequencies, such as exist in concurrent multiple ultrasound frequency systems. Synchronized sweeping frequencies in succession prevent this damage. However, it is important that the sweeping frequencies have a non-constant sweep rate to eliminate a second source of resonant damage that exists in many modern day sweeping ultrasonic systems.

The history of applying multiple ultrasound frequencies sequentially starts in 1998 with U.S. Pat. No. 5,834,871 which taught a universal transducer design and driving it from different frequency generators that were selected by a multiplexer. The above described primitive relay system from Ney Ultrasonics was available that same year.

Starting in 1999, follow-on U.S. Pat. Nos. 6,002,195, 6,016,821, 6,181,051 and 6,433,460 disclose improvements on delivering different frequencies in succession to universal transducers and preventing resonant damage to parts being cleaned. In 2000, CAE Ney Ultrasonics replaced the primitive system and sold generators that produced multiple frequencies to drive universal transducers at frequencies selected by a binary code as programmed by a PLC. In 2001 to 2004, U.S. Pat. Nos. 6,313,565; 6,462,461; 6,538,360 and 6,822,372 issued and further protected the multiple ultrasound frequencies in succession technology and the circuitry required to produce these generators. In 2002, Blackstone~NEY Ultrasonics introduced a seven frequency generator driving universal transducers from 40 kHz to 270 kHz.

Three classes of ultrasonic cleaning and processing equipment exist, the equipment with an operating center frequency in the range of 18 kHz to 100 kHz is normally referred to as ultrasonic equipment, the equipment with an operating center frequency in the range of 100 kHz to 350 kHz is sometimes referred to as microsonic equipment and the equipment with an operating center frequency in the range of 350 kHz to 4 MHz is normally referred to as megasonic equipment. Each different frequency put into a cleaning solution removes a different size and type of contamination with optimum efficiency; therefore, a universal transducer array that could produce one or more frequencies from each of the three frequency ranges is a significant improvement over state of the art equipment.

There is a primary problem to realizing this universal transducer array.

Megasonics transducers do not have a resonance in the ultrasonic and microsonic frequency ranges and therefore cannot be used to produce intense sound waves at these lower frequencies. Ultrasonic or microsonic transducers do not have a useful resonance in the megasonic frequency range and therefore cannot produce intense sound waves at a nominal 1 MHz frequency.

The present invention overcomes the above limitations a wide range multiple frequency transducer array that will economically produce intense sound in the ultrasonic, microsonic and megasonic frequency ranges.

Prior art ultrasound systems also lack performance at megasonic frequencies due to the limitation of one resonant frequency. The present invention overcomes this limitation and teaches improved performance at higher microsonics frequencies and at megasonic frequencies.

SUMMARY OF THE INVENTION

As defined in the technical literature, "ultrasound", "ultrasonic" and "ultrasonics" generally refer to acoustic disturbances in a frequency range above about eighteen kilohertz (khz) and which extend upwards to over five megahertz (Mhz). As is commonly used in the cleaning industry and as used herein, "ultrasonic" will generally refer to acoustic disturbances in a frequency range above about eighteen kilohertz and extending up to about 99 khz. Ultrasound and ultrasonics will be used to mean the complete range of acoustic disturbances from about 18 khz to 5 Mhz, except when they are use with terms such as "lower frequency" ultrasound, "low frequency" ultrasound, "lower frequency" ultrasonics, or "low frequency" ultrasonics, then they will mean ultrasound between about 18 khz and 99 khz. "Megasonics" or "megasonic" refer to acoustic disturbances between about 351 khz and 5 Mhz. The prior art has manufactured "low frequency" and "megasonic" ultrasound systems. Typical prior art low frequency systems, for example, operate at 25 khz, 40 khz, and as high as 90 khz. Typical prior art megasonic systems operate between 600 khz and 2 Mhz. Certain aspects of the invention apply to low frequency ultrasound and to megasonics. However, certain aspects of the invention apply to ultrasound in the 100 khz to 350 khz region, a frequency range which is sometimes denoted herein as "microsonic" or "microsonics." The upper end of the microsonic frequency range from about 300 khz to 350 khz is called herein "higher microsonics" or "higher frequency microsonic".

As used herein, "resonant transducer" means a transducer operated at a frequency or in a range of frequencies that correspond to a one-half wavelength (lambda) of sound in the transducer stack. "Harmonic transducer" means a transducer operated at a frequency or in a range of frequencies that correspond to 1 lambda, 1.5 lambda, 2 lambda or 2.5 lambda of sound, and so on, in the transducer stack. The harmonics of a practical physical structure are often not exact integer multiples of the fundamental frequency, the literature sometimes refer to these non-integer harmonics as overtones. Herein, harmonics will mean resonances higher in frequency than the fundamental resonant frequency. "Bandwidth" means the range of frequencies in a resonant or harmonic region of a transducer over which the acoustic power output of a transducer remains between 50% and 100% of the maximum value.

As used herein, a "delicate part" refers to those parts which are undergoing a manufacture, process, or cleaning operation within liquid subjected to ultrasound energy. By way of example, one delicate part is a semiconductor wafer which has extremely small features and which is easily damaged by cavitation implosion. Another delicate part is a modern jet engine turbine blade which can fracture if excited into resonant vibration. A delicate part often defines components in the computer industry, including disk drives, semiconductor components, and the like.

As used herein, "hz" refers to hertz which is cycles per second, "khz" refers to kilohertz and a frequency magnitude of one thousand hertz. "Mhz" refers to megahertz and a frequency magnitude of one million hertz.

As used herein, "successive frequencies" are two or more waveforms that are produced, one at a time, in a series fashion, where at least two different frequencies exist within the set of waveforms. At the output of a generator, these waveforms generally form an AC voltage. In an ultrasound tank, these waveforms are normally represented by an ultrasound wave in the liquid.

As used herein, successive frequencies are said to "sweep" when the period or the half period of two or more of the waveforms are unequal to each other.

Sweeping frequency generators change their output frequency through successive frequencies in a bandwidth, e.g., sweeping from the lowest frequency in a chosen bandwidth through the bandwidth to the highest frequency in the chosen bandwidth, then sweeping from this highest frequency through the bandwidth back to the lowest frequency. The function of time for these frequency changes is typically linear, but other functions of time, such as part of an exponential, are possible. As used herein, "sweep frequency" refers to the reciprocal of the time that it takes for successive frequencies to make a round trip, for example, change from one frequency through the other frequencies and back to the original frequency. Although sweep rate might technically be interpreted as the rate of change from one successive frequency to the next, the more common usage for sweep rate will be used herein; that is, "sweep rate" means the same as sweep frequency. It is generally undesirable to operate an ultrasound transducer at a fixed, single frequency because of the resonances created at that frequency. Therefore, an ultrasound generator can sweep the operational frequency through some or all of the available frequencies within the transducer's bandwidth at a "sweep rate." Accordingly, particular frequencies have only short duration during the sweep cycle (i.e., the time period for sweeping the ultrasound frequency up and down through a range of frequencies within the bandwidth). "Sweep the sweep rate" or "double sweeping" or "dual sweep" refer to an operation of changing the sweep rate as a function of time. In accord with the invention, "sweeping the sweep rate" generally refers to the operation of sweeping the sweep rate so as to reduce or eliminate resonances generated at a single sweep frequency. "Random sweep rate" or "chaotic sweep rate" refer to sweep rates where the successive sweep rates are numbers that are described by no well defined function, i.e., random or chaotic numbers.

The present invention concerns the applied uses of ultrasound energy, and in particular the application and control of ultrasonics to clean and process parts within a liquid. Generally, in accord with the invention, one or more ultrasound generators drive one or more ultrasound transducers, or arrays of transducers, coupled to a liquid to clean and/or process the part. The liquid is preferably held within a tank; and the transducers mount on or within the tank to impart ultrasound into the liquid. In this context, the invention is particularly directed to one or more of the following aspects and advantages:

By utilizing harmonics of certain clamped ultrasound transducers, the invention generates, in one aspect, ultrasound within the liquid in a frequency range of between about 100 khz to 350 khz (i.e., "microsonic" frequencies). This has certain advantages over the prior art. In particular, unlike prior art ultrasonic systems which operate at less than 100 khz, the invention eliminates or greatly reduces damaging cavitation implosions within the liquid. Further, the transducers operating in this frequency range provide relatively uniform microstreaming, such as provided by megasonics; but they are also relatively rugged and reliable, unlike megasonic transducer elements. In addition, and unlike megasonics, microsonic waves are not highly collimated, or "beam-like," within liquid; and therefore efficiently couple into the geometry of the ultrasound tank. Preferably, the application of microsonic frequencies to liquid occurs simultaneously with a sweeping of the microsonic frequency within the transducer's harmonic bandwidth. That is, microsonic transducers (clamped harmonic transducers) are most practical when there is a sweep rate of the applied microsonic frequency. This combination reduces or eliminates (a) standing waves within the liquid, (b) other resonances, (c) high energy cavitation implosions, and (d) non-uniform sound fields, each of which is undesirable for cleaning or processing semiconductor wafers and delicate parts.

The ultrasound transducers or arrays of the invention typically have a finite bandwidth associated with the range of frequencies about a resonant or harmonic frequency. When driven at frequencies within the bandwidth, the transducers generate acoustic energy that is coupled into the liquid. In one aspect, the invention drives the transducers such that the frequency of applied energy has a sweep rate within the bandwidth; and that sweep rate is also varied so that the sweep rate is substantially non-constant during operation. For example, the sweep rate can change linearly, randomly, chaotically or as some other function of time. In this manner, the invention reduces or eliminates resonances which are created by transducers operating with a single sweep rate, such as provided in the prior art.

At least one ultrasound generator of the invention utilizes amplitude modulation (AM). However, unlike the prior art, this AM generator operates by selectively changing the AM frequency over time. In a preferred aspect of the invention, the AM frequency is swept through a range of frequencies which reduce or eliminate low frequency resonances within the liquid and the part being processed. Accordingly, the AM frequency is swept through a range of frequencies; and this range is typically defined as about 10-40% of the optimum AM frequency. The optimum AM frequency is usually between about 1 hz and 10 khz. Therefore, for example, if the optimum AM frequency is 1 khz, then the AM frequency is swept through a frequency range of between about 850 hz and 1150 hz. In addition, the rate at which these frequencies are varied is usually less than about $\frac{1}{10}$th of the optimum AM frequency. In this example, therefore, the AM sweep rate is about 100 hz. These operations of sweeping the AM frequency through a range of frequencies and at a defined AM sweep rate reduce or eliminate unwanted resonances which might otherwise occur at the optimum AM frequency. In another aspect of the invention, for delicate parts with very low frequency resonances, the AM frequency is changed randomly or chaotically or the AM sweep rate is swept at a function of time with a frequency about $\frac{1}{10}$th of the AM sweep rate. This random or chaotic AM frequency in combination with the random or chaotic sweep rate of (3) provides elimination of low frequencies in a cleaning liquid, therefore, eliminating low frequency resonances. This combination is sometimes referred to as CRAM.

The invention provides AM control by selecting a portion of the rectified power line frequency (e.g., 60 hz in the United States and 50 hz in Europe). In one aspect, this AM control is implemented by selecting a portion of the leading quarter sinusoid in a full wave amplitude modulation pattern that ends at the required amplitude in the zero to 90 degrees and the 180 degrees to 270 degrees regions. Another AM control is implemented by selecting a portion of the leading quarter sinusoid in a half wave amplitude modulation pattern that ends at the required amplitude in the zero to 90 degrees region.

The invention can utilize several tanks, transducers and generators simultaneously to provide a wet bath of different chemistries for the delicate part. In one aspect, when two or more generators are operating at the same time, the invention synchronizes their operation to a common FM signal so that each generator can be adjusted, through AM, to control the process characteristics within the associated tank. In this manner, undesirable beating effects or cross coupling between multiple tanks are reduced or eliminated. In a preferred aspect, a master generator provides a common FM signal to the other generators, each operating as a slave generator coupled to the master generator, and each slave generator provides AM selectively. In addition, because the transducers in the several tanks are sometimes swept through the frequencies of the transducer's bandwidth, the FM control maintains overall synchronization even though varying AM is applied to the several transducers. The multi-generator FM synchronization also applies to single tank ultrasound systems. That is, the invention supports the synchronized operation of a plurality of generators that are connected to a single tank. In this case, each generator has an associated harmonic transducer array and is driven with a common FM signal and AM signal so that the frequencies within the tank are synchronized, in magnitude and phase, to reduce or eliminate unwanted resonances which might otherwise occur through beating effects between the multiple generators and transducers.

In another aspect, the invention utilizes two or more transducers, in combination, to broaden the overall bandwidth of acoustical energy applied to the liquid around the primary frequency or one of the harmonics. For example, the invention of one aspect has two clamped transducers operating at their first, second third, or fourth harmonic frequency between about 100 khz and 350 khz. The center harmonic frequency of each is adjusted so as to be different from each other. However, their bandwidths are made to overlap such that an attached generator can drive the transducers, in combination, to deliver ultrasound to the liquid in a broader bandwidth. In a preferred aspect, two or more transducers, or transducer arrays, operate at unique harmonic frequencies and have finite bandwidths that overlap with each of the other transducers. If, for example, each transducer has a bandwidth of 4 khz, then two such transducers can approximately provide a 8 khz bandwidth, and three such transducers can approximately provide a 12 khz bandwidth, and so on.

In one aspect, the invention provides a single tank system which selects a desired frequency, or range of frequencies, from a plurality of connected ultrasound generators. Specifically, two or more generators, each operating or optimized to generate a range of frequencies, are connected to a mux; and the system selects the desired frequency range, and hence the right generator, according to the cavitation implosion energy that is desired within the tank chemistry.

The invention has additional and sometimes greater advantages in systems and methods which combine one or more of the features in the above paragraphs.

The following patents, each incorporated herein by reference, provide useful background to the invention in the area of ultrasound generators: U.S. Pat. Nos. 3,152,295; 3,293,456; 3,629,726; 3,638,087; 3,648,188; 3,651,352; 3,727,112; 3,842,340; 4,044,297; 4,054,848; 4,069,444; 4,081,706; 4,109,174; 4,141,608; 4,156,157; 4,175,242; 4,275,363; and 4,418,297. Further, U.S. Pat. Nos. 4,743,789 and 4,736,130 provide particularly useful background in connection with ultrasound generators that are suitable for use with certain aspects of the invention, and are, accordingly incorporated herein by reference.

Clamped ultrasound transducers suitable for use with the invention are known in the art. For example, the following patents, each incorporated herein by reference, provide useful background to the invention: 3,066,232; 3,094,314; 3,113,761; 3,187,207; 3,230,403; 3,778,758; 3,804,329 and RE 25,433.

Techniques for mounting or affixing transducers within the tank, and of arranging the transducer and/or tank geometry are, for example, described in U.S. Pat. Nos. 4,118,649; 4,527,901; 4,543,130; and 4,836,684. Each of these patents is also incorporated by reference.

Single chamber ultrasound processing systems are described, for example, in U.S. Pat. Nos. 3,690,333; 4,409, 999; 5,143,103; and 5,201,958. Such systems provide additional background to the invention and are, accordingly, incorporated herein by reference.

In one aspect, the invention provides a system for delivering broadband ultrasound to liquid. The system includes first and second ultrasound transducers. The first transducer has a first frequency and a first ultrasound bandwidth, and the second transducer has a second frequency and a second ultrasound bandwidth. The first and second bandwidths are overlapping with each other and the first frequency is different from the second frequency. An ultrasound generator drives the transducers at frequencies within the bandwidths. Together, the first and second transducers and the generator produce ultrasound within the liquid and with a combined bandwidth that is greater than either of the first and second bandwidths.

In another aspect, the system of the invention includes a third ultrasound transducer that has a third frequency and a third ultrasound bandwidth. The third bandwidth is overlapping with at least one of the other bandwidths, and the third frequency is different from the first and second frequencies. The generator in this aspect drives the third transducer within the third bandwidth so as to produce ultrasound within the liquid and with a combined bandwidth that is greater than either of the first, second and third bandwidths.

Preferably, each of the transducers are clamped so as to resist material strain and fatigue. In another aspect, each of the first and second frequencies are harmonic frequencies of the transducer's base resonant frequency. In one aspect, these harmonic frequencies are between about 100 khz and 350 khz.

In another aspect, the system includes at least one other synergistic ultrasound transducer that has a synergistic frequency and a synergistic ultrasound bandwidth. As above, the synergistic bandwidth is overlapping with at least one of the other bandwidths, and the synergistic frequency is different from the first and second frequencies. The generator drives the synergistic transducer within the synergistic bandwidth so as to produce ultrasound within the liquid and with a combined bandwidth that is greater than any of the other bandwidths. In one aspect, this synergistic frequency is a harmonic frequency between about 100 khz and 350 khz.

In other aspects, the bandwidths of combined transducers overlap so that, in combination, the transducers produce ultrasound energy at substantially all frequencies within the combined bandwidth. Preferably, the combined operation provides ultrasound with relatively equal power for any frequency in the combined bandwidth. Using the full width half maximum (FWHM) to define each bandwidth, the bandwidths preferably overlap such that the power at each frequency within the combined bandwidth is within a factor of two of ultrasound energy produced at any other frequency within the combined bandwidth.

In another aspect, a system is provided for delivering ultrasound to liquid. The system has an ultrasound transducer with a harmonic frequency between about 100 khz and 350 khz and within an ultrasound bandwidth. A clamp applies compression to the transducer. An ultrasound generator drives the transducer at a range of frequencies within the bandwidth so as to produce ultrasound within the liquid.

In still another aspect, the system can include at least one other ultrasound transducer that has a second harmonic frequency within a second bandwidth. As above, the second frequency is between about 100 khz and 350 khz, and the second bandwidth is overlapping, in frequency, with the ultrasound bandwidth. The generator drives the transducers at frequencies within the bandwidths so as to produce ultrasound within the liquid and with a combined bandwidth that is greater than the bandwidth of a single transducer.

Another aspect of the invention provides a system for delivering ultrasound to liquid. In such a system, one or more ultrasound transducers have an operating frequency within an ultrasound bandwidth. An ultrasound generator drives the transducers at frequencies within the bandwidth, and also changes the sweep rate of the frequency continuously so as to produce non-resonating ultrasound within the liquid.

Preferably, the generator of the invention changes the sweep rate frequency in one of several ways. In one aspect, for example, the sweep rate is varied as a function of time. In another aspect, the sweep rate is changed randomly or chaotically. Typically, the sweep rate frequency is changed through a range of frequencies that are between about 10-50% of the optimum sweep rate frequency. The optimum sweep rate frequency is usually between about 1 hz and 1.2 khz; and, therefore, the range of frequencies through which the sweep rate is varied can change dramatically. By way of example, if the optimum sweep rate is 500 hz, then the range of sweep rate frequencies is between about 400 hz and 600 hz; and the invention operates by varying the sweep rate within this range linearly, randomly or chaotically, or as a function of time, so as to optimize processing characteristics within the liquid.

The invention further provides a system for delivering ultrasound to liquid. This system includes one or more ultrasound transducers, each having an operating frequency within an ultrasound bandwidth. An amplitude modulated ultrasound generator drives the transducers at frequencies within the bandwidth. A generator subsystem also changes the modulation frequency of the AM, continually, so as to produce ultrasound within the liquid to prevent low frequency resonances at the AM frequency.

Preferably, the subsystem sweeps the AM frequency at a sweep rate between about 1 hz and 100 hz. For extremely sensitive parts and/or tank chemistries, the invention can further sweep the AM sweep rate as a function of time so as to eliminate possible resonances which might be generated by the AM sweep rate frequency. This sweeping of the AM sweep rate occurs for a range of AM sweep frequencies generally defined by 10-40% of the optimum AM sweep rate. For example, if the optimum AM sweep rate is 150 hz, then one aspect of the invention changes the AM sweep rate through a range of about 130 hz and 170 hz.

In one aspect, the invention also provides amplitude control through the power lines. Specifically, amplitude modulation is achieved by selecting a portion of a leading quarter sinusoid, in a full wave amplitude modulation pattern, that ends at a selected amplitude in a region between zero and 90 degrees and between 180 degrees and 270 degrees of the sinusoid. Alternatively, amplitude control is achieved by selecting a portion of a leading quarter sinusoid, in a half wave amplitude modulation pattern, that ends at a selected amplitude between zero and 90 degrees of the sinusoid.

In still another aspect, a system of the invention can include two or more ultrasound generators that are synchronized in magnitude and phase so that there is substantially zero frequency difference between signals generated by the generators. Preferably, a timing signal is generated between the generators to synchronize the signals. In one aspect, a FM generator provides a master frequency modulated signal to each generator to synchronize the signals from the generators.

A generator of the invention can also be frequency modulated over a range of frequencies within the bandwidth of each transducer. In another aspect, the frequency modulation occurs over a range of frequencies within the bandwidth of each transducer, and the generator is amplitude modulated over a range of frequencies within the bandwidth of each transducer.

The systems of the invention generally include a chamber for holding the solution or liquid which is used to clean or process objects therein. The chamber can include, for example, material such as 316L stainless steel, 304 stainless steel, polytetrafluoroethylene, fluorinated ethylene propylene, polyvinylidine fluoride, perfluoro-alkoxy, polypropylene, polyetheretherketone, tantalum, Teflon coated stainless steel, titanium, hastalloy, and mixtures thereof.

It is preferable that the transducers of the system include an array of ultrasound transducer elements.

The invention also provides a method of delivering broadband ultrasound to liquid, including the steps of: driving a first ultrasound transducer with a generator at a first frequency and within a first ultrasound bandwidth, and driving a second ultrasound transducer with the generator at a second frequency within a second ultrasound bandwidth that overlaps at least part of the first bandwidth, such that the first and second transducers, in combination with the generator, produce ultrasound within the liquid and with a combined bandwidth that is greater than any of the first and second bandwidths.

In other aspects, the method includes the step of compressing at least one of the transducers, and/or the step of driving the first and second transducers at harmonic frequencies between about 100 khz and 350 khz.

Preferably, the method includes the step of arranging the bandwidths to overlap so that the transducers and generator produce ultrasound energy, at each frequency, that is within a factor of two of ultrasound energy produced by the transducers and generator at any other frequency within the combined bandwidth.

The application of broadband ultrasound has certain advantages. First, it increases the useful bandwidth of multiple transducer assemblies so that the advantages to sweeping ultrasound are enhanced. The broadband ultrasound also gives more ultrasound intensity for a given power level because there are additional and different frequencies spaced further apart in the ultrasound bath at any one time. Therefore, there is less sound energy cancellation because only frequencies of the same wavelength, the same amplitude and opposite phase cancel effectively.

In one aspect, the method of the invention includes the step of driving an ultrasound transducer in a first bandwidth of harmonic frequencies centered about a microsonic frequency in the range of 100 khz and 350 khz. For protection, the transducer is preferably compressed to protect its integrity.

Another method of the invention provides the following steps: coupling one or more ultrasound transducers to the liquid, driving, with a generator, the transducers to an operating frequency within an ultrasound bandwidth, the transducers and generator generating ultrasound within the liquid, changing the frequency within the bandwidth at a sweep rate, and continuously varying the sweep rate as a function of time so as to reduce low frequency resonances.

In other aspects, the sweep rate is varied according to one of the following steps: sweeping the sweep rate as a function of time; linearly sweeping the sweep rate as a function of time; and randomly or chaotically sweeping the sweep rate. Usually, the optimum sweep frequency is between about 1 hz and 1.2 khz, and therefore, in other aspects, the methods of the invention change the sweep rate within a range of sweep frequencies centered about an optimum sweep frequency. Typically, this range is defined by about 10-50% of the optimum sweep frequency. For example, if the optimum sweep frequency is 800 hz, then the range of sweep frequencies is between about 720 hz and 880 hz. Further, and in another aspect, the rate at which the invention sweeps the sweep rate within this range is varied at less than about $\frac{1}{10}$th of the optimum frequency. Therefore, in this example, the invention changes the sweep rate at a rate that is less than about 80 hz.

Another method of the invention provides for the steps of (a) generating a drive signal for one or more ultrasound transducers, each having an operating frequency within an ultrasound bandwidth, (b) amplitude modulating the drive signal at a modulation frequency, and (c) sweeping the modulation frequency, selectively, as to produce ultrasound within the liquid.

The invention is particularly useful as an ultrasound system which couples acoustic energy into a liquid for purposes of cleaning parts, developing photosensitive polymers, and stripping material from surfaces. The invention can provide many sound frequencies to the liquid by sweeping the sound through the bandwidth of the transducers. This provides at least three advantages: the standing waves causing cavitation hot spots in the liquid are reduced or eliminated; part resonances within the liquid at ultrasound frequencies are reduced or eliminated; and the ultrasound activity in the liquid builds up to a higher intensity because there is less cancellation of sound waves.

In one aspect, the invention provides an ultrasound bath with transducers having at least two different resonant frequencies. In one configuration, the resonant frequencies are made so that the bandwidths of the transducers overlap and so that the impedance versus frequency curve for the paralleled transducers exhibit maximum flatness in the resonant region. For example, when a 40 khz transducer with a 4.1 khz bandwidth is put in parallel—i.e., with overlapping bandwidths—with a 44 khz transducer with a 4.2 khz bandwidth, the resultant bandwidth of the multiple transducer assembly is about 8 khz. If transducers with three different frequencies are used, the bandwidth is approximately three times the bandwidth of a single transducer.

In another aspect, a clamped transducer array is provided with a resonant frequency of 40 khz and a bandwidth of 4 khz. The array has a second harmonic resonant frequency at 104 khz with a 4 khz harmonic bandwidth. Preferably, the bandwidth of this second harmonic frequency resonance is increased by the methods described above for the fundamental frequency of a clamped transducer array.

In one aspect, the invention provides a method and associated circuitry which constantly changes the sweep rate of an ultrasound transducer within a range of values that is in an optimum process range. For example, one exemplary process can have an optimum sweep rate in the range 380 hz to 530 hz. In accord with one aspect of the invention, this sweep rate constantly changes within the 380 hz to 530 hz range so that the sweep rate does not set up resonances within the tank and set up a resonance at that rate.

The invention provides for several methods to change the sweep rate. One of the most effective methods is to generate a random or chaotic change in sweep rate within the specified range. A simpler method is to sweep the sweep rate at some given function of time, e.g., linearly. One problem with sweeping the sweep rate is that the sweeping function of time has a specific frequency which may itself cause a resonance. Accordingly, one aspect of the invention is to sweep this time function; however, in practice, the time function has a specific frequency lower than the lowest resonant frequency of the semiconductor wafer or delicate part, so there is little need to eliminate that specific frequency.

Most prior art ultrasound systems are amplitude modulated at a low frequency, typically 50 hz, 60 hz, 100 hz, or 120 hz. One ultrasound generator, the proSONIK™ sold by Ney Ultrasonics Inc., and produced according to U.S. Pat. No. 4,736,130, permits the generation of a specific amplitude modulation pattern that is typically between 50 hz to 5 khz. However, the specific amplitude modulation frequency can itself be a cause of low frequency resonance in an ultrasound bath if the selected amplitude modulation frequency is a resonant frequency of the delicate part.

Accordingly, one aspect of the invention solves the problem of delicate part resonance at the amplitude modulation frequency by randomly or chaotically changing or sweeping the frequency of the amplitude modulation within a bandwidth of amplitude modulation frequencies that satisfy the process specifications. For cases where substantially all of the low frequencies must be eliminated, random or chaotic changes of the modulation frequency are preferred. For cases where there are no resonances in a part below a specified frequency, the amplitude modulation frequency can be swept at a frequency below the specified frequency.

Random or chaotic changing or sweeping of the amplitude modulation frequency inhibits low frequency resonances because there is little repetitive energy at a frequency within the resonant range of the delicate part or semiconductor wafer. Accordingly, a resonant condition does not build up, in accord with the invention, providing obvious advantages.

The invention also provides relatively inexpensive amplitude control as compared to the prior art. One aspect of the invention provides amplitude control with a full wave or half wave amplitude modulated ultrasound signal. For full wave, a section of the 0 degrees to 90 degrees and the 180 degrees to 270 degrees quarter sinusoid is chosen which ends at the required (desired) amplitude. For example, at the zero crossover of the half sinusoid (0 degrees and 180 degrees), a monostable multivibrator is triggered. It is set to time out before 90 degrees duration, and specifically at the required amplitude value. This timed monostable multivibrator pulse is used to select that section of the quarter sinusoid that never exceeds the required amplitude.

In one aspect, the invention also provides an adjustable ultrasound generator. One aspect of this generator is that the sweep rate frequency and the amplitude modulation pattern frequency are randomly or chaotically changed or swept within the optimum range for a selected process. Another aspect is that the generator drives an expanded bandwidth clamped piezoelectric transducer array at a harmonic frequency from 100 khz to 350 khz.

Such a generator provides several improvements in the problematic areas affecting lower frequency ultrasonics and megasonics: uncontrolled cavitation implosion, unwanted resonances, unreliable transducers, and standing waves. Instead, the system of the invention provides uniform microstreaming that is critical to semiconductor wafer and other delicate part processing and cleaning.

In another aspect of the invention, an array of transducers is used to transmit sound into a liquid at its fundamental frequency, e.g., 40 khz, and at each harmonic frequency, e.g., 72 khz or 104 khz. The outputs of generators which have the transducer resonant frequencies and harmonic frequencies are connected through relays to the transducer array. One generator with the output frequency that most closely producers the optimum energy in each cavitation implosion for the current process chemistry is switched to the transducer array.

In yet another aspect, the invention reduces or eliminates low frequency beat resonances created by multiple generators by synchronizing the sweep rates (both in magnitude and in phase) so that there is zero frequency difference between the signals coming out of multiple generators. In one aspect, the synchronization of sweep rate magnitude and phase is accomplished by sending a timing signal from one generator to each of the other generators. In another aspect, a master FM signal is generated that is sent to each "slave" power module, which amplifies the master FM signal for delivery to the transducers. At times, the master and slave aspect of the invention also provides advantages in eliminating or reducing the beat frequency created by multiple generators driving a single tank.

However, when multiple generators are driving different tanks in the same system, this master and slave aspect may not be acceptable because the AM of the FM signal is usually different for different processes in the different tanks. Accordingly, and in another aspect, a master control is provided which solves this problem. The master control of the invention has a single FM function generator (sweeping frequency signal) and multiple AM function generators, one for each tank. Thus, every tank in the system receives the same magnitude and phase of sweep rate, but a different AM as set on the control for each generator.

The invention also provides other advantages as compared to the prior art's methods for frequency sweeping ultrasound within the transducer's bandwidth. Specifically, the invention provides a sweeping of the sweep rate, within the transducer's bandwidth, such that low frequency resonances are reduced or eliminated. Prior art frequency sweep systems had a fixed sweep frequency that is selectable, once, for a given application. One problem with such prior art systems is that the single low frequency can set up a resonance in a delicate part, for example, a read-write head for a hard disk drive.

The invention also provides advantages in that the sweep frequency of the sweep rate can be adjusted to conditions within the tank, or to the configuration of the tank or transducer, or even to a process chemistry.

The invention also has certain advantages over prior art single chamber ultrasound systems. Specifically, the methods of the invention, in certain aspects, use different frequency ultrasonics for each different chemistry so that the same optimum energy in each cavitation implosion is maintained in each process or cleaning chemistry. According to other aspects of the invention, this process is enhanced by selecting the proper ultrasound generator frequency that is supplied at the fundamental or harmonic frequency of the transducers bonded to the single ultrasound chamber.

In another aspect, the invention provides ultrasound transducer apparatus. In the apparatus, at least one polarized piezoelectric ceramic element is sandwiched between a front mass and a back mass. The polarized piezoelectric ceramic element has electrical contacts or electrodes mounted on either face and is responsive to voltages applied to the contacts or electrodes so as to produce ultrasound energy. A connecting element—e.g., a bolt—connects the back mass to the front mass and compresses the polarized piezoelectric ceramic element therebetween. In accord with the invention, the front mass and/or the back mass are shaped so that the apparatus produces substantially uniform power as a function of frequency over a range of frequencies. In another aspect, the shape of the driver and/or back mass are selected so as to provide a varying power function as a function of frequency.

In another aspect, a multi-frequency ultrasound generator is provided. In one aspect, the generator includes a constant power output circuit with means for switching the center frequency of the output signal selectively. The switching means operates such that little or no intermediate frequencies are output during transition between one center frequency and another.

Another multi-frequency generator of the invention includes two or more circuits which independently create ultrasound frequencies. By way of example, one circuit can generate 40 khz ultrasound energy; while another circuit can generate 104 khz energy. A switching network connects the plurality of circuits such that the generator is shut down and relay switching takes place in a zero voltage condition. As above, therefore, the switching occurs such that little or no intermediate frequencies are output during transition between one center frequency and another.

In still another aspect, a two stage ultrasound processing system is provided. The system includes (a) one or more transducers with a defined ultrasound bandwidth defined by an upper frequency and a lower frequency. The system further includes (b) a frequency generator for driving the transducers from the upper frequency to the lower frequency over a selected or variable time period and (c) a process tank connected with the transducers so as to generate ultrasound energy within the tank at frequencies defined by the generator. During a given cycle, the generator drives the transducers from the upper frequency to the lower frequency. Once the lower frequency is reached, a frequency control subsystem controls the generator so as to drive the transducers again from upper to lower frequency and without driving the transducers from lower to upper frequencies. In this manner, only decreasing frequencies—per cycle—are imparted to process chemistries. The system thus provides for removing contamination as the downward cycling frequencies cause the acoustic energy to migrate in an upwards motion inside the tank which in turn pushes contamination upwards and out of the tank.

In another aspect of the invention, the two stage ultrasound processing system includes means for cycling from upper-to-lower frequencies every half cycle. That is, once the transducers are driven from upper to lower frequencies over a first half cycle, the generator recycles such that the next half cycle again drives the transducers from upper to lower frequencies. Alternatively, after driving the transducers from upper to lower frequencies for a first half cycle, the system inhibits the flow of energy into the tank over a second half cycle.

The two stage ultrasound processing systems of the invention can be continuous or intermittent. That is, in one preferred aspect, the system cycles from upper to lower frequencies and then from lower to upper frequencies in a normal mode; and then only cycles from upper to lower frequencies in a contamination removing mode.

In still another aspect, the invention provides a sensing system which is disposed within the process liquid and monitors certain process characteristics within an ultrasonic process tank. The sensing system preferably is a sensing probe, which includes an enclosure, e.g., made from polypropylene, that transmits ultrasound energy therethrough. The enclosure houses a liquid (sample liquid) that is responsive to the ultrasonic energy in some manner such as to create free radicals and ions from which conductivity can be measured. This conductivity provides an indication as to the number of cavitation implosions per unit volume being imparted to the process chemistry within the tank. A conduit from the enclosure to a location external to the process chemistry is used to measure the characteristics of the sample liquid in response to the energy. In other aspects, a thermocouple is included within the enclosure and/or on an external surface of the enclosure (i.e., in contact with the process chemistry) so as to monitor temperature changes within the enclosure and/or within the process chemistry. According to one aspect, the sample liquid is different from the process liquid. In another aspect, the sample liquid also has the characteristic that it produces chemiluminescence when exposed to cavitation and a photo sensor is enclosed within the sample liquid. Other characteristics within the tank and/or enclosure can be monitored over time so as to create time-varying functions that provide other useful information about the characteristics of the processes within the tank.

In one aspect, the invention provides an ultrasound system for moving contaminants upwards within a processing tank, which holds process liquid. An ultrasound generator produces ultrasound drive signals through a range of frequencies as defined by an upper frequency and a lower frequency. A transducer connected to the tank and the generator responds to the drive signals to impart ultrasound energy to the liquid. A controller subsystem controls the generator such that the drive signals monotonically change from the upper frequency to the lower frequency to drive contaminants upwards through the liquid.

In one aspect, the controller subsystem cyclically produces the drive signals such that the generator sweeps the drive signals from the upper frequency to the lower frequency over a first half cycle, and from the lower frequency to the higher frequency over a second one half cycle. The subsystem of this aspect inhibits the drive signals over the second half cycle to provide a quiet period to the liquid.

In other aspects, the first and second one-half cycles can have different time periods. Each successive one-half cycle can have a different time period such that a repetition rate of the first and second half cycles is non-constant. Or, the first one-half cycle can have a fixed period and the second one-half cycle can be non-constant.

In one aspect, the first half cycle corresponds to a first time period and the second one half cycle corresponds to a second time period, and the subsystem varies the first or second time periods between adjacent cycles.

Preferably, the subsystem includes means for shutting the generator off during the second one half cycle.

In another aspect, the subsystem includes an AM modulator for amplitude modulating the drive signals at an AM frequency. In one aspect, the AM modulator sweeps the AM frequency. In another aspect, the AM modulator sweeps the AM frequency from a high frequency to a low frequency and without sweeping the AM frequency from the low frequency to the high frequency. The subsystem can further inject a quiet or degas period before each monotonic AM frequency sweep.

In another aspect, there is provided an ultrasound system for moving contaminants upwards within a processing tank, including: a processing tank for holding process liquid, an ultrasound generator for generating ultrasound drive signals through a range of frequencies defined between an upper frequency and a lower frequency, at least one transducer connected to the tank and the generator, the transducer being responsive to the drive signals to impart ultrasound energy to the liquid, and a controller subsystem for controlling the generator through one or more cycles, each cycle including monotonically sweeping the drive signals from the upper frequency to the lower frequency, during a sweep period, and recycling the generator from the lower frequency to the upper frequency, during a recovery period, the sweep period being at least nine times longer than the recovery period.

In one aspect, the controller subsystem varies a time period for each cycle wherein the time period is non-constant.

In still another aspect, an ultrasound system is provided for moving contaminants upwards within a processing tank, including: a processing tank for holding process liquid; an ultrasound generator for generating ultrasound drive signals; at least one transducer connected to the tank and the generator, the transducer being responsive to the drive signals to impart ultrasound energy to the liquid; and an amplitude modulation subsystem for amplitude modulating the drive signals through a range of AM frequencies characterized by an upper frequency and a lower frequency, the subsystem monotonically changing the AM frequency from the upper frequency to the lower frequency to drive contaminants upwards through the liquid.

In one aspect, the generator sweeps the drive signals from upper to lower frequencies to provide additional upwards motion of contaminants within the liquid.

In another aspect, the AM frequencies are between about 1.2 khz and a lower frequency of 1 hz. The AM frequencies can also cover a different range, such as between about 800 hz and a lower frequency of 200 hz.

In another aspect, the invention provides a multi-generator system for producing ultrasound at selected different frequencies within a processing tank of the type including one or more transducers. A generator section has a first generator circuit for producing first ultrasound drive signals over a first range of frequencies and a second generator circuit for producing second ultrasound drive signals over a second range of frequencies. The generator section has an output unit connecting the drive signals to the transducers. Each generator circuit has a first relay initiated by a user-selected command wherein either the first or the second drive signals are connected to the output unit selectively.

In one aspect, a 24VDC supply provides power for relay coils.

In another aspect, each generator circuit has a second relay for energizing the circuit. Two time delay circuits can also be included for delay purposes: the first time delay circuit delaying generator circuit operation over a first delay period from when the second relay is energized, the second time delay circuit delaying discontinuance of the first relay over a second delay period after the generator circuit is commanded to stop. The first delay period is preferably longer than the second delay period such that no two generators circuits operate simultaneously and such that all generator circuits are inactive during switching of the first relay.

Each relay can include a 24 VDC coil. A selecting device, e.g., a PLC, computer, or selector switch, can be used to select the operating generator circuit. At selection, 24 VDC connects to the two relays of this operating generator circuit. Preferably, each relay coil operates at a common voltage level.

In one aspect, a variable voltage ultrasound generator system is provided, including: an ultrasound generator; a switching regulator for regulating a 300 VDC signal to +12V and +15V lines, the generator being connected to the +12V and +15V lines; and a power factor correction circuit connected to AC power. The power factor correction circuit provides 300 VDC output to the generator and to the regulator. The generator thus being automatically operable from world voltage sources between 86 VAC and 264 VAC.

In another aspect, a variable voltage ultrasound generator system is provided, including: an ultrasound generator; and a universal switching regulator (known to those skilled in the art), connected to AC power, for regulating a set of DC voltages to the generator. The generator thus being automatically operable from world voltage sources between 86 VAC and 264 VAC.

In another aspect, a double compression transducer is provided for producing ultrasound within an ultrasound tank. The transducer has a front mass and a back mass. At least one piezoceramic is sandwiched between the front mass and back mass. A bias bolt with an elongated bias bolt body between a bias bolt head and a threaded portion extends through the front mass and the piezoceramic and is connected with the back mass (either by screwing into the back mass or by a nut screwed onto the bias bolt adjacent the back mass). The bias bolt also forms a through-hole interior that axially extends between the head and the threaded portion. A second bolt with an elongated body between a second bolt head and a threaded tip is disposed within the bias bolt. The second bolt head is rigidly attached to the tank and a nut is screwed onto the threaded tip and adjacent to the back mass. The bias bolt thus provides a first level of compression of the piezoceramic. The second bolt provides a second level of compression of the front mass and the tank, particularly when epoxy is used to bond between the front mass and the tank.

In still another aspect, a variable voltage ultrasound generator system is provided. The system includes an ultrasound generator and a constant peak amplitude triac circuit connected to AC power. The triac circuit converts the AC power to a 121.6 voltage peak, or less, AC signal. A bridge rectifier and filter connects to the AC signal to rectify and filter the AC signal and to generate a DC voltage less than (86)*(Square Root of 2) volts. A switching regulator regulates the DC voltage to 12 VDC and 15 VDC; and the generator connects to the DC voltage, the 12 VDC and the 15 VDC. In this manner, the generator is thus automatically operable from world voltage sources between 86 VAC and 264 VAC.

In another aspect, the successive multiple ultrasound frequency invention described herein is a new class of liquid cleaning and processing equipment where there is one transducer array and one generator that produces a series string of different frequencies within two or more non-overlapping continuous frequency ranges. The transducer array is capable of responding to electrical frequency signals to produce intense sound energy at any frequency within two or more distinct frequency bands. The generator is capable of supplying an electrical frequency signal at any frequency within continuous frequency ranges contained within two or more of the transducer array's frequency bands.

The generator and transducer array produce a series string of different frequency sound waves. The first produced frequency is typically followed by a different second frequency that is in the same frequency range as the first frequency, then this second frequency is typically followed by a different third frequency that is in the same frequency range as the first two frequencies, and this pattern continues for at least the lifetime of a sound wave in the liquid (typically 20 to 70 milliseconds). This results in multiple closely related frequencies of the same frequency range adding up within the liquid to a value of high intensity sound. This high intensity sound field is typically maintained long enough to accomplish a specific part of the cleaning or processing cycle, then the electrical frequency signal output of the generator is controlled to jump to a frequency in a different frequency range, typically in a different frequency band, where different frequencies are again strung together for at least the lifetime of a sound wave in the liquid.

This invention is an improvement over prior art multiple frequency systems because by stringing together different frequencies from the same frequency range for at least the lifetime of a sound wave in the liquid, the sound intensity of these closely related frequencies builds up to a higher value than with any of the prior art multiple frequency systems. This higher intensity sound field does the improved cleaning or processing within the frequency range and then the system jumps to another frequency range where the cleaning or processing effect is different. Again, in the second frequency range the sound intensity builds up to a higher value than with any prior art multiple frequency system and, therefore, the improvement in cleaning or processing occurs within this second frequency range. Also, by maintaining the production of sound in each frequency range for a minimum of 20 milliseconds, there is substantially no intense sound energy produced at frequencies outside of the frequency ranges, this further adds to the build up of the intensity of the sound energy. Each of these improved effects in each of the different frequency ranges adds up to a process that is superior to prior art methods.

A variation of the invention substitutes a fraction of a cycle of a frequency strung together with other fractions of a cycle of sound at different frequencies within a given frequency range before jumping to a different frequency range. Another variation inserts a degas time between jumps from one frequency range to another. Another variation controls the generator to cycle through the frequency ranges in different orders, i.e., several permutations of the frequency ranges are introduced into the liquid during the cleaning or processing cycle. Another variation defines each permutation of a frequency range to be a cleaning packet and the order in which these cleaning packets are delivered to the liquid is varied to produce different cleaning effects. Still other variations introduce phase lock loops, duty cycle control, amplitude control, PLC control, computer control, quiet times, active power control, series resistor VCO control, DAC VCO control, cavitation probe feedback to the generator and digital code frequency selection. In general, this invention is useful in the frequency spectrum 9 khz to 5 Mhz.

The foregoing and other objects of are achieved by the invention, which in one aspect comprises a system for coupling sound energy to a liquid, including at least two transducers forming a transducer array adapted for coupling to a liquid in a container. The transducer array is constructed and arranged so as to be capable of producing intense sound energy in the liquid at any frequency within at least two non-overlapping frequency bands. The system further includes a signal generator adapted for producing a driver signal for driving the transducer array at any frequency from one or more continuous frequency ranges within at least two of the frequency bands. The signal generator drives the transducer array to produce the intense sound energy characterized by a series string of different frequencies within one of the continuous frequency ranges. The generator further drives the transducer array to discontinuously jump amongst the frequency ranges, so as to generate intense sound energy characterized by a series string of different frequencies within at least one additional frequency range in at least one additional frequency band.

Another embodiment of the invention further includes a controller for controlling the frequency of the ultrasound energy within the series string of different frequencies. The controller also controls a duration of each frequency in the series string.

In another embodiment of the invention, the intense sound energy in the series string of different frequencies is characterized by a staircase function.

In another embodiment of the invention, the intense sound energy in the series string of different frequencies is characterized by a series of monotonically decreasing frequencies.

In another embodiment of the invention, the series of monotonically decreasing frequencies occurs for at least ninety percent of an interval during which the transducer array couples intense sound energy to the liquid.

In another embodiment of the invention, the intense sound energy in the series string of different frequencies is characterized by a series of frequencies defined by a predetermined function of time.

In another embodiment of the invention, the intense sound energy in the series string of different frequencies is characterized by a series of frequencies swept from a first frequency to a second frequency at a constant sweep rate.

In another embodiment of the invention, the series of frequencies is swept at a non-constant sweep rate.

In another embodiment of the invention, the intense sound energy in the series string of different frequencies is characterized by a random or chaotic series of frequencies.

In another embodiment of the invention, the intense sound energy in the series string of different frequencies is characterized by at least a first group of frequencies from a first frequency band, and a second group of frequencies from a second frequency band, such that at least two groups of frequencies adjacent in time are from different frequency bands.

In another embodiment of the invention, the series string of different frequencies further includes at least one degas interval between periods of time having ultrasound energy.

In another embodiment of the invention, the intense sound energy in the series string of different frequencies is characterized by at least a first group of frequencies from a first frequency band, and a second group of frequencies also from the first frequency band, such that at least two groups of frequencies adjacent in time are from the same frequency band In another embodiment of the invention, the intense sound energy in each of the series string of different frequencies is characterized by at least a fraction of a cycle of the distinct frequency.

In another embodiment of the invention, the fraction of a cycle is one-half of a cycle, and each successive one-half cycle represents a different frequency.

In another embodiment of the invention, the intense sound energy includes frequencies selected from the frequency spectrum 9 khz to 5 Mhz.

In another embodiment of the invention, the frequency ranges are characterized by a center frequency. The center frequency of each higher frequency range is a non-integer multiple of the center frequency of the lowest frequency range, so as to prevent one or more Fourier frequencies of a periodic wave from forming in the liquid.

In another embodiment of the invention, the controller includes a PLC or a computer.

Another embodiment of the invention further includes a probe adapted for measuring one or more parameters associated with the liquid corresponding to sound-produced effects in the liquid. The controller alters the generator driver signal as both a predetermined function of the measured parameters, and according to the desired purpose of the system.

In another embodiment of the invention, each specific frequency range is represented by a distinct digital code. The controller initiates a transition from a first frequency range to a second frequency range in response to the digital code transitioning from a digital code representative of the first frequency range to the digital code representative of the second frequency range.

In another embodiment of the invention, the center frequency of each frequency range corresponds to an output of a voltage controlled oscillator. The output of the voltage controlled oscillator corresponds to an input control signal, and the input control signal is determined by a series string of resistors. The total string of resistors produces the lowest frequency range and each higher string of resistors produces each higher frequency range.

In another embodiment of the invention, the intense sound energy includes ultrasound energy.

In another embodiment of the invention, the intense sound energy in the series string of different frequencies occurs continuously for at least 20 milliseconds, within each of the continuous frequency ranges.

In another embodiment of the invention, the output power level of the driver signal is actively maintained by comparing an actual output power level to a specified output power level, and adjusting parameters of the driver signal to make the actual output power level substantially equal to the specified output power level. The parameters of the driver signal may be either amplitude, duty cycle, or some combination thereof.

In another embodiment of the invention, the intense sound energy characterized by the series string of different frequencies further includes one or more quiet time intervals characterized by a substantial absence of intense sound energy.

In another embodiment of the invention, the quiet time intervals are distributed periodically among the intervals of intense sound energy. In yet another embodiment, the quiet time intervals are distributed randomly or chaotically among the intervals of intense sound energy.

In another embodiment of the invention, the quiet time intervals are distributed among the intervals of intense sound energy according to a predetermined function of time.

In another embodiment of the invention, the center frequency for each frequency range is optimized by an automatic adjustment from a circuit that maintains a substantially zero phase shift between an associated output voltage and output current at the center frequency.

In another embodiment of the invention, the order of frequency range transitions varies such that several permutations of frequency ranges can be introduced into the liquid. In other embodiments, each permutation of frequency ranges is defined as a specific cleaning packet, and the order in which the cleaning packets are introduced into the liquid is changed such that each different order produces a different cleaning effect.

In another embodiment of the invention, substantially no intense sound energy is produced at frequencies outside of the frequency ranges.

In another embodiment of the invention, the container holding the liquid is constructed from materials resistant to detrimental effects of the liquids. These materials may include tantalum, polyetheretherketone, titanium, polypropylene, Teflon, Teflon coated stainless steel, or combinations thereof, or other similar materials known to those in the art.

In another embodiment of the invention, the signal generator is capable of producing an infinite number of frequencies contained within each of the unconnected continuous frequency ranges.

In another embodiment of the invention, the signal generator produces an output signal including the FM information for synchronizing other generators or power modules.

In another embodiment of the invention, the center frequency of each frequency range corresponds to an output of a voltage controlled oscillator. The output of the voltage controlled oscillator corresponds to an input control signal, and the input control signal is generated by a DAC (digital-to-analog converter). In other embodiments, the digital input to the DAC produces a stepped staircase analog output from the DAC, resulting in a stepped, staircase sweeping function within a frequency range. In yet another embodiment, the digital input to the DAC produces a random or chaotic staircase analog output from the DAC, resulting in a random or chaotic staircase sweeping function within a frequency range.

In another aspect, the invention comprises a system for coupling sound energy to a liquid. The system includes at least two transducers forming a transducer array adapted for coupling to a liquid in a tank, and the transducer array is constructed and arranged so as to be capable of producing intense sound energy in the liquid at any frequency within at least two non-overlapping frequency bands. The system further includes a signal generator adapted for producing a driver signal for driving the transducer array at any frequency from one or more continuous frequency ranges within at least two of the frequency bands. The signal generator drives the transducer array so as to produce intense sound energy characterized by a plurality of changing frequencies within a first frequency range, followed by a plurality of changing frequencies within a second frequency range. The system so operating reduces a strong antinode below the liquid-to-air interface.

In another aspect, the invention comprises a system for coupling sound energy to a liquid, that includes at least two transducers forming a transducer array adapted for coupling to a liquid in a tank. The transducer array is constructed and arranged so as to be capable of producing intense sound energy in the liquid at any frequency within at least two distinct frequency bands. The system further includes a signal generator adapted for producing a driver signal for driving the transducer array at any frequency from one or more continuous frequency ranges within the at least two frequency bands. The center frequencies of the higher frequency ranges are non-integer multiples of the center frequency of the lowest frequency range to prevent two or more Fourier frequencies of a periodic wave from forming in the liquid. The signal generator drives the transducer array to produce sound energy corresponding to a first set of frequencies from a first frequency range, then produces sound energy corresponding to a second set of frequencies from a second frequency range. The transition from the first frequency range to the second frequency range is discontinuous and occurs after a time interval at least as long as the lifetime of sound energy in the container for frequencies from the first frequency range. The sound energy corresponding to the second set of frequencies continues for a time interval at least as long as the lifetime of sound energy in the container for frequencies from the second frequency range.

In another aspect, the invention comprises multiple frequency generator capable of producing an output signal characterized by any frequency within two or more non-contiguous, continuous frequency ranges. The generator is controlled to change the frequency within a frequency range, and then to change frequencies from one frequency range to a second frequency range before beginning the changing of frequencies in this second frequency range.

In another aspect, the invention comprises a method of delivering successive multiple ultrasound frequencies of intense sound waves to a liquid. The method includes the step of coupling to the liquid an array of transducers that are capable of producing sound energy in the liquid at an infinite number of different frequencies contained within two or more non-contiguous, continuous frequency bands. The method also includes the step of driving the transducer array with a generator capable of producing substantially all of the frequencies within continuous frequency ranges contained within two or more of the transducer array frequency bands. The method further includes the step of controlling the generator so that the produced frequencies change within the frequency ranges according to a function of time, and the frequencies jump amongst the frequency ranges.

In another aspect, the present invention is directed to the creation of an AC switch by electronic circuitry or electromechanical devices, such as relays. The AC switch as presented in this invention will exchange a modifying circuitry (which contains resistive, reactive, and active components) into and out of the power section of an ultrasound generator. Therefore, the output of the ultrasound generator will be modified by the modification circuitry disclosed, by way of example, herein. The AC switch is operatively connected to the modification circuitry. It switches the modification circuitry into and out of the output stage of the generator. The control circuitry is associated with the AC switch and is adapted to turn off and turn on the AC switch. The AC switch will swap resistive, reactive and active components and networks of these components into and out of the power section of ultrasound frequency generators. The present invention provides a simple and reliable manner to increase the number of parameters and diversify the capabilities of an ultrasound generator.

The AC switch introduces a modification circuit that is able to (1) maintain full power output from a multiple frequency ultrasound generator as the center frequency of the generator is changed, (2) step sweep the output of an ultrasound oscillator, and (3) vary the output power and amplitude of a non self-oscillating ultrasound generator. A fixed frequency oscillator can be modified to accomplish certain of these functions and to sweep frequency. This is accomplished by the step sweeping and successive AC switching in of capacitors and/or inductors (i.e. modification circuitry).

This patent will suggest a number of applications in which the AC switch is created by triacs. A triac is a three terminal semiconductor, which controls current in either direction. The triac is suited to create a simple and less expensive AC switch than the use of transistors. Nevertheless, it will be obvious to those skilled in the art that other circuitry can be substituted for triacs. One example of such other circuitry, which simulates a triac, is one that includes back to back silicon-controlled rectifiers. Also, a series/parallel active device configuration or bi-directional lateral insulated gate bipolar transistor, can act as the AC switch.

The phrase "modification circuitry" as used herein is defined as resistive, reactive and active components and networks of these components. The circuitry will have two main leads and one or more control leads available for active components or networks containing active components. One of ordinary skill in the art will readily appreciate that it is possible to introduce a different value of a resistive or reactive component through the use of a transformer; therefore, in some cases a transformer winding or tap can be the part of the modification circuitry that is switched by the AC switch.

The modification circuitry is placed in parallel with an AC switch when it is required that the modification circuitry be inserted into a conduction line of the ultrasound generator. The modification circuitry is placed in series with an AC switch when it is required that the modification circuitry be inserted between two nodes of the ultrasound generator. When connected in series, the modification circuitry is inserted at any time in the cycle by turning on the AC switch. In the case of a parallel connection, the modification circuitry is removed from the generator when the AC switch is on. The reverse effect will happen when the AC switch is turned off. The addition of a control circuitry to the AC switch supplies turn on and off signals to the AC switch. Where the AC switch is a triac, the control circuitry will provide (1) a turn off signal to the ultrasound generator for a period of time at least as long as the triac turn off time, (2) the turn off signal to the triac for a period of time at least as long as the triac turn off time, and (3) concurrent signals for a period of time at least as long as the triac turn off time. The use of this control circuitry is necessary due to the fact that the speed of triacs is too slow to allow them to go off when conducting an ultrasound current.

Another embodiment of the invention includes modification circuitry capable of modifying the following parameters of the output of an ultrasound generator: frequency; amplitude; power; impedance; and waveform. The parameter will change in accordance to the purpose of the application or generator. The modification includes at least one capacitor, one inductor, or one resistor. Finally, it can also include an active/passive network with a control circuitry adapted to control the active components in the network.

In another embodiment of the invention, a control circuitry capable of supplying a turn off signal to the AC switch for a duration D1 is illustrated. If the AC switch is a triac, the control circuitry will also supply a turn off signal D2 to the generator, where D1 and D2 are concurrent for a time equal to or greater than the triac turn off time. The same will apply if the AC switch is comprised of back to back silicon controlled rectifiers. In the case of the modification of the output frequency of an ultrasound oscillator, the "controller" will represent the control circuit. This controller can be further modified to selectively activate or deactivate components so as to step sweep the output frequency of an oscillator.

Another embodiment of the invention is a system for coupling ultrasound to a liquid, comprising two or more transducers adapted for coupling to a liquid, the transducers constructed and arranged so as to be capable of producing ultrasound in the liquid at frequencies within at least two frequency bands, and one or more ultrasound generators adapted for producing driver signals for driving the transducers at frequencies in one or more frequency ranges within each of the at least two frequency bands; wherein at least one frequency range is within the microsonic range of frequencies; and, wherein the driver signals in the microsonic range of frequencies are synchronized with a common FM signal; and, wherein the driver signals of the one or more ultrasound generators drive the transducers to produce ultrasound in the liquid characterized by a frequency that sweeps at random, chaotic or pseudo random sweep rates within at least one of the frequency ranges in one of the at least two frequency bands; and, wherein the sweep is monotonic from high frequency to low frequency with a recovery time from low frequency to high frequency that is a shorter time than the monotonic sweep; and, wherein the driver signals are amplitude modulated at a modulation frequency that changes randomly, chaotically or pseudo randomly; and, wherein the one or more ultrasound generators each have an output stage, which comprises, a) modification circuitry which modifies the output stage; b) an AC switch, operatively connected to the modification circuitry, which switches the modification circuitry into and out of the output stage of the ultrasound generator; and c) control circuitry, associated with the AC switch and with the one or more ultrasound generators, which is adapted to turn off and turn on the AC switch, wherein the control circuitry, AC switch and modification circuitry changes the one or more ultrasound generator driver signals to further drive the transducers to change frequency to a different frequency range in a different frequency band, so as to generate ultrasound characterized by a frequency that sweeps at random, pseudo random or chaotic sweep rates within at least one additional frequency range in at least one additional frequency band of the at least two frequency bands. In yet another embodiment of the invention, this system adds power control to the ultrasound by an amplitude modulated driver signal that has off times that vary randomly, chaotically or pseudo randomly while maintaining a specified duty cycle for power control.

Another embodiment of the invention is a system for coupling ultrasound to a liquid, comprising one or more transducers adapted for coupling to a liquid, the transducers constructed and arranged so as to be capable of producing ultrasound in the liquid at frequencies within at least two frequency bands, and an ultrasound generator adapted for producing a driver signal for driving the transducers at frequencies in one or more frequency ranges within each of the at least two frequency bands; wherein the driver signal of the ultrasound generator drives the transducers to produce ultrasound in the liquid characterized by successive frequencies within at least one of the frequency ranges in one of the at least two frequency bands; and, wherein the ultrasound generator has an output stage, which comprises, a) modification circuitry which modifies the output stage; b) an AC switch, operatively connected to the modification circuitry, which switches the modification circuitry into and out of the output stage of the ultrasound generator; and c) control circuitry, associated with the AC switch and with the ultrasound generator, which is adapted to turn off and turn on the AC switch, wherein the control circuitry, AC switch and modification circuitry changes the ultrasound generator driver signal to further drive the transducers to change frequency to a different frequency range in a different frequency band, so as to generate ultrasound characterized by successive frequencies within at least one additional frequency range in at least one additional frequency band of the at least two frequency bands.

Another embodiment of the invention is a system for coupling ultrasound to a liquid, comprising, two or more transducers adapted for coupling to a liquid, the transducers constructed and arranged so as to be capable of producing ultrasound in the liquid at frequencies within at least two frequency bands, and, one or more ultrasound generators adapted for producing driver signals for driving the transducers at frequencies in one or more frequency ranges within each of the at least two frequency bands; wherein at least one frequency range is within the microsonic range of frequencies; and, wherein the driver signals of the one or more ultrasound generators drive the transducers to produce ultrasound in the liquid characterized by a frequency that sweeps at random, chaotic or pseudo random sweep rates within at least one of the frequency ranges in one of the at least two frequency bands; and, wherein the driver signals are amplitude modulated at a modulation frequency that changes randomly, chaotically or pseudo randomly; and, wherein the one or more ultrasound generators each have an output stage, which comprises, a) modification circuitry which modifies the output stage; b) an AC switch, operatively connected to the modification circuitry, which switches the modification circuitry into and out of the output stage of the ultrasound generator; and c) control circuitry, associated with the AC switch and with the one or more ultrasound generators, which is adapted to turn off and turn on the AC switch, wherein the control circuitry, AC switch and modification circuitry changes the one or more ultrasound generator driver signals to further drive the transducers to change frequency to a different frequency range in a different frequency band, so as to generate ultrasound characterized by a frequency that sweeps at random, pseudo random or chaotic sweep rates within at least one additional frequency range in at least one additional frequency band of the at least two frequency bands.

Another embodiment of the invention is a system for coupling ultrasound to a liquid, comprising at least two transducers adapted for coupling to a liquid, the transducers constructed and arranged so as to be capable of producing ultrasound in the liquid at frequencies within at least two frequency bands; an ultrasound generator adapted for producing a driver signal for driving the transducers at frequencies in one or more frequency ranges within each of the at least two frequency bands; wherein at least one of the frequency ranges is in the microsonic range of frequencies; and, wherein the driver signal of the ultrasound generator drives the transducers to produce ultrasound in the liquid characterized by successive frequencies within at least one of the frequency ranges in one of the at least two frequency bands; the ultrasound generator changes the driver signal to further drive the transducers to change frequency to a different frequency range in a different frequency band, so as to generate ultrasound characterized by successive frequencies within at least one additional frequency range in at least one additional frequency band of the at least two frequency bands.

Another embodiment of the invention is a system for coupling ultrasound to a liquid, comprising two or more transducers adapted for coupling to a liquid, the transducers constructed and arranged so as to be capable of producing ultrasound in the liquid at frequencies within at least two frequency bands, and, one or more ultrasound generators adapted for producing driver signals for driving the transducers at frequencies in one or more frequency ranges within each of the at least two frequency bands; wherein the driver signals of the one or more ultrasound generators drive the transducers to produce ultrasound in the liquid characterized by a frequency that sweeps at random, chaotic or pseudo random sweep rates within at least one of the frequency ranges in one of the at least two frequency bands; and, wherein the driver signals are continuous wave; and, wherein the one or more ultrasound generators each have an output stage, which comprises a) modification circuitry which modifies the output stage; b) an AC switch, operatively connected to the modification circuitry, which switches the modification circuitry into and out of the output stage of the ultrasound generator; and c) control circuitry, associated with the AC switch and with the one or more ultrasound generators, which is adapted to turn off and turn on the AC switch, wherein the control circuitry, AC switch and modification circuitry changes the one or more ultrasound generator driver signals to further drive the transducers to change frequency to a different frequency range in a different frequency band, so as to generate ultrasound characterized by a frequency that sweeps at random, pseudo random or chaotic sweep rates within at least one additional frequency range in at least one additional frequency band of the at least two frequency bands.

Another embodiment of the invention is an ultrasound generator having an output signal that is frequency modulated with a sweeping frequency waveform and amplitude modulated with a changing frequency; wherein the sweep rate of the sweeping frequency waveform changes randomly, chaotically or pseudo randomly; and, wherein the amplitude modulation frequency changes randomly, chaotically or pseudo randomly.

Another embodiment of the invention is an ultrasound generator having an output signal that is frequency modulated with a sweeping frequency waveform and has continuous wave for its amplitude modulation; wherein the sweep rate of the sweeping frequency waveform changes randomly, chaotically or pseudo randomly.

Another embodiment of the invention is a frequency drive signal (referred to herein as the improved cavitation efficiency drive signal) where the drive signal is provided during a first defined time period and at a first frequency during a beginning portion of the first defined time period, and the drive signal is provided at a second frequency during an ending portion of the first defined time period with the drive signal sweeping from the first frequency to the second frequency during this first defined time period. The frequency of the drive signal is varied from the second frequency to a third frequency; and the drive signal is provided during a second defined time period. This drive signal increases the efficiency of cavitation and can be employed with any of the generator or generator and transducer array systems described in this specification.

Another embodiment of the invention is for improving cleaning or processing by producing a first form of cavitation and a second form of cavitation in a liquid comprising a succession of time periods with at least one time period wherein the first form of cavitation is produced in the liquid, and, at least one of the successive time periods wherein the second form of cavitation is produced in the liquid, wherein the first form of cavitation is predominantly stable cavitation, and, wherein the second form of cavitation is predominantly transient cavitation. This method of improving performance with two forms of cavitation can be employed with any of the generator or generator and transducer array systems described in this specification.

In another embodiment of the invention the second form of cavitation is produced by the improved cavitation efficiency drive signal. A drive signal incorporating the first form of cavitation in at least one time period and the second form of cavitation in the form of the improved efficiency drive signal in another time period can be employed with any of the generator or generator and transducer array systems described in this specification.

In another embodiment of the invention, a method for inactivation of organisms in liquids includes establishing a sequence of one or more periods of predominantly stable cavitation in the liquid and one or more periods of predominantly transient cavitation in the liquid, the respective periods being sufficient to effect a predetermined inactivation of the organisms. In the preferred aspect of the invention the method for the inactivation for microorganisms in liquids further includes adding to the liquid one or more microbiologically active chemicals prior to the establishing steps.

In another embodiment of the invention, combinations of eight process parameters, i.e., multiple frequencies, predominantly stable cavitation, predominantly transient cavitation, a succession of predominantly stable and predominantly transient cavitation, UV light, electric current, an electrolyte and microbiologically active chemicals, are employed to improve the inactivation of organisms, i.e., to reduce the time that it takes to achieve a specified inactivation.

In another embodiment of the invention, a method for inactivation of organisms in aqueous liquids comprises adding an electrolyte to the liquid and passing an electric current through the liquid, whereby the inactivation is effected.

In another embodiment of the invention, a method for inactivation of organisms in liquids comprises applying successive multiple ultrasound frequencies to the liquid, whereby the inactivation is effected.

In another embodiment of the invention involving concurrent multiple ultrasound frequencies, the inventor has found that when an optimum spacing D for transducers results in less power density than is required by the process, the solution is to use random transducer spacing where the radiating membrane surface is uniformly covered by the number of transducers needed to supply the required power density. For a concurrent multiple ultrasound frequency system, the random spacing has one of two configurations. If the transducers are the same type of universal transducer with the ability to produce two or more different frequencies, then the randomly spaced transducers are wired into two or more arrays where adjacent transducers are typically in different arrays. If the transducers are unique for each of the two or more different frequencies, then the randomly spaced transducers include a mix of different frequency transducers such that adjacent transducers are typically a different frequency.

The destructive and constructive interference of the different frequency sound waves results in less transient cavitation compared to sweeping single frequency systems because the resultant wave in the liquid has many frequencies that typically exist for one cycle or less, except for frequencies at or near the average of the individual frequencies. Transient cavitation produced by normal power ultrasonics (defined herein as typically 100 watts per gallon for small volumes on the order of five gallons to 20 watts per gallon for larger volumes on the order of 100 gallons) typically requires several cycles for the cavitation bubble to oscillate up to the critical energy level required for a transient collapse, therefore, for that ultrasonic energy at frequencies where one cycle or less is available, the bubbles grow and then decay, producing microstreaming, but seldom a transient collapse. Although this conventional operation of a concurrent multiple ultrasound frequency system is lacking where predominantly transient cavitation is required, the growth and decay of bubbles simulates the effects of stable cavitation and therefore, this conventional operation of a concurrent multiple ultrasound frequency system will be used herein as one additional method to produce predominantly stable cavitation.

For processes where transient cavitation is required, the present invention improves the amount of transient cavitation from a concurrent multiple ultrasound frequency system by supplying the ultrasonic power to the tank in synchronized high peak power different frequency ultrasonic bursts. This produces the spectrum of frequencies that typically exist for one cycle or less, however, when the synchronized ultrasonic bursts have sufficient peak power to grow the bubbles to the energy levels required for transient cavitation collapse in one cycle or less, then there is transient cavitation at each of these frequencies. The inventor has found that in a normal power system, if a minimum of 84 percent of the energy per cycle is delivered in a maximum of 27 percent of the cycle time, the conditions for improved transient cavitation occur. As higher percentages of the energy are delivered in shorter amounts of the cycle time, the efficiency of transient cavitation improves.

It should be noted that the intermixed random spacing is the preferred transducer configuration for this invention, however, any spacing, intermixed or not intermixed, results in the improved cavitation density of the broad spectrum of transient cavitation that results from the synchronized high peak power different frequency ultrasonic bursts. It should also be noted that the drive signal in each of the synchronized bursts is typically a sweeping frequency, however, single frequency bursts also improve the amount of transient cavitation compared to prior art systems with the same powers and frequencies.

In another embodiment of the invention a system is configured to be capable of supplying both concurrent multiple ultrasound frequencies and successive multiple ultrasound frequencies in series to a liquid. The generator is controlled to supply each type of ultrasound for the programmed periods to accomplish the desired process. This method provides greater efficiency for processes where the unique advantages of each type of ultrasound (concurrent multiple ultrasound frequencies and successive multiple ultrasound frequencies) are useful for part of the process. This embodiment is best achieved with multiple arrays of universal transducers. Consider as an example, two arrays of universal transducers with a first multiple frequency generator driving the first array of universal transducers and with a second multiple frequency generator driving the second array of universal transducers. A controller controls these two generators such that they produce concurrent multiple ultrasound frequencies when the first generator is controlled to operate in a first frequency range while the second generator is controlled to operate in a second frequency range. When the controller controls both generators to operate in the same frequency range, the system produces the first in a series of successive multiple ultrasound frequencies. By programming the controller to work in each mode is series, both concurrent multiple ultrasound frequencies and successive multiple ultrasound frequencies in series are supplied to a liquid. It is noted that some processes are improved when the individual frequency ranges in a set of successive ultrasound frequencies are separated by a time period of concurrent multiple frequency ultrasound frequencies. This special case will be defined herein to be included when both concurrent multiple ultrasound frequencies and successive multiple ultrasound frequencies in series are referred to.

In one form of the invention, two or more transducers (or arrays of transducers) may be driven by a frequency spectrum including distinct frequencies (e.g., F1 and F2 in the case of two transducers or two transducer arrays) for a period of time. Followed by one or more transducers or arrays of transducers being driven by different frequency spectra (e.g., in the case of a single transducer a third frequency F3) for a second period of time (F3 may be equal to F1 or F2 or may be a different frequency). The latter transducers may be one or more of the former transducers or they may be distinct from the former transducers. The application of the different frequency spectra may be in the above described sequence or reversed in time. The time periods can be contiguous or not as desired.

In another embodiment of the invention a new wide range multiple frequency transducer that will operate at regions in each area of the wide frequency range from ultrasonic to microsonic to megasonic is a sandwich type transducer. The unique concept that makes megasonics operation practical in this sandwich type transducer is that the thickness of each piezoelectric ceramic is designed such that an integer number of half wavelengths of sound exist in the ceramic at the megasonics frequency; and the back mass and the front mass with its bonded surface each contain an integer number of half wavelengths plus one quarter of a wavelength at the megasonics frequency. Good design practice calls for the clamping bolt or other clamping assembly to be recessed from the outer surface of the back mass and/or from the radiating surface of the front mass so its load bearing surface or surfaces are at nodal points of the megasonics half wavelengths within the front mass and/or the back mass. Another unique feature of this inventive sandwich type transducer structure (Langevin type structure) when operated at megasonics frequencies is the heat dissipating ability of the stacked structure. This allows reliable off resonance operation of the transducer in ranges around the megasonics center frequency, which allows sweeping in the megasonics frequency range. The inventor has found that sweeping megasonics has advantages over the state of the art single frequency megasonics. The collimated megasonic characteristic of the prior art is reduced by sweeping megasonics and the process efficiency is improved because there is less absorption of sound energy when sweeping compared to prior art single frequency megasonics.

This transducer operates at the lower ultrasonic and/or microsonic frequencies in the same fashion as a Langevin transducer with harmonics, i.e., the lowest frequency is the half wavelength resonance of the complete stack and higher frequencies are harmonics or overtones of this fundamental resonance.

In another embodiment of the invention a multiple frequency band ultrasound transducer for producing vibratory motion at a drive surface comprises a transducer assembly extending along the transducer axis of the transducer assembly including:

i. a piezoelectric assembly including a stack of p polarized piezoelectric ceramic elements extending along the transducer axis between a piezoelectric assembly top surface and a piezoelectric assembly bottom surface, each of the polarized piezoelectric ceramic elements having an element top surface and an element bottom surface, and being characterized by a thickness $P_i$ along the transducer axis, where i is an integer 1, 2, . . . , p, each of the element top surfaces and the element bottom surfaces having an electrically conductive layer disposed thereon, and including means for coupling a drive signal to the electrically conductive layers, ii. a tank wall extending between a tank wall top surface and a tank wall bottom surface, the tank wall having a thickness T in the direction of the transducer axis, the thickness T being small relative to other thicknesses in the transducer assembly, the tank wall top surface forming the drive surface, and the tank wall bottom surface bonded to a front mass effectively adding a thickness T/2 to the front mass;

iii. the front mass extending between the tank wall bottom surface and the piezoelectric assembly top surface, the front mass having a thickness D in the direction of the transducer axis;

iv. a back mass extending between a bottom transducer surface and the bottom piezoelectric assembly surface, the back mass having a thickness B in the direction of the transducer axis;

v. a compression assembly including means for applying a compressive force F across the front mass and the back mass; whereby the front mass, the piezoelectric assembly, the back mass and the tank wall are dimensioned so that in response to the compressive force F:

$P_i$ is equal to $n_i \lambda_p/2$ $D+T/2$ is equal to $m_1 \lambda_D/2 + \lambda_D/4$ B is equal to $m_2 \lambda_B/2 + \lambda_B/4$ where $n_1$, $m_1$ and $m_2$ are integers and $\lambda_p$ is the characteristic acoustic wavelength of the polarized piezoelectric ceramic elements, and $\lambda_B$ and $\lambda_D$, are the characteristic acoustic wavelengths of the back mass and the front mass, respectively [where $\lambda=v/f$] wherein the transducer is characterized by a vibratory fundamental first frequency having wavelength $\lambda_{f1}$ equal to $$2\left(\sum_i P_i + D + T/2 + B\right)$$

and a vibratory second frequency having wavelength $\lambda_{f2}$ equal to $2\lambda_P$.

The invention is next described further in connection with preferred embodiments, and it will become apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which:

FIGS. 16-26 show transducer and back mass embodiments for systems, methods and transducers of the invention.

FIGS. 34 and 35 show alternative timing cycles through which the system of FIG. 33 applies ultrasound from upper to lower frequencies;

FIGS. 42 and 43 show multi-frequency ultrasound systems constructed according to the invention;

FIG. 44 illustrates a process control system and ultrasound probe constructed according to the invention;

FIG. 64 shows a side view of a printed circuit board coupled with transducers as a single unit, in accord with the invention; and FIG. 65 shows a top view of the unit of FIG. 64;

FIG. 72A shows in diagram form the multiple frequency system according to the present invention;

FIG. 72B shows, in graphical form, characteristics of the transducer array of FIG. 72A;

FIG. 72C shows, in graphical form, characteristics of the generator of FIG. 72A;

FIG. 73B shows, in schematic form, additional components of the generator of FIG. 73A;

FIG. 96A shows graphs of single frequency particle removal for process time x and for process time 20x.

FIG. 96B shows graphs of particle removal for seven successive multiple ultrasound frequencies each with a process time of x for a total process time of 7x and the combined effect graph.

DESCRIPTION OF THE PREFERRED EMBODIMENTS

Figure 1:
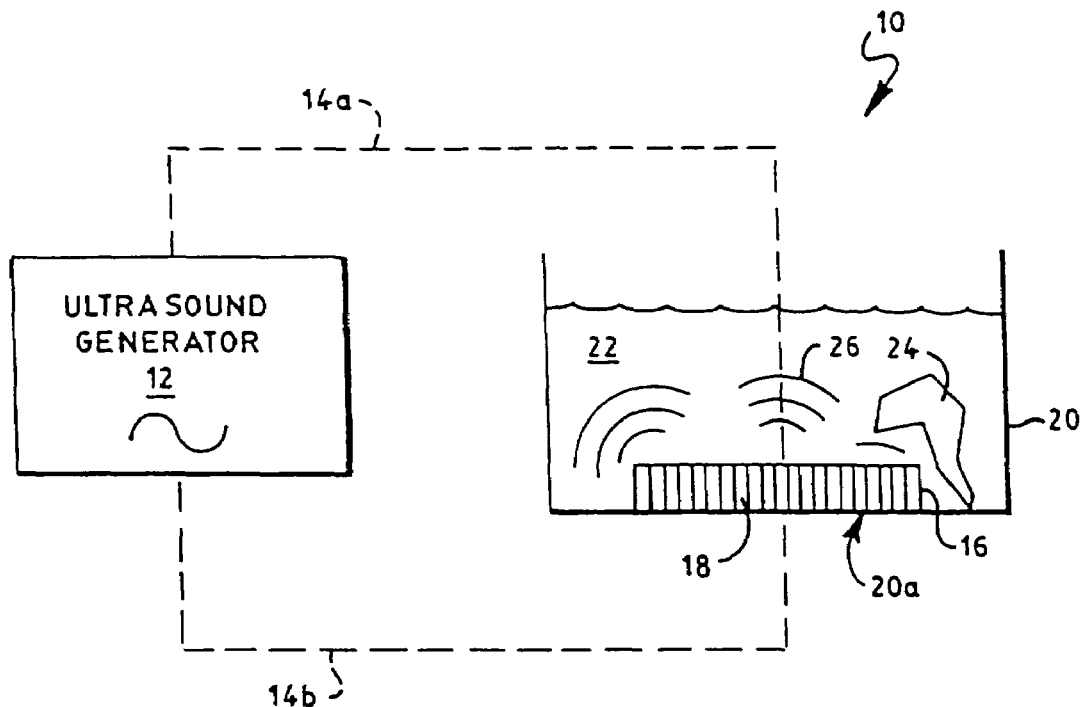
FIG. 1 shows a cut-away side view schematic of an ultrasound processing system constructed according to the invention.
Figure 2:
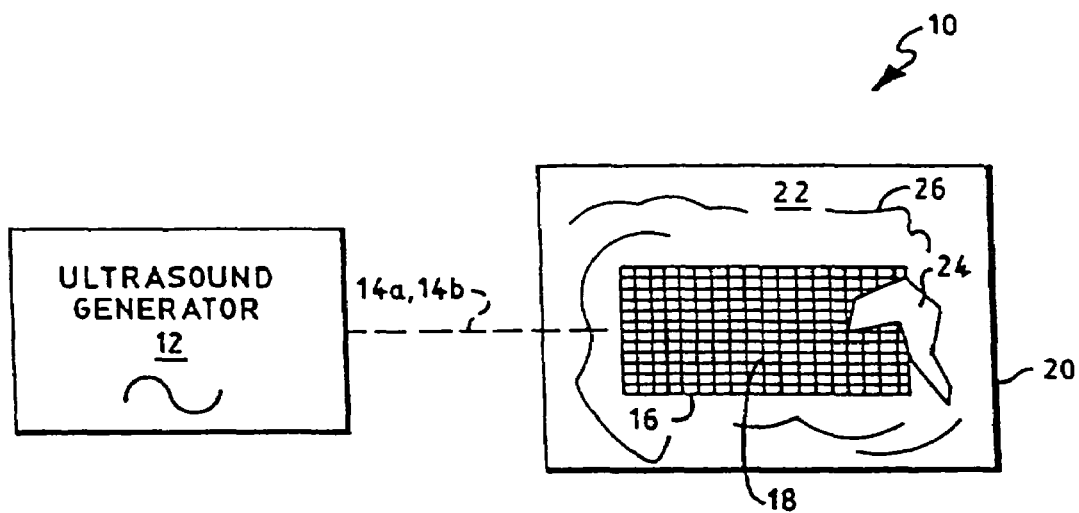
FIG. 2 shows a top view schematic of the system of FIG. 1.

FIGS. 1 and 2 show schematic side and top views, respectively, of an ultrasound processing system 10 constructed according to the invention. An ultrasound generator 12 electrically connects, via electrical paths 14a, 14b, to an ultrasound transducer 16 to drive the transducer 16 at ultrasound frequencies above about 18 khz, and usually between 40 khz and 350 khz. Though not required, the transducer 16 is shown in FIG. 1 as an array of transducer elements 18. Typically, such elements 18 are made from ceramic, piezoelectric, or magnetostrictive materials which expand and contract with applied voltages or current to create ultrasound. The transducer 16 is mounted to the bottom, to the sides, or within the ultrasound treatment tank 20 through conventional methods, such as known to those skilled in the art and as described above. A liquid 22 fills the tank to a level sufficient to cover the delicate part 24 to be processed and/or cleaned. In operation, the generator 12 drives the transducer 16 to create acoustic energy 26 that couples into the liquid 22.

Although the transducer 16 is shown mounted to the bottom of the tank 20, those skilled in the art will appreciate that other mounting configurations are possible and envisioned. The transducer elements 18 are of conventional design, and are preferably "clamped" so as to compress the piezoelectric transducer material.

Figure 3:
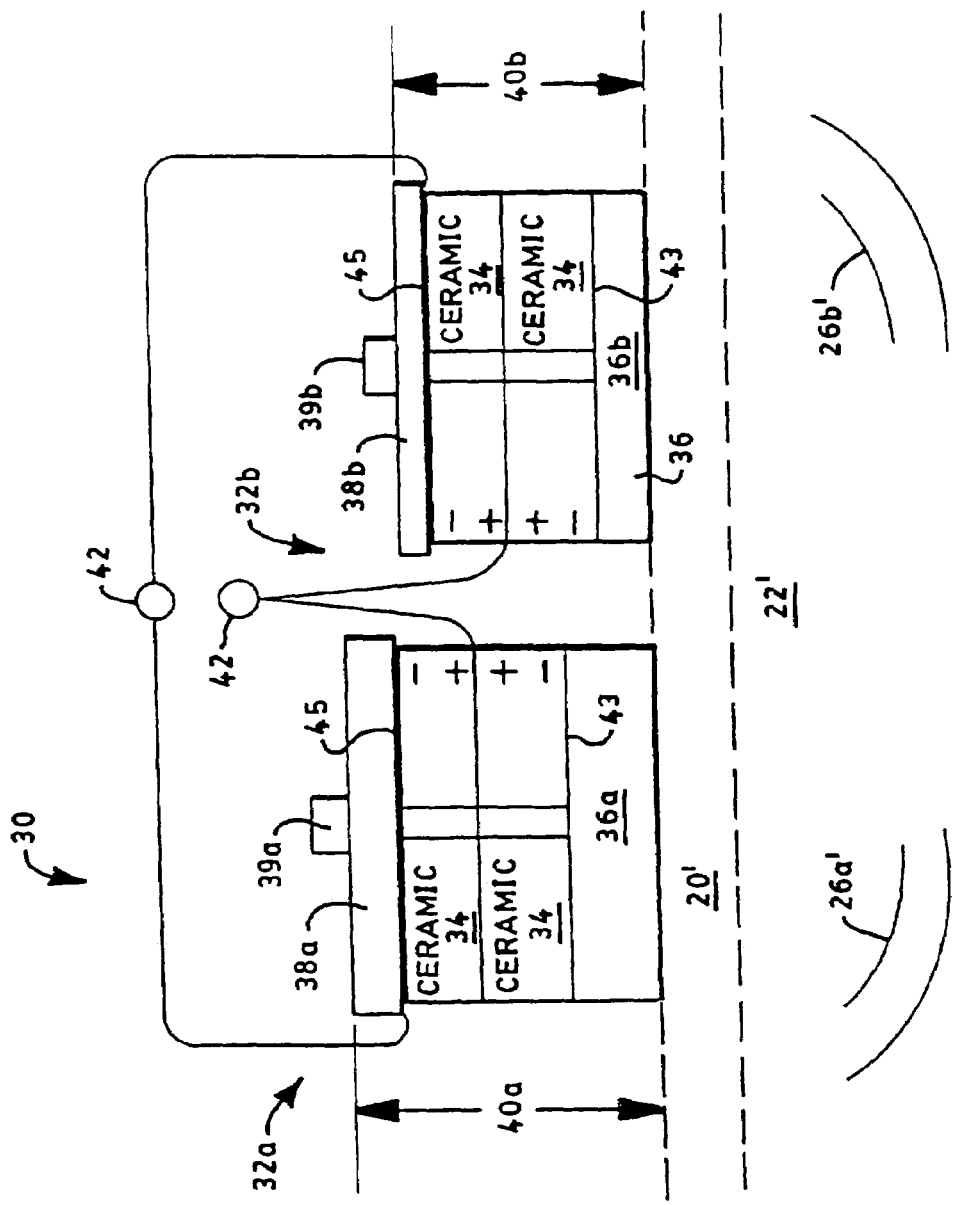
FIG. 3 shows a schematic illustration of a multi-transducer system constructed according to the invention and used to generate broadband ultrasound in a combined bandwidth.

FIG. 3 illustrates a two transducer system 30. Transducer 32a, 32b are similar to one of the elements 18, FIG. 1. Transducer 32a includes two ceramic sandwiched elements 34, a steel back mass 38a, and a front mass 36a that is mounted to the tank 20'. Transducer 32b includes two ceramic sandwiched elements 34, a steel back mass 38b, and a front mass 36b that is mounted to the tank 20'. Bolts 39a, 39b pass through the masses 38a, 38b and screw into the drive masses 36a, 36b, respectively, to compresses the ceramics 34. The transducers 32 are illustratively shown mounted to a tank surface 20'.

The transducers 32a, 32b are driven by a common generator such as generator 12 of FIG. 1. Alternatively, multiple generators can be used. The ceramics 34 are oriented with positive "+" orientations together or minus "−" orientations together to obtain cooperative expansion and contraction within each transducer 32. Lead-outs 42 illustrate the electrical connections which connect between the generator and the transducers 32 so as to apply a differential voltage there-across. The bolts 39a, 39b provide a conduction path between the bottoms 43 and tops 45 of the transducers 32 to connect the similar electrodes, shown here as—and—, of the elements 34.

The thicknesses 40a, 40b of transducers 32a, 32b, respectively, determine the transducer's fundamental resonant frequency. For purposes of illustration, transducer 32a has a fundamental frequency of 40 khz, and transducer 32b has a fundamental frequency of 44 khz. Transducers 32a, 32b each have a finite ultrasound bandwidth which can be adjusted, slightly, by those skilled in the art. Typically, however, the bandwidths are about 4 khz. By choosing the correct fundamental frequencies, therefore, an overlap between the bandwidths of the two transducers 32a, 32b can occur, thereby adding additional range within which to apply ultrasound 26a', 26b' to liquid 22'.

Figure 4:
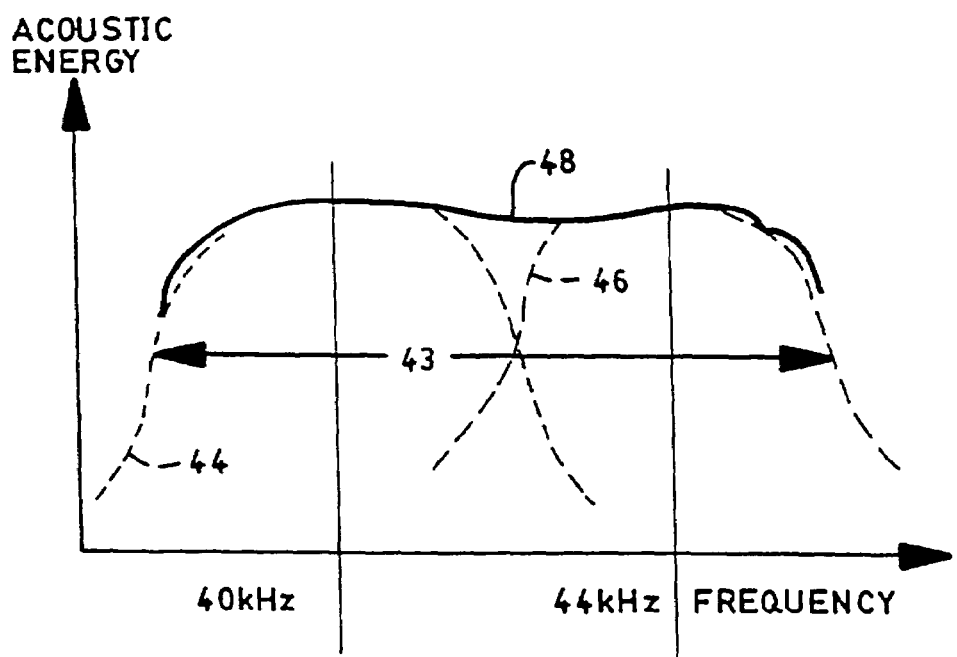
FIG. 4 graphically illustrates the acoustic disturbances produced by the two transducers of FIG. 3.

The acoustic energy 26' applied to the liquid 22' by the combination of transducers 32a, 32b is illustrated graphically in FIG. 4. In FIG. 4, the "x" axis represents frequency, and the "y" axis represents acoustical power. The outline 44 represents the bandwidth of transducer 32a, and outline 46 represents the bandwidth of transducer 32b. Together, they produce a combined bandwidth 43 which produces a relatively flat acoustical energy profile to the liquid 22', such as illustrated by profile 48. The flatness of the bandwidth 43 representing the acoustical profile 48 of the two transducers 32a, 32b is preferably within a factor of two of any other acoustical strength within the combined bandwidth 43. That is, if the FWHM defines the bandwidth 43; the non-uniformity in the profile 48 across the bandwidth 43 is typically better than this amount. In certain cases, the profile 48 between the two bandwidths 44 and 46 is substantially flat, such as illustrated in FIG. 4.

The generator connected to lead-outs 42 drives the transducers 32a, 32b at frequencies within the bandwidth 43 to obtain broadband acoustical disturbances within the liquid 22'. As described herein, the manner in which these frequencies are varied to obtain the overall disturbance is important. Most preferably, the generator sweeps the frequencies through the overall bandwidth, and at the same time sweeps the rate at which those frequencies are changed. That is, one preferred generator of the invention has a "sweep rate" that sweeps through the frequencies within the bandwidth 43; and that sweep rate is itself varied as a function of time. In alternative embodiments of the invention, the sweep rate is varied linearly, randomly, chaotically or as some other function of time to optimize the process conditions within the tank 20'.

With further reference to FIGS. 1 and 2, each of the elements 18 can have a representative bandwidth such as illustrated in FIG. 4. Accordingly, an even larger bandwidth 43 can be created with three or more transducers such as illustrated by transducers 32a, 32b. In particular, any number of combined transducers can be used. Preferably, the bandwidths of all the combined transducers overlap to provide an integrated bandwidth such as profile 48 of FIG. 4. As such, each transducer making up the combined bandwidth should have a unique resonant frequency.

Those skilled in the art understand that each of the transducers 18 and 32a, 32b, FIGS. 2 and 3, respectively, have harmonic frequencies which occur at higher mechanical resonances of the primary resonant frequency. It is one preferred embodiment of the invention that such transducers operate at one of these harmonics, i.e., typically the first, second, third or fourth harmonic, so as to function in the frequency range of 100 khz to 350 khz. This frequency range provides a more favorable environment for acoustic processes within the tanks 20, 20' as compared to low frequency disturbances less than 100 khz. For example, ultrasound frequencies around the 40 khz frequency can easily cause cavitation damage in the part 24. Further, such frequencies tend to create standing waves and other hot spots of spatial cavitation within the liquid.

Figure 5:
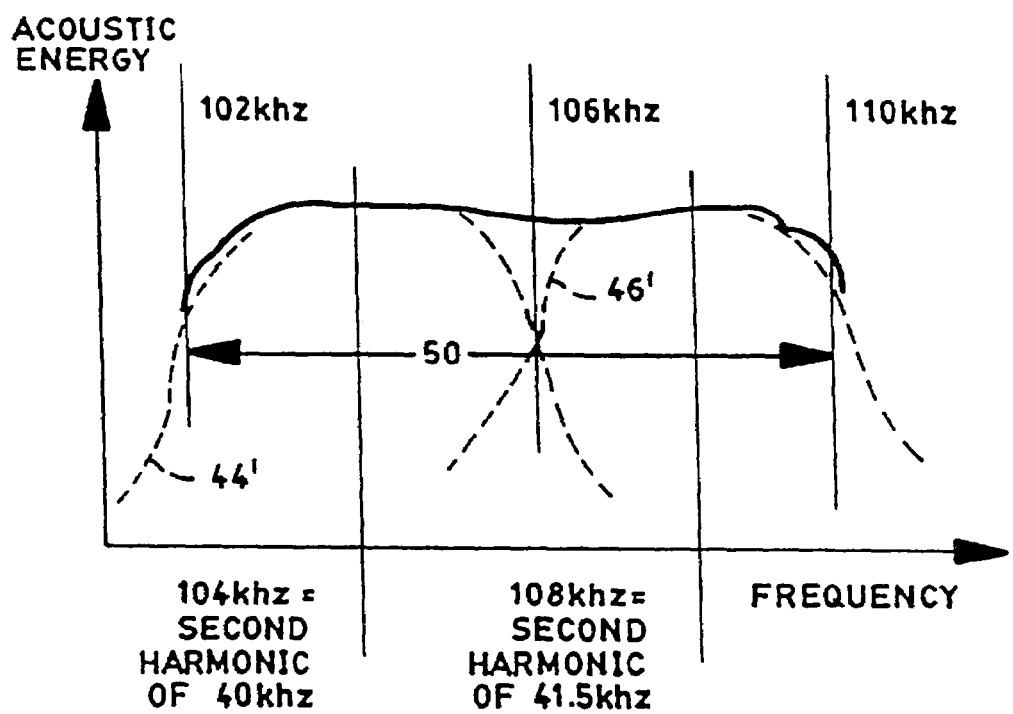
FIG. 5 graphically illustrates the broadband acoustic disturbances produced by harmonics of a multi-transducer system constructed according to the invention.

Accordingly, the benefits of applying a broadband acoustic disturbance to the liquid also apply to the 100-350 khz microsonic frequencies. Similar to FIG. 4, FIG. 5 illustrates a combined bandwidth 50 of harmonic frequencies in the range 100-350 khz. Specifically, FIG. 5 shows the combined bandwidth 50 that is formed by the bandwidth 44' around the second harmonic of the 40 khz frequency, and the bandwidth 46' around the second harmonic of the 41.5 khz frequency.

Figure 6:
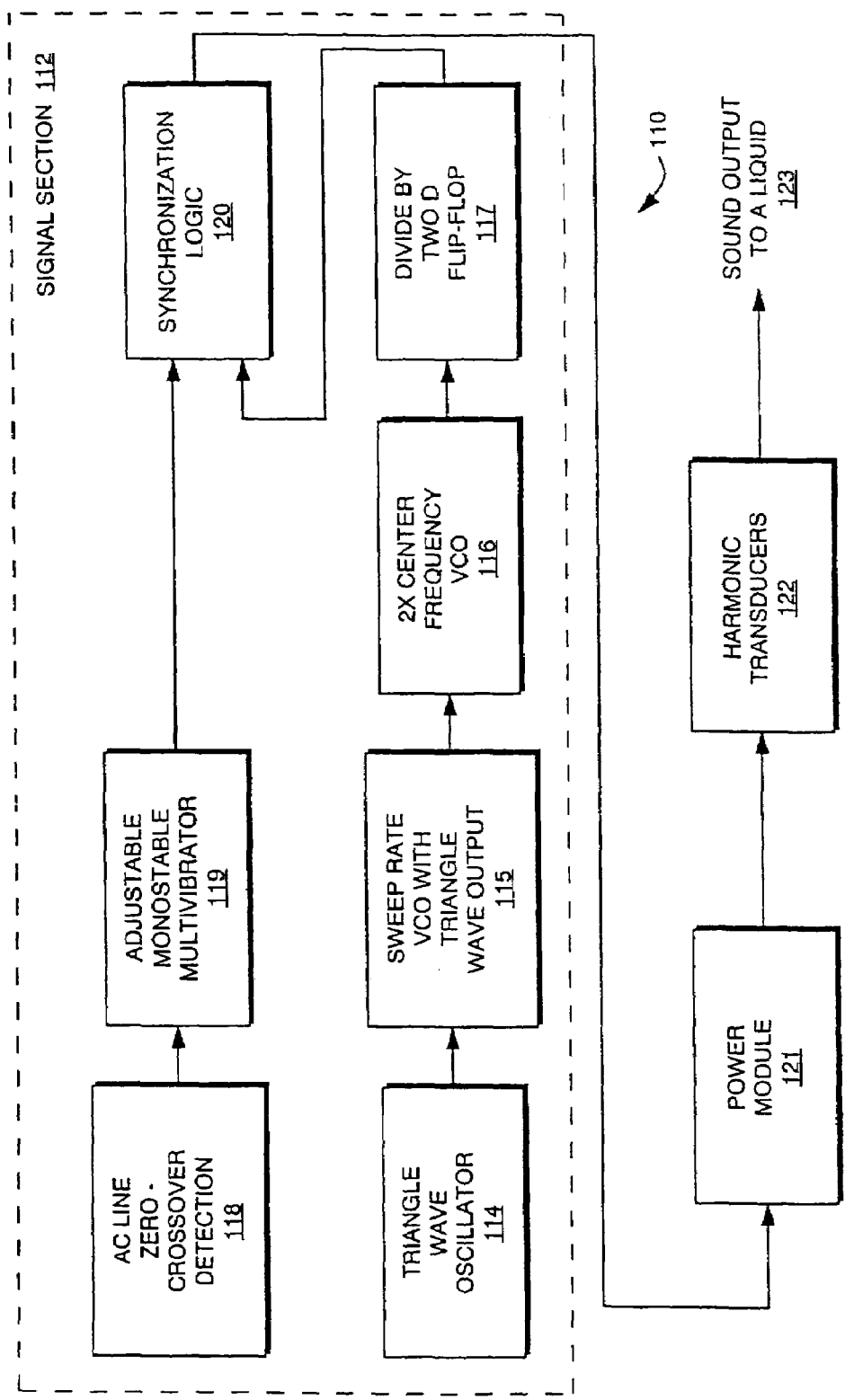
FIG. 6 shows a block diagram illustrating one embodiment of a system constructed according to the invention.

FIG. 6 shows in block diagram embodiment of a system 110 constructed according to the present invention. The system 110 includes a signal section 112 which drives a power module 121. The power module 121 powers the harmonic transducer array 122. The transducer array 122 is coupled to a liquid 123 by one of several conventional means so as to generate acoustic energy within the liquid 123. By way of example, the array 122 is similar to the array 16 of FIG. 1; and the liquid 123 is similar to the liquid 22 of FIG. 1.

The signal section 112 includes a triangle wave oscillator 114 with a frequency typically below 150 hz. The purpose of the oscillator 114 is to provide a signal that sweeps the sweep rate of the ultrasound frequencies generated by the transducer arrays 122.

The oscillator 114 is fed into the input of the sweep rate VCO 115 (Voltage Controlled Oscillator). This causes the frequency of the output of VCO 115 to linearly sweep at the frequency of the oscillator 114. The optimum sweep rate frequency output of VCO 115 is typically from about 10 hz, for magnetostrictive elements, to about 1.2 khz, for piezoelectrics. Therefore, the optimum center sweep rate frequency can be anywhere within the range of about 10 hz to 1.2 khz, and that sweep rate is varied within a finite range of frequencies about the center sweep frequency. This finite range is typically set to about 10-50% of the center sweep rate frequency. For example, the center sweep rate frequency for one process might be 455 hz, so the VCO 115 output is set, for example, to sweep from 380 hz to 530 hz. If, additionally, the oscillator 114 is set to 37 hz, then the output of VCO 115 changes frequency, linearly, from 380 hz to 530 hz, and back to 380 hz at thirty seven times per second.

The output of VCO 115 feeds the VCO input of the 2 X center frequency VCO 116. The VCO 116 operates as follows. If, for example, the center frequency of VCO 116 is set to 208 khz and the bandwidth is set to 8 khz, the center frequency linearly changes from 204 khz to 212 khz and back to 204 khz in a time of 1.9 milliseconds (i.e., 1/530 hz) to 2.63 milliseconds (i.e., 1/380 hz). The specific time is determined by the voltage output of the oscillator 114 at the time of measurement. Since the voltage output of oscillator 114 is constantly changing, the time it takes to linearly sweep the center frequency from 204 khz to 212 khz and back to 204 khz is also constantly changing. In this example, the time changes linearly from 1.9 milliseconds to 2.63 milliseconds and back to 1.9 milliseconds at thirty seven times per second.

The oscillator 114, VCO 115 and VCO 116 operate, in combination, to eliminate the repetition of a single sweep rate frequency in the range of 10 hz to 1.2 khz. For example, the highest single frequency that exists in the stated example system is 37 hz. If an unusual application or process were found whereby a very low frequency resonance around 37 hz exists, then the oscillator 114 would be replaced by a random or chaotic voltage generator to reduce the likelihood of exciting any modes within the part.

The VCO 116 drives a divide-by-two D flip-flop 117. The purpose of the D flip-flop 117 is to eliminate asymmetries in the waveform from the VCO 116. The output of the D flip-flop 117 is thus a square wave that has the desired frequency which changes at a sweep rate that is itself sweeping. In the stated example, the output square wave from D flip-flop 117 linearly changes from 102 khz to 106 khz and back to 102 khz at different times in the range of 1.9 milliseconds to 2.63 milliseconds. This sweeping of the sweep rate is sometimes referred to herein as "double sweep" or "double sweeping."

The AC line zero-crossover detection circuit 118 produces a signal with a rise time or narrow pulse at or near the time that the AC line voltage is at zero or at a low voltage, i.e., at or near zero degrees. This signal triggers the adjustable monostable multivibrator 119. The timed pulse out of monostable multivibrator 119 is set to a value between zero degrees and ninety degrees, which corresponds to a time from zero to 4.17 milliseconds for a 60 hz line frequency.

If the maximum amplitude were desired, for example, the monostable multivibrator 119 is set to a time of 4.17 milliseconds for a 60 hz line frequency. For an amplitude that is 50% of maximum, the monostable multivibrator 119 is set to 1.389 milliseconds for a 60 hz line frequency. In general, the monostable multivibrator 119 time is set to the arcsine of the amplitude percent times the period of the line frequency divided by 360 degrees.

The double sweeping square wave output of the D flip-flop 117 and the timed pulse output of the monostable multivibrator 119 feed into the synchronization logic 120. The synchronization logic 120 performs three primary functions. First, it only allows the double sweeping square wave to pass to the output of the synchronization logic 120 during the time defined by the pulse from the monostable multivibrator 119. Second, the synchronization logic 120 always allows a double sweeping square wave which starts to be completed, even if the monostable multivibrator 119 times out in the middle of a double sweeping square wave. And lastly, the synchronization logic 120 always starts a double sweeping square wave at the beginning of the ultrasound frequency, i.e., at zero degrees.

The output of synchronization logic 120 is a double sweeping square wave that exists only during the time defined by the monostable multivibrator 119 or for a fraction of a cycle past the end of the monostable multivibrator 119 time period. The synchronization logic 120 output feeds a power module 121 which amplifies the pulsed double sweeping square wave to an appropriate power level to drive the harmonic transducers 122. The transducers 122 are typically bonded to a tank and deliver sound waves into the liquid within the tank. These sound waves duplicate the pulsed double sweeping characteristics of the output of the signal section 112.

Figure 7:
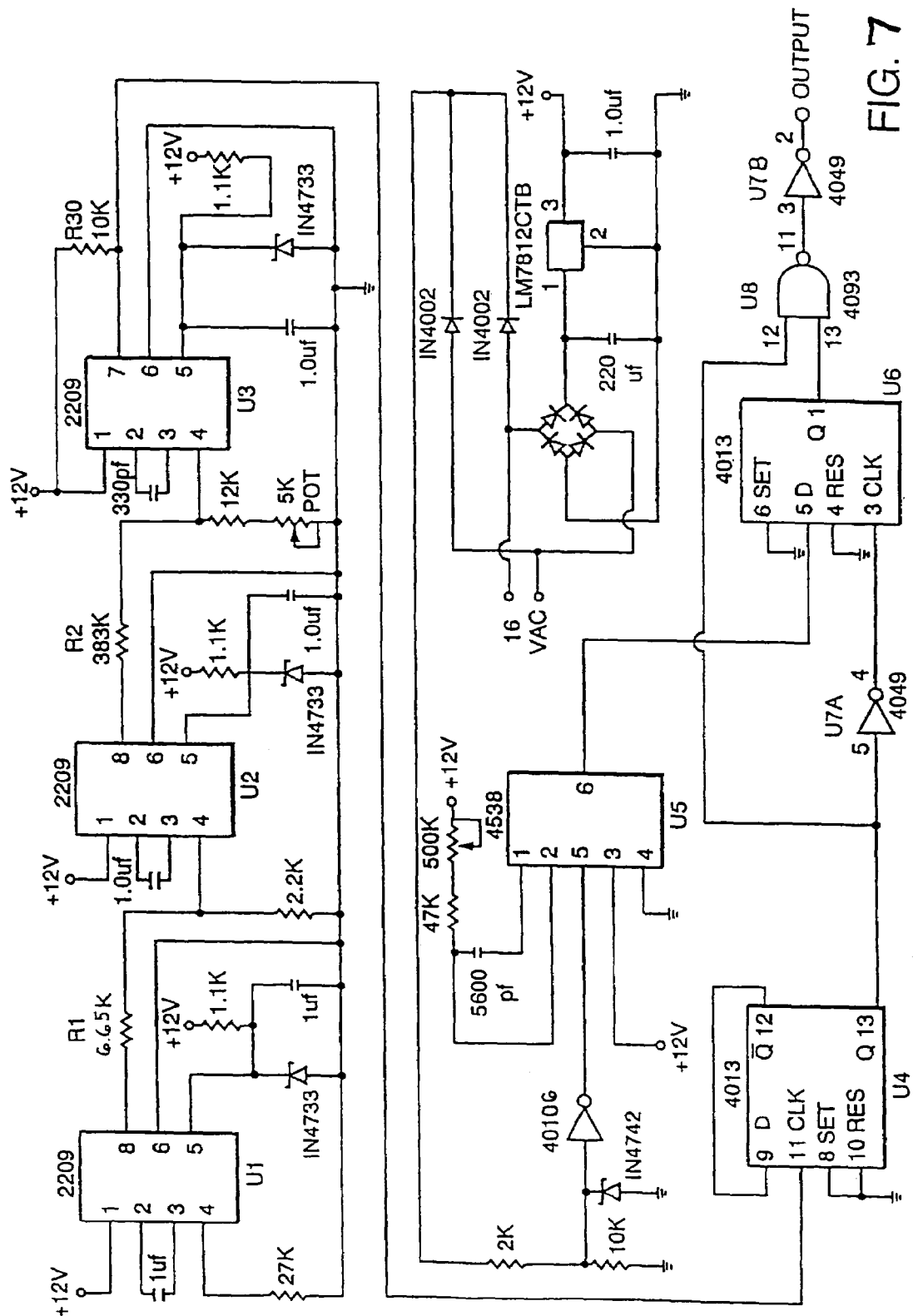
FIG. 7 shows a schematic embodiment of the signal section of the system of FIG. 6.

FIG. 7 shows a schematic embodiment of the signal section 112 in FIG. 6. U1 is a XR-2209 precision oscillator with a triangle wave output at pin 8. The frequency of the XR-2209 is 1/(RC)=1/((27 Kohm) (1 microfarad))=37 hz. This sets the frequency of the triangle wave oscillator 114, FIG. 6, to sweep the sweep rate at 37 hz. The other components associated with the XR-2209 are the standard configuration for single supply operation of this integrated circuit.

U2 is a XR-2209 precision oscillator with a triangle wave output at pin8. The center frequency of U2 is 1/(RC)=1/((2.2 Kohm) (1 microfarad))=455 hz. The actual output frequency is proportional to the current flowing out of pin4 of U2. At 455 hz, this current is 6 volts/2.2 Kohm=2.73 milliampers. It is generally desirable, according to the invention, to sweep the 455 hz sweep rate through a total change of 150 hz, i.e., 75 hz either side of 455 hz. Since 75 hz/455 hz=16.5%, the current flowing out of pin 4 must change by 16.5% in each direction, that is, by (16.5%) (2.73 milliampers)=0.45 milliampers. The triangle wave from U1 causes this change. The triangle wave changes from 3 volts to 9 volts; therefore, there is 3 volts on either side of 6 volts at pin4 of U2 to cause the 0.45 milliampers change. By making R1=3 volts/0.45 milliampers=6.67 Kohm, the sweep rate is changed 75 hz either side of 455 hz. The actual R1 used in FIG. 7 is 6.65 Kohm, a commercially available value giving an actual change of 75.2 hz.

U3 is an XR-2209 precision oscillator with a center frequency of approximately 1/(RC)=1/((12 Kohm+2.5 Kohm) (330 microfarad))=209 khz with the potentiometer set to its center position of 2.5 Kohm. In the actual circuit, the potentiometer is adjusted to about 100 ohms higher to give the desired 208 khz center frequency. Out of U3 pin4 flows 6 volts/(12 Kohm+2.5 Kohm+100 ohms)=0.41 milliampers. To change the center frequency a total of 8 khz, the 0.41 milliampers is changed by 4 khz/208 khz=1.92%, or 7.88 microampers. This means that R2=3 volts/7.88 microampers=381 Kohm. In FIG. 7, however, the commercial value of 383 Kohm was used.

U3 pin7 has a square wave output that is changing from 204 khz to 212 khz and back to 204 khz at a rate between 380 hz and 530 hz. The actual rate is constantly changing thirty seven times a second as determined by U1.

U4 is a D flip-flop in a standard divide by two configuration. It squares up any non 50% duty cycle from U3 and provides a frequency range of 102 khz to 106 khz from the 204 khz to 212 khz U3 signal.

The output of U4 feeds the synchronization logic which is described below and after the description of the generation of the amplitude control signal.

The two 1N4002 diodes in conjunction with the bridge rectifier form a full wave half sinusoid signal at the input to the 40106 Schmidt trigger inverter. This inverter triggers when the half sinusoid reaches about 7 volts, which on a half sinusoid with an amplitude of 16 times the square root of two is close enough to the zero crossover for a trigger point in a practical circuit. The output of the 40106 Schmidt trigger falls which triggers U5, the edge triggered 4538 monostable multivibrator wired in a trailing edge trigger/retriggerable configuration. The output of U5 goes high for a period determined by the setting on the 500 Kohm potentiometer. At the end of this period, the output of U5 goes low. The period is chosen by setting the 500 Kohm potentiometer to select that portion of the leading one-quarter sinusoid that ends at the required amplitude to give amplitude control. This timed positive pulse feeds into the synchronization logic along with the square wave output of U4.

The timed pulse U5 feeds the D input of U6, a 4013 D-type flip flop. The square wave from U4 is invented by U7a and feeds the clock input of U6. U6 only transfers the signal on the D input to the output Q at the rise of a pulse on the clock input, Pin3. Therefore, the Q output of U6 on Pin1 is high when the D input of U6 on Pin3 is high and the clock input of U6 on Pin3 transitions high. This change in the Q output of U6 is therefore synchronized with the change in the square wave from U4.

The synchronized high Q output of U6 feeds U8 Pin13, a 4093 Schmidt trigger NAND gate. The high level on Pin13 of U8 allows the square wave signal to pass from U8 Pin12 to the output of U8 at Pin11.

In a similar way, U8 synchronizes the falling output from U5 with the square wave from U4. Therefore, only complete square waves pass to U8 Pin11 and only during the time period as chosen by monostable multivibrator U5. The 4049 buffer driver U7b inverts the output at U8 Pin11 so it has the same phase as the square wave output from U4. This signal, U7b Pin2 is now the proper signal to be amplified to drive the transducers.

Figure 8A:
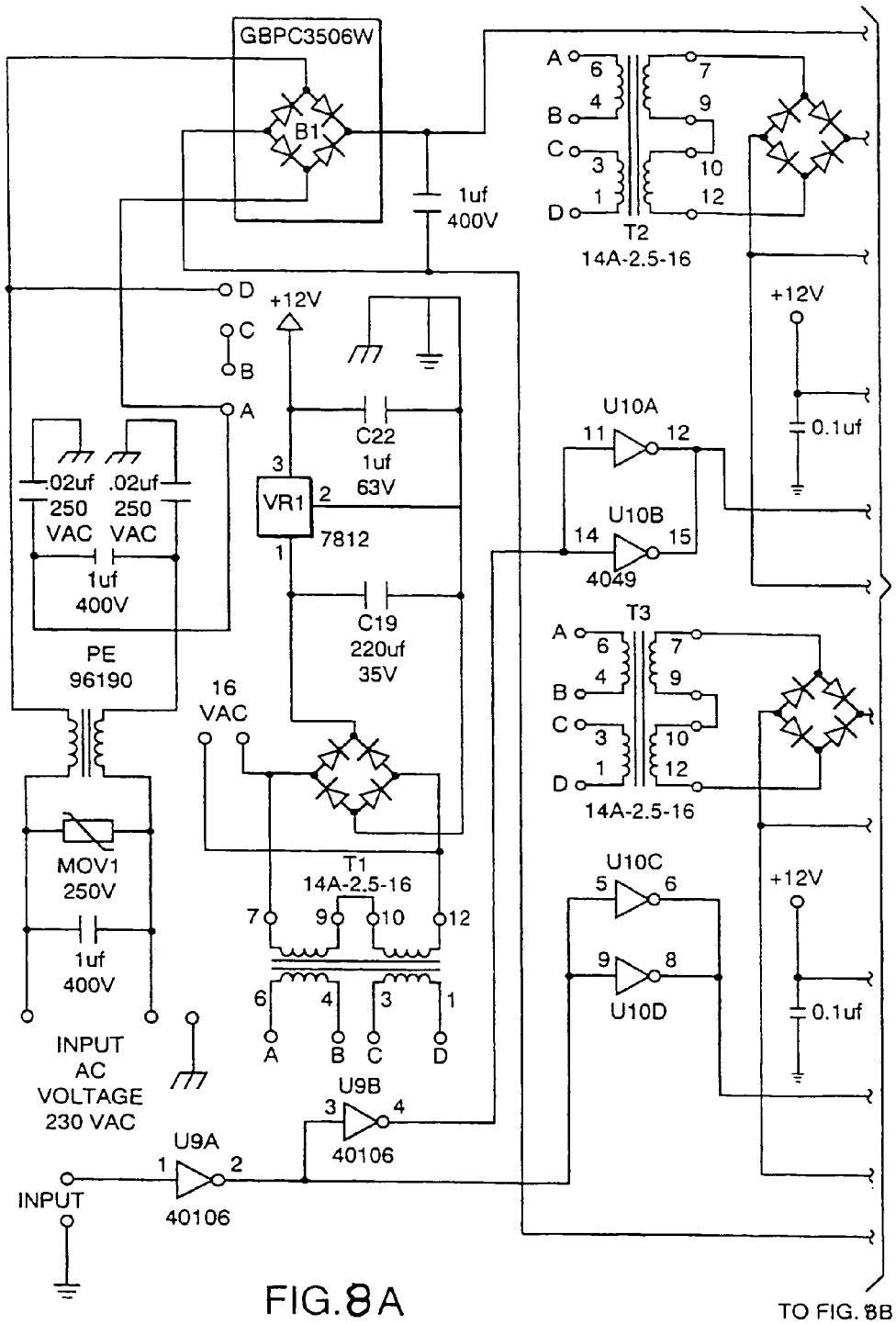
FIGS. 8A and 8B show a schematic embodiment of the power module section of the system of FIG. 6.
Figure 8B:
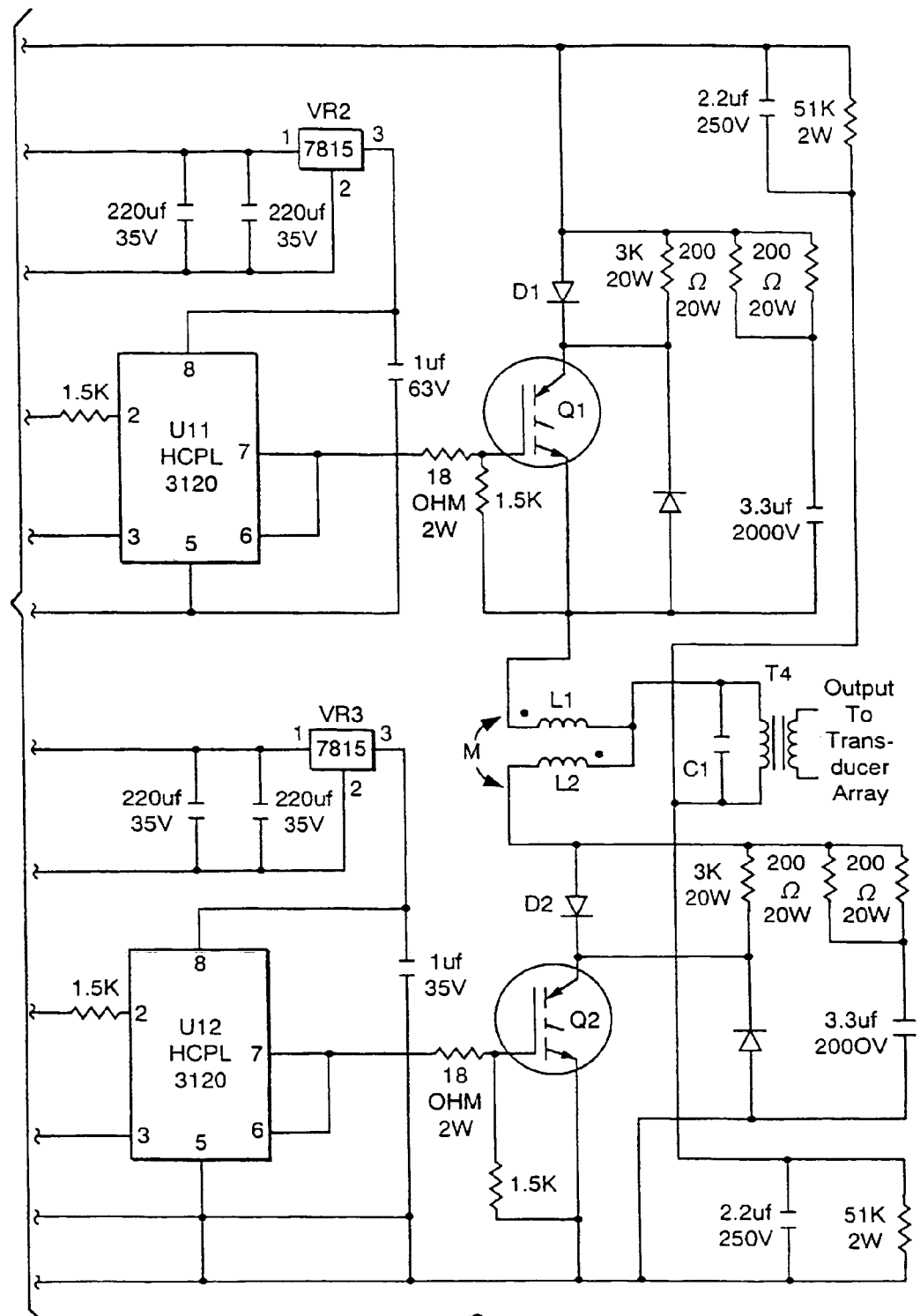

FIGS. 8A and 8B represent a circuit that increases the signal from U7b Pin 2 in FIG. 7 to a power level for driving the transducers 122, FIG. 6. There are three isolated power supplies. The first one, including a T1, a bridge, C19, VR1 and C22, produces +12VDC for the input logic. The second and third isolated power supplies produce +15 VDC at VR2 Pin3 and VR3 Pin3 for gate drive to the IGBTs (insulated gate bipolar transistors).

The signal input to FIGS. 8A and 8B have its edges sharpened by the 40106 Schmidt trigger U9a. The output of U9a feeds the 4049 buffer drivers U10c and U10d which drive optical isolator and IGBT driver U12, a Hewlett Packard HCPL3120. Also, the output of U9a is inverted by U9b and feeds buffer drivers U10a and U10b which drive U11, another HCPL3120.

This results in an isolated drive signal on the output of U11 and the same signal on the output of U12, only 180 degrees out of phase. Therefore, U11 drives Q1 on while U12 drives Q2 off. In this condition, a power half sinusoid of current flows from the high voltage full wave DC at B1 through D1 and Q1 and L1 into C1. Current cannot reverse because it is blocked by D1 and the off Q2. When the input signal changes state, U11 turns off Q1 and U12 turns on Q2, a half sinusoid of current flow out of C1 through L2 and D2 and Q2 back into C1 in the opposite polarity. This ends a complete cycle.

The power signal across C1 couples through the high frequency isolation transformer T4. The output of T4 is connected to the transducer or transducer array.

Figure 9A:
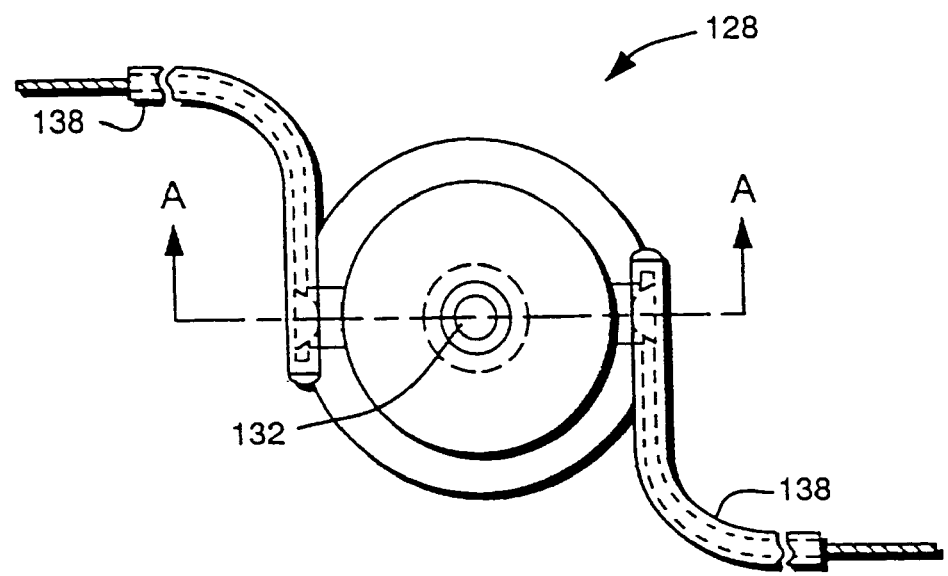
FIG. 9A is a top view of the harmonic transducer of FIG. 9.
Figure 9:
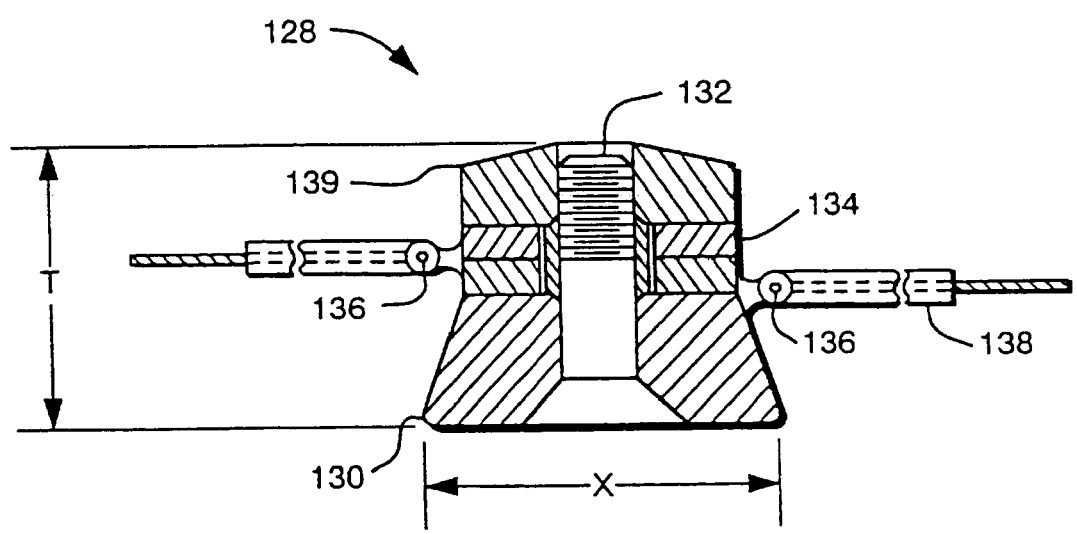
FIG. 9 is a cross-sectional side view of a harmonic transducer constructed according to the invention and driven by the power module of FIGS. 8A and 8B.

FIG. 9 shows a cross-sectional side view of one clamped microsonic transducer 128 constructed according to the invention; while FIG. 9A shows a top view of the microsonic transducer 128. The microsonic transducer 128 has a second harmonic resonant frequency of 104 khz with a 4 khz bandwidth (i.e., from 102 khz to 106 khz). The cone-shaped back mass 139 flattens the impedance verses frequency curve to broaden the frequency bandwidth of the microsonic transducer 128. Specifically, the back mass thickness along the "T" direction changes for translational positions along direction "X." Since the harmonic resonance of the microsonic transducer 128 changes as a function of back mass thickness, the conical back mass 139 broadens and flattens the microsonic transducer's operational bandwidth.

The ceramic 134 of microsonic transducer 128 is driven through oscillatory voltages transmitted across the electrodes 136. The electrodes 136 connect to an ultrasound generator (not shown), such as described above, by insulated electrical connections 138. The ceramic 134 is held under compression through operation of the bolt 132. Specifically, the bolt 132 provides 5,000 pounds of compressive force on the piezoelectric ceramic 134. This transducer invention will be referred to herein as the "reverse bolt construction" transducer.

Figure 10:
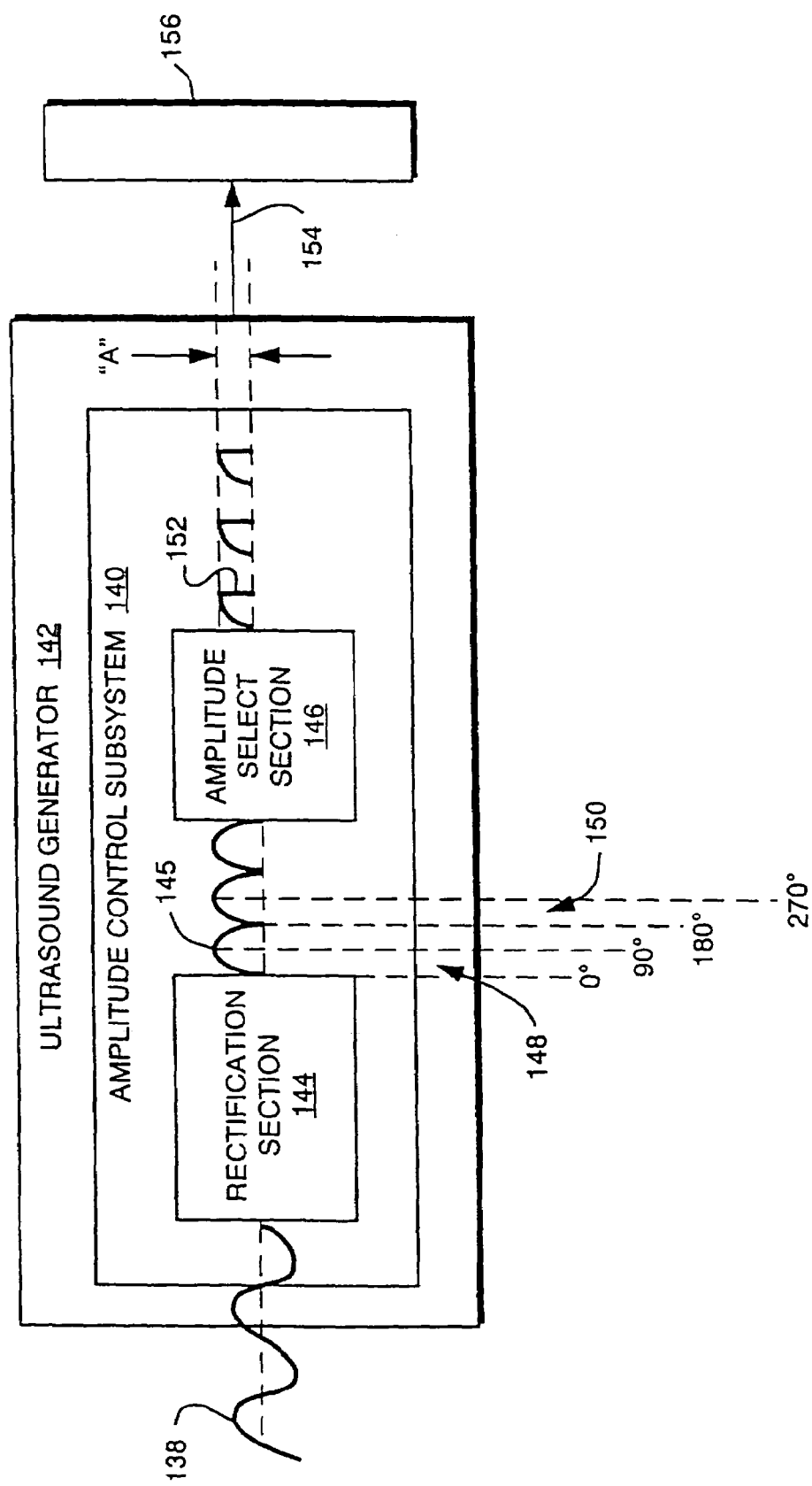
FIG. 10 is a schematic illustration of an amplitude control subsystem constructed according to the invention.
Figure 10A:
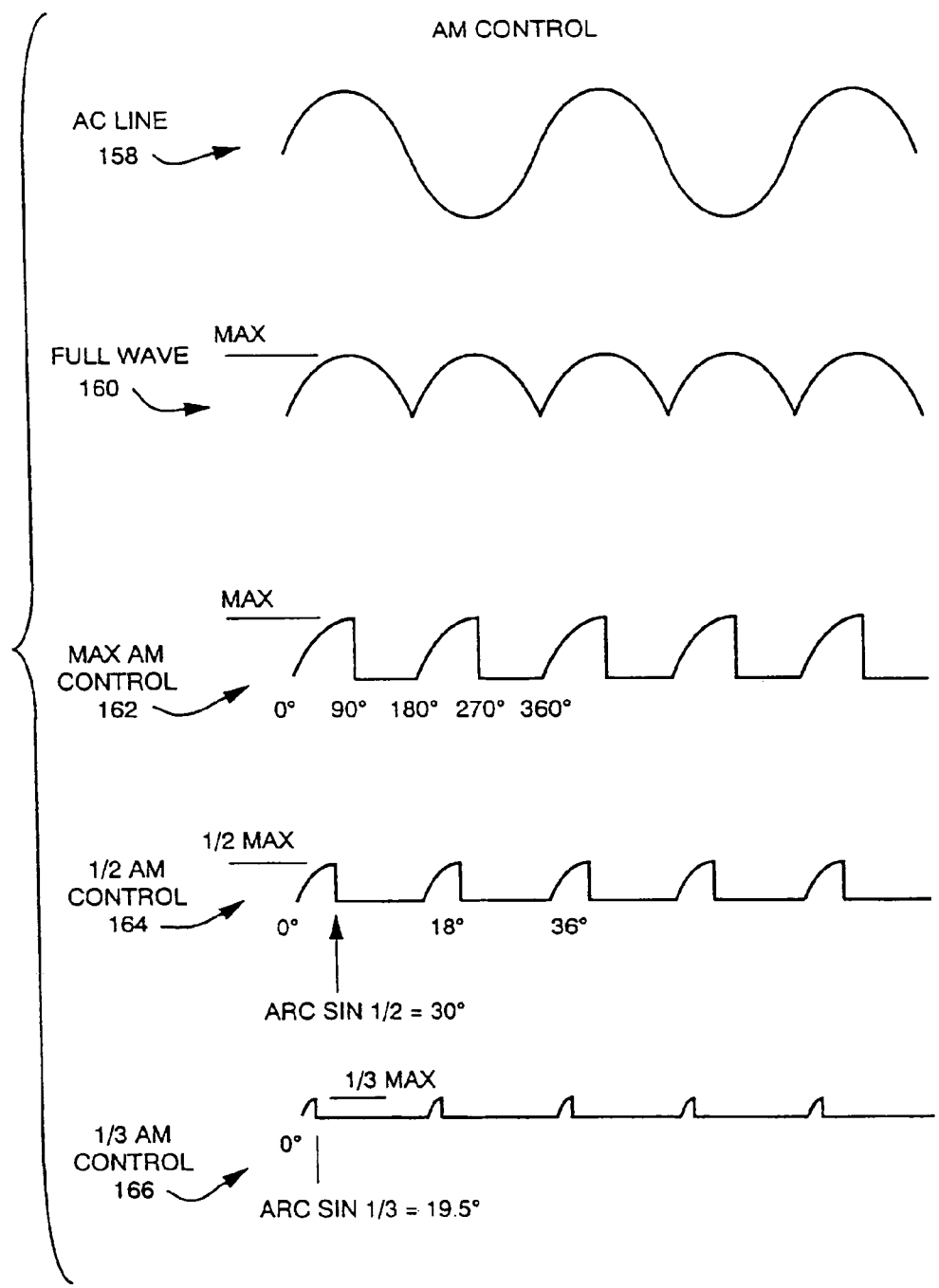
FIG. 10A shows illustrative amplitude control signals generated by an amplitude control subsystem such as in FIG. 10.

Amplitude control according to one embodiment of the invention is illustrated in FIGS. 10 and 10A. Specifically, FIG. 10 shows an amplitude control subsystem 140 that provides amplitude control by selecting a portion of the rectified line voltage 145 which drives the ultrasound generator amplitude select section 146. The signal section 112, FIG. 6, and particularly the monostable multivibrator 119 and synchronization logic 120, provide similar functionality. In FIG. 10, the amplitude control subsystem 140 operates with the ultrasound generator 142 and connects with the power line voltage 138. The rectification section 144 changes the ac to dc so as to provide the rectified signal 145.

The amplitude select section 146 selects a portion of the leading quarter sinusoid of rectified signal 145 that ends at the desired amplitude, here shown as amplitude "A," in a region 148 between zero and 90 degrees and in a region 150 between 180 degrees and 270 degrees of the signal 145. In this manner, the amplitude modulation 152 is selectable in a controlled manner as applied to the signal 154 driving the transducers 156 from the generator 142, such as discussed in connection with FIGS. 3 and 4.

FIG. 10A shows illustrative selections of amplitude control in accord with the invention. The AC line 158 is first converted to a full wave signal 160 by the rectifier 144. Thereafter, the amplitude select section 146 acquires the signal amplitude selectively. For example, by selecting the maximum amplitude of 90 degrees in the first quarter sinusoid, and 270 degrees in the third quarter sinusoid, a maximum amplitude signal 162 is provided. Similarly, a one-half amplitude signal 164 is generated by choosing the 30 degrees and 210 degrees locations of the same sinusoids. By way of a further example, a one-third amplitude signal 166 is generated by choosing 19.5 degrees and 199.5 degrees, respectively, of the same sinusoids.

Those skilled in the art will appreciate that the rectification section 144 can also be a half-wave rectifier. As such, the signal 145 will only have a response every other one-half cycle. In this case, amplitude control is achieved by selecting a portion of the leading quarter sinusoid that ends at a selected amplitude between zero and 90 degrees of the sinusoid.

The ultrasound generator of the invention is preferably amplitude modulated. Through AM control, various process characteristics within the tank can be optimized. The AM control can be implemented such as described in FIGS. 3,4,10 and 10A, or through other prior art techniques such as disclosed in U.S. Pat. No. 4,736,130.

This "sweeping" of the AM frequency is accomplished in a manner that is similar to ultrasound generators which sweep the frequency within the bandwidth of an ultrasound transducer. By way of example, U.S. Pat. No. 4,736,130 describes one ultrasound generator which provides variable selection of the AM frequency through sequential "power burst" generation and "quiet time" during a power train time. In accord with the invention, the AM frequency is changed to "sweep" the frequency in a pattern so as to provide an AM sweep rate pattern.

Figure 11:
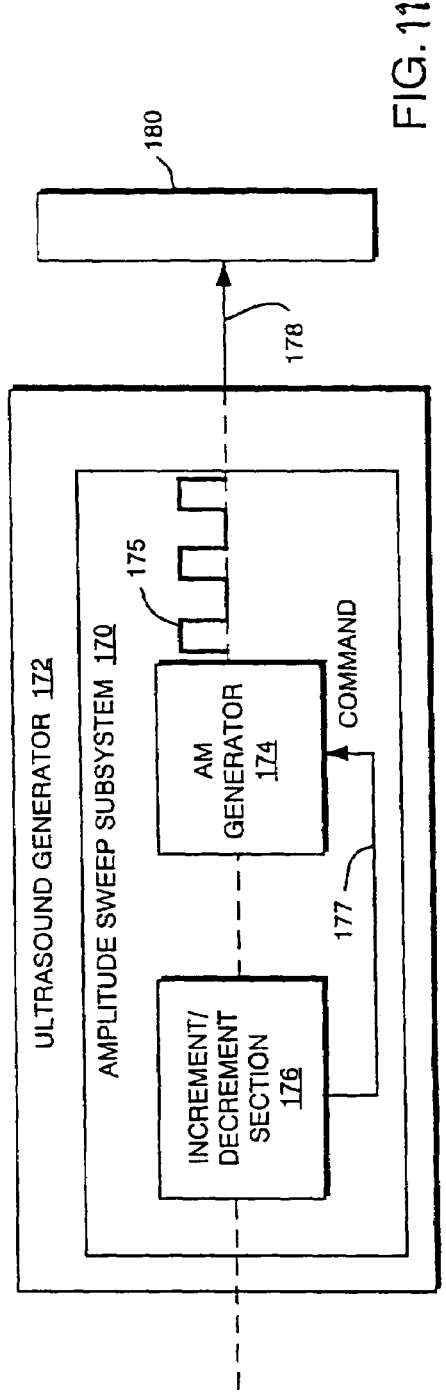
FIG. 11 shows a schematic illustration of an AM sweep subsystem constructed according to the invention.

FIG. 11 illustrates an AM sweep subsystem 170 constructed according to the invention. The AM sweep subsystem 170 operates as part of, or in conjunction with, the ultrasound generator 172. The AM generator 174 provides an AM signal 175 with a selectable frequency. The increment/decrement section 176 commands the AM generator 174 over command line 177 to change its frequency over a preselected time period so as to "sweep" the AM frequency in the output signal 178 which drives the transducers 180.

Figure 11A:
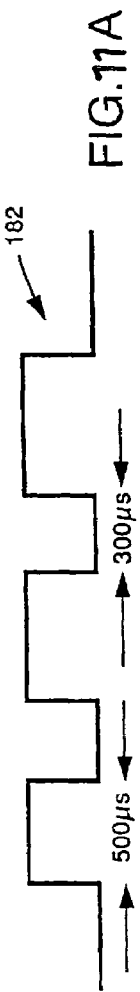
FIG. 11A shows a typical AM frequency generated by an AM generator.
Figure 11B:
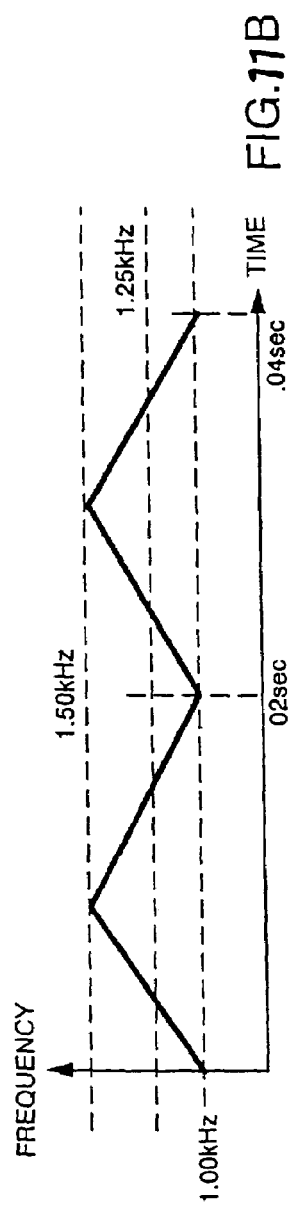
FIG. 11B graphically shows AM sweep frequency as a function of time for a representative sweep rate, in accord with the invention.

U.S. Pat. No. 4,736,130 describes one AM generator 56, FIG. 1, that is suitable for use as the generator 174 of FIG. 11. By way of example, FIG. 11A illustrates one selectable AM frequency signal 182 formed through successive 500 µs power bursts and 300 µs quiet times to generate a 1.25 khz signal (e.g., 1/(300 µs+500 µs)=1.25 khz). If, for example, the AM frequency is swept at 500 hz about a center frequency of 1.25 khz, such as shown in FIG. 11, then the frequency is commanded to vary between 1.25 khz+250 hz and 1.25 khz−250 hz, such as illustrated in FIG. 11B. FIG. 11B illustrates a graph of AM frequency versus time for this example.

Figure 12:
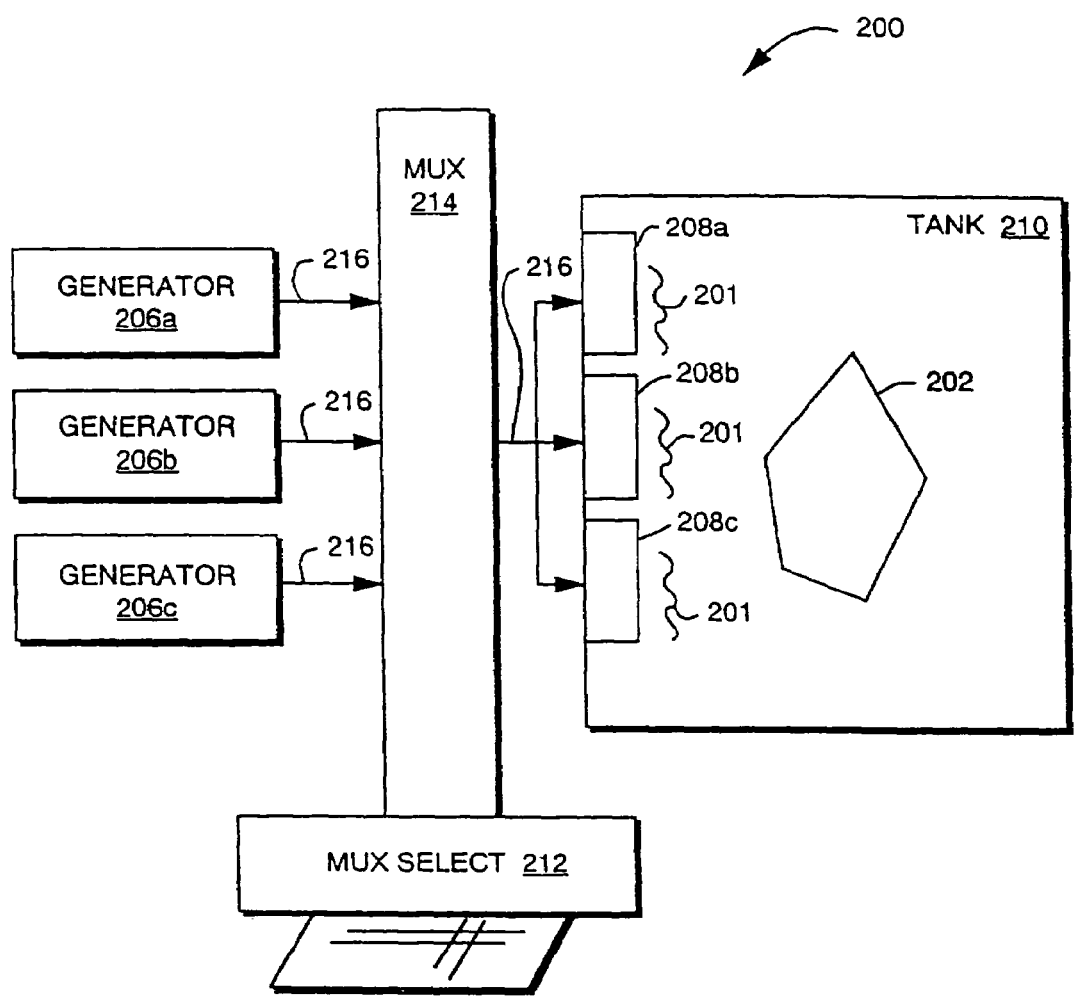
FIG. 12 illustrates a multi-generator, multi-frequency, single tank ultrasound system constructed according to the invention.

FIG. 12 schematically illustrates a multi-generator, single tank system 200 constructed according to the invention. In many instances, it is desirable to select an ultrasound frequency 201 that most closely achieves the cavitation implosion energy which cleans, but does not damage, the delicate part 202. In a single tank system such as in FIG. 12, the chemistries within the tank 210 are changed, from time to time, so that the desired or optimum ultrasound frequency changes. The transducers and generators of the prior art do not operate or function at all frequencies, so system 200 has multiple generators 206 and transducers 208 that provide different frequencies. By way of example, generator 206a can provide a 40 khz primary resonant frequency; while generator 206b can provide the first harmonic 72 khz frequency. Generator 206c can provide, for example, 104 khz microsonic operation. In the illustrated example, therefore, the generators 206a, 206b, 206c operate, respectively, at 40 khz, 72 khz, and 104 khz. Each transducer 208 responds at each of these frequencies so that, in tandem, the transducers generate ultrasound 201 at the same frequency to fill the tank 210 with the proper frequency for the particular chemistry.

In addition, each of the generators 206a-206c can and do preferably sweep the frequencies about the transducers' bandwidth centered about the frequencies 40 khz, 72 khz and 104 khz, respectively; and they further sweep the sweep rate within these bandwidths to reduce or eliminate resonances which might occur at the optimum sweep rate.

When the tank 210 is filled with a new chemistry, the operator selects the optimum frequency through the mux select section 212. The mux select section connects to the analog multiplexer ("mux") 214 which connects to each generator 206. Specifically, each generator 206 couples through the mux 214 in a switching network that permits only one active signal line 216 to the transducers 208. For example, if the operator at mux select section 212 chooses microsonic operation to optimize the particular chemistry in the tank 210, generator 206c is connected through the mux 214 and drives each transducer 208a-208c to generate microsonic ultrasound 201 which fills the tank 210. If, however, generator 206a is selected, then each of the transducers 208 are driven with 40 khz ultrasound.

Figure 13:
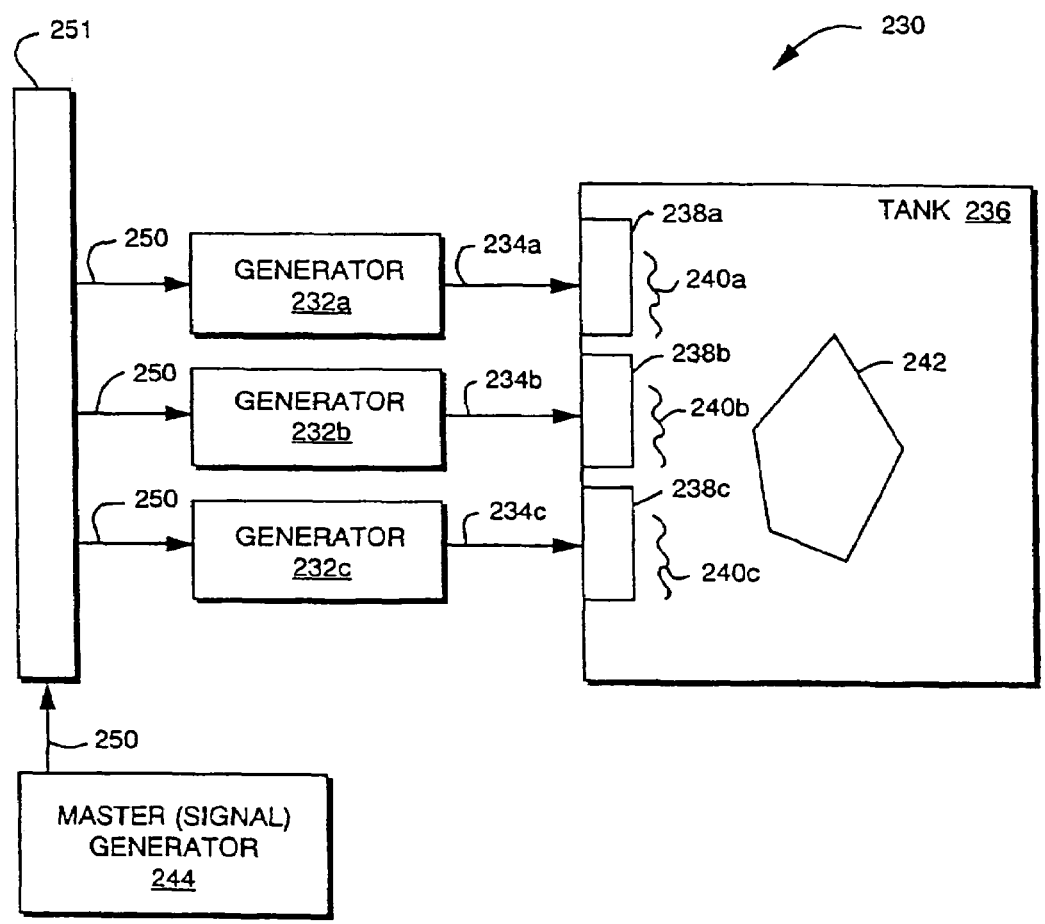
FIG. 13 illustrates a multi-generator, common-frequency, single tank ultrasound system constructed according to the invention.

FIG. 13 illustrates a multi-generator, common frequency ultrasound system 230 constructed according to the invention. In FIG. 13, a plurality of generators 232 (232a-232c) connect through signal lines 234 (234a-234c) to drive associated transducers 238 (238a-238c) in a common tank 236. Each of the transducers 238 and generators 232 operate at the same frequency, and are preferably swept through a range of frequencies such as described above so as to reduce or eliminate resonances within the tank 236 (and within the part 242).

In order to eliminate "beating" between ultrasound energies 240a-240c of the several transducers 238a-238c and generators 232a-232c, the generators 232 are each driven by a common FM signal 250 such as generated by the master signal generator 244. The FM signal is coupled to each generator through signal divider 251.

In operation, system 230 permits the coupling of identical frequencies, in magnitude and phase, into the tank 236 by the several transducers 238. Accordingly, unwanted beating effects are eliminated. The signal 250 is swept with FM control through the desired ultrasound bandwidth of the several transducers to eliminate resonances within the tank 236; and that sweep rate frequency is preferably swept to eliminate any low frequency resonances which can result from the primary sweep frequency.

Those skilled in the art should appreciate that system 230 of FIG. 13 can additionally include or employ other features such as described herein, such as AM modulation and sweep, AM control, and broadband transducer.

Figure 14:
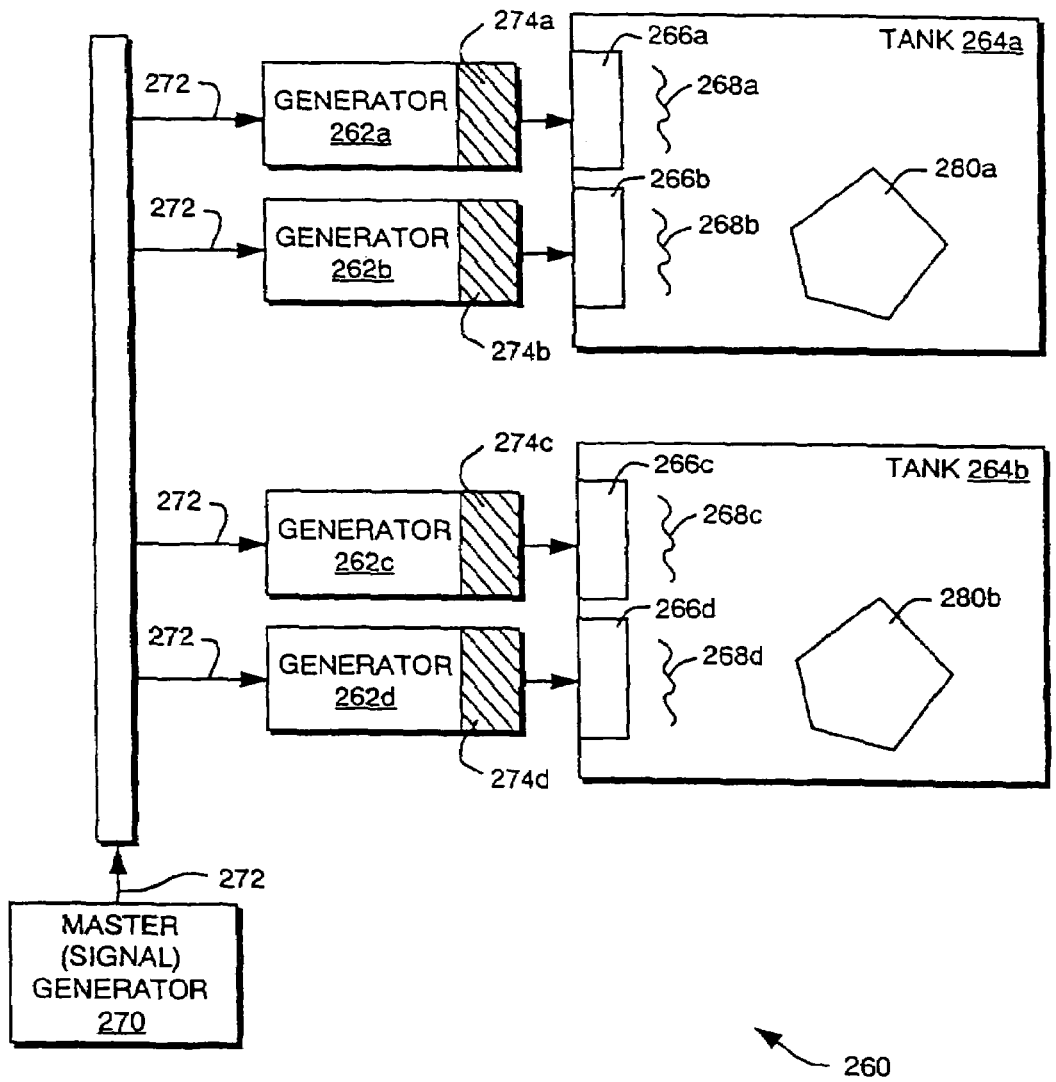
FIG. 14 illustrates a multi-tank ultrasound system constructed according to the invention.

FIG. 14 illustrates a multi-tank system 260 constructed according to the invention. One or more generators 262 drive each tank 264 (here illustrated, generators 262a and 262b drive tank 264a; and generators 264c and 264d drive tank 264b). Each of the generators 262 connects to an associated ultrasound transducer 266a-d so as to produce ultrasound 268a-d in the associated tanks 264a-b.

The common master signal generator 270 provides a common FM signal 272 for each of the generators 262. Thereafter, ultrasound generators 262a-b generate ultrasound 268a-b that is identical in amplitude and phase, such as described above. Similarly, generators 262c-d generate ultrasound 268c-d that is identical in amplitude and phase. However, unlike above, the generators 262 each have an AM generator 274 that functions as part of the generator 262 so as to select an optimum AM frequency within the tanks 264. In addition, the AM generators 274 preferably sweep through the AM frequencies so as to eliminate resonances at the AM frequency.

More particularly, generators 274a-b generate and/or sweep through identical frequencies of the AM in tank 264a; while generators 274c-d generate and/or sweep through identical frequencies of AM in tank 264b. However, the AM frequency and/or AM sweep of the paired generators 274a-b need not be the same as the AM frequency and/or AM sweep of the paired generators 274c-d. Each of the generators 274 operate at the same carrier frequency as determined by the FM signal 270; however each paired generator set 274a-b and 274c-d operates independently from the other set so as to create the desired process characteristics within the associated tank 264.

Accordingly, the system 260 eliminates or prevents undesirable cross-talk or resonances between the two tanks 264a-b. Since the generators within all tanks 264 operate at the same signal frequency 270, there is no effective beating between tanks which could upset or destroy the desired cleaning and/or processing characteristics within the tanks 264. As such, the system 260 reduces the likelihood of creating damaging resonances within the parts 280a-b. It is apparent to those skilled in the art that the FM control 270 can contain the four AM controls 274a-d instead of the illustrated configuration.

Figure 14A:
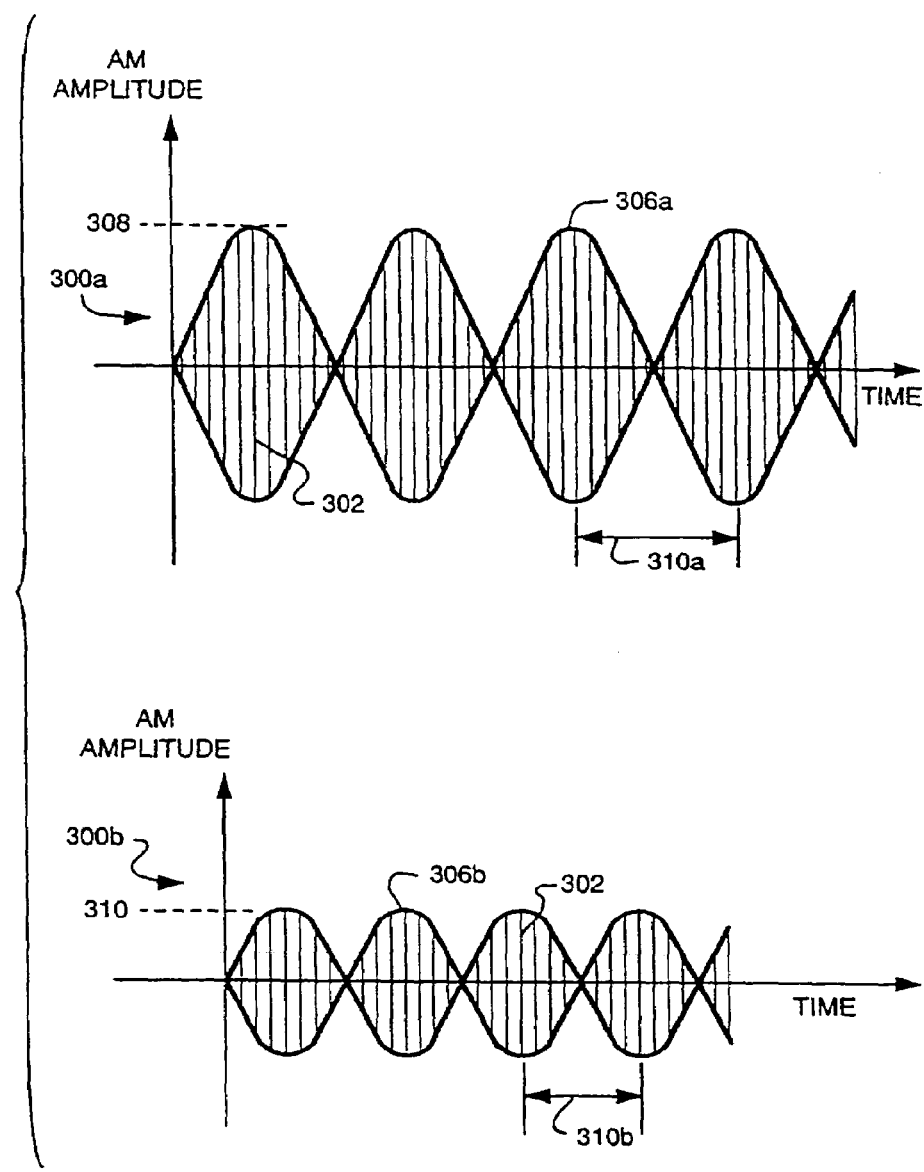
FIG. 14A shows representative AM waveform patterns as controlled through the system of FIG. 14.

FIG. 14A shows two AM patterns 300a, 300b that illustrate ultrasound delivered to multiple tanks such as shown in FIG. 14. For example, AM pattern 300a represents the ultrasound 268a of FIG. 14; while AM pattern 300b represents the ultrasound 268c of FIG. 14. With a common FM carrier 302, as provided by the master generator 270, FIG. 14, the ultrasound frequencies 302 can be synchronized so as to eliminate beating between tanks 264a, 264b. Further, the separate AM generators 274a and 274c provide capability so as to select the magnitude of the AM frequency shown by the envelope waveform 306. As illustrated, for example, waveform 306a has a different magnitude 308 as compared to the magnitude 310 of waveform 306b. Further, generators 374a, 374c can change the periods 310a, 310b, respectively, of each of the waveforms 306a, 306b selectively so as to change the AM frequency within each tank.

Figure 15A:
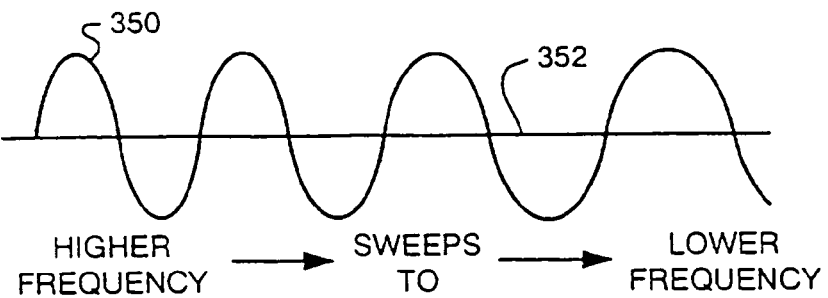
FIGS. 15A, 15B and 15C graphically illustrate methods of sweeping the sweep rate in accord with the invention.
Figure 15B:
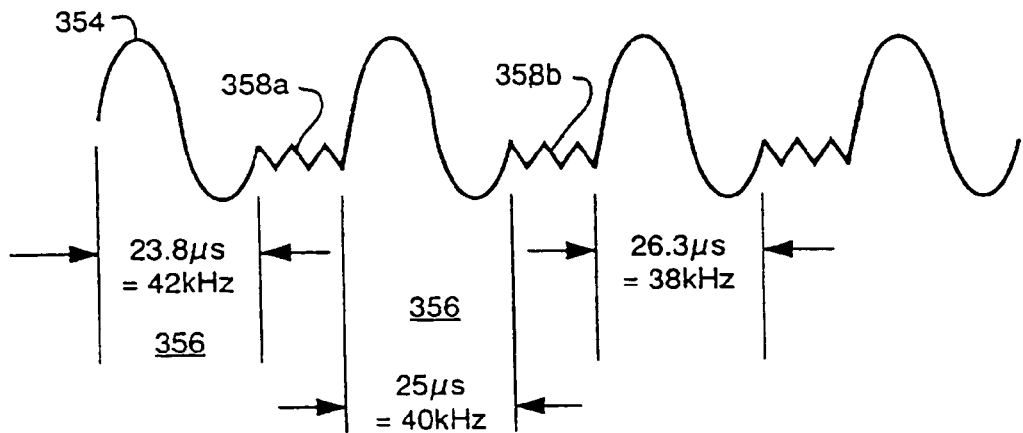
Figure 15C:
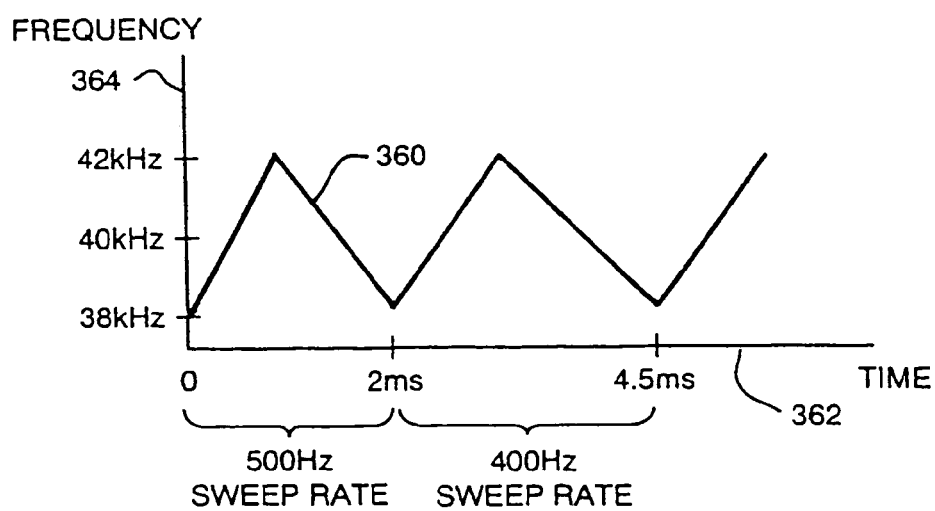

FIGS. 15A, 15B and 15C graphically illustrate the methods of sweeping the sweep rate, in accord with the invention. In particular, FIG. 15A shows an illustrative condition of a waveform 350 that has a center frequency of 40 khz and that is varied about the center frequency so as to "sweep" the frequency as a function of time along the time axis 352. FIG. 15B illustrates FM control of the waveform 354 which has a varying period 356 specified in terms of time. For example, a 42 khz period occurs in 23.8 microseconds while a 40 khz period occurs in 25 microseconds. The regions 358a, 358b are shown for ease of illustration and represent, respectively, compressed periods of time within which the system sweeps the waveform 354 through many frequencies from 42 khz to 40 khz, and through many frequencies from 40 khz to 38 khz.

FIG. 15C graphically shows a triangle pattern 360 which illustrates the variation of sweep rate frequency along a time axis 362.

The invention thus attains the objects set forth above, among those apparent from preceding description. Since certain changes may be made in the above apparatus and methods without departing from the scope of the invention, it is intended that all matter contained in the above description or shown in the accompanying drawing be interpreted as illustrative and not in a limiting sense.

It is also to be understood that the following claims are to cover all generic and specific features of the invention described herein, and all statements of the scope of the invention which, as a matter of language, might be said to fall there between.

FIGS. 16-20 illustrate alternative back mass configurations according to the invention. Unlike the configuration of FIG. 3, the back masses of FIGS. 16-20 are shaped to flatten or modify the power output from the entire transducer when driven over a range of frequencies such as shown in FIG. 4. Specifically, FIG. 16 includes a back mass 58 that, for example, replaces the back mass 38 of FIG. 3. A portion of the bolt 39 is also shown. As illustrated, the back mass 58 has a cut-away section 60 that changes the overall acoustic resonance of the transducer over frequency. Similarly, the back mass 58a of FIG. 17 has a curved section 60a that also changes the overall acoustic resonance of the transducer over frequency. FIGS. 18, 19 and 20 similarly have other sloped or curved sections 60b, 60c, and 60d, within back masses 58b, 58c and 58d, respectively, that also change the overall acoustic resonance of the transducer.

The exact configuration of the back mass depends upon the processing needs of the ultrasound being delivered to a tank. For example, it is typically desirable to have a flat or constant power over frequency, such as shown in FIG. 4. Accordingly, for example, the back mass and/or front mass can be cut or shaped so as to help maintain a constant power output such that the energy generated by the transducer at any given frequency is relatively flat over that bandwidth. Alternatively, the back mass can be cut or shaped so as to provide a varying power output, over frequency, such as to compensate for other non-linearities within a given ultrasound system.

Figure 27:
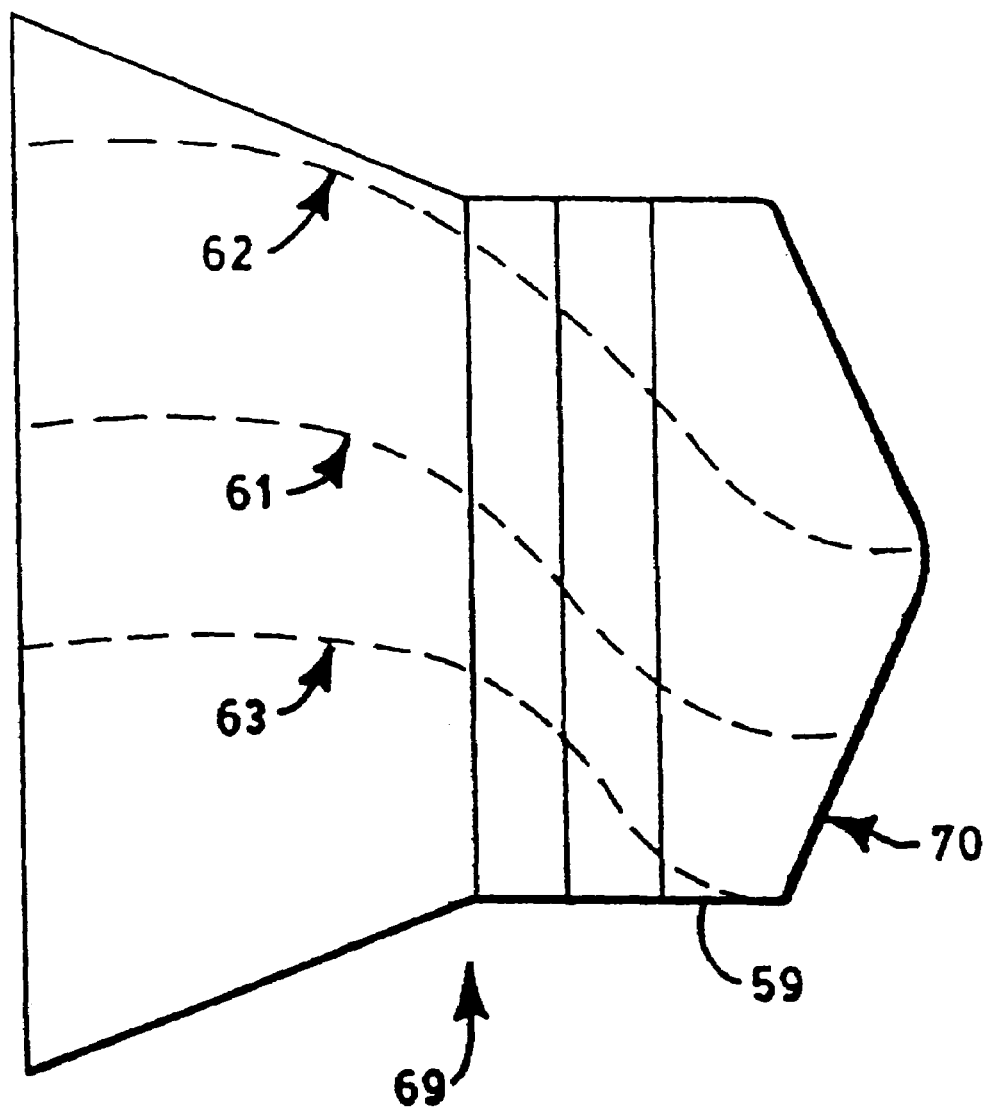
FIG. 27 shows representative standing waves within one transducer of the invention.

FIG. 27 illustratively shows how standing waves are formed within one transducer 69 of the invention over various frequencies 61, 62, 63. Because of the shaped surface 70 of the back mass 59, there are no preferred resonant frequencies of the transducer 69 as standing waves can form relative to various transverse dimensions of the transducer 69. By way of example, frequency 62 can represent 38 khz and frequency 63 can represent 42 khz.

FIG. 21 illustrates still another transducer 80 of the invention that provides for changing the power output as a function of frequency. The front mass 82 and the back mass 84 are connected together by a bolt 86 that, in combination with the driver 82 and back mass 84, compress the ceramics 88a, 88b. The configuration of FIG. 21 saves cost since the front mass 82 has a form fit aperture-sink 90 (the bolt head 86a within the sink 90 are shown in a top view in FIG. 22) that accommodates the bolt head 86a. A nut 86b is then screwed onto the other end of the bolt 86 and adjacent to the back mass 84 such that a user can easily access and remove separate elements of the transducer 80.

The front mass 82 and/or back mass 84 (the "back mass" also known as "back mass" herein) are preferably made from steel. The front mass 82 is however often made from aluminum. Other materials for the front mass 82 and/or the back mass 84 can be used to acquire desired performance characteristics and/or transducer integrity.

Figure 23:
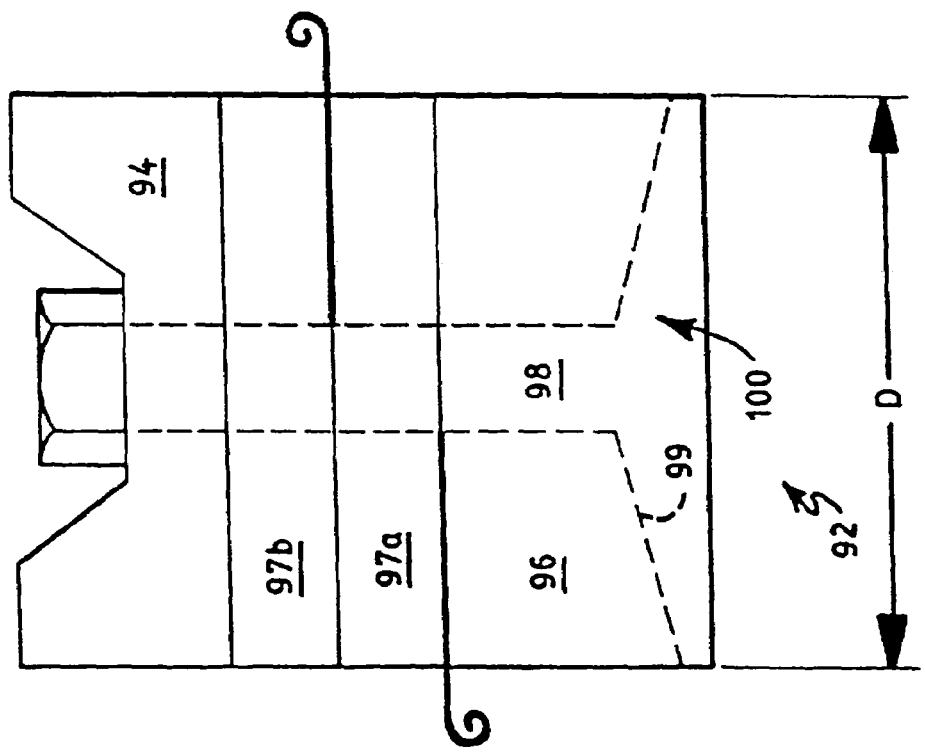

FIG. 23 shows another transducer 92 that includes a back mass 94 and a front mass 96. A bolt 98 clamps two ceramic elements 97a, 97b together and between the back mass 94 and driver 96; and that bolt 98 has a bolt head 100 that is approximately the same size as the diameter "D" of the transducer 92. The bolt head 100 assists the overall operation of the transducer 92 since there is no composite interface of the bolt 98 and the driver 96 connected to the tank. That is, the bond between the tank and the transducer 92 is made entirely with the bolt head 100. By way of comparison, the bond between the tank and the transducer 80, FIG. 21, occurs between both the bolt 86 and the driver 82. A sloped region 99 provides for varying the power output over frequency such as described herein.

Figure 24:
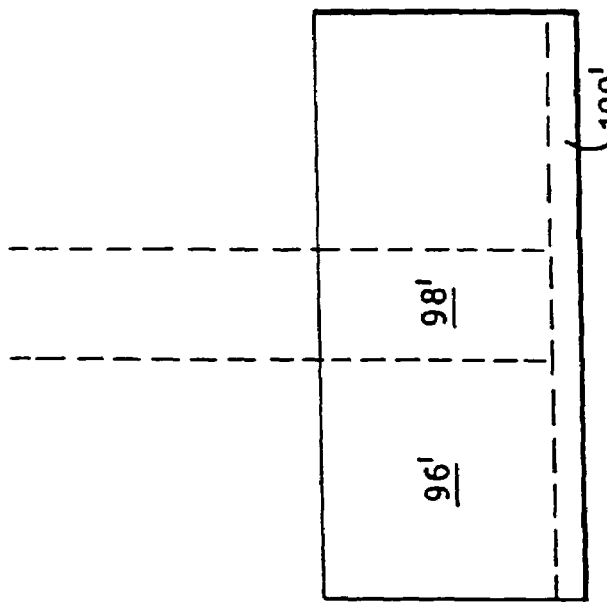

FIG. 24 illustrates one end 102 of a transducer of the invention that is similar to FIG. 23 except that there is no slope region 99; and therefore there is little or no modification of the power output from the transducer (at least from the transducer end 102).

Figure 25:
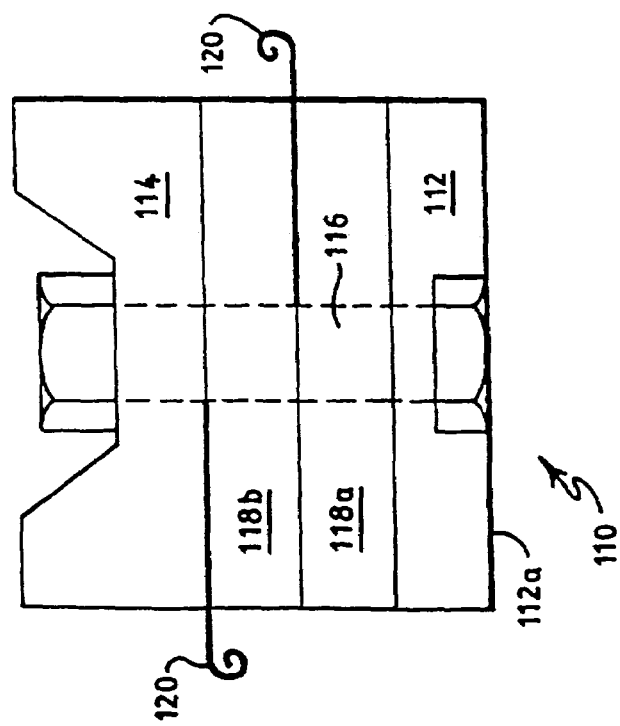

FIGS. 15 and 16 show further transducer embodiments of the invention. FIG. 25 shows a transducer 110 that includes a driver 112, back mass 114, bolt 116, ceramic elements 118a, 118b, and electrical lead-outs 120. The back mass is shaped so as to modify the transducer power output as a function of frequency. The driver 112 is preferably made from aluminum.

Figure 26:
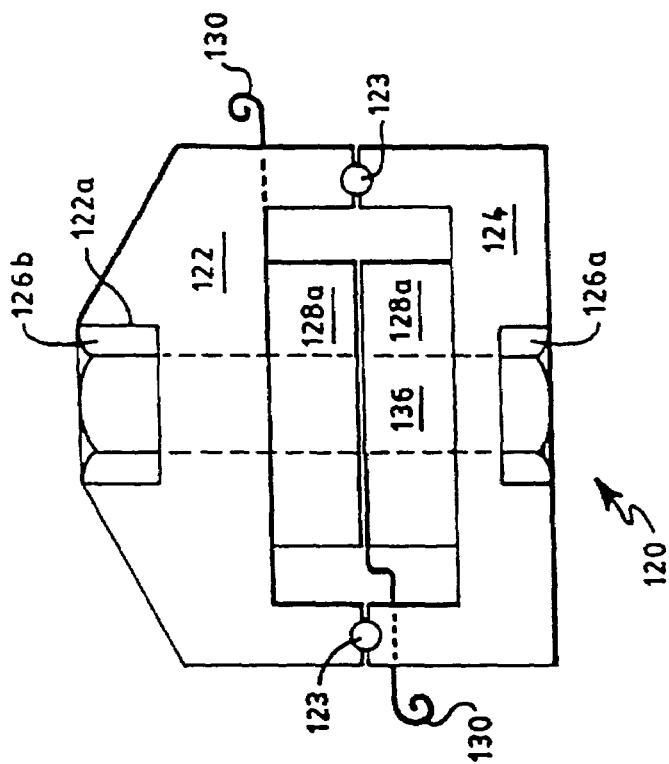

FIG. 26 illustrates an alternative transducer 120 that includes a back mass 122, driver 124, bolt 126, ceramic elements 128a, 128b, and lead outs 130. One or both of the back mass and driver 122, 124 are made from steel. However, the front mass 124 is preferably made from aluminum. The bolt head 126a is fixed within the driver 124; and a nut 126b is screwed onto the bolt 126 to reside within a cut-out 122a of the back mass 122. The back mass 122 and front mass 129 are sealed at the displacement node by an O-ring 123 to protect the electrical sections (i.e., the piezoelectric ceramics and electrodes) of the transducer 120 under adverse environmental conditions.

The designs of FIGS. 23-24 have advantages over prior art transducers in that the front mass in each design is substantially flush with the tank when mounted to the tank. That is, the front masses have a substantially continuous front face (e.g., the face 112a of FIG. 25) that mounts firmly with the tank surface. Accordingly, such designs support the tank surface, without gap, to reduce the chance of creating cavitation implosions that might otherwise eat away the tank surface and create unwanted contaminants.

Figure 28:
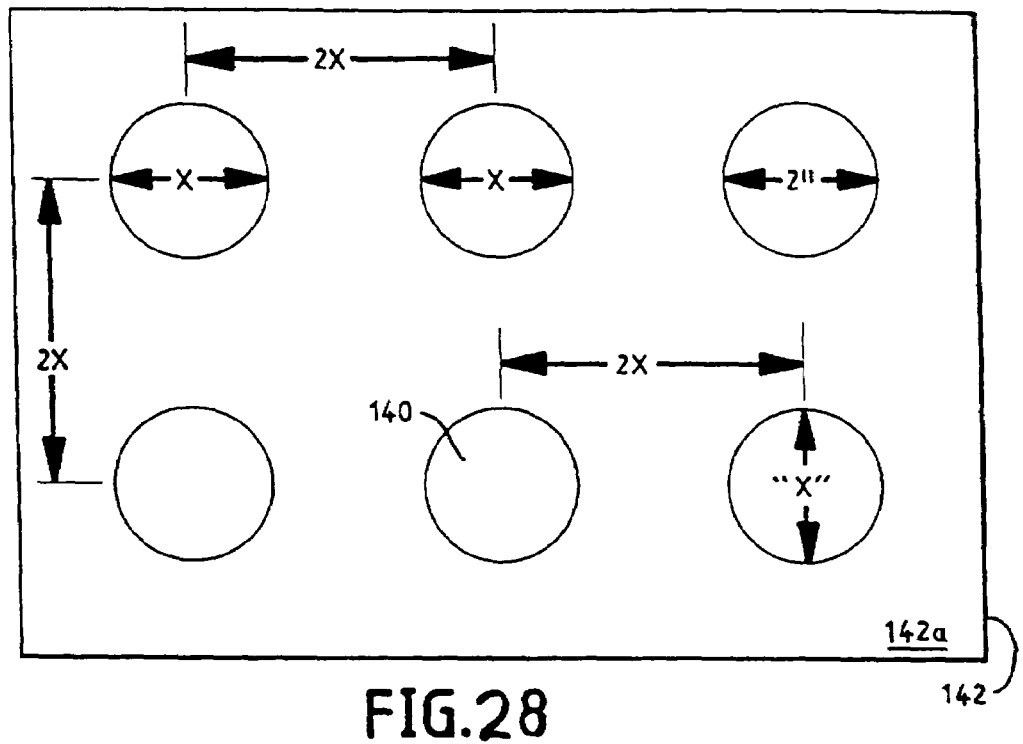
FIG. 28 illustrates preferential placement and mounting of multiple transducers relative to a process tank, in accord with the invention.
Figure 29:
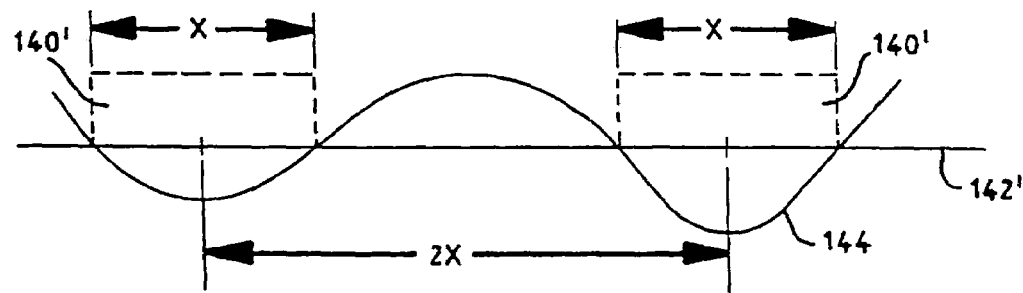
FIG. 29 illustrates a representative standing wave relative to the process tank as formed by the arrangement of FIG. 28.

FIG. 28 shows one preferred arrangement (in a bottom view) for mounting multiple transducers 140 to the bottom 142a of a process tank 142. Specifically, the lateral spacing between transducers 140—each with a diameter X—is set to 2X to reduce the cavitation implosions around the transducers 140 (which might erode the generally expensive tank surface 142a). By way of example, if the transducer 140 has a two inch diameter (i.e., X=2"), then the spacing between adjacent transducers 140 is four inches. Other sizes can of course be used and scaled to user needs and requirements. FIG. 29 illustrates, in a cross sectional schematic view, a standing wave 144 that is preferentially created between adjacent transducers 140' with diameters X and a center to center spacing of 2X. The standing wave 144 tends to reduce cavitation and erosion of the tank 142' surface.

Surface cavitation is intense cavitation that occurs at the interface between the solution within the tank and the radiating surface upon which the ultrasound transducers are mounted. There are several problems associated with surface cavitation damage. First, it is often intense enough to erode the material of the radiating surface. This can eventually create a hole in the radiation surface, destroying the tank. The erosion is also undesirable because it introduces foreign materials into the cleaning solution. Surface cavitation further generates cavitation implosions with higher energy in each cavitation implosion than exists in the cavitation implosions in the process chemistry. If the cavitation implosions in the process chemistry are at the proper energy level, than there is the possibility that the higher energy cavitation implosions at the surface cavitation will cause pitting or craters in the parts under process. In addition, the energy that goes into creating the surface cavitation is wasted energy that is better used in creating bulk cavitation.

Figure 30:
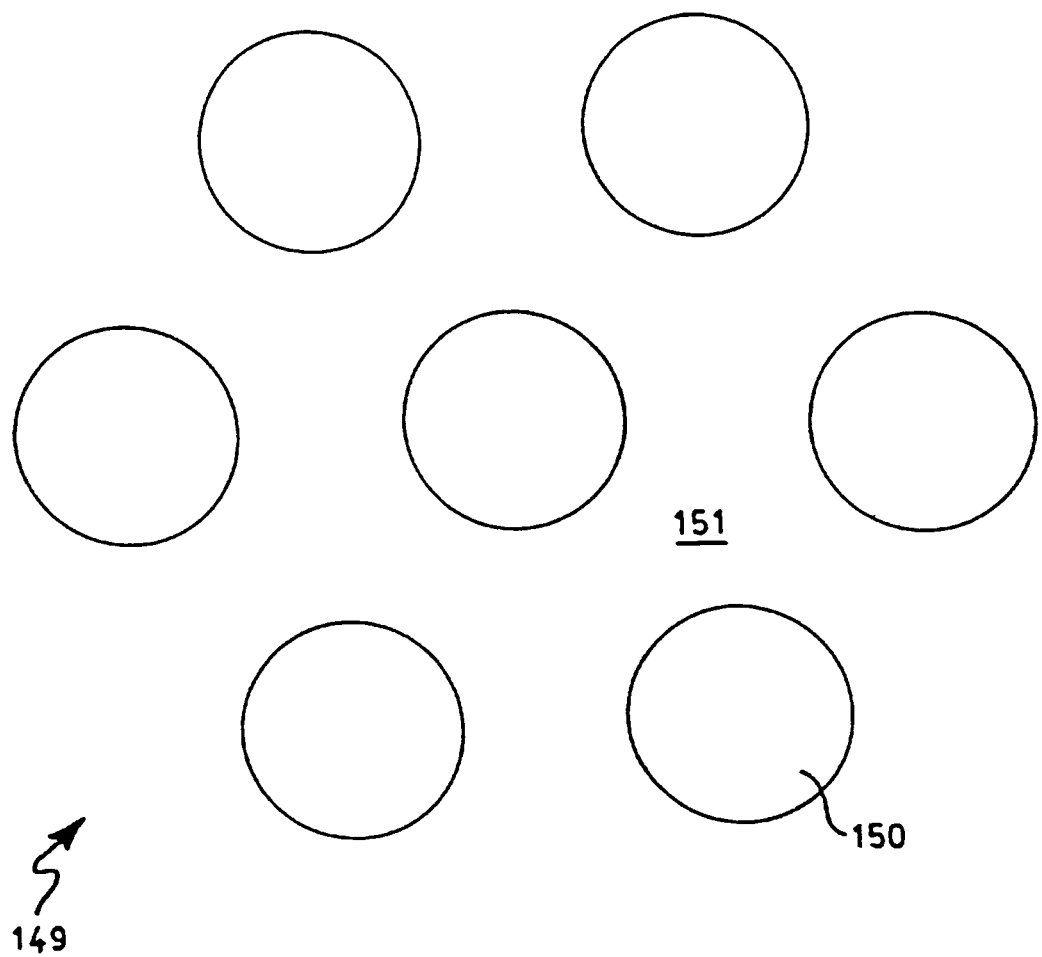
FIG. 30 illustrates another preferential pattern of placing transducers onto a mounting surface such as an ultrasound tank, in accord with the invention.
Figure 31:
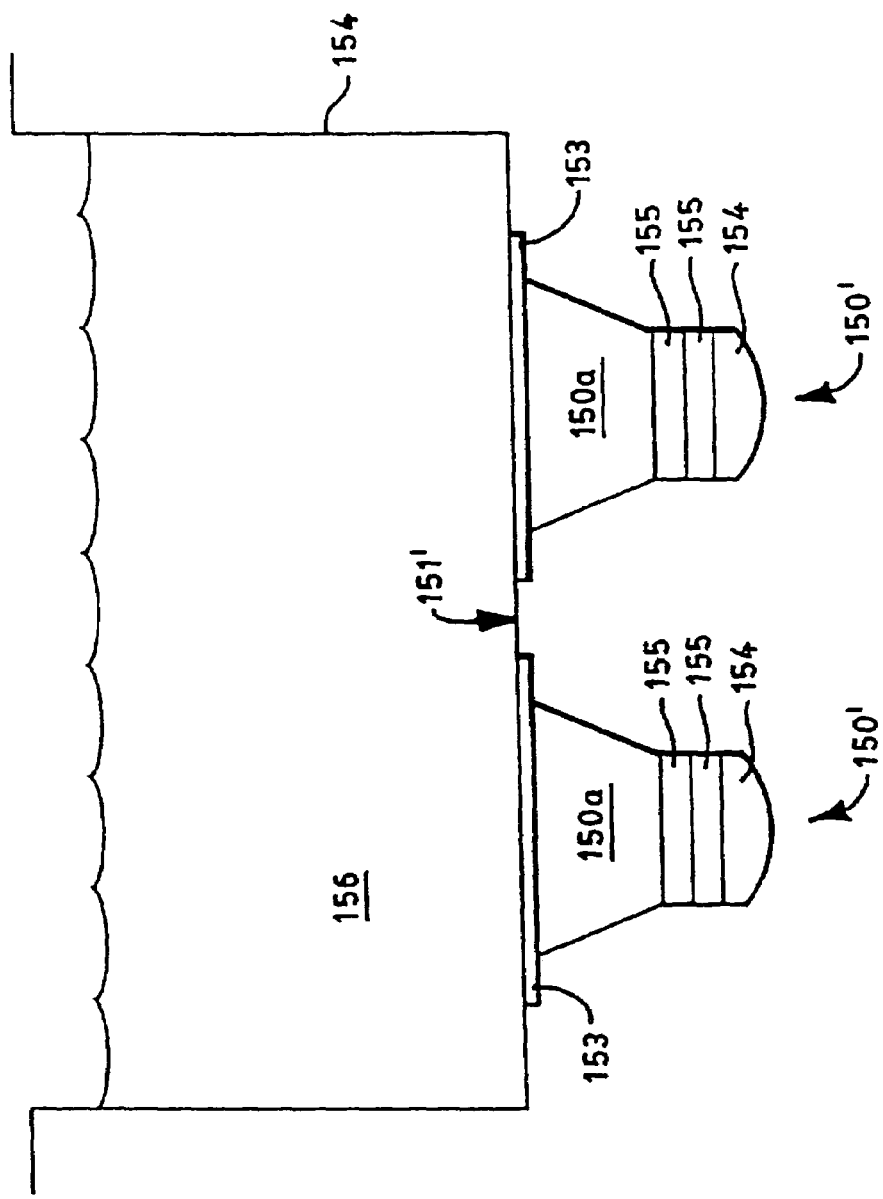
FIG. 31 illustrates, in a side view, the mounting of two transducers (such as the transducers of FIG. 30) to a tank, in accord with the invention.
Figure 32:
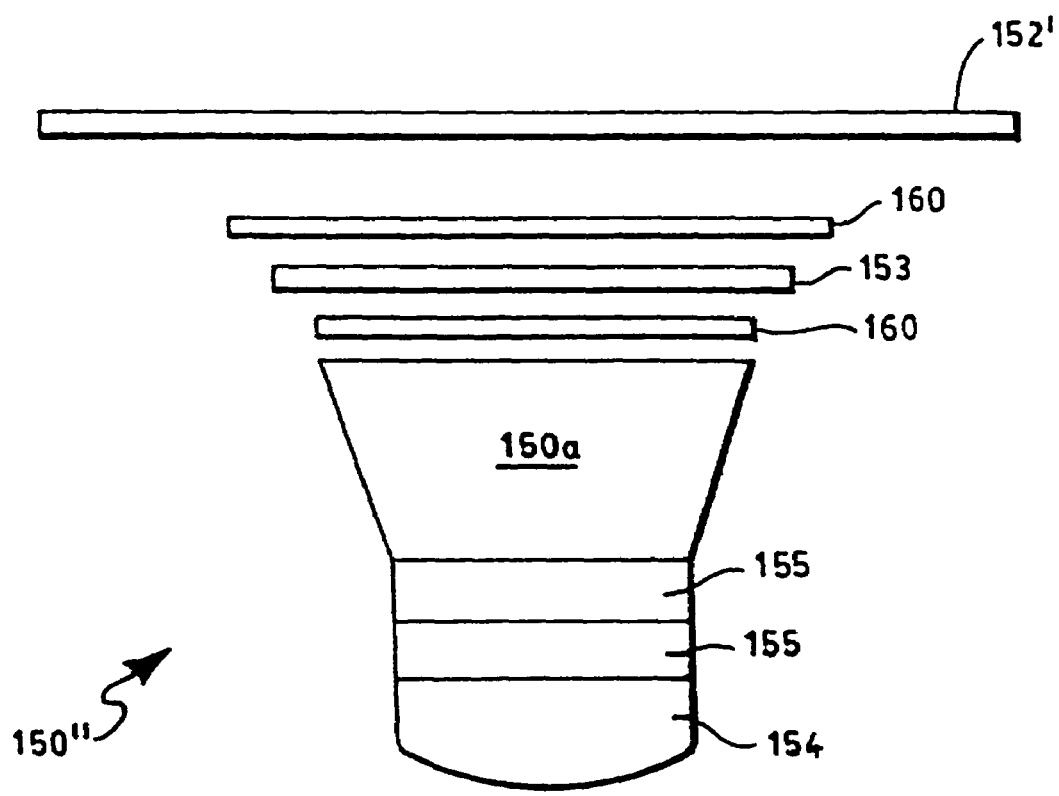
FIG. 32 shows an exploded side view of further features of one transducer such as shown in FIG. 31.

FIG. 30 illustrates a closed hex spacing pattern 149 of transducer elements 150 that causes the radiating membrane 151 (i.e., the surface of the tank to which the elements are bonded to) to vibrate in a sinusoidal pattern such that surface cavitation is prevented or reduced. In a side view, FIG. 31 illustrates a G-10 isolator 153 bonded between two of the transducers 150' (and specifically the front mass 150a) and the radiating surface 151', i.e., the wall of the tank 154 holding the process chemistry 156. The G-10 153 operates to further reduce unwanted surface cavitation, often times even when the closed hex spacing pattern of FIG. 30 is not possible. Polarized piezoelectric ceramic elements 155 are sandwiched between the front mass 150a and back mass 154. FIG. 32 shows an exploded side view of one of the G-10 mounted transducer 150" of FIG. 31. Layers of epoxy 160 preferably separate the G-10 isolator 153 from the transducer 150" and from the surface 152'.

Most ultrasound processes, including cleaning, have two distinct stages. The first stage is usually preparation of the liquid and the second stage is the actual process. The system 200 of FIGS. 33-35 reduces the time for liquid preparation and accomplishes the task to a degree where shorter process times are possible.

Figure 33:
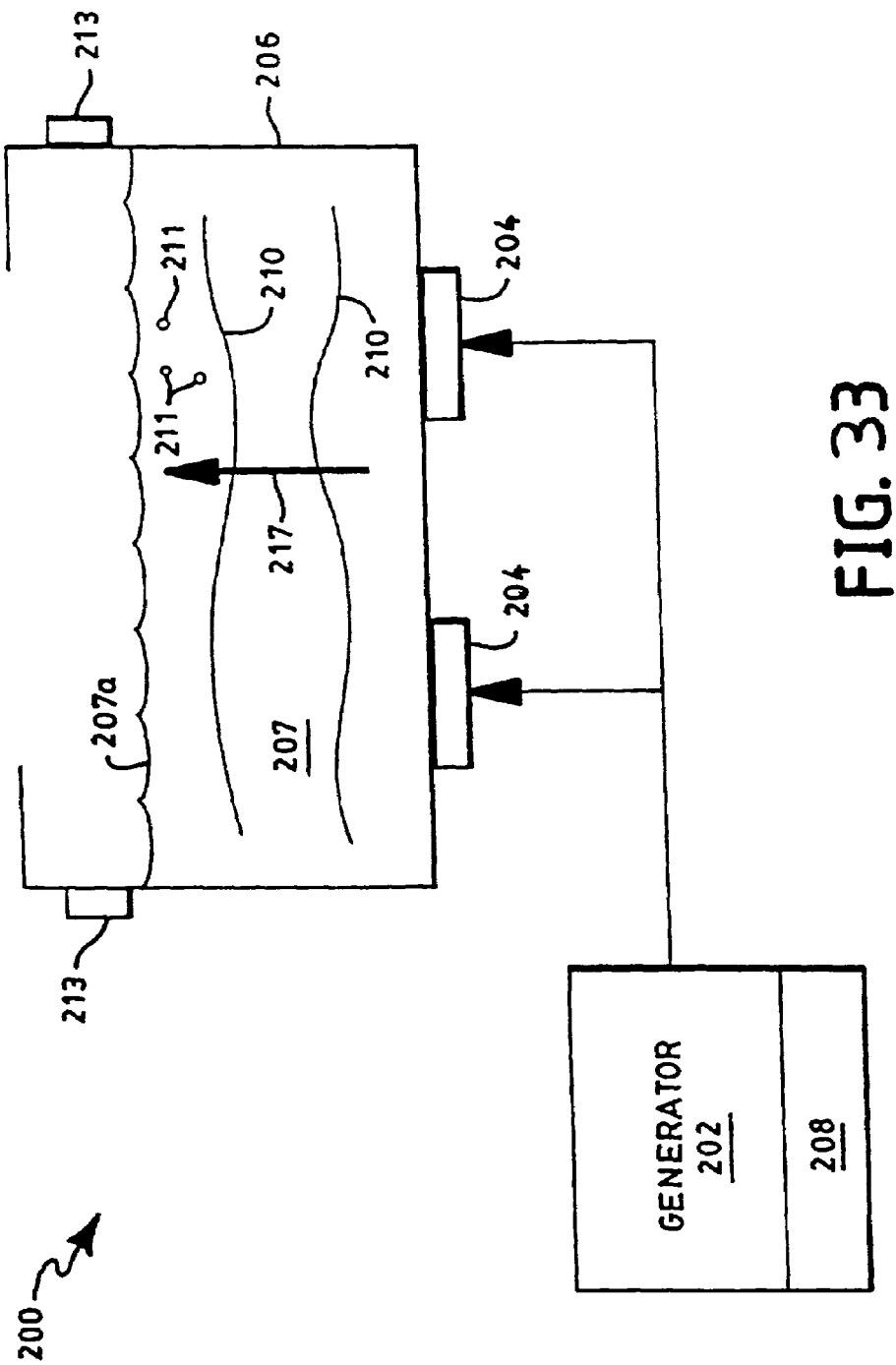
FIG. 33 illustrates a two stage ultrasound delivery system constructed according to the invention.

The invention of FIG. 33 utilizes the sound fields as an upward driving force to quickly move contaminants to the surface 207a of the liquid 207. This phenomenon is referred to herein as "power up-sweep" and generally cleans the liquid more quickly and thoroughly so that part processing can be done with less residual contamination.

More particularly, FIG. 33 shows a system 200 constructed according to the invention. A generator 202 drives a plurality of transducers 204 connected to a process tank 206, which holds a process chemistry 207. The generator 202 drives the transducers 204 from an upper frequency ($f_{upper}$) to a lower frequency ($f_{lower}$), a shown in FIG. 35. Once $f_{lower}$ is reached, a frequency control subsystem 208 controls the generator 202 so as to drive the transducers 204 again from $f_{upper}$ to $f_{lower}$ and without driving the transducers from $f_{lower}$ to $f_{upper}$. In this manner, only decreasing frequencies are imparted to the process chemistry 207; and acoustic energy 210 migrates upwards (along direction 217), pushing contamination 211 upwards and out of the tank 206.

As shown in FIG. 34, the two stage ultrasound processing system 200 can alternatively cycle the transducers 204 from $f_{upper}$ to $f_{lower}$ every other half cycle, with a degas, quiet or off half cycle 222 between each power burst. The control subsystem 208 of this embodiment thus includes means for inhibiting the flow of energy into the tank 206 over a second half cycle so that the quiet period 222 is realized. It is not necessary that the time periods of the first and second one-half cycles 222a, 222b, respectively, be equal.

FIGS. 34 and 35 also show that the rate at which the frequencies are swept from $f_{upper}$ to $f_{lower}$ can vary, as shown by the shorter or longer periods and slope of the power bursts, defined by the frequency function 220.

The generator 202 preferably produces frequencies throughout the bandwidth of the transducers 204. The generator 202 is thus preferably a sweep frequency generator (described in U.S. Pat. Nos. 4,736,130 and 4,743,789) or a dual sweep generator (described in International Patent Application PCT/US97/12853) that will linearly or non-linearly change frequency from the lowest frequency in the bandwidth to the highest frequency in the bandwidth; and that will thereafter reverse direction and sweep down in frequency through the bandwidth. The invention of FIG. 35 has an initial stage where the sweeping frequency only moves from the highest bandwidth frequency to the lowest bandwidth frequency. Once the lowest frequency is reached, the next half cycle is the highest frequency and the sweep starts again toward the lowest frequency. An alternative (FIG. 34) is to shut the ultrasonics off when the lowest frequency is reached and reset the sweep to the highest frequency. After an ultrasonics quiet period 222, another sweep cycle from high frequency to low frequency occurs. This "off" period followed by one directional sweep is repeated until contamination removal is complete; and then the processing can start in a normal way. Alternatively, a power up-sweep mode can be utilized for improved contamination removal during processing.

The reason that contamination is forced to the surface 207a of the process chemistry 207 in the system of FIG. 33 is because the nodal regions move upward as frequency is swept downward. Contamination trapped in nodal regions are forced upward toward the surface as nodes move upward. Generally, the system of FIG. 33 incorporates a type of frequency modulation (FM) where frequency changes are monotonic from higher to lower frequencies. Transducers 204 mounted to the bottom of the process tank 206 generate an ever expanding acoustic wavelength in the upward direction 217 (i.e., toward the surface 207a of the process chemistry 207). This produces an acoustic force 210 which pushes contamination 211 to the surface 207a where the contamination 211 overflows the weirs 213 for removal from the tank 206.

Those skilled in the art should appreciate that methods and systems exist for sweeping the applied ultrasound energy through a range of frequencies so as to reduce resonances which might adversely affect parts within the process chemistry. See, e.g., U.S. Pat. Nos. 4,736,130 and 4,743,789 by the inventor hereof and incorporated by reference. It is further known in ultrasound generators to "sweep the sweep rate" so that the sweep frequency rate is changed (intermittently, randomly, with a ramp function, or by another function) to reduce other resonances which might occur at the sweep rate. By way of example, the inventor of this application describes such systems and methods in connection with FIGS. 3, 4, 5A, 5B, 22A, 22B and 22C of International Application No. PCT/US97/12853, which is herein incorporated by reference.

Figure 36:
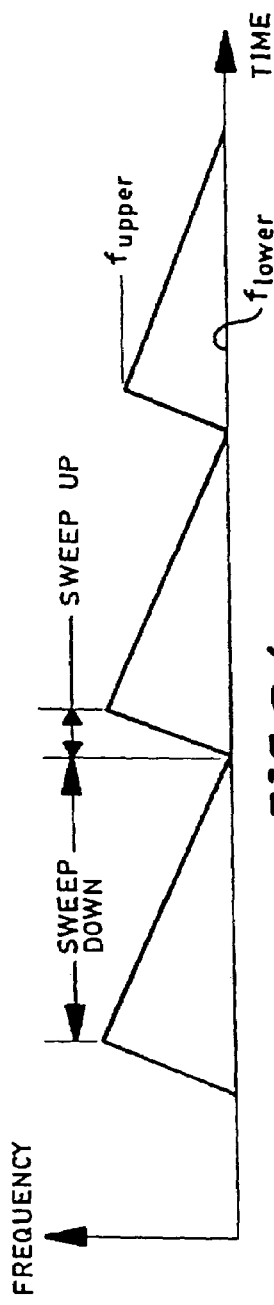
FIGS. 36-40 show alternate sweep down cyclical patterns for applying a power-up sweep pattern in accord with the invention.

The variable slope of the frequency function 220 of FIGS. 34 and 35 illustrates that the time period between successive power up sweeps, from $f_{upper}$ to $f_{lower}$, preferably changes so as to "sweep the sweep rate" of the power up sweep. Accordingly, the power up-sweep preferably has a non-constant sweep rate. There are several ways to produce a non-constant power up-sweep rate, including:

As illustrated in FIG. 36, sweep down in frequency (i.e., from $f_{upper}$ to $f_{lower}$) at a relatively slow rate, typically in the range of 1 hz to 1.2 khz, and sweep up in frequency (i.e., from $f_{lower}$ to $f_{upper}$) during the recovery time at a rate about ten times higher than the sweep down frequency rate. Vary the rate for each cycle. This cycle is repeated during processing.

Figure 37:
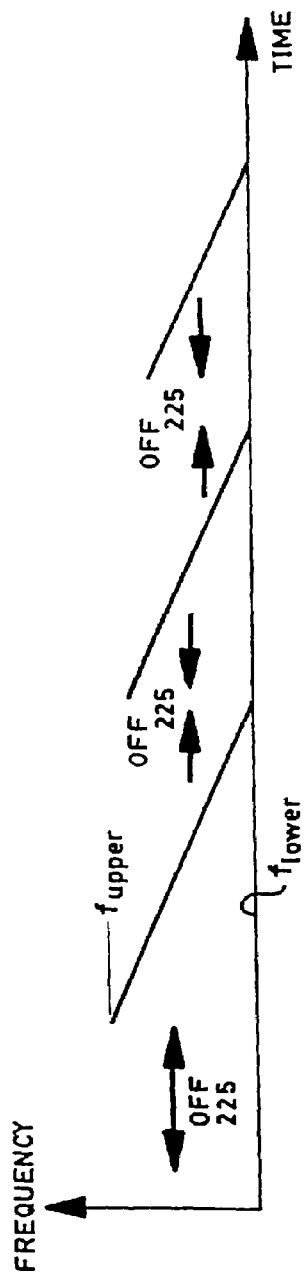

As illustrated in FIG. 37, sweep down in frequency at a relatively slow rate and shut the generator 202 off (such as through the control subsystem 208) at periods 225' when the lowest frequency $f_{lower}$ in the bandwidth (bandwidth=$f_{upper}$-$f_{lower}$) is reached. During the off time 225', a degassing period 222 can occur as in FIG. 34 due to buoyancy of the gas bubbles; and the subsystem 208 resets the generator 202 to the highest frequency for another relatively slow rate of sweeping from $f_{upper}$ to $f_{lower}$, each time reducing contaminants. Vary the time of the degas period. Repeat this cycle during processing.

Figure 38:
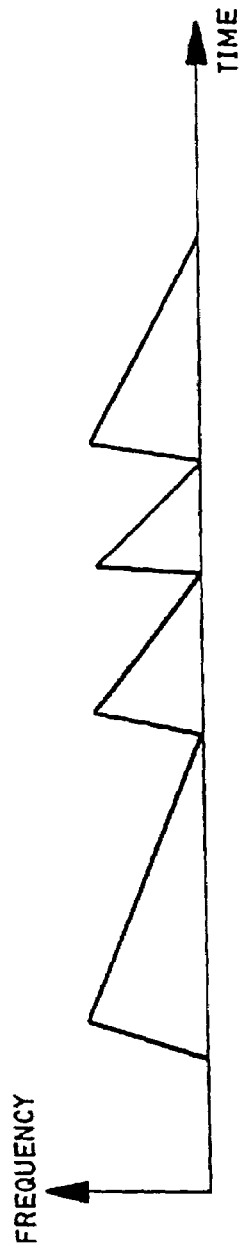

As a function of time, change or "sweep" the power up-sweep rate at optimum values (1 hz to 1.2 khz) of the rate, as shown in FIG. 38. The change in the upward sweep rate and the change in the downward sweep rate can be synchronized or they can be random or chaotic with respect to one another.

Figure 39:
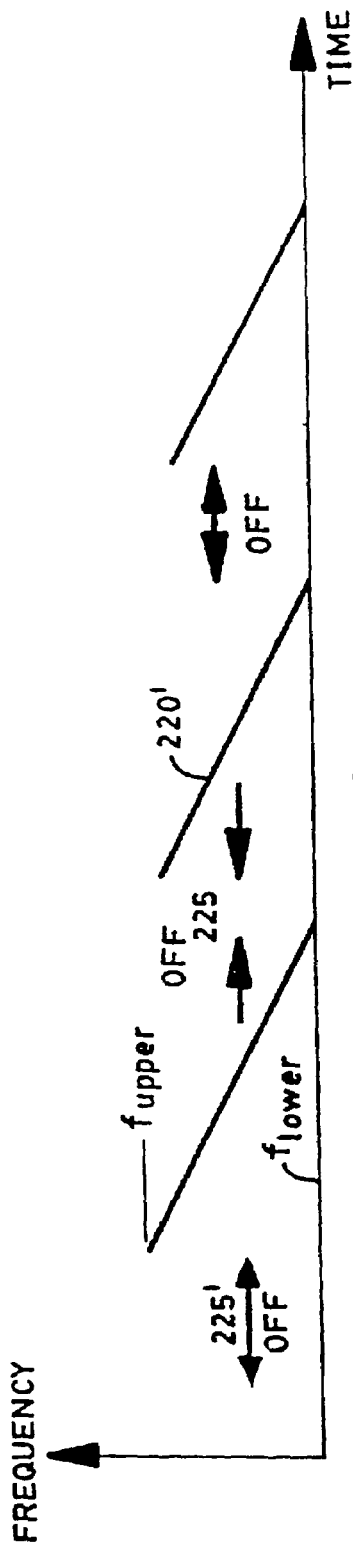

For the case where there is a degas period, such as in FIGS. 34 and 39 (i.e. the recovery period when the generator is off or unconnected while resetting from low frequency to high frequency), vary the length of the degas period 222 (FIG. 34), 225' (FIG. 39) randomly or as a function of time such as through a linear sweep rate time function. This technique has an advantage for cases where there is one optimum power up-sweep rate (i.e., the rate of frequency change between $f_{upper}$ and $f_{lower}$) and, accordingly, low frequency resonances are eliminated by changing the overall rate. In such a technique, the slope of the frequency function 220' in FIG. 39, is constant, though the period of each degas period 225' changes according to some predefined function.

Figure 40:
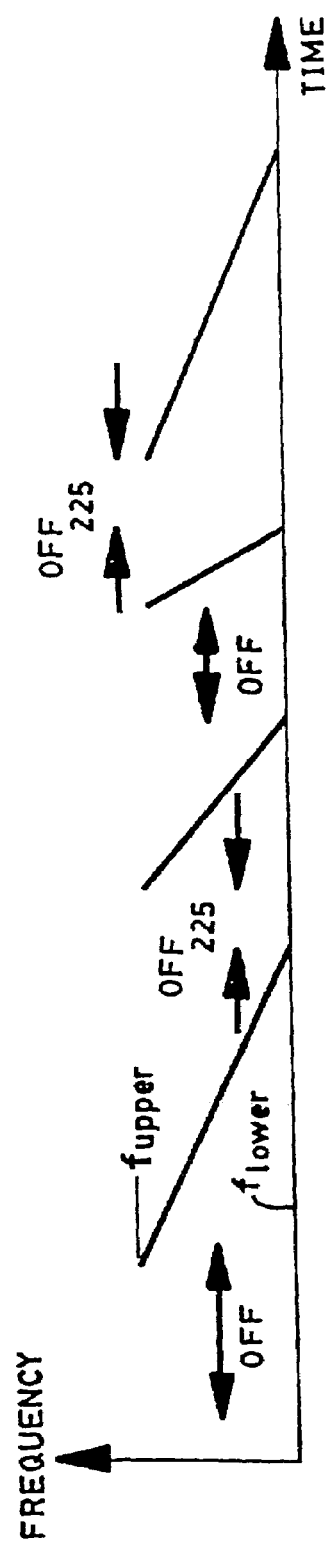

As shown in FIG. 40, sweep the rate with a combination of (c) and (d) techniques above.

Note that in each of FIGS. 34-40, the x-axis represents time (t) and the y-axis represents frequency f.

FIG. 41 shows a schematic 250 illustrating the most general form of generator circuitry providing both non-constant power up-sweep rate and non-constant degas period, as described above.

FIG. 42 shows a system 300 including a generator 302 and transducers 304 that can be switched, for example, to either 72 khz or 104 khz operation. The transducers 304 operate to inject sonic energy 305 to the process chemistry 307 within the tank 306. Because of the impedance characteristics at these frequencies, the generator 302 includes a constant power output circuit 306 that changes the center frequency output from the generator 302 while maintaining constant output power. The circuit 306 includes a switch section 308 that switches the output frequency from one frequency to the next with no intermediate frequencies generated at the output (i.e., to the transducers 304).

A similar system 310 is shown in FIG. 43, where switching between frequencies does not utilize the same power circuit. In FIG. 43, the generator 312 includes at least two drive circuits for producing selected frequencies $f_1$ and $f_2$ (these circuits are illustratively shown as circuit ($f_1$), item 314, and circuit ($f_2$), item 316). Before the reactive components in either of the circuits 314, 316 can be switched to different values, the output circuit 318 shuts down the generator 312 so that stored energy is used up and the relay switching occurs in a zero voltage condition.

From the above, one skilled in the art should appreciate that the system 310 can be made for more than two frequencies, such as for 40 khz, 72 khz and 104 khz. Such a system is advantageous in that a single transducer array can be used for each of the multiple frequencies, where, for example, its fundamental frequency is 40 khz, and its first two harmonics are 72 khz and 104 khz.

An alternative system is described in connection with FIG. 71.

FIG. 44 illustrates a system 400 and a sensing system 402, which is a sensing probe disposed with the process liquid 407. A generator 404 connects to transducers 406 to impart ultrasonic energy 403 to the process chemistry 407 within the tank 408. The sensing probe 402 includes an enclosure 410 that houses a liquid 412 that is responsive to ultrasound energy within the liquid 407. The enclosure 410 is made from a material (e.g., polypropylene) that transmits the energy 403 therethrough. In response to the energy 403, changes in or energy created from liquid 412 are sensed by the analysis subsystem 414. By way of example, the liquid 412 can emit spectral energy or free radicals, and these characteristics can be measured by the subsystem 414. Alternatively, the conduit 416 can communicate electrical energy that indicates the conductivity within the enclosure. This conductivity provides an indication as to the number of cavitation implosions per unit volume within the process chemistry 407. The conduit 416 thus provides a means for monitoring the liquid 412. A thermocouple 420 is preferably included within the enclosure 410 and/or on the enclosure 410 (i.e., in contact with the process chemistry 407) so as to monitor temperature changes within the enclosure 410 and/or within the process chemistry 407. Other characteristics within the tank 408 and/or enclosure 410 can be monitored by the subsystem 414 over time so as to create time-varying functions that provide other useful information about the characteristics of the processes within the tank 408. For example, by monitoring the conductivity and temperature over time, the amount of energy in each cavitation explosion may be deduced within the analysis subsystem 414, which preferably is microprocessor-controlled.

Figure 45:
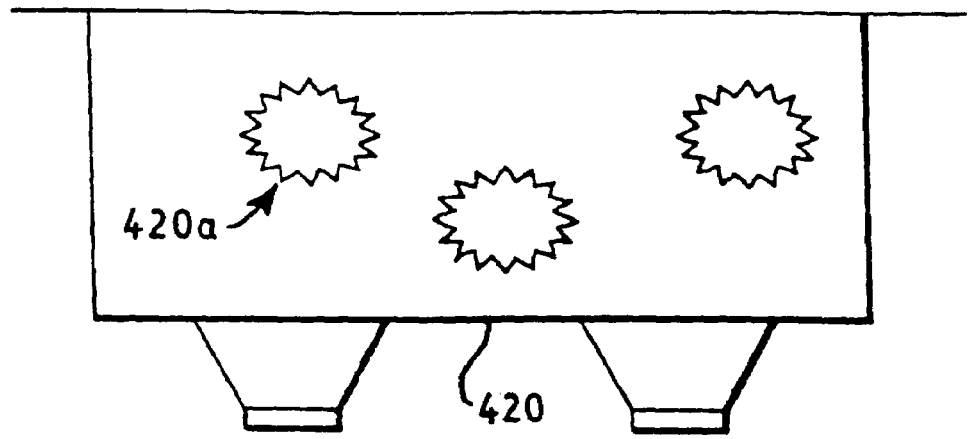
FIGS. 45 and 46 illustrate two process tanks operating with equal input powers but having different cavitation implosion activity.
Figure 46:
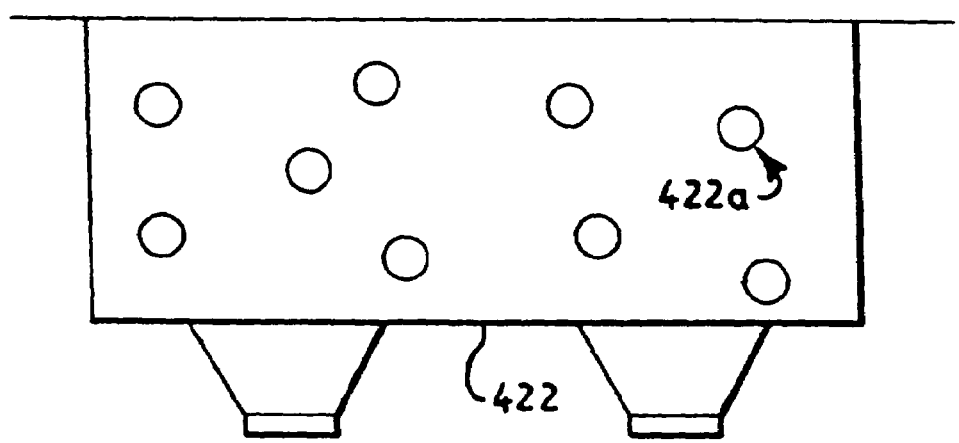

The prior art is familiar with certain meters which measure sound characteristics and cavitations within an ultrasonic tank. Each of the meters gives one number, usually in units of watts per gallon, and sometimes in undefined units such as cavities. However, the activity in a cavitating ultrasonic tank is very complex and no single number adequately describes this activity. For example, as shown in FIGS. 45 and 46, it is possible to have two ultrasonic tanks 420, 422, both having the same input power (i.e. watts per gallon) but each having very different ultrasonic activity characteristics. The first tank 420 might have relatively few high energy cavitation implosions 420a while the second tank 422 has many low energy cavitation implosions 422a (specifically, FIGS. 45 and 46 show cavitation implosions 420a, 422a during a fixed time period in the two tanks 420, 422 having equal input energies). At least two numbers are thus necessary to describe this situation: the energy in each cavitation implosion and the cavitation density. The energy in each cavitation implosion is defined as the total energy released in calories from a single cavitation event; and the cavitation density is defined as the number of cavitation events in one cubic centimeter of volume during a 8.33 millisecond time period. Note, in Europe and other countries with fifty Hz power lines, the cavitation events in one cubic centimeter are counted over a ten millisecond time period and multiplied by 0.833. This technique provides the most accurate measurement for the common ultrasonic systems that have their amplitude modulation pattern synchronized by two times the power line frequency.

In most ultrasonic systems, the cavitation density also varies as a function of time. Accordingly, this is a third characteristic that should be measured when measuring ultrasonic activity in a tank.

Figure 47:
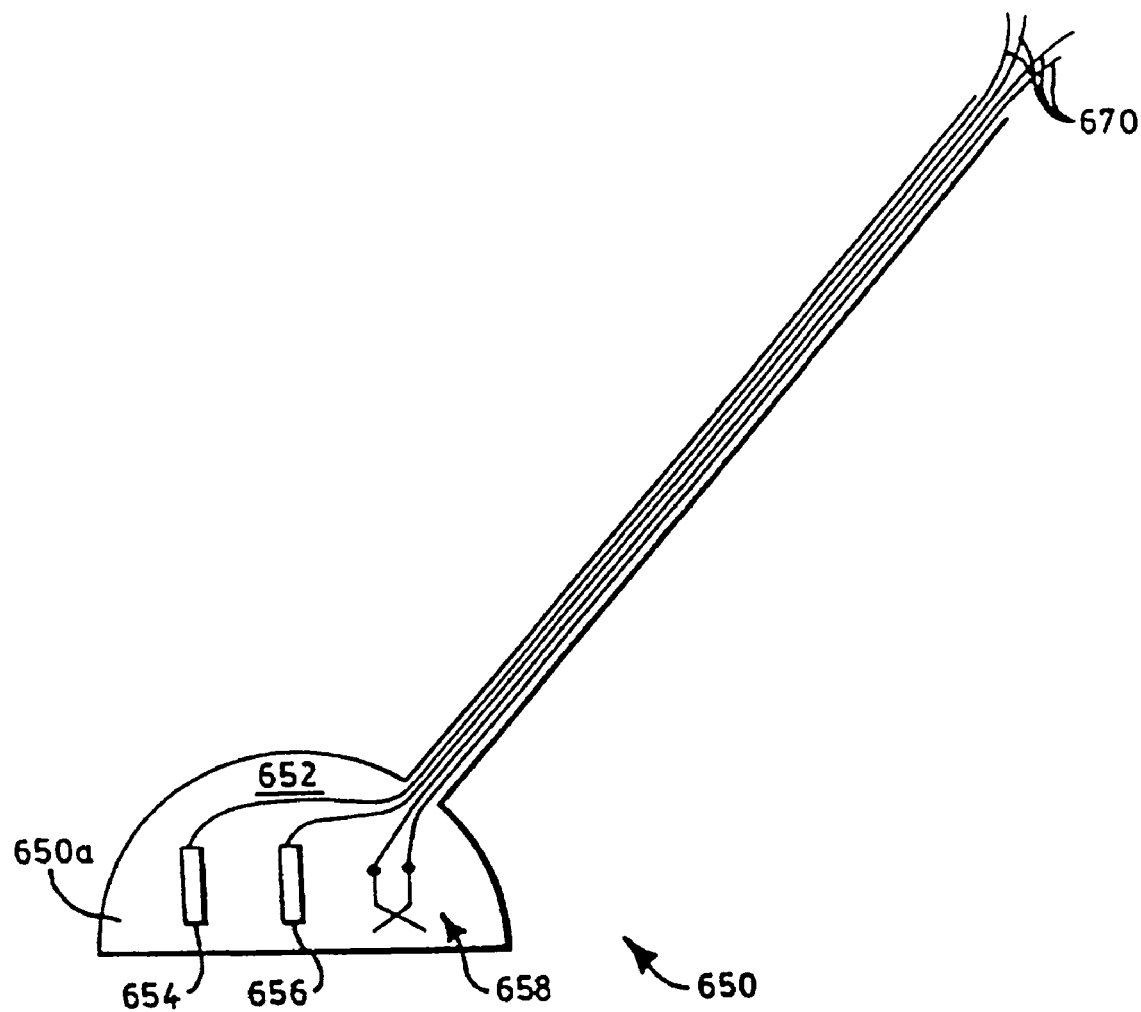
FIG. 47 illustrates a process probe constructed according to the invention and for monitoring process characteristics within a process chemistry such as within an ultrasound tank.

FIG. 47 thus illustrates a sensing system, which is a sensing probe 650 and which permits the calculation of these important parameters. Specifically, the sensing probe 650 measures average conductivity, conductivity as a function of time, and change in temperature.

A characteristic of ultrasonic cavitation in aqueous solutions is the production of free radicals, ions and super oxides. These by-products of the cavitation increase the conductivity of the aqueous solution. A measure of the conductivity is thus a function of the number of cavitation implosions present in the aqueous sample, and the time variation of this conductivity is a measure of how the cavitation density varies as a function of time.

Another characteristic of cavitation is that it heats the aqueous solution. This is because all the energy released during each cavitation implosion becomes heat energy. By measuring the change in temperature of the aqueous sample, therefore, and by knowing its mass and specific heat, one can calculate the total energy released from the cavitation by the following formula: energy (calories) equals specific heat (no units, i.e., a ratio) times mass (grams) times the change in temperature (degrees C.). When the amount of energy released is known, as well as the number of cavitation implosions that released this energy, a division of the quantities gives the energy in each cavitation implosion.

The sensing probe 650 is similar in operation to the sensing probe 402 of FIG. 34 and includes a fixed sample volume of aqueous solution 652 (or other chemistry that changes conductivity in an ultrasonic field) contained in the sensing probe tip 650a. The sensing probe tip 650a is designed to cause minimal disturbance to the ultrasonic field (e.g., the field 403 of FIG. 34). Accordingly, the sensing probe tip 650a is preferably made of a material that has nearly the same acoustic impedance as the liquid being measured and that has low thermoconductivity. Polypropylene works well since it and water have nearly the same acoustic impedance.

The sensing probe 650 thus includes, within the sensing probe tip 650a, two electrodes 654, 656 to measure conductivity, and a temperature measuring device (e.g., a thermocouple) 658 to monitor the temperature of the fixed mass of aqueous solution 652. These sensing devices 654, 656 and 658 are connected to data wires for sampling of the sensing device responses. A data collection instrument (e.g., an A/D sensor interface board and a computer) connects to the wires 670 out of the sensing probe 650 to measure temperature rise as a function of time, DeltaT=g(t), and to evaluate this quantity over a specific time period t', in seconds, i.e., DeltaT=g(t'). The data collection instrument also measures the initial conductivity, $C_0$, without ultrasonics, and the conductivity as a function of time, C=h(t), within the ultrasonic field. Fixed constants associated with the sensing probe should also be stored, including the specific heat (p) of the liquid 652, the volume (V) of the liquid 652 (in cubic centimeters), the mass (m) of the liquid 652 (in grams), and the functional relationship $n=f(C,C_0)$ between conductivity and the number of cavitation implosions occurring in the sensing probe tip 650a in 8.33 milliseconds determined by counting the sonoluminescence emissions over a 8.33 millisecond period and plotting this versus the conductivity measurement. The instrument then calculates the ultrasonic parameters from this information according to the following formulas:

$$\text{cavitation density} = D = n/V = f(C,C_0)/V$$

$$\text{energy in each cavitation implosion} = E = (0.00833)(p)(m)(g(t'))/f(C,C_0)/t'$$

$$\text{cavitation density as a function of time} = f(h(t))N$$

These three measured parameters are then fed back to the generator to continuously control the output of the generator to optimum conditions. FIG. 38 shows a complete system 675 for monitoring and processing data from such a sensing probe 650' and for modifying applied ultrasound energy 676 applied to the process chemistry 678. Specifically, the system 675 monitors the parameters discussed above and, in real time, controls the generator 680 to adjust its output drive signals to the transducers 682 at the tank 684. The data collection instrument 685 connects to the wiring 670' which couples directly to the sensing devices within the sensing probe tip 650'. The instrument 685 generates three output signal lines corresponding to measured parameters: the "A" signal line corresponds to the energy in each cavitation implosion, the "B" signal line corresponds to the cavitation density output, and the "C" signal line corresponds to the cavitation density as a function of time. These signal lines A-C are input to separate comparators 686a, 686b and 686c. The comparators 686a-c are coupled to signal lines D-F, respectively, so that the input signal lines A-C are compared to user selected optimum values for each of the parameters. Typically, the user employs empirical experimentation to arrive at the optimum values for a particular tank 684 and chemistry 678. The results from the comparators 686 are input to the control system 690, which controls the generator 680 (those skilled in the art should appreciate that the controller 690 and generator 680 can be, and preferably are, coupled as a single unit).

The energy in each cavitation implosion decreases as the frequency of the ultrasonics 676 increases and as the temperature of the solution 678 increases. The energy in each cavitation implosion is measured and compared to the optimum value (set by signal lines D-F) for the process, and if the measured value has a higher energy value than the optimum value, as determined by the comparators 686, the center frequency of the generator 680 is increased (by the controller 690 receiving data at the "center frequency input control") until the values are equal. If there is not enough range in the center frequency adjustment to reach the optimum value, then the temperature of the solution 678 is increased by the control system 690 until the optimum value is reached. An alternative is to utilize a switchable frequency generator, as described above, so as to change the drive frequency to one where the energy in each cavitation implosion is not greater than the optimum value, and without changing the solution temperature.

The cavitation density increases as the ultrasonic power into the tank 684 increases. Therefore, the cavitation density measurement fed back to the generator 680 is compared against the optimum value of cavitation density for the process; and if the measured value is lower than the optimum value, the generator output power is increased (by the controller 690 receiving data at the "power control") until the two values are equal. If the measured value is greater than the optimum value, the generator output power is decreased until the values are equal.

Cavitation density as a function of time is controlled by the amplitude modulation (AM) pattern of the generator output 692. Therefore the measured cavitation density as a function of time is measured and the generator's AM pattern is adjusted (via the controller 690 receiving data at the "AM Control") until the measured function equals the optimum function.

Figure 47A:
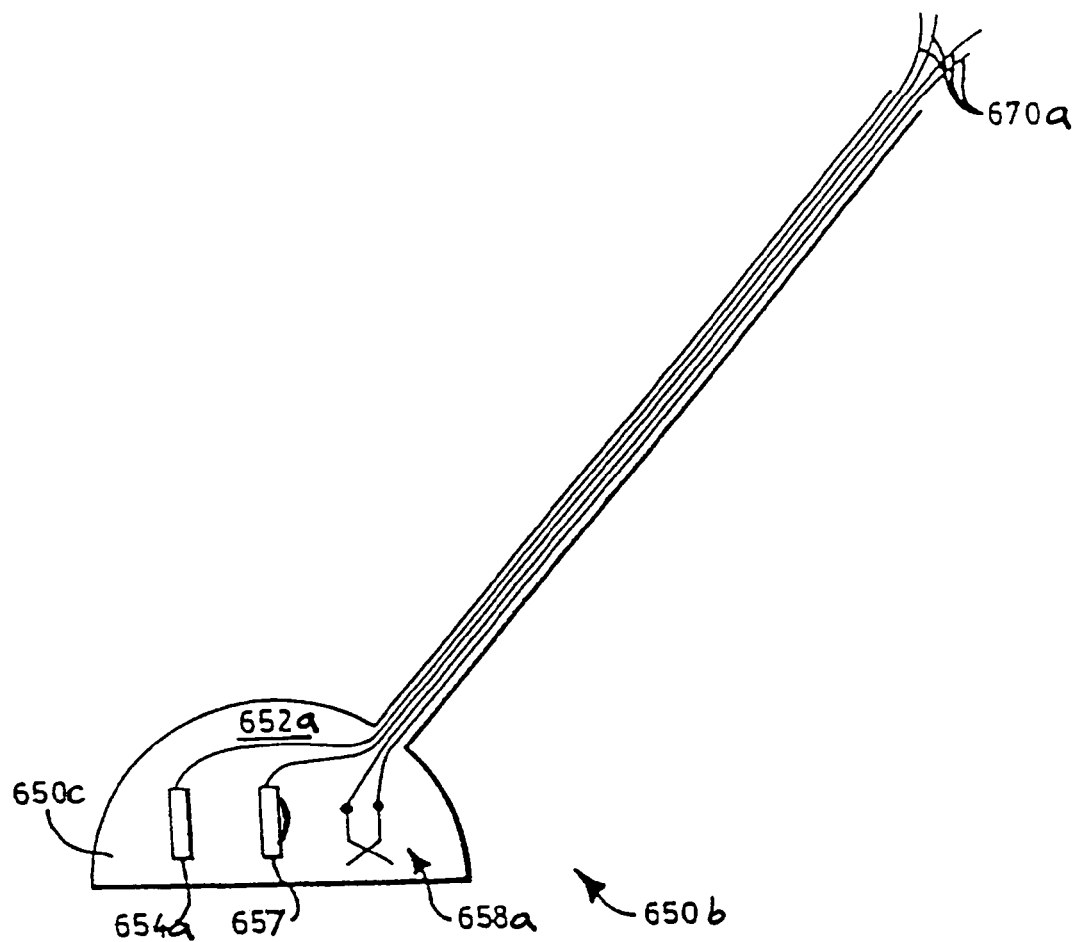
FIG. 47A illustrates a photon sensing process probe constructed according to the invention and for monitoring process characteristics within a process chemistry such as within an ultrasound tank.
Figure 48:
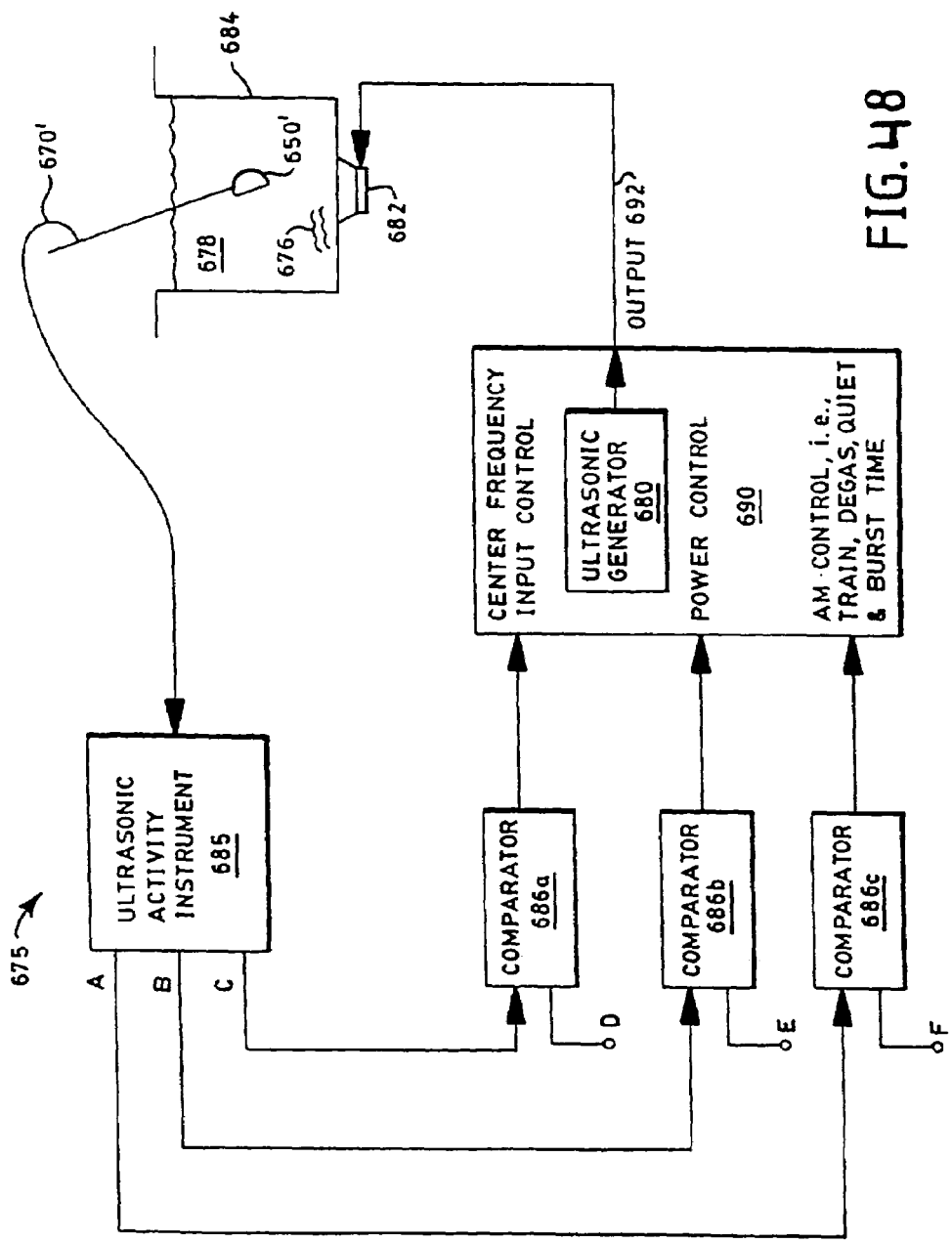
FIG. 48 shows a schematic view of a system incorporating the probe of FIG. 47 and further illustrating active feedback control of energy applied to an ultrasound tank, in accord with the invention.

FIG. 47A illustrates a second embodiment of a sensing probe 650b of the invention which permits the calculation of parameters of the cavitation within the ultrasound treatment tank, such as cavitation density and energy in each cavitation implosion. Specifically, the sensing probe 650b also measures light emissions from the sample liquid 652a which has materials adapted to generate chemiluminescence in the presence of cavitation. Examples of suitable sample liquids are o-aminophthalhydrazide mixed with hydrogen peroxide and cobalt Co(II) or anthracene hydrazide. The sensing device that measures the light emissions is a photo sensor 657. In one embodiment, the photo sensor 657 includes a photoelectric sensing device. Examples of photo sensors 657 that can be used in the sensing probe 650b are a photo multiplier tube, a CCD (charge coupled device), a photo tube, a photodiode, a CMOS light sensor, or a photo transistor. According to one preferred embodiment of the present invention, the sample liquid is different from the process liquid.

A characteristic of the sample liquid 652a is that it produces photons when exposed to ultrasonic cavitation. These photons are measured by the photo sensor 657 to provide information about the cavitation field. According to one preferred embodiment, the photo sensor 657 is a photo multiplier tube, and the individual photons are measured and counted by the photo multiplier tube. The measurement of the photons provides a measure of the energy and the number of cavitation implosions present in the sample liquid, and the variation of this photon counting over time is a measure of how the cavitation density varies as a function of time. In alternative embodiments, if a more primitive device is used for the photo sensor 657, for example, a photo diode, the average intensity of the light output within the sample liquid can be measured, which provides a measure of the total energy in the cavitation implosions present in the sample liquid, and the variation of this total energy over time is a measure of how the cavitation density varies as a function of time. Alternatively, more than one photo sensors, which belong to different types of photo sensors, may be used within the sensing probe 650b.

The sensing probe in FIG. 47A shows three different sensing devices, a conductivity sensor 654a (shown as one unit for simplicity, but actually has two sensing probes between which the conductivity is measured), a photo sensor 657 and a thermocouple 658a. From the above description, it is clear to one skilled in the art that using these three sensing devices in the sample liquid provides more than one independent measurement for one or more of the cavitation parameters within the tank. For example, both the photo sensor and the temperature sensor can be used to measure the total cavitation energy. One advantage of the combination of multiple sensors is that it can be used to calculate errors and thereby reduce errors in the final measured values. The cost and complexity of the sensing probe can be reduced by using any lower combination of one or more of the sensing devices, with a corresponding reduction in the amount and/or accuracy of information about the cavitation field.

Figure 49:
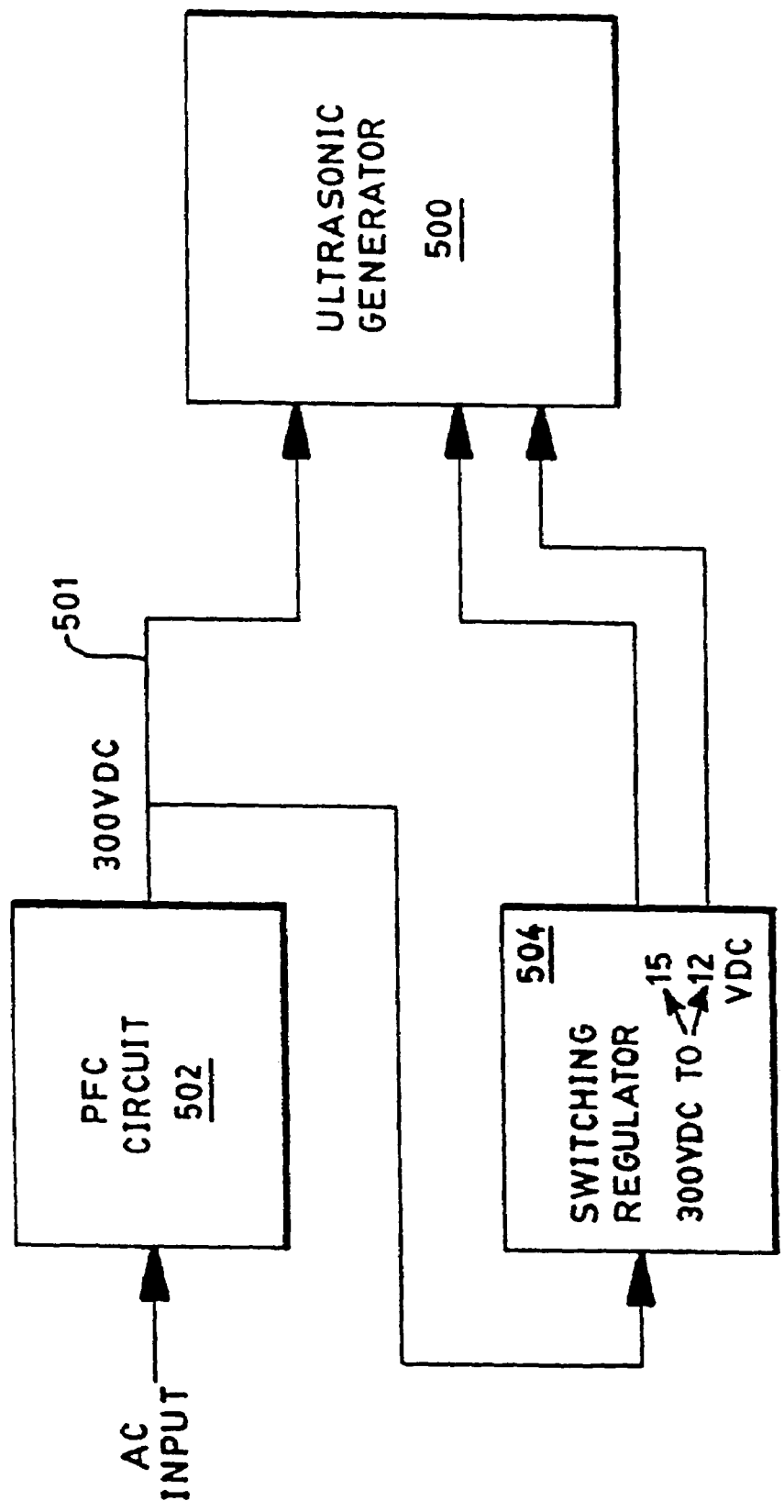
FIGS. 49-51 illustrate alternative embodiments of ultrasound generators with universal voltage input, in accord with the invention.
Figure 50:
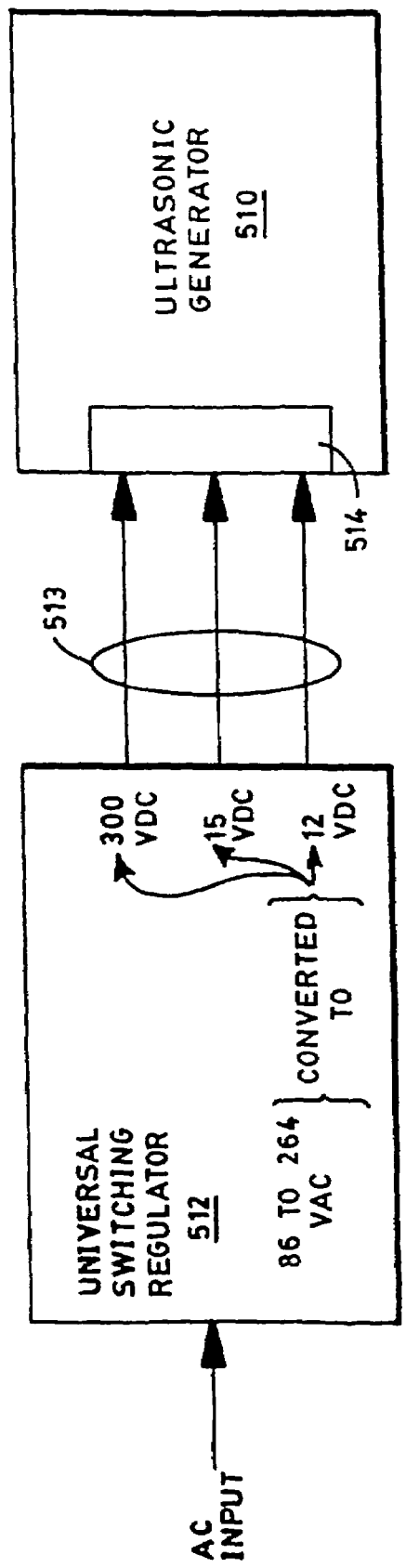
Figure 51:
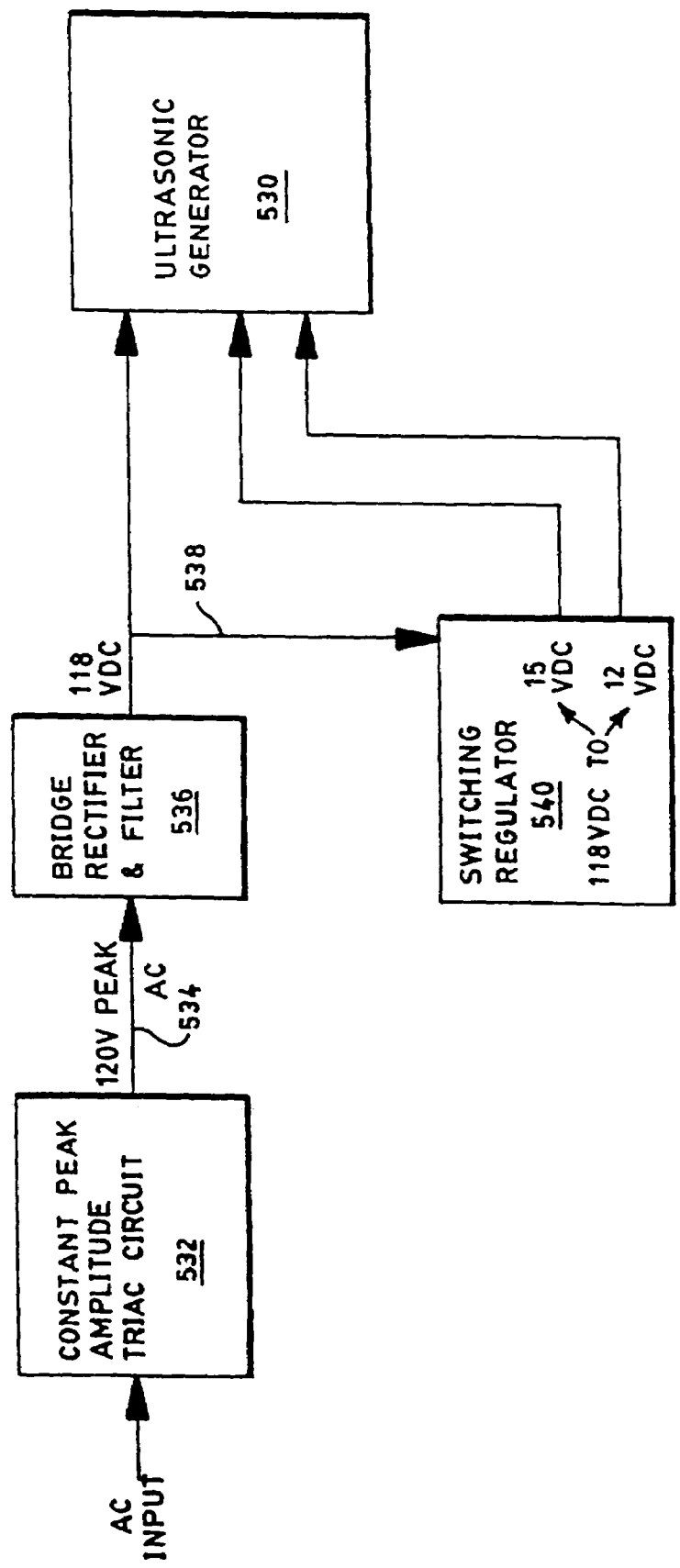

FIGS. 49-51 illustrate separate embodiments of universal voltage input ultrasound generators, in accord with the invention. These embodiments are made to solve the present day problems associated with separate designs made for countries with differing power requirements (in volts A-C, or "VAC"), such as:

| | |
|---|---|
| 100 VAC | Japan, and intermittently during brown-outs in the U.S. |
| 120 VAC | U.S. |
| 200 VAC | Japan |
| 208 VAC | U.S. |
| 220 VAC | Most of Europe except Scandinavia and U.K. |
| 240 VAC | U.S., U.K., Norway, Sweden and Denmark |
| "Z" VAC | Corresponding to unusual voltages found in France and other world locations |

These voltages are obviously problematic for industry suppliers of ultrasound generators, who must supply the world markets. The invention of FIGS. 49-51 eliminates the chance that a particular world consumer receives an incorrect generator by providing universal voltage generators that operate, for example, between 86 VAC and 264 VAC.

In FIG. 49, an ultrasound generator 500 is shown connected to a 300 VDC source 501. A power factor correction (PFC) circuit 502 connects to the front end of the generator 500 to produce a regulated 300 VDC. A switching regulator 504 regulates the 300 VDC to +12V and +15V. The generator 500 can be represented, for example, as the circuit of FIG. 41, except that the "high voltage supply" is replaced by the PFC circuit 502 and the +12V and +15V are replaced with control voltages from the regulator 504.

FIG. 50 illustrates a generator 510 connected to a universal input switching regulator 512. The regulator 512 generates a set 513 of DC voltages for the generator 510. The generator 510 includes circuitry 514 that operates with the set 513. The generator 510 can be represented, for example, as the circuit of FIG. 41, except that the "high voltage supply" and the +12V and +15V are replaced with output voltages from the regulator 512.

Those skilled in the art should appreciate that methods and systems exist for utilizing the power line to acquire amplitude control for ultrasound generators. By way of example, the inventor of this application describes such systems and methods in connection with FIGS. 3, 4, 5A, 5B and 7 of International Application No. PCT/US97/12853. Specifically, an amplitude control subsystem is achieved by rectifying the AC power line and selecting a portion of the rectified line voltage that ends at the desired amplitude (such as between zero and 90 degrees or between 180 degrees and 270 degrees of the signal). In this manner, amplitude modulation is selectable in a controlled manner as applied to the signal driving the transducers from the generator. For example, by selecting the maximum amplitude of 90 degrees in the first quarter sinusoid, and 270 degrees in the third quarter sinusoid, a maximum amplitude signal is provided. Similarly, a one-half amplitude signal is generated by choosing the 30 degrees and 210 degrees locations of the same sinusoids. By way of a further example, a one-third amplitude signal is generated by choosing 19.5 degrees and 199.5 degrees, respectively, of the same sinusoids.

FIG. 51 illustrates a generator 530 which operates at a DC voltage less than or equal to $(86)(\sqrt{2})$ volts. As in amplitude control, a triac 532 is used to select that portion of the power line voltage with an amplitude equal to the generator DC voltage requirements. The signal 534 is rectified and filtered by the bridge rectifier and filter 536 to obtain the constant DC voltage 538 in the range less than or equal to (86)*(Square Root 2) volts. The generator 530 can be represented, for example, as the circuit of FIG. 41, except that the "high voltage supply" is replaced by the voltage from the bridge rectifier and filter 536 and the +12V and +15V are replaced with output voltages from the regulator 540, as above.

In another embodiment, the selected AC voltage angle can be reduced to lower the DC voltage to reduce the amplitude of the ultrasound drive signal.

The "power up sweep" features of the invention also apply to amplitude modulation, where an AM pattern of the AM frequency varies according to the power up-sweep techniques discussed above, and preferably at the same time with the techniques of "sweep the sweep rate", as discussed herein. With power up-sweep AM, the AM pattern modulation creates an additional upward force on contamination while eliminating low frequency resonances.

Figure 52:
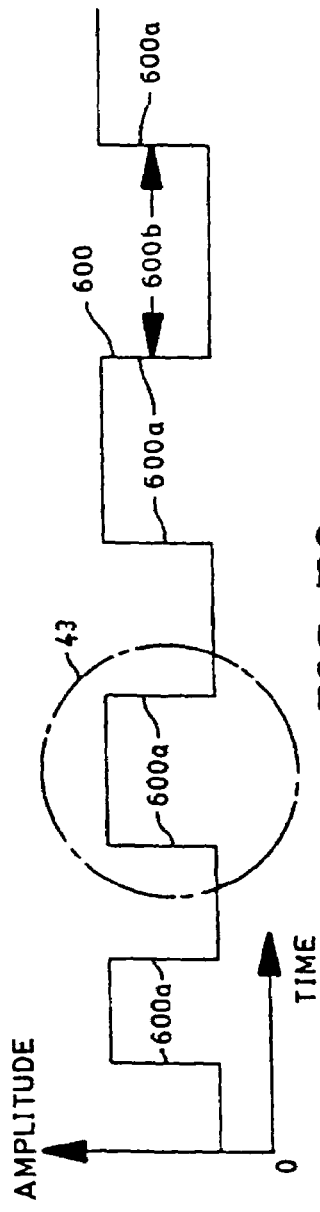
FIG. 52 graphically illustrates an AM burst pattern in accord with the invention.
Figure 53:
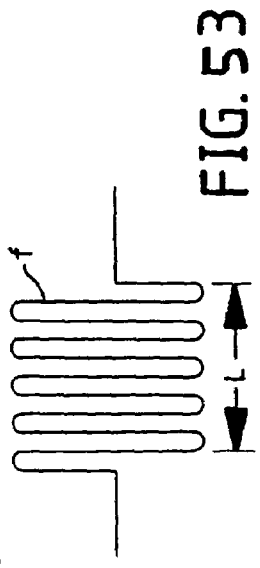
FIG. 53 illustrates one burst of primary frequency ultrasound within one of the non-zero AM periods.

FIG. 52 illustrates an AM (amplitude modulation) pattern 600 of the invention, where the frequency of the AM is constantly decreasing with increasing time t. More particularly, ultrasound bursts of energy (as shown in FIG. 53, with a frequency f) are contained within each of the non-zero portions 600*a* of the pattern 600. As time increases, longer and longer bursts of energy are applied to the associated transducers. In the optimum case, the ultrasound frequency within each burst of FIG. 53 varies with a power up sweep, from $f_{upper}$ to $f_{lower}$, as discussed above.

Figure 54:
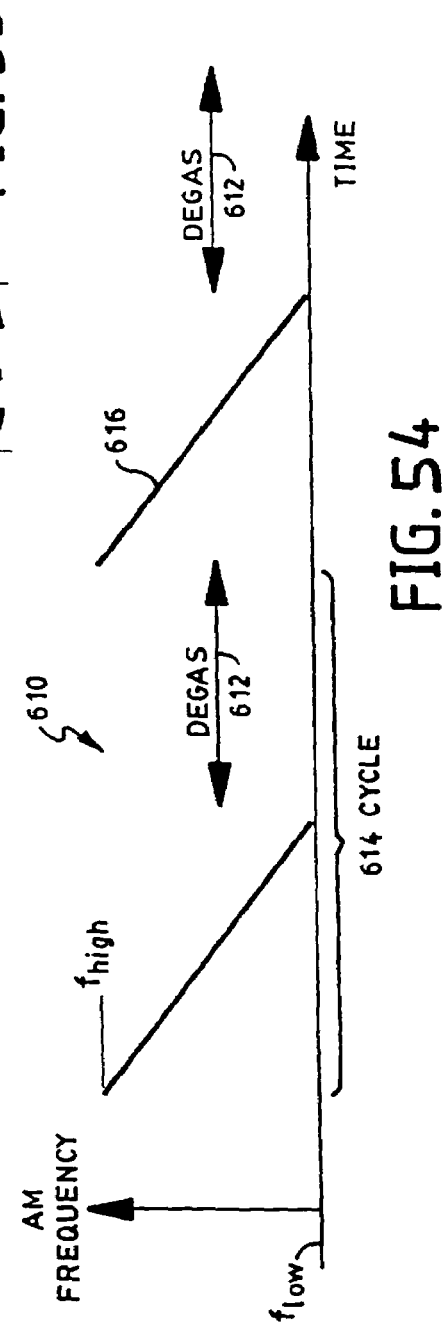
FIG. 54 illustrates an AM sweep pattern, in accord with the invention.

FIG. 54 shows a plot 610 of AM frequency verses time t. As shown, the AM frequency monotonically changes from a high frequency, $f_{high}$, to a low frequency, $f_{low}$. When $f_{low}$ is reached, a degas or quiet period 612 is typically introduced before the cycle 614 repeats.

Note that the sweep rate of the change of the AM frequency along the slope 616 can and preferably does change at a non constant sweep rate. The rate of AM frequency change can thus be non-constant. The degas period 612 can also be non constant. The degas period 612 can also be substantially "0", so that no time is permitted for degas.

Generally, there are three ways to change the AM frequency. The burst length "L" (FIG. 53) can be changed, the time between bursts can be changed (e.g., the periods 600*b*, FIG. 52, where the amplitude is zero); or both parameters can be changed simultaneously.

Figure 55:
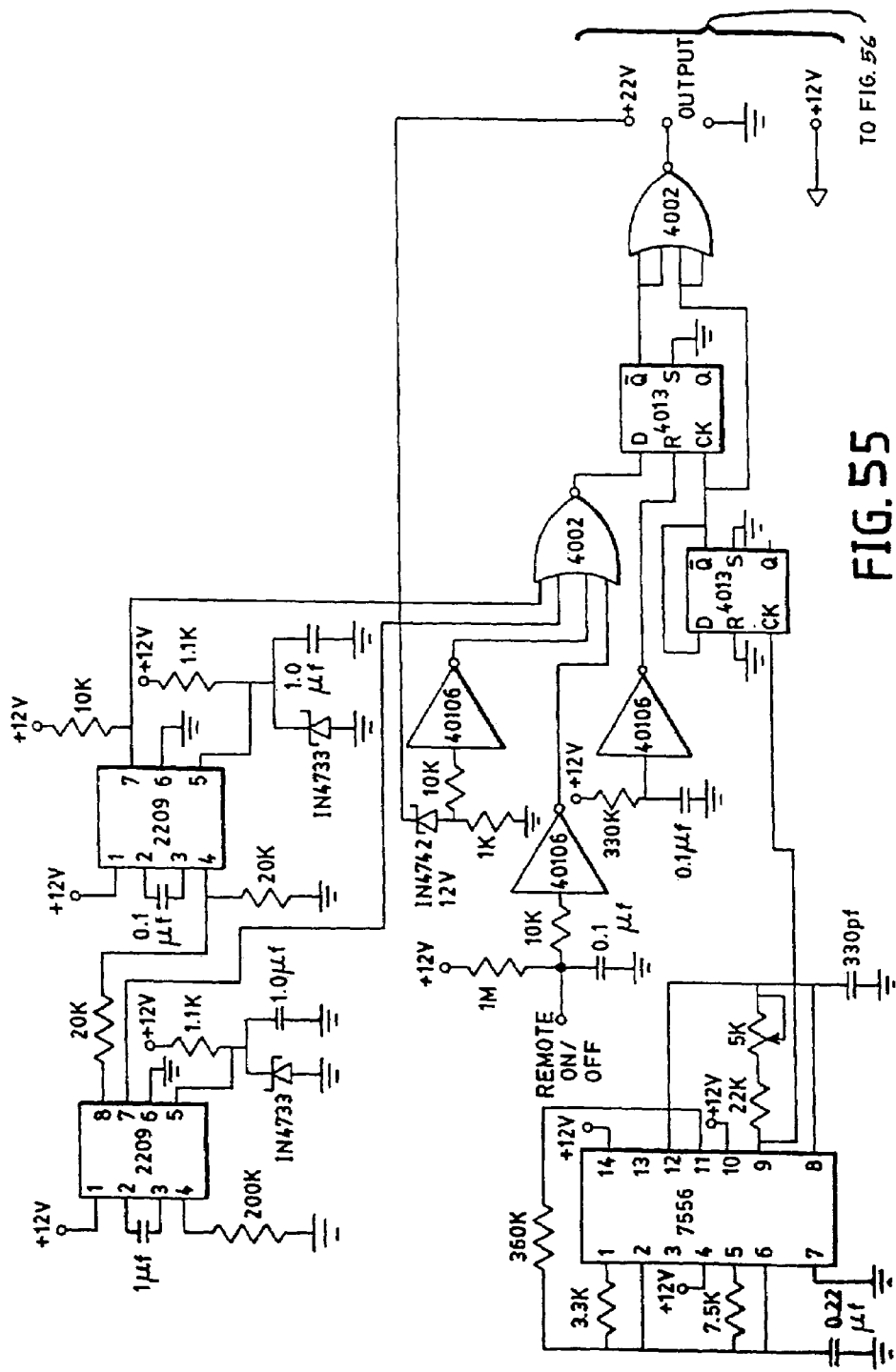
FIGS. 55, 56 and 57 schematically show one AM power up-sweep generator circuit constructed according to the invention.
Figure 56:
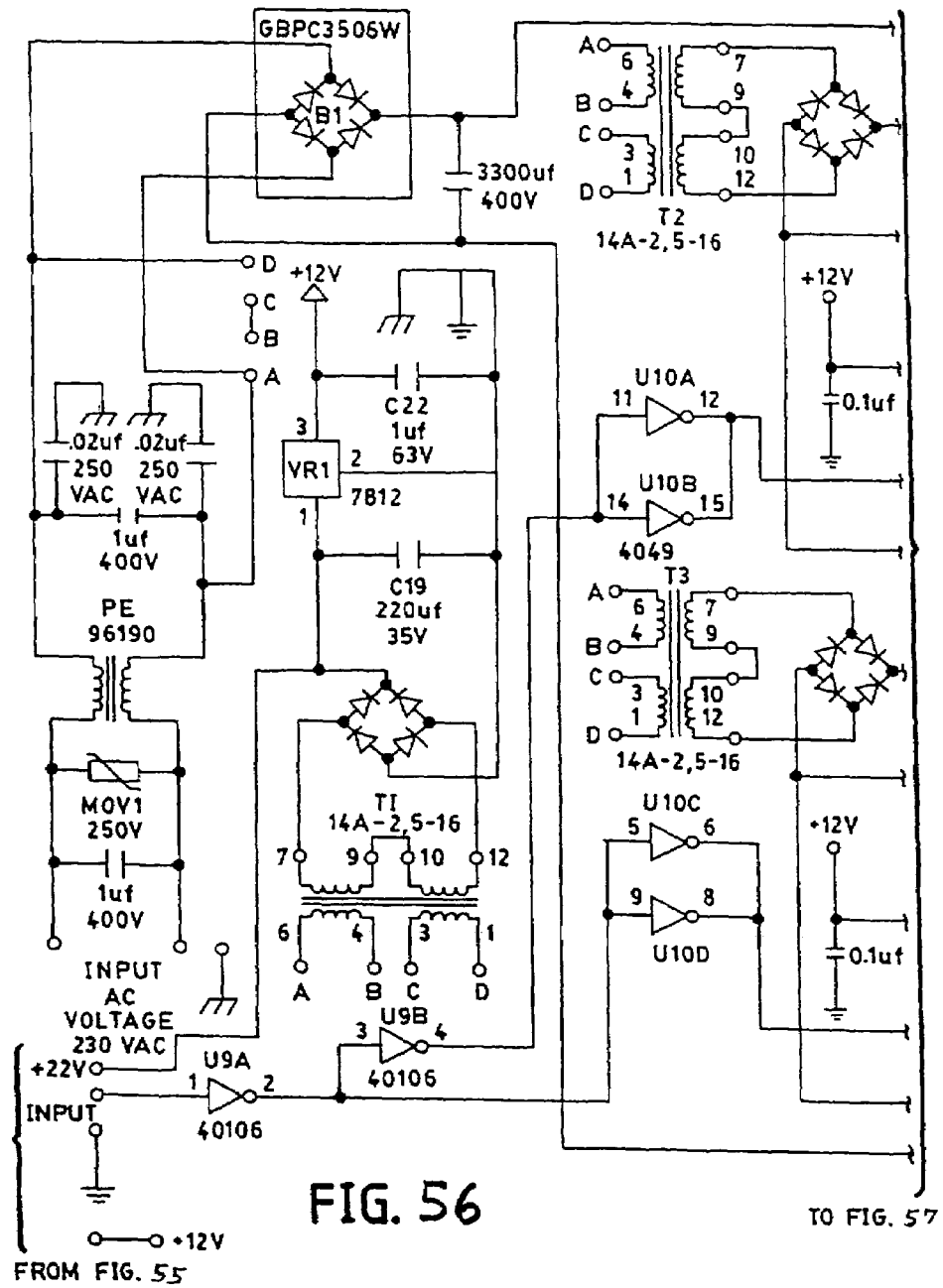
Figure 57:
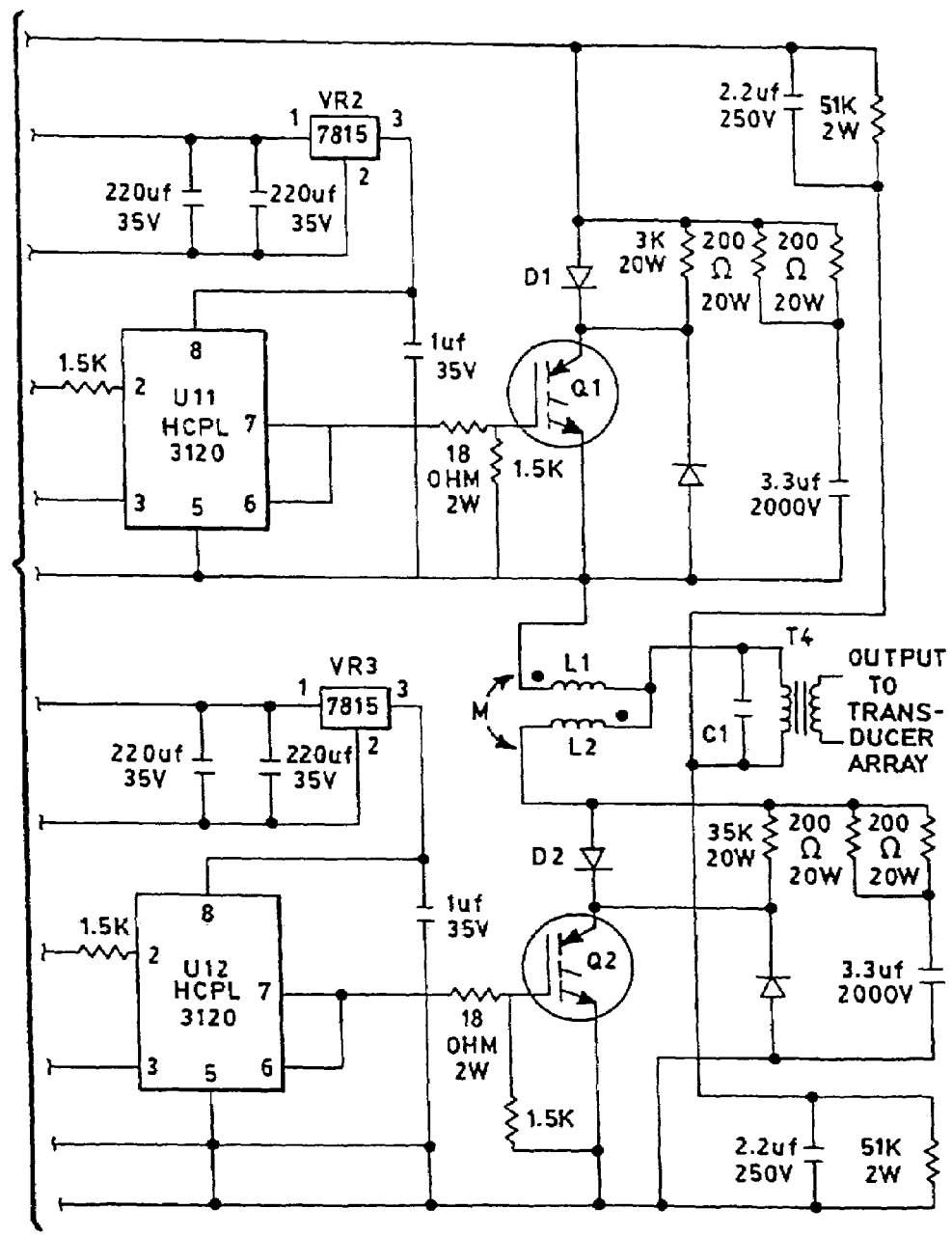

FIGS. 55, 56 and 57 schematically illustrate electronics for one ultrasound generator with AM power up-sweep capability, in accord with the invention.

A common feature in prior art tanks (ultrasound and non-ultrasonic) is a quick dump rinse feature (QDR) where a large valve in the bottom of the tank opens to allow the solution in the tank to quickly drain out of the tank. This QDR feature reduces the contamination residing on the parts under process as compared to the contamination that would reside if the liquid were removed more slowly from the tank, or if the parts were pulled out of the tank.

Figure 58:
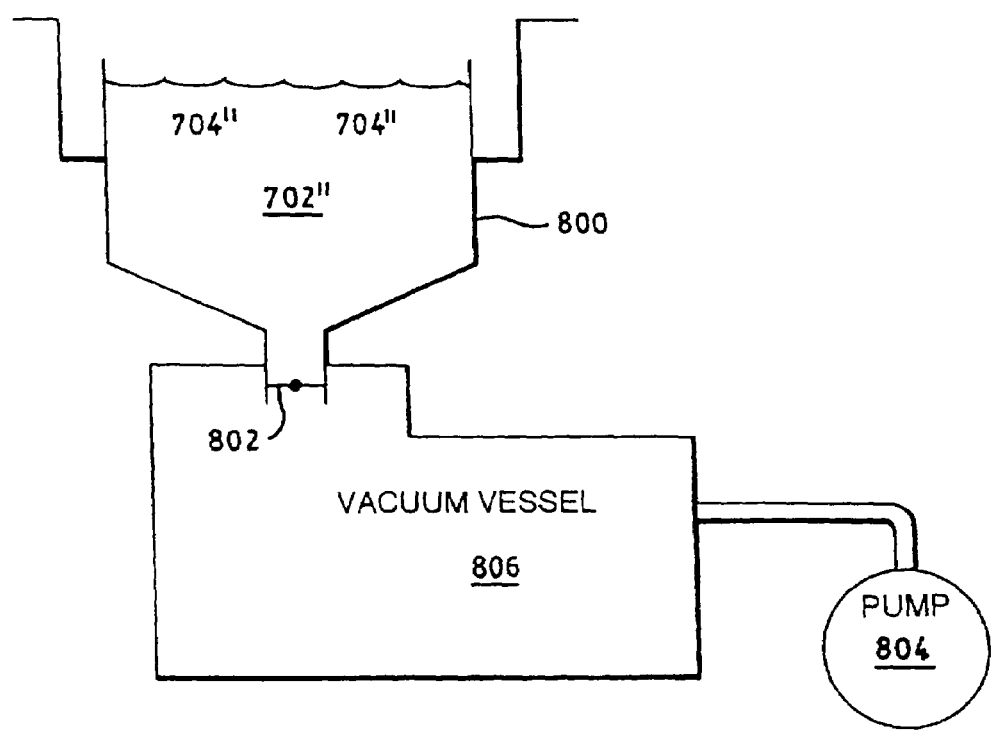
FIG. 58 shows a quick dump rinse (QDR) tank constructed according to the invention.

FIG. 58 illustrates a QDR tank 800 modified in accord with the invention to speed up the rate of liquid removal from the tank. The large valve output 802 is connected to a vacuum reservoir 804 that is evacuated to a pressure below atmospheric pressure during the cleaning cycle. When the valve 802 is opened to dump the liquid 702", the difference between atmospheric pressure and the pressure in the vacuum vessel 806 forces the liquid 702" out of the tank 800, thus shortening the drain time and further reducing the residual contamination.

Figure 59:
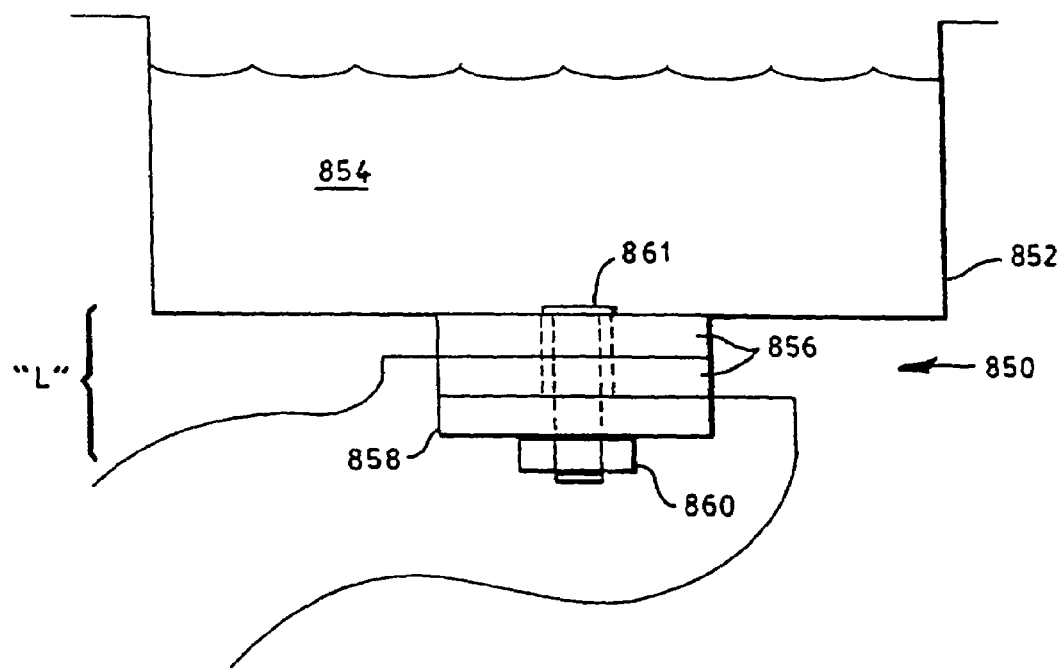
FIG. 59 shows an improved high frequency transducer constructed according to the invention.

The conventional stacked transducer consists of a front mass, active polarized piezoelectric ceramic elements and a back mass. The length "L" of the transducer (from front mass to back mass) basically determines the transducer's primary and harmonic frequencies. As the fundamental frequency of the transducer becomes higher, the thickness of each of the transducer elements is reduced until they become impractical. FIG. 59 shows a transducer 850 constructed according to the invention which reduces this impracticality.

In FIG. 59, the transducer 850 is shown connected to an ultrasound processing tank 852, which holds process chemistry 854. The transducer includes two polarized piezoelectric ceramic elements 856 that are compressed between the back mass 858 and the tank 852. Specifically, a bias bolt 860 connects through the transducer 850 and connects directly into a weld 861 at the tank 852. Accordingly, there is no front mass; and thus the transducer length "L" can be divided between the polarized piezoelectric ceramic elements 856 and the back mass 858. This division makes it possible to make a stacked transducer 850 with a higher fundamental frequency (and higher harmonics too).

Another configuration of the transducer in FIG. 59 uses one polarized piezoelectric ceramic element 856 in the center of the stack and an insulating ceramic front mass or quartz front mass between the polarized piezoelectric ceramic element and the tank 852. Another configuration of FIG. 59 also replaces back mass 850 with a ceramic back mass. These transducers of the FIG. 59 type are referred to herein as the "welded stud type construction" transducers.

Most transducers discussed herein are longitudinal vibrators with elements sandwiched by a center bolt that holds the transducer assembly together and that provides a compressive bias to the active piezoelectric components (i.e., sandwiched between the a front mass and back mass or back mass). Since piezoelectric ceramic is strong under compression, but weak in tension, the constant compressive force provided by the spring constant of the bolt greatly improves the reliability of this transducer over other configurations.

The longitudinal vibrating transducer is normally connected to the tank or other surface that is to receive the sound energy by epoxy or brazing, or by a mechanical stud, or by a combination of these schemes.

Figure 60:
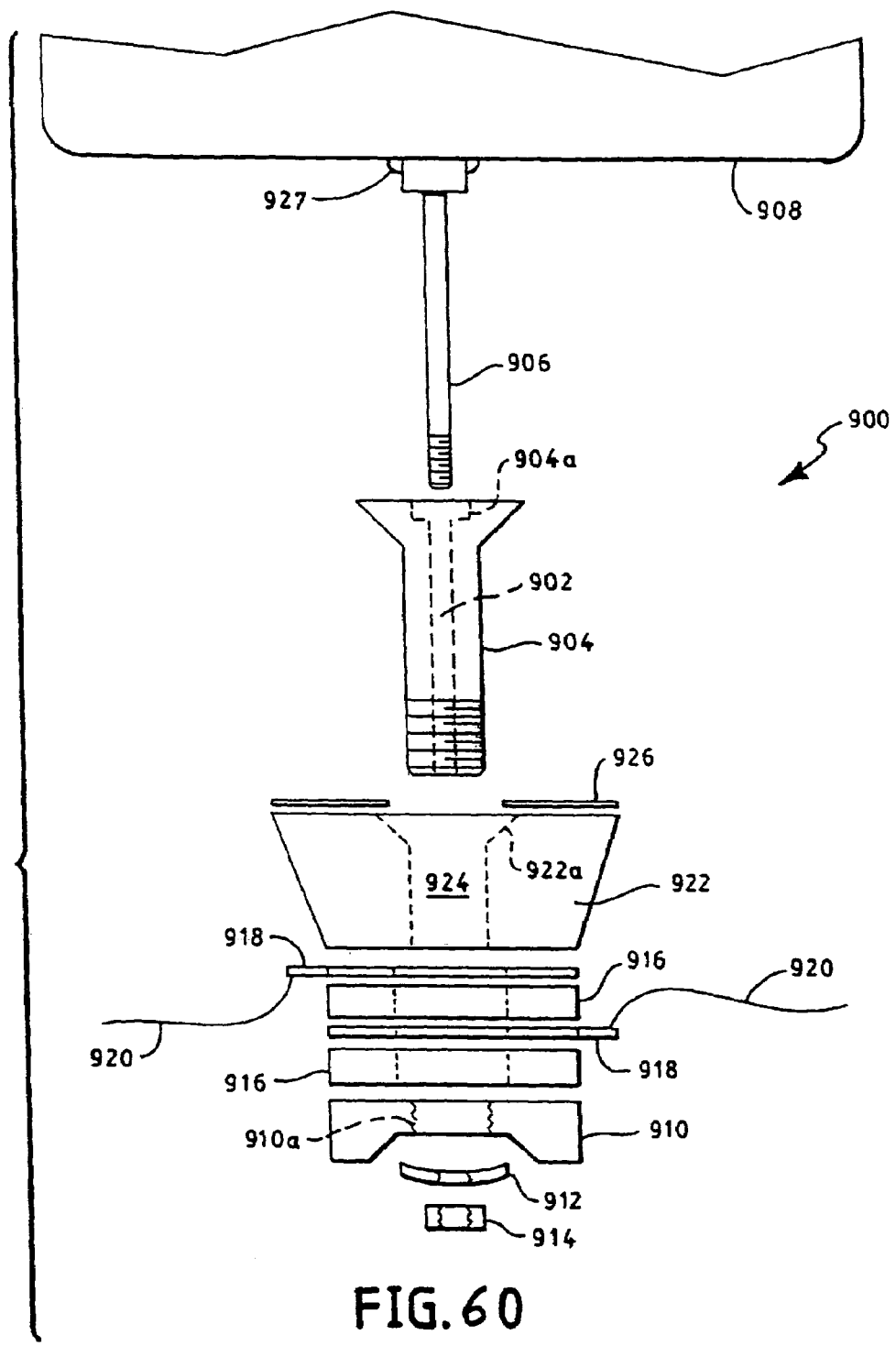
FIG. 60 illustrates, in a side exploded view, a double compression transducer constructed according to the invention.

The invention of FIG. 60 illustrates a transducer 900 constructed according to the invention and shown in an exploded view. The transducer 900 has "double compression", as discussed below, to increase its reliability over the prior art. Specifically, the bias bolt 904 has a through-hole 902 in its center. The center hole 902 receives a second bolt 906 that is welded to the surface of the tank 908 (illustrated by weld joint 910). When integrated, the second bolt 906 protrudes out past the tail mass 927 (i.e., the back mass) of the transducer 900 by way of a Belleville disc spring washer 912 and nut 914, which screws onto bolt 906.

As in other transducers herein, the transducer 900 includes piezoelectric ceramics 916, associated electrodes 918, and lead-outs 920 for the electrodes 918.

The bias bolt 904 thus provides the first compressive force similar to other transducers herein. That is, the bolt 904 slides through the front mass 922 via the through-hole 924, and continues on through the ceramics 916. The back mass 910 has threads 910*a* which mate with the bolt 904; and thus the bolt 904 screws into the back mass 910. By tightening the bolt 904 into the back mass 910, the bolt 904 firmly seats into the counter-sink 922*a* of the front mass 922 and compression is applied to the ceramics 916.

As an alternative, the threads in the back mass 910 can be thru-holed; and a nut against the back mass can replace the threads to support compression bias on the piezoceramic 916.

The second compressive force derives from the operation of the second bolt 906, which compresses the epoxy 926 after seating within the counter-sink 904*a* of the first bolt 904 and after tightening the nut 914 onto the bolt 906. The front mass 922 is then bonded to the tank 908 via an epoxy layer 926. The second compressive force keeps a compressive bias on the epoxy 926 bond between the front mass 922 and the tank surface 908.

As an alternative, it is possible to eliminate the Belleville disc spring washer 912 and rely entirely on the spring tension in the second bolt 906; but the added feature of the Belleville disc spring washer 912 provides a larger displacement before tension goes to zero.

The second compressive bias of transducer 900 provides at least three improvements over the prior art. First, during the epoxy curing process, the bias keeps force on the epoxy bond 926 (even if the epoxy layer thickness changes during a liquid state) resulting in a superior bond. Second, during operation of the transducer 900, the reliability of the bond 926 is enhanced because of the constant mechanical compressive force. That is, epoxy bonds are weakest in shear forces, and reasonably strong in tension but superior in compression. Third, during abnormal conditions (e.g., a mechanical jar to the bonding surface) that might dislodge a conventionally bonded transducer, the second compression force with its spring characteristics absorbs the mechanical shock and protects the epoxy bond.

Those skilled in the art should appreciate that the double compression transducer 900 provides increased reliability when mounted with most any surface, and not simply an ultrasound tank 908.

Figure 61:
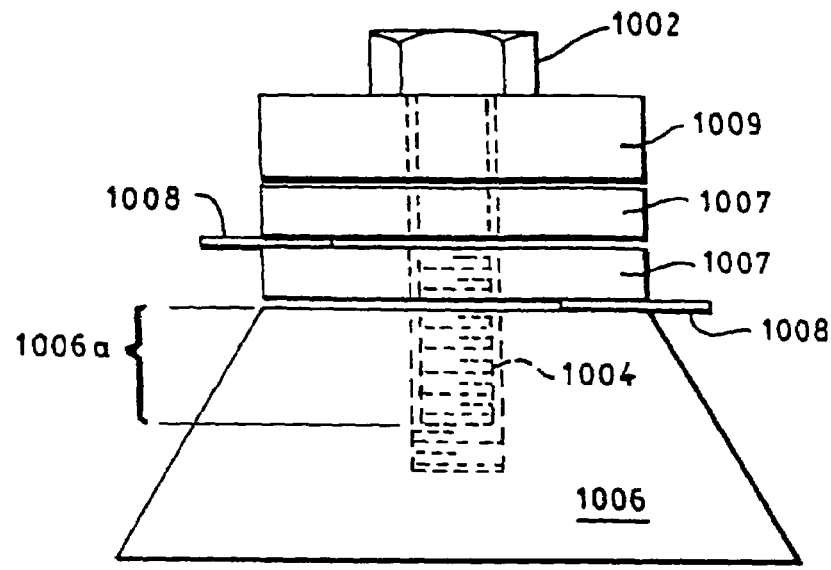
FIG. 61 shows a prior art transducer with a bias bolt threaded into the upper part of the front mass.

FIG. 61 shows a cross-sectional view of a conventional stacked transducer 1000 with a bias bolt 1002 that screws into threads 1004 in the aluminum front mass 1006. The threads 1004 are only within the top portion 1006a of the front mass 1006. The transducer includes the normal piezoceramics 1007, electrodes 1008, and rear mass 1009.

Figure 62:
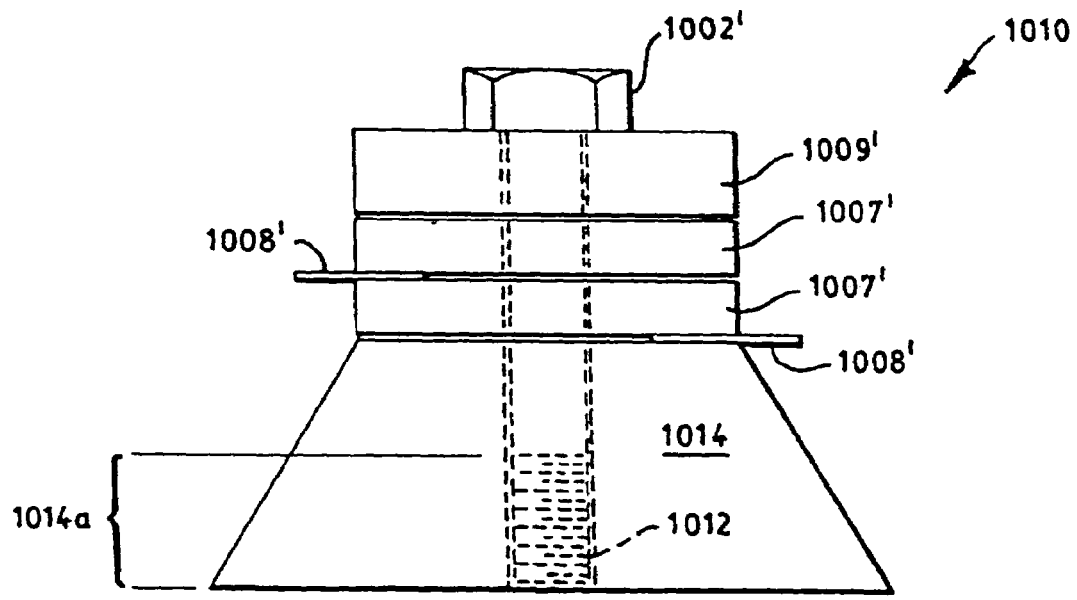
FIG. 62 shows an improved transducer, constructed according to the invention; with a bias bolt threaded into a lower part of the front mass.

FIG. 62 shows an alternative transducer 1010 constructed according to the invention. In transducer 1010, the threads 1012 within the front mass 1014 are at bottom portion 1014a so that bias pressure is not concentrated on the top threads (as in FIG. 61) where the surface of the aluminum can be deformed in operation, decreasing bias pressure. The elements 1002', 1007', 1008' and 1009' have similar function as in FIG. 61; except that they are sized and shaped appropriately to accommodate the thread repositioning at the bottom 1014a of the driver 1014.

Figure 63:
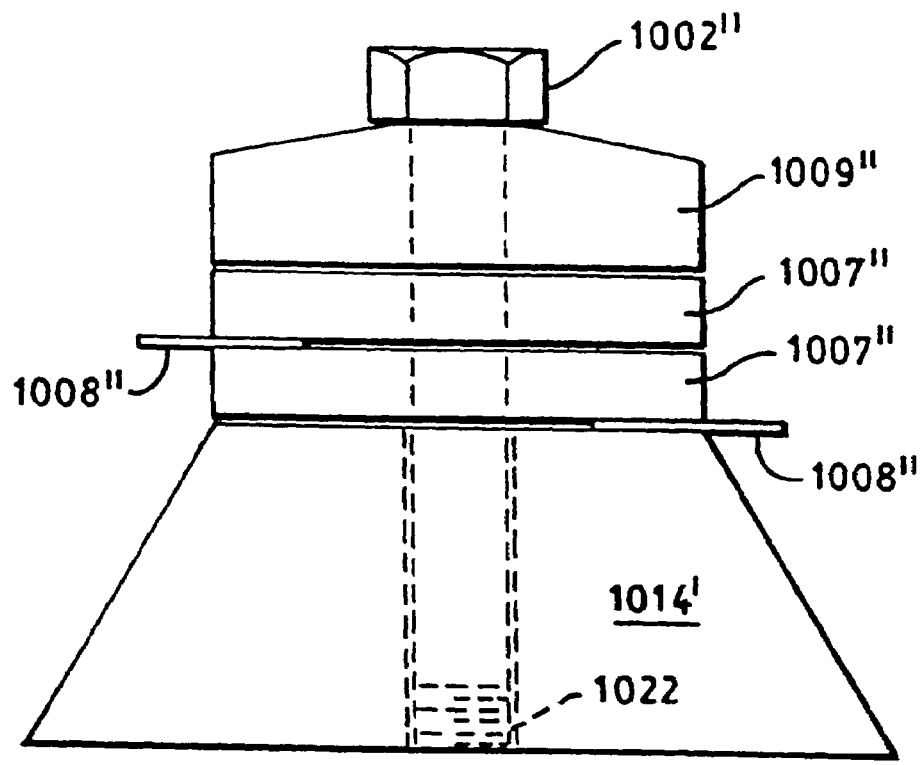
FIG. 63 illustrates one transducer of the invention utilizing a steel threaded insert to reduce stress on the front mass.

FIG. 63 illustrates a transducer 1020 that is similar to the transducer 1010, FIG. 62, except that a helical insert 1022 is used instead of the threads 1012. The helical insert 1022 is preferably made from steel and will not plastically deform under normal transducer stresses. The helical insert 1022 thus prevents distortion of the aluminum driver 1014' under the normal stresses of the transducer 1020. Note that the helical insert can similarly replace the threads 1004 of the prior art transducer 1000 to provide similar advantages in preventing distortion.

FIG. 64 illustrates a side view of one embodiment of the invention including a printed circuit board (PCB) 1030 connected with ultrasound transducers 1032 such as described herein (including, for example, piezoelectric ceramics 1034). The PCB 1030 contains circuitry and wiring so as to function as an ultrasound generator and for the electrodes of the transducers 1032. As such, the PCB 1030 can drive the transducers 1032 to produce ultrasound 1036 when powered. By way of example, the PCB 1030 can include the circuitry of FIG. 41A, 41B and 41C.

The PCB 1030 and transducers 1032 are also substantially "integral" in construction so as to be a single unit. This provides structural integrity, and reduces the cost and size of the system.

FIG. 65 shows a top view of the PCB 1030 of FIG. 64. For purposes of illustration, the top surface 1030a of the PCB 1030 is shown with electrodes 1038 for the positive side of the piezoelectric ceramic 1034. The electrodes 1038 are preferably connected by wiring 1048 (e.g., circuit board land patterns) to provide for common voltage input to the transducers 1032. There is a similar electrode pattern on the bottom side (not shown) of the PCB 1030 that makes contact with the transducer's front mass 1032b, which is in electrical contact with the bias bolt 1032a (FIG. 64). The bolt 1032a connects through the transducer 1032 and into the back mass 1032c, providing electrical feedthrough to the negative electrode of the piezoelectric ceramic 1034. The PCB 1030 thus provides two electrodes for each transducer 1032 and all the interconnect wiring for the transducers 1032 such as by etching the PCB pattern. The ultrasound generator is also provided with the PCB 1030 circuitry (illustrated by circuit board components 1040) with its output connected into the transducer electrodes as part of the PCB artwork.

Figure 66:
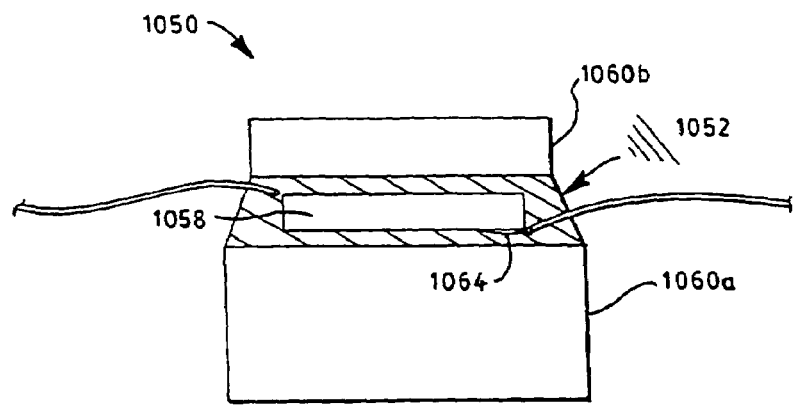
FIG. 66 shows an acid-resistant transducer constructed according to the invention.

FIG. 66 illustrates an acid resistant transducer 1050 with internal piezoelectric compression. By way of background, the above description has described certain transducers that utilize metal masses to lower the resonant frequency of the piezoelectric ceramics and a bolt to keep a compressive bias on the polarized piezoelectric ceramic elements. In harsh environments, e.g., sulfuric acid process tanks, the metallic elements of the transducer are prone to acid attack and therefore are a reliability risk. The transducer 1050 of FIG. 66 resolves this problem by eliminating the metal masses and the bolt. The compressive force on the piezoelectric ceramic 1058 is obtained by an epoxy 1052 that contracts upon curing. The metal "back mass" and the metal "front mass" such as described above are replaced by a non-metallic material 1060. In FIG. 66, the front mass 1060a and back mass 1060b are thus both made from a non-metallic material such as quartz.

The internal piezoceramics 1058 connect to wiring to drive the elements 1058 in the normal way. To protect the wiring and ceramics, it can be made from Teflon which is soldered to the ceramic 1058 by known methods, such as illustrated by solder joint 1064. This transducer will be referred to herein as the "acid transducer type construction".

Figure 41A:
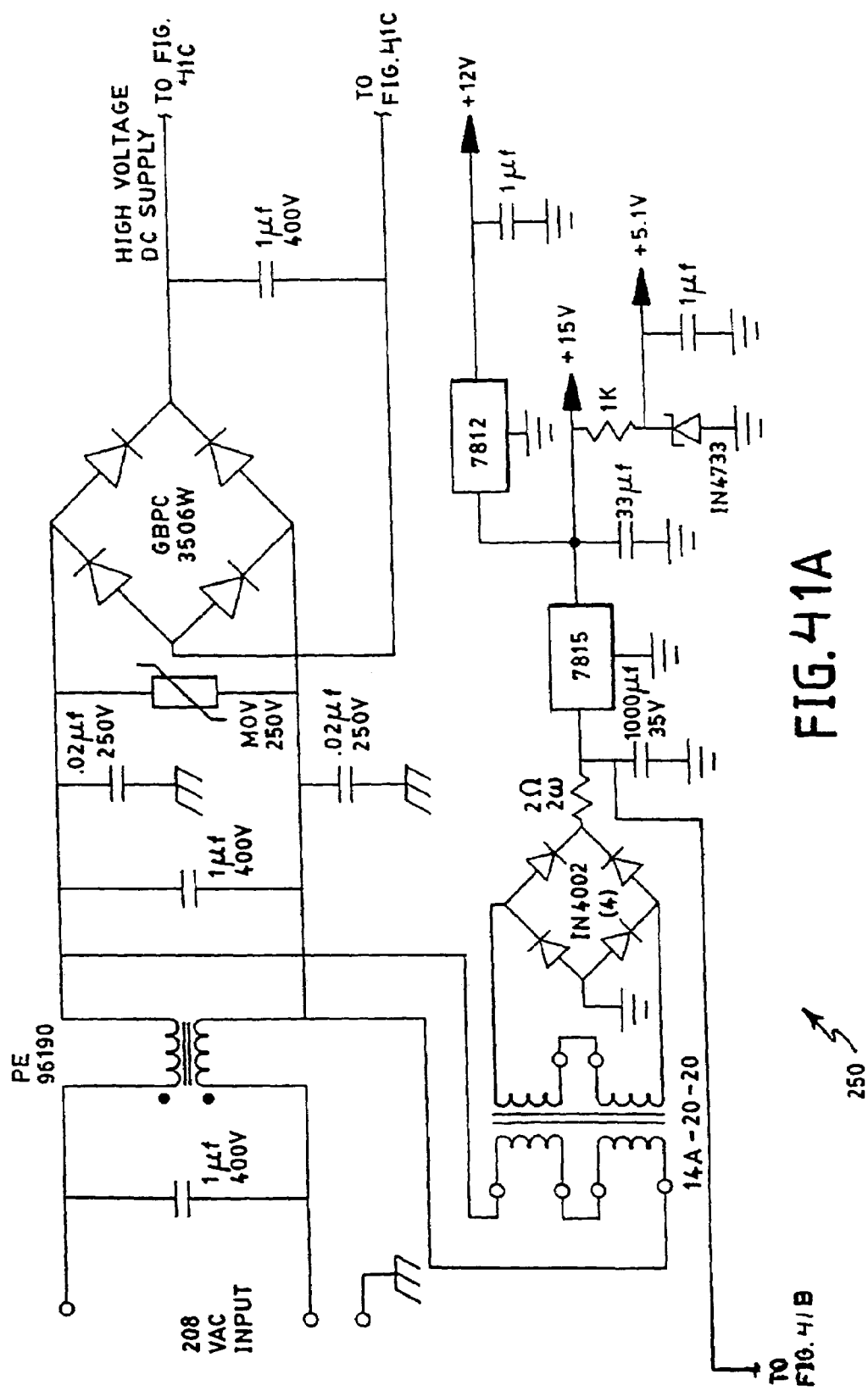
FIG. 41A, 41B and 41C schematically illustrate ultrasound generator circuitry for providing dual sweeping power-up sweep and variable degas periods, in accord with the invention.
Figure 41B:
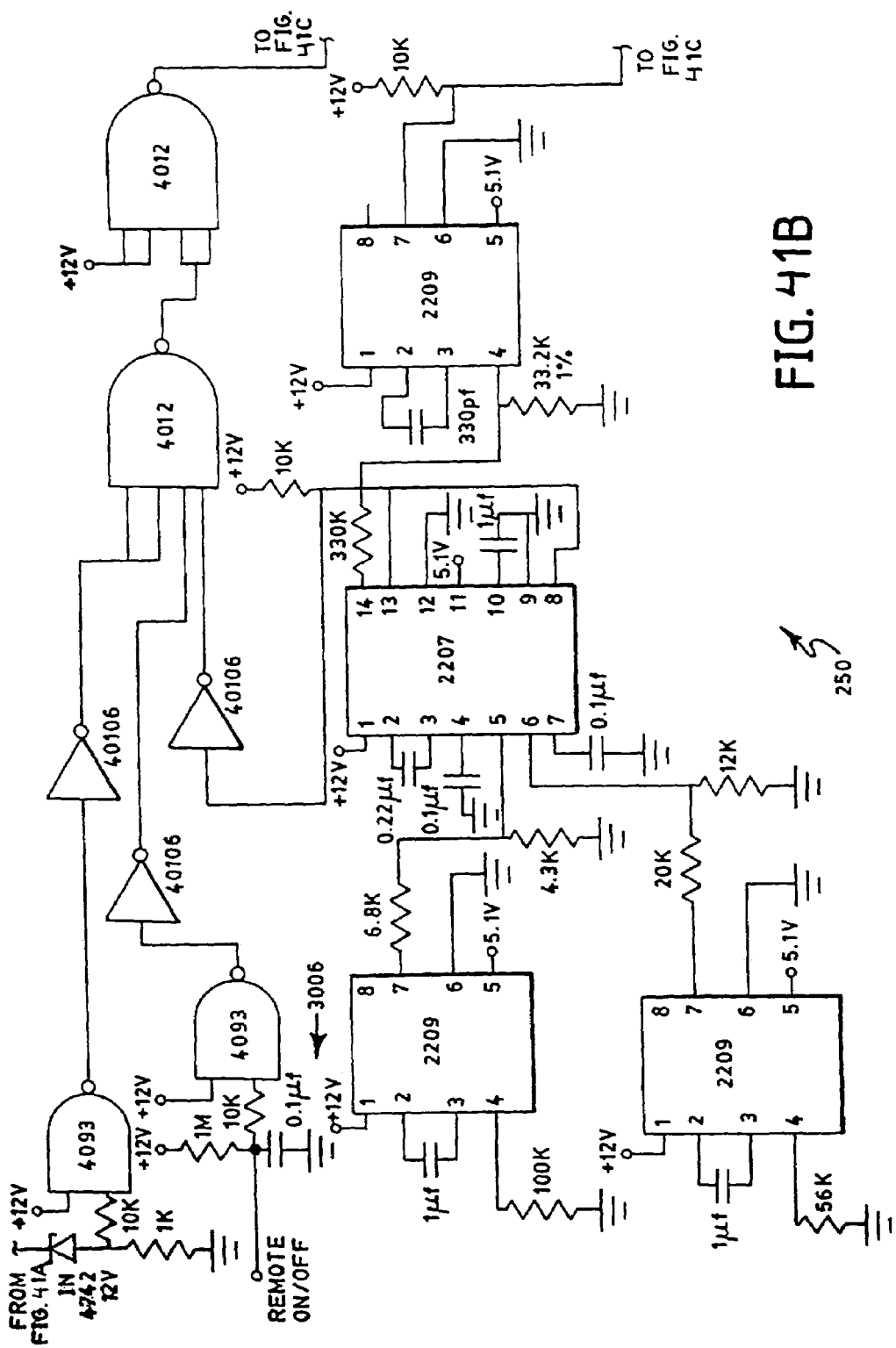
Figure 41C:
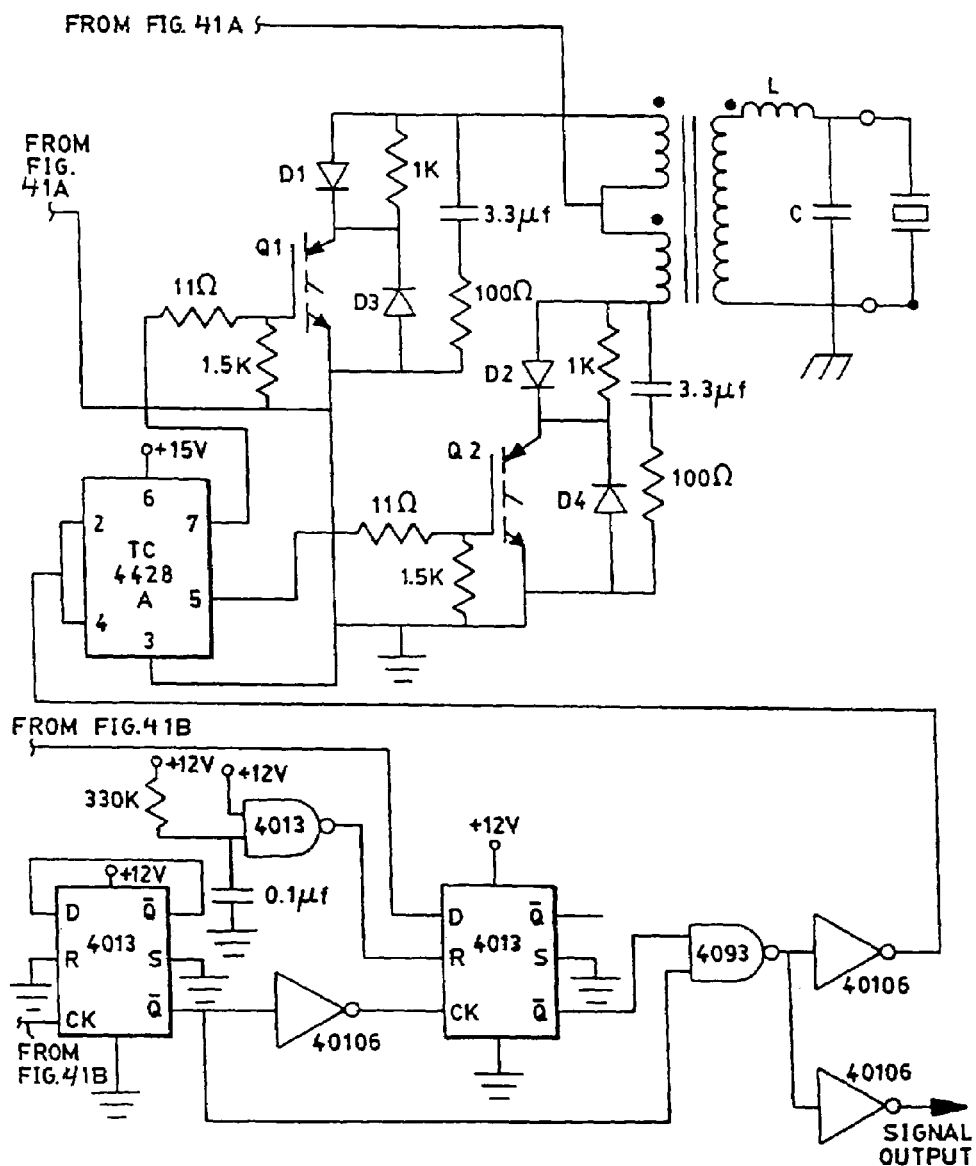
Figure 67:
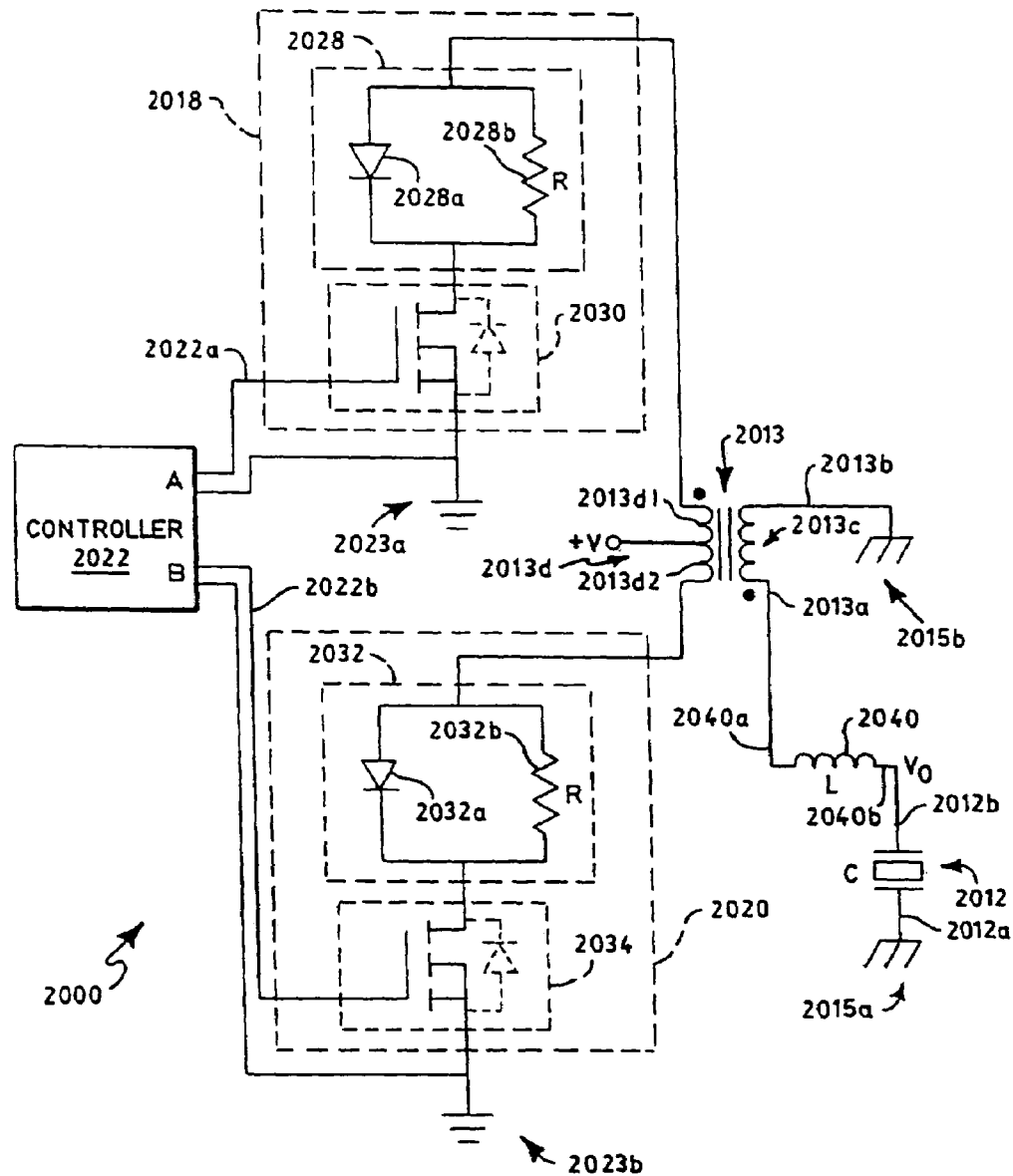
FIG. 67 schematically shows one power up-sweep generator circuit of the invention.

FIG. 67 illustrates a generator circuit 2000 used to implement power up-sweep such as described herein (e.g., such as described in connection with FIG. 41A, 41B and 41C, except that FIG. 41A, 41B and 41C uses IGBTs as the switching devices and FIG. 67 uses MOSFETs). In FIG. 67, circuit 2000 includes a capacitive element 2012 with terminal 2012a connected to earth ground 2015a. The other terminal 2012b connects to terminal 2040b of inductor 2040. Terminal 2040a of inductor 2040 connects to terminal 2013a of the secondary 2013c of transformer 2013. Terminal 2013b of secondary 2013c connects to earth ground 2015b. The circuit 2000 includes two drive networks 2018 and 2020, and a controller 2022.

Drive network 2018 includes a blocking network 2028 and a multi-state power switch network 2030, which is coupled to the controller 2022 by way of line 2022a. The drive network 2020 includes a blocking network 2032 and a multi-state power switch network 2034, which is coupled to the controller 2022 by way of line 2022b.

In drive network 2018, the blocking network 2028 and switch network 2030 provide a unidirectional current flow path characterized by a first impedance from the potential +V through the first primary winding 2013d1 of center-tapped primary winding 2013d of transformer 2013 when the switch network 2030 is in a first (conductive) state. The networks 2028 and 2030 provide an oppositely directed current flow path characterized by a second impedance from circuit ground 2023a through 2013d1 to the potential +V when the switch network 2030 is in a second (non-conductive) state. The first impedance of the flow path established when network 2030 is in its first state is lower than the second impedance of the flow path established when the network 2030 is in its second state.

In drive network 2020, the blocking network 2032 and switch network 2034 provide a unidirectional current flow path characterized by a third impedance from the potential +V through the second primary winding 2013d2 of center-tapped primary winding 2013d of transformer 2013 when the switch network 2032 is in a first (conductive) state. The networks 2032 and 2034 provide an oppositely directed current flow path characterized by a fourth impedance from circuit ground 2023b through 2013d2 to the potential +V when the switch network 2034 is in a second (non-conductive) state. The third impedance of the flow path established when network 2034 is in its first state is lower than the fourth impedance of the flow path established when the network 2030 is in its second state.

The impedance (Z) of drive network 2018 when switch network 2030 is in its second state may be primarily determined by resistor 2028b (of value "R"), in which case Z has a value substantially equal to R for current flow in a direction toward +V, and a "near-infinity" value (i.e. relatively high) for current flow away from +V. In other embodiments, Z may be non-linear, normally lower at the beginning of operation in the second state and higher at times after the second state begins. For example, a metal oxide varistor (MOV) in parallel with a resistor (R) may be the primary determining factor for Z. In this case, at the beginning of operation in the second state when the voltage across Z is high, the low impedance of the on MOV primarily determines Z and later in the second state, as the voltage drops below the MOVs breakdown potential, Z is primarily determined by R.

A similar situation occurs for the impedance of drive network 2020 when switch network 2034 is in its second state.

Where the circuit 2000 is adapted to drive an ultrasound transducer, the capacitive element 2012 may be an electrostrictive device suitable for use as an ultrasound transducer. With such a configuration, for example, the controller 2022 may effectively control the circuit 2000 to drive such ultrasound transducers at a selectively controlled frequency. In various forms of the invention, the controller 2022 may be adaptively controlled so as to track variations in the resonant frequency for the respective ultrasound transducers, or to frequency modulate the frequency with a function such as a power up-sweep function, described above.

In operation, the controller 2022 cyclically switches the switch network 2030 between its first and second states at a frequency f (f=1/T), where f is less than or equal to $f_r$ ($f_r$=1/$T_r$), where $f_r$ is the resonant frequency of the series LC network formed by 2012 and 2040, approximately equal to 1/(2*PI*Square Root(LC)), where PI is approximately 3.14159. During each cycle, network 2030 is controlled to be in its first state for a period greater than or equal to $T_r$/2, but less than or equal to T/2, at the beginning of each cycle. Network 2030 is controlled to be in its second state for the remainder of each cycle.

Similarly, the controller 2022 also cyclically switches the switch network 2032 between its first and second states at the frequency f (f=1/T). During each cycle, network 2032 is controlled to be in its first state for a period greater than or equal to $T_r$/2, but less than or equal to T/2, at the beginning of each cycle. Network 2032 is controlled to be in its second state for the remainder of each cycle. In the presently described embodiment, the start time for each cycle of the switching of network 2030 is offset by T/2 from the start time for each cycle of the switching of network 2034. In other forms, the start time for the cycle of the switching network 2030 may be offset by at least $T_r$/2 and less than $T_r$/2+D, where D equals T-$T_r$.

An AC voltage waveform ($V_o$) at frequency f is impressed across the capacitive element 2012. Generally, this voltage waveform $V_0$ passes from low to high and from high to low with a sinusoidal waveshape (at frequency $f_r$). After rising from its low peak level to its high peak level, the voltage waveform stays substantially at its high peak level (except for droop due to resistive losses) for a period ½(T-$T_r$), or D/2, before passing from that high peak level to its low peak level. Similarly, upon returning to the low peak level, the voltage waveform $V_0$ remains at that level (except for droop due to resistive losses) for a period ½(T-$T_r$), or D/2, before again passing to the high peak level.

Thus, the voltage impressed across capacitive element 2012 rises and falls at the resonant frequency $f_r$, with the capacitive element 2012 being maintained in its fully charged state for a "dead" time which is adjustably dependent upon the switching frequency f of the controller 2022. Accordingly, the drive frequency to the element 2012 may be adjustably controlled.

Where the element 2012 is an ultrasound transducer, circuit 2000 is used to drive that transducer at a frequency adjusted to match the optimal drive frequency. In various embodiments, variations in that optimal drive frequency may be detected and the controller may be adjusted in closed loop fashion to adaptively track such variations.

Blocking network 2028 includes a diode 2028a in parallel with a resistor 2028b, and the blocking network 2032 includes a diode 2032a and a resistor 2032b. The single inductor (L) 2040 operates in resonance with the element 2012.

Circuit 2000 is particularly useful with "fast" switching devices (such as bipolar, MOS and IGBT transistors) which do not require an extended turn-off time. In operation, the capacitive element 2012 and transformer 2013 function like the circuit of FIG. 41, except that circuit 2000 utilizes FETs instead of IGBTs (insulated gate bipolar transistors) for the terminal power switching devices. The power devices 2030, 2034 are also connected to circuit ground, eliminating the need for separate isolated power supplies, reducing the cost of the generator.

In another implementation of circuit 2000, FIG. 67, the inductor 2040 is not a separate component, but rather is incorporated into the transformer 2013 by way of leakage inductance. This leakage inductance performs the same function as inductor 2040 and the leakage inductance is controlled by the coupling of transformer 2013, e.g., by setting a gap in the transformer's core as is known in the art. This circuit of the FIG. 67 type is referred to herein as the "zero current switching inverter circuit".

Figure 70:
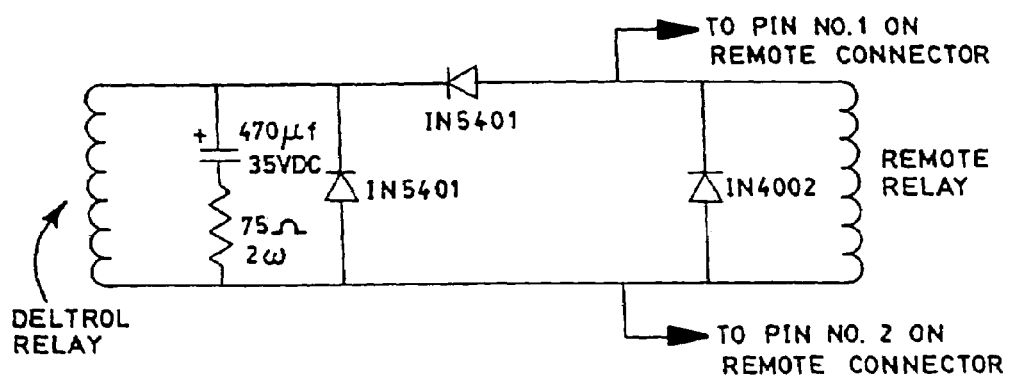
FIG. 70 schematically shows a circuit coupled to the rotary switch of FIG. 68.
Figure 68:
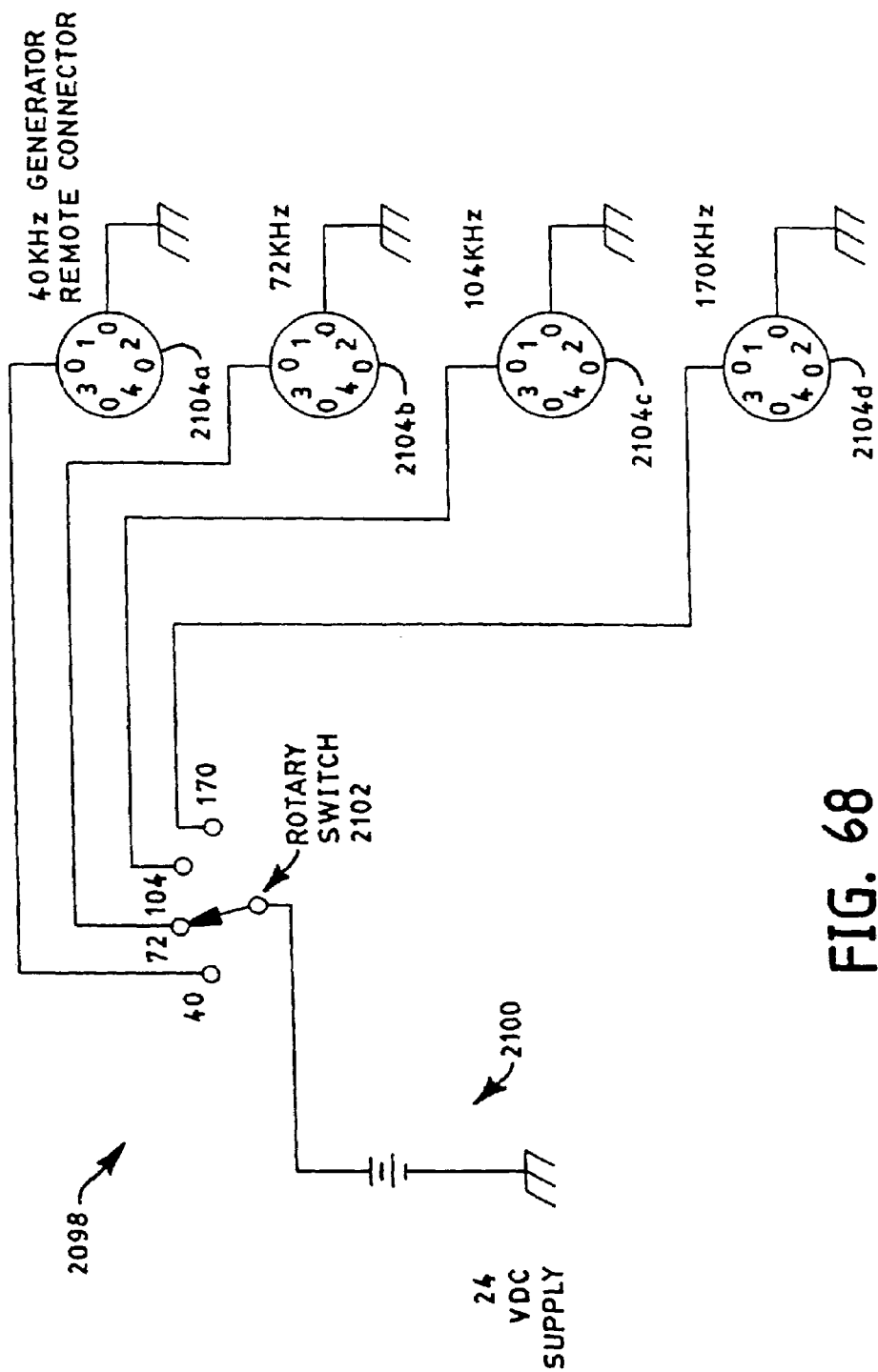
FIG. 68 illustrates a wiring schematic that couples a common voltage supply to one generator of a system that includes multiple generators, in accord with the invention.
Figure 69:
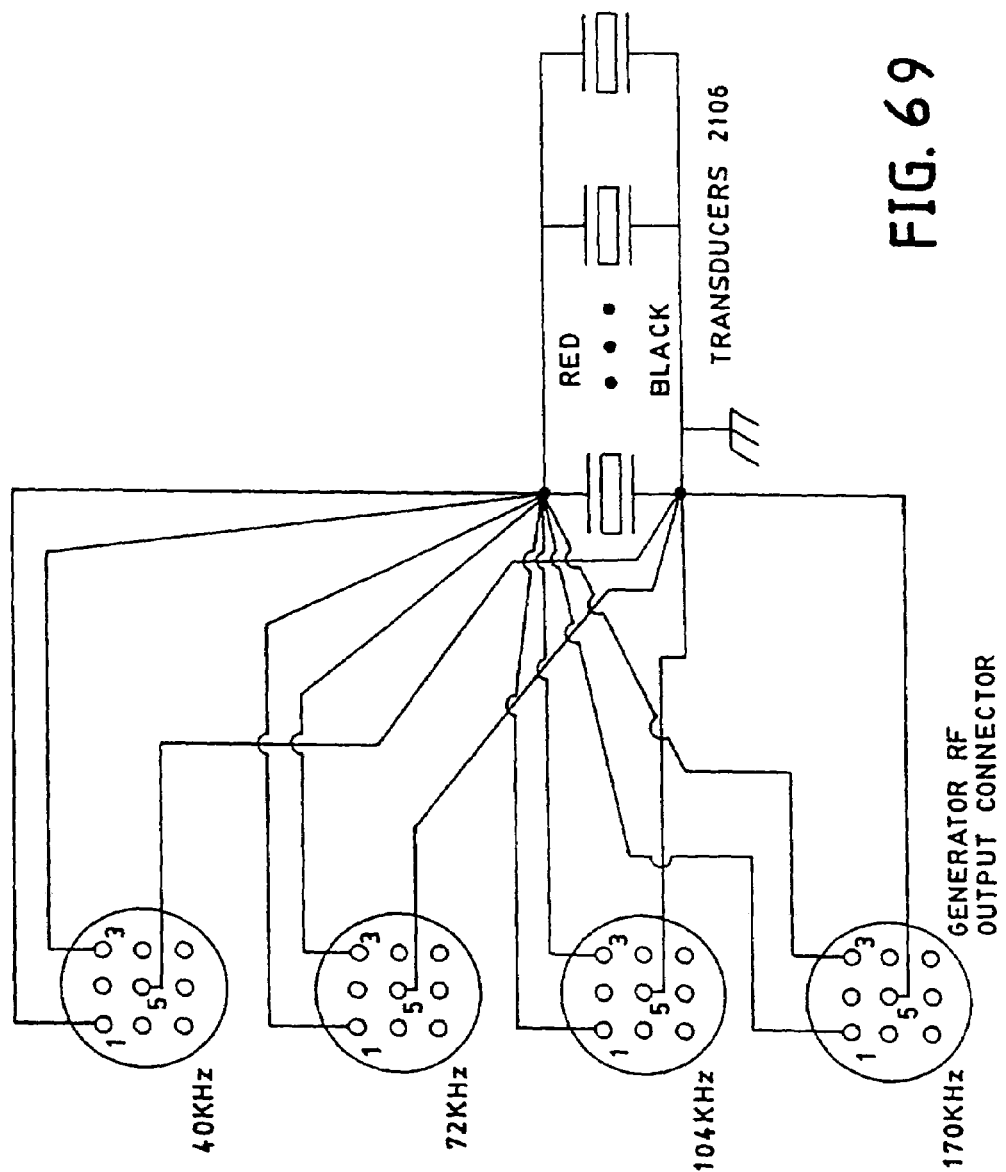
FIG. 69 shows a wiring schematic to couple the generators to a single processing tank with transducers.

With further reference to FIG. 43, one embodiment of the invention couples multiple generator frequencies to a common tank 306' and transducers 304'. FIG. 68 schematically shows additional switch circuitry corresponding and connecting to a different generator frequency, e.g., 2104a for 40 khz, 2104*b* for 72 khz, 2104*c* for 104 khz, and 2104*d* for 170 khz). Which ever generator thus connects to the 24VDC supply between pins "1" and "2" on its corresponding remote connector 2104 will drive the common process tank, as shown in FIG. 69. The generators can have a remote on/off relay in the form of FIG. 70, which illustrates coupling between a Deltrol relay and the remove relay. The connector-to-tank wiring is further illustrated in FIG. 69. In FIG. 69, each generator within the system connects to each of the plurality of transducers 2106 within the tank; though only one generator actively drives the transducers 2106 depending upon the position of the switch 2102.

In operation, power is applied to one generator (e.g., the 40 khz generator coupled to remote connector 2104*a*) via the 24VDC signal from the rotary switch 2102. The following sequence then occurs with respect to FIGS. 58-60: 2098 compatible with this embodiment. In FIG. 68, a common 24VDC supply 2100 couples to a user-selectable switch 2102 (e.g., a rotary switch) to provide drive energy to remote connectors 2104*a*-*d* (each connector 2104

| Time | Event |
| --- | --- |
| 7 milliseconds | Remote relay #1 energizes starting the ½sec. timer #1 |
| 10 milliseconds | Deltrol relay #1 connects the tank to the 40 khz generator |
| 0.5 seconds | ½sec. timer #1 starts the 40 khz generator, the tank runs at 40 khz |

If the rotary switch 2102 is turned to the next position, e.g., to the 72 khz generator position, the following sequence occurs (assuming, worst case, that the rotary switch is moved very fast so there is zero time between the 40 khz position and the 72 khz position):

| Time | Event |
| --- | --- |
| 0 milliseconds | 24 VDC is removed from remote relay #1 |
| 0 milliseconds | 24 VDC is removed from Deltrol relay #1 |
| 5 milliseconds | 40 khz generator turns off |
| 7 milliseconds | 72 khz remote relay #2 energizes starting the ½ sec. timer #2 |
| 10 milliseconds | Deltrol relay #2 connects tank to 72 khz generator |
| 250 milliseconds | Deltrol relay #1 disconnects 40 khz generator from the tank |
| 0.5 seconds | ½sec. timer #2 starts the 72 khz generator, the tank runs at 72 khz |

To avoid this "worst case" scenario, extra margin is provided by providing an off position between each rotary switch generator position. That is, the rotary switch can be labeled as follows:

OFF-40 khz-OFF-72 khz—OFF-104 khz—OFF-170 khz

Generators connected within this system preferably have a four socket reverse sex square flange AMP CPC receptacle with arrangement 11-4 (AMP part number 206430-1) installed on the rear of the generator. The mating four pin plug (AMP part number 206429-1) has the following pin connections:

| | |
| --- | --- |
| Pin#1 | +24 VDC referenced to Pin #2 connects the generator or power module to the transducers and turns the generator on |

-continued

| | |
| --- | --- |
| Pin#2 | return for 24 VDC signal, can be grounded |
| Pin#3 | anode of LED to indicate RF current flow |
| Pin#4 | cathode of LED to indicate RF current flow |

The cable from the AMP plug is for example a Manhattan/Cot PIN M39025 control cable with four #24 AWG wires, with the following color codes: Pin#1 red; Pin#2 green; Pin#3 blue; and Pin#4 white.

Generators within this system can have a nine socket reverse sex square flange AMP CPC receptacle with arrangement 17-9 (AMP part number 211769-1) installed on the rear of the generator according to the following connections.

Socket #1: +RF output
Socket #2: not used
Socket #3: +RF output
Socket #4: −DC test point
Socket #5: −RF output, ground
Socket #6: cable shield, ground
Socket #7: +DC output interlock
Socket #8: +DC input interlock
Socket #9: waveform test point The mating nine pin plug (AMP part number 211768-1) can have the following pin outs and color code when supplied with a three wire RF cable.

Pin#1: +RF output red
Pin #3: +RF output red
Pin #5: −RF output green/yellow

All pin#5*s* can for example be wired together and connected to the −RF transducer lead. All pin #1's are then connected together and connected to the +RF transducer lead coming from one-half of the transducers. All pin #3's are then connected together to the +RF transducer lead coming from the other one-half of the transducers. The only exception to this is when the generators do not all drive the same number of transducers.

Figure 71:
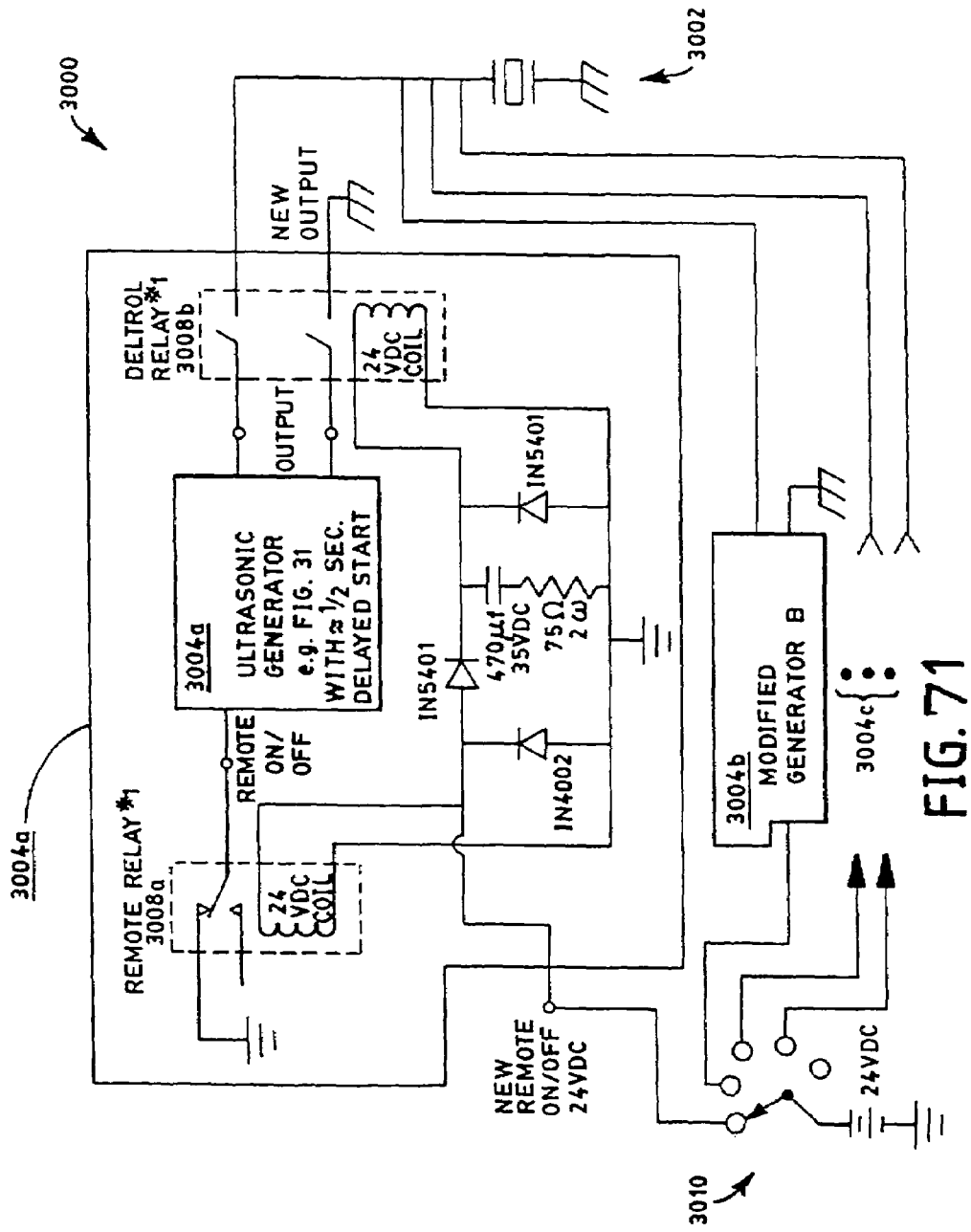
FIG. 71 shows a multi-generator system constructed according to the invention.

FIG. 71 schematically shows a multi-generator system 3000 used to drive common transducers 3002. One advantage of the system 3000 is that multiple generators 3004 can alternatively drive the transducer 3002; and it is assured that no two generators operate simultaneously. Each generator 3004 preferably represents a different drive frequency. Generator 3004*a* represents, for example, the generator set forth by circuitry of FIG. 41 (except that preferably, a ½ second delay is installed into circuit 250 by adjusting capacitor 3006 to one microfarad instead of 1/10 microfarad, which provides only 50 milliseconds delay). The relays 3008*a*, 3008*b* for example can be implemented similar to the relay schematic of FIG. 70.

The rotary switch 3010 (e.g., similar to the switch 2102, FIG. 68) permits user selection between any of the generators 3004. Generator 3004*b* can thus be switched in to drive the transducer 3002 with a different frequency. Those skilled in the art should appreciate that additional generators 3004*c*, 3004*d*, can be installed into the system 3000 as desired, with additional frequencies. Those skilled in the art should appreciate that the rotary switch 3010 can be replaced by a PLC or computer control to provide similar generator selection.

As used herein, "lifetime" of a sound wave in a liquid contained in a tank or other container is defined as the time for the sound wave to decay from 90% to 10% of its intensity value after the sound energy input to the tank or container is stopped. Lifetime is a function of the sound frequency, type of liquid, shape and material of the container, and loading of the container.

As used herein, "degas time", "quiet time", "transition time" and "off time" are periods of time when the generator is supplying no electrical frequency drive signal to the array of transducers.

As used herein, "permutations of frequency ranges" means different orders of supplying the frequency ranges to the liquid. For example, if there are four frequency ranges, there are twenty-four permutations of these four frequency ranges.

As used herein, "cleaning packet" is defined as a permutation of frequency ranges.

As used herein, "intense" sound energy is defined as sound energy having amplitude suitable for cleaning and processing components; such amplitudes typically produce cavitation as is well known to those in the art.

As used herein, "frequency band" is defined as a continuous set of frequencies over which a transducer array can generate intense sound energy. These frequency bands are typically located around the fundamental frequency and the harmonics of the transducer array.

FIG. 72A shows a diagram of a multiple frequency cleaning system 10 constructed according to the present invention. A signal generator 12 (also referred to herein as 'generator') connects via electrical paths 14, 15, 16 to a transducer array consisting of paralleled transducers 17, 18, 19. The transducer array is driven by the generator 12 to produce multiple frequency sound waves 26 in liquid 22 which is contained in tank 20. Tank 20 is typically constructed of 316L stainless steel, but other tanks or containers such as those constructed of tantalum, polyetheretherketone, titanium, polypropylene, Teflon, Teflon coated stainless steel, or other material or combination of materials can be used. These alternate materials are most appropriate when the liquid 22 is an aggressive chemistry that will degrade or erode 316L stainless steel.

FIG. 72B shows a graph of the sound intensity produced by the transducer array verses the frequency of the sound. BW1 21 is a first frequency band of frequencies produced by the transducer array and BW2 23 is a second frequency band of frequencies produced by the transducer array. Since these frequency bands are continuous along the frequency axis, there are an infinite number of frequencies contained in each frequency band that can be excited by the generator. The first frequency band typically occurs around the fundamental frequency of the transducer and the other frequency bands typically occur around the transducer harmonics. It is possible to not use the frequency band around the fundamental frequency and to select two or more of the frequency bands around harmonic resonances for the operating areas of the transducer array.

FIG. 72C shows a graph of the generator output voltage verses frequency. R1 25 is a first range of frequencies produced by the generator, with R1 25 being a frequency subset of BW1 21. R2 27 is a second range of frequencies produced by the generator, with R2 27 being a frequency subset of BW2 23.

FIG. 9 shows a cross-sectional view of one transducer 128 constructed according to the invention; while FIG. 9A shows a top view of the transducer 128. Two or more transducers are connected in parallel to form an array of transducers. The parallel array of transducers formed from transducers 128 exhibit frequency bands that are centered on 39.75 khz, 71.5 khz, 104 khz, 131.7 khz, 167.2 khz and 250.3 khz.

In FIGS. 9 and 9A, the ceramic 134 of transducer 128 is driven through oscillatory voltages transmitted across the electrodes 136. The electrodes 136 connect to a generator (not shown), such as described above, by insulated electrical connections 138. The ceramic 134 is held under compression through operation of the bolt 132 providing compressive force by way of the front mass 130 and the back mass 139.

Figure 73A:
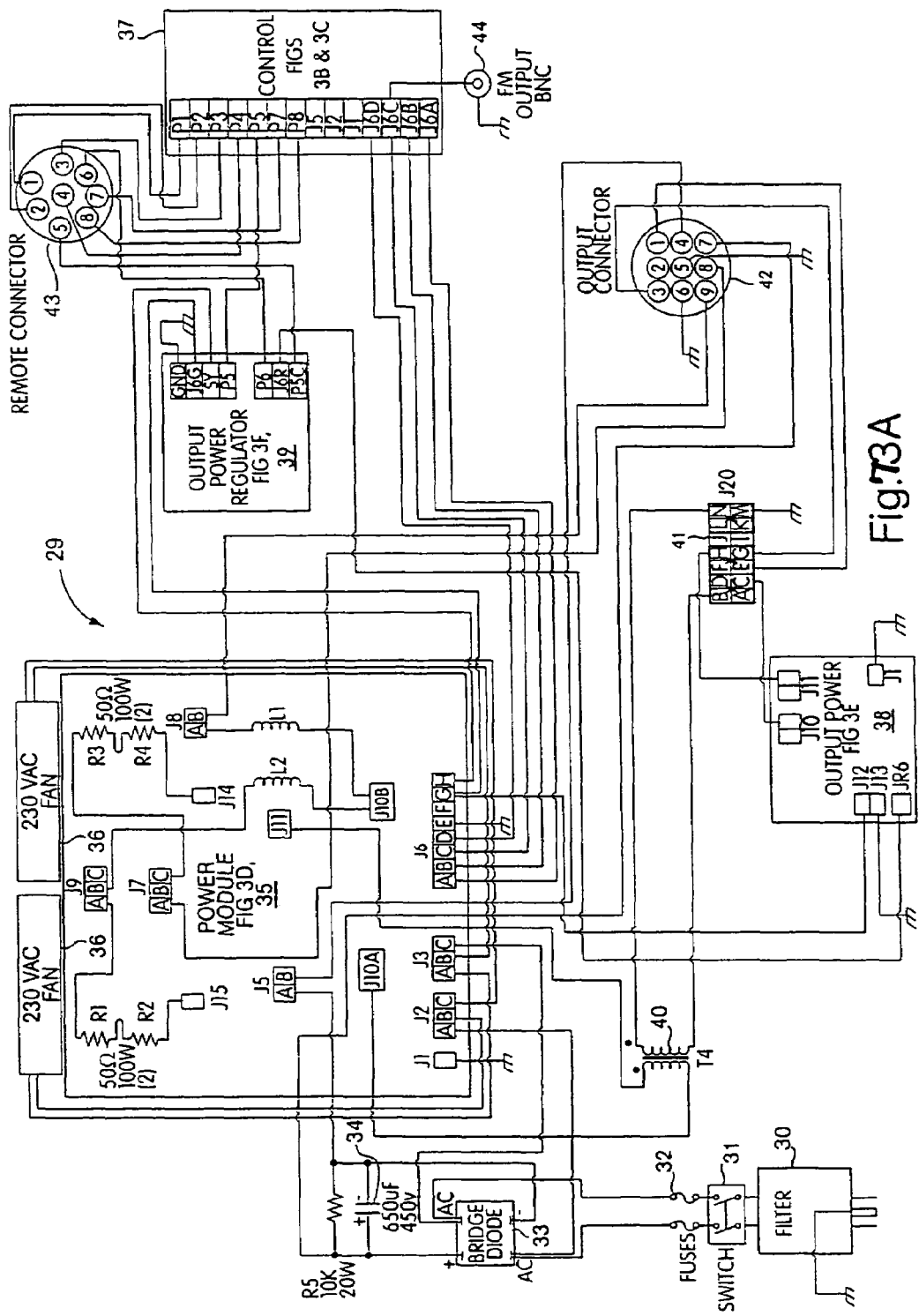
FIG. 73A shows, in schematic form, a portion of a generator built to produce multiple frequency drive signals for an array of transducers formed from paralleled transducers of FIG. 9.

FIG. 73A shows the basic schematic for a generator 29 built according to the invention, with FIGS. 73B, 73C, 73D, 73E and 73F showing the component details of the circuit blocks in FIG. 73A. The generator 29 receives AC power from the power line into filter 30, the purpose of filter 30 is to prevent high frequency noise voltages produced by the generator from entering the AC power lines. Switch 31 controls the AC power to generator 29 and fuses 32 protect the system from over current conditions. Bridge diode 33 in combination with filter capacitor 34 converts the AC line voltage to a DC voltage. The power module 35 converts the DC voltage to the needed frequencies to drive the transducer array (not shown) as described above. The control 37 supplies the frequency modulation (FM) and the amplitude modulation (AM) information to the power module 35. The output power circuit 38 measures the power delivered to the transducer array and supplies this information to the output power regulator 39. The output power regulator 39 compares the signal from output power circuit 38 with the desired output power supplied through pin 5 of remote connector 43 and supplies the difference information to control 37 so the AM can be adjusted to make the actual output power substantially equal to the desired output power.

In FIG. 73A BNC connector 44 supplies the FM information to other generators (often called power modules) that need to be synchronized with this generator 29 for the purpose of eliminating beat frequencies. Terminal 41 serves as a junction connection for the power output lines. Transformer 40 isolates the generator 29 from the transducer array and output connector 42 supplies the output drive signals to the transducer array.

Figure 73C:
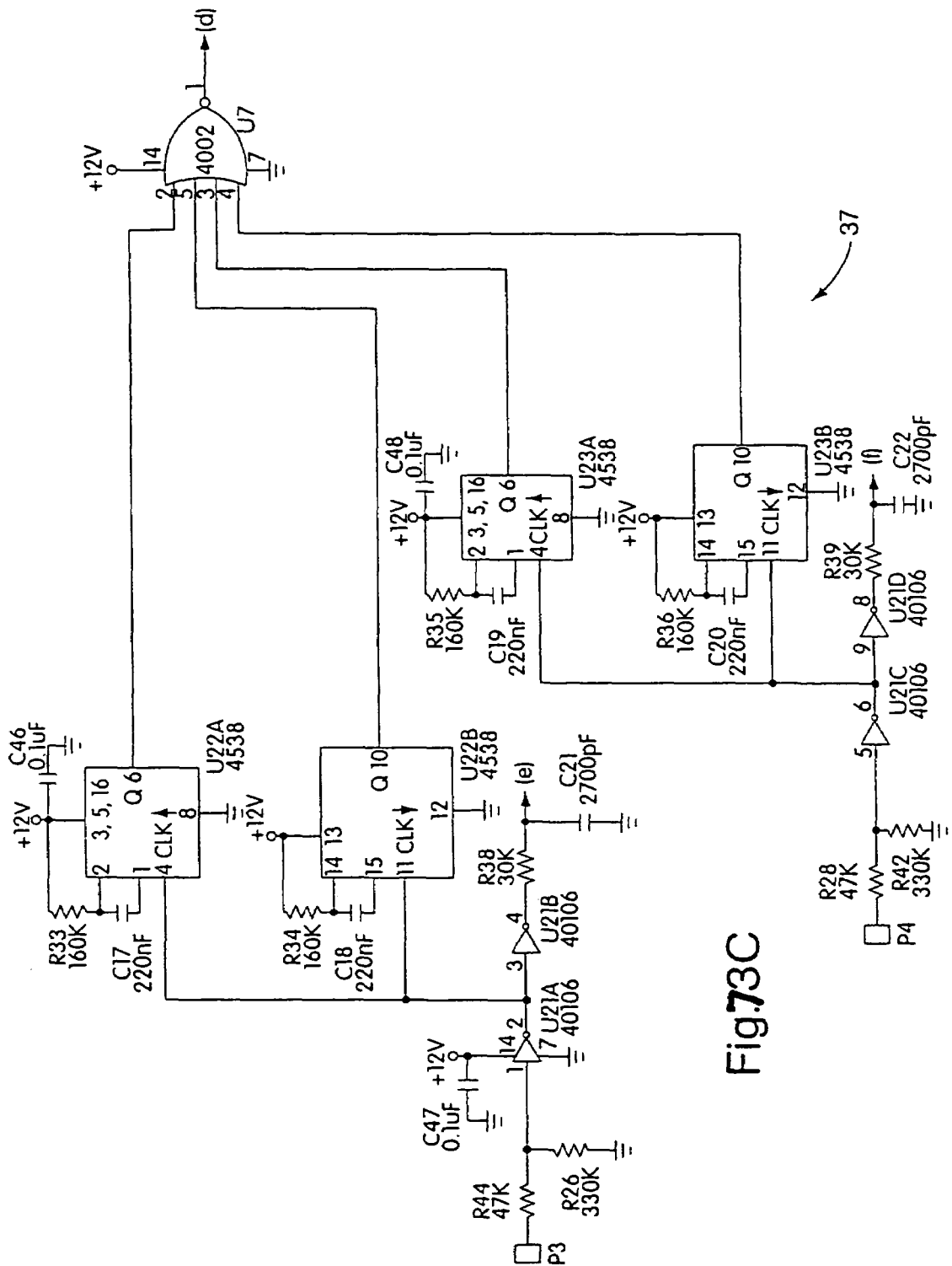
FIG. 73C shows, in schematic form, additional components of the generator of FIG. 73A.

FIGS. 73B and 73C show in schematic form the component details of control 37. VCO (voltage controlled oscillator) U13 produces a triangle wave at output pin 8 that sweeps the sweep rate signal generated by VCO U8. Besides generating the sweep rate signal, U8 also makes this sweep rate signal non-symmetrical so that most of the time (greater than 90%) the sweep rate is from high frequency to low frequency so the transducers substantially respond to a monotonic frequency change direction. VCO U14 generates two times the needed drive frequency from the sweeping information produced by U13 and U8 and from the binary code supplied to P3 and P4 in FIG. 73C. The specific binary code and center frequencies (after the U11:B divide by two flip flop) for the component values shown in FIGS. 73B and 73C are when P3,P4 are 1,1 the center frequency is 39.75 khz, when P3,P4 are 0,1 the center frequency is 71.5 khz, when P3,P4 are 1,0 the center frequency is 104 khz and when P3,P4 are 0,0 the center frequency is 167.2 khz. The series string of resistors consisting of RV40, R40, RV72, R73, RV104, R105, RV170 and R171 determine the center frequency of the signal from pin 7 of U14 by responding to the binary code. For example, when P3,P4 are 1,1 output pin 3 of gate U10:A is an open circuit, output pin 5 of gate U9:B is an open circuit and output pin 3 of gate U9:A is an open circuit. This results in the total series string of resistors RV40, R40, RV72, R73, RV104, R105, RV170 and R171 being connected to pin 4 of U14 and this produces the center frequency two times 39.75 khz. As a second example, when P3,P4 are 0,1 output pin 3 of gate U10:A is an open circuit, output pin 5 of gate U9:B is an open circuit and output pin 3 of gate U9:A is a short circuit. This results in the resistors RV40 and R40 being shorted out and now the series string of resistors RV72, R73, RV104, R105, RV170 and R171 are connected to pin 4 of U14 and this produces the center frequency two times 71.5 khz. As a third example, when P3,P4 are 1,0 output pin 3 of gate U10:A is an open circuit, output pin 5 of gate U9:B is a short circuit and output pin 3 of gate U9:A is a open circuit. This results in the resistors RV40, R40, RV72 and R73 being shorted out and now the series string of resistors RV104, R105, RV170 and R171 are connected to pin 4 of U14 and this produces the center frequency two times 104 khz. And lastly as a forth example, when P3,P4 are 0,0 output pin 3 of gate U10:A is a short circuit, output pin 5 of gate U9:B is a open circuit and output pin 3 of gate U9:A is a open circuit. This results in the resistors RV40, R40, RV72, R73, RV104 and R105, being shorted out and now the series string of resistors RV170 and R171 are connected to pin 4 of U14 and this produces the center frequency two times 167.2 khz. The frequency is continually changing around the chosen center frequency by the current input from R31 which is connected to U14 pin 4. The current into R31 is a result of the sweeping of the sweep rate signal produced by VCOs U13 and U8 as described above. U11:B divides by two the frequencies produced by U14 and this is inverted by U6D, U6E and U6F before being output to J6C for connection to the power module 35 as shown in FIG. 73A.

It should be noted that the center frequencies of this design are not integer multiples of the lowest (fundamental) frequency. The integer multiples of 39.75 khz are 79.5 khz, 119.25 khz, 159 khz, 198.75 khz, 238.5 khz, 278.25 khz, etc. None of these integer multiples are equal to the center frequencies of this design or the complete set of center frequencies possible with the transducer design in FIGS. 9 and 9A, i.e., 39.75 khz, 71.5 khz, 104 khz, 131.7 khz, 167.2 khz and 250.3 khz. This eliminates the possibility of generating the components of a Fourier series and therefore prevents the possibility of a periodic wave that can damage a part by exciting it into resonance.

It should also be noted that rather than a binary code to specify the frequency ranges, it is possible to use a BCD code or any other digital code to specify the frequency ranges. It is also possible to accomplish the same selection function with an analog level, for example, the analog level could be put into an ADC (analog to digital converter) and the ADC output could be used to drive the binary selection circuitry.

FIG. 73B (sheet 1 of 2) is a schematic of that part of control 37 that generates an AM signal on J6D which is output to the power module 35 for the following purposes: to control the output power of the generator; to allow the insertion of quiet times, degas times, transition times and off times into the generator output; to shut the generator off in the event of a fault condition such as low voltage or over temperature; and to start the generator up safely in the correct logic states. The power is controlled by a zero to five-volt level on P5. This voltage feeds the plus input to operational amplifier U16 that compares this voltage to the ramp voltage on the operational amplifier's minus input. The ramp is formed by RV1, R18 and C5 and it is reset by U10B. When the ramp voltage exceeds the voltage level on P5, the output of the operational amplifier U16 changes from +12 VDC to zero, this ripples through four gates that invert the signal four times and therefore a zero is on J6D which terminates the sound burst at the correct time to control the power to the level specified by the voltage on P5. The insertion of quiet times, degas times, transition times and off times into the generator output are accomplished by setting the appropriate input to NAND gate U12 to a zero. A change in the binary code to P3 or P4 in FIG. 73C causes a transition time zero to occur on input pin 3 of U12. A 12 to 50 VDC signal on P7 causes a zero on pin 11 of U12 for the insertion of a quiet time, degas time or off time. Zero inputs to the appropriate inputs of U12 are also the way fault signals shut down the generator. A low voltage on the power lines causes Schmitt trigger U1A pin 1 to go low which results in a zero on pin 10 of U12. An over temperature condition is sensed by U3 and it puts out a zero to pin 4 of U12 when this over temperature condition occurs. The generator is allowed to assume all the correct logic states by the delayed start hold off caused by R20 and C26.

FIG. 73C has four monostable multivibrators that introduce a degas time or off time between discontinuous jumps from one frequency range to the next frequency range. These degas times allow the sound waves from the prior frequency range to decay before sound waves from the new frequency range are introduced into the liquid. This is accomplished in the FIG. 73C schematic section of control 37 by any transition on the binary input lines P3 and/or P4 causing a transition on at least one of the monostable multivibrators U22A, U22B, U23A or U23B producing an output pulse the length of the degas time. This pulse travels through U7 and feeds pin 3 of U12 in FIG. 73B (sheet 1 of 2) where the AM is shut down for the length of the degas pulse.

Figure 73D:
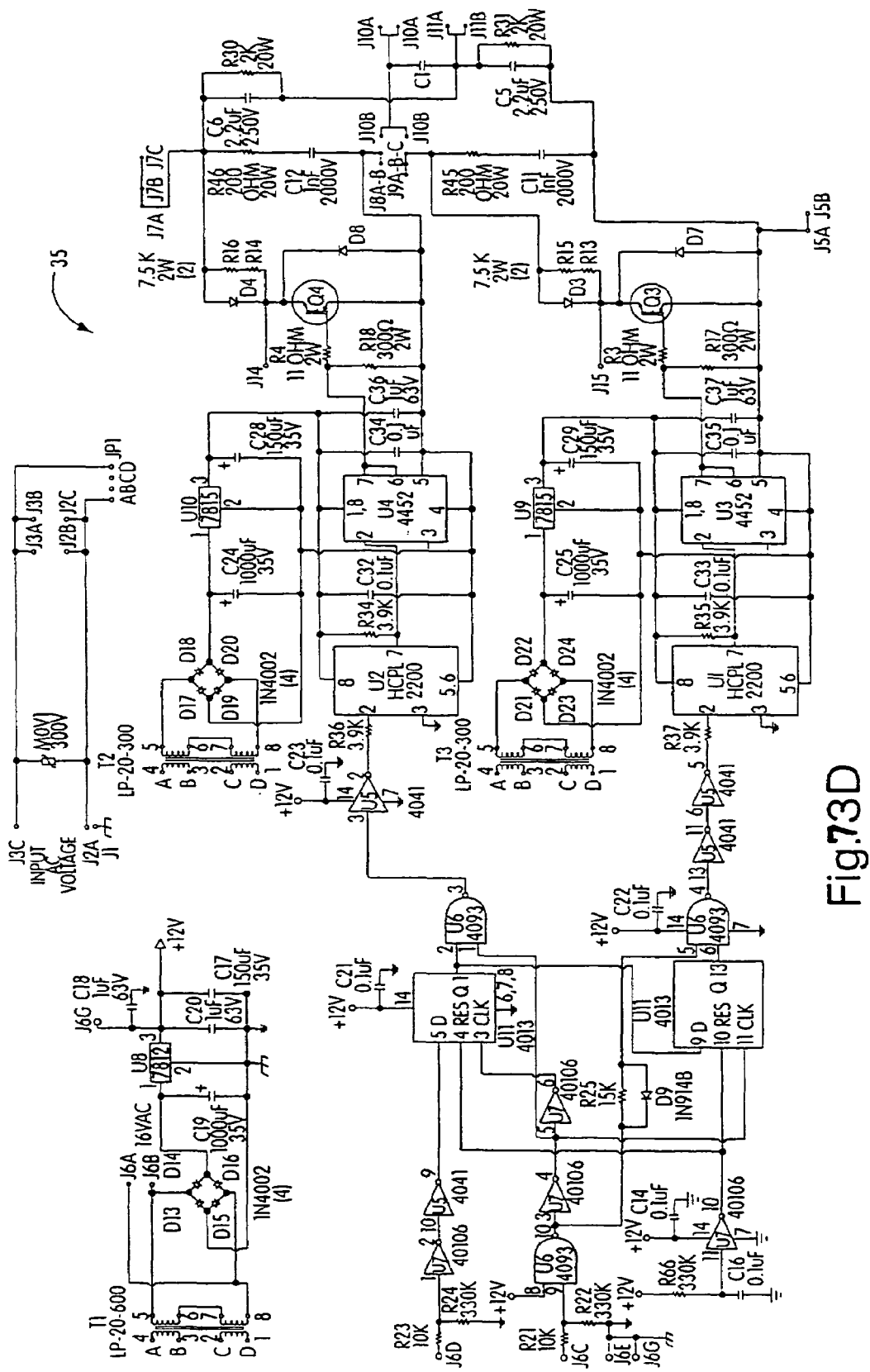
FIG. 73D shows, in schematic form, additional components of the generator of FIG. 73A.

FIG. 73D is a schematic of the power module 35. The front end logic consisting of U5, U6, U7 and U11 accepts and synchronizes the FM and AM signals from the control 37. The power section of power module 35 converts the synchronized FM and AM signals to levels appropriate for driving the transducers. This power section will respond to the infinite number of different frequencies that are possible with this multiple frequency system. The power circuit is well known to people skilled in the art and is described in U.S. Pat. No. 4,743,789.

Figure 73E:
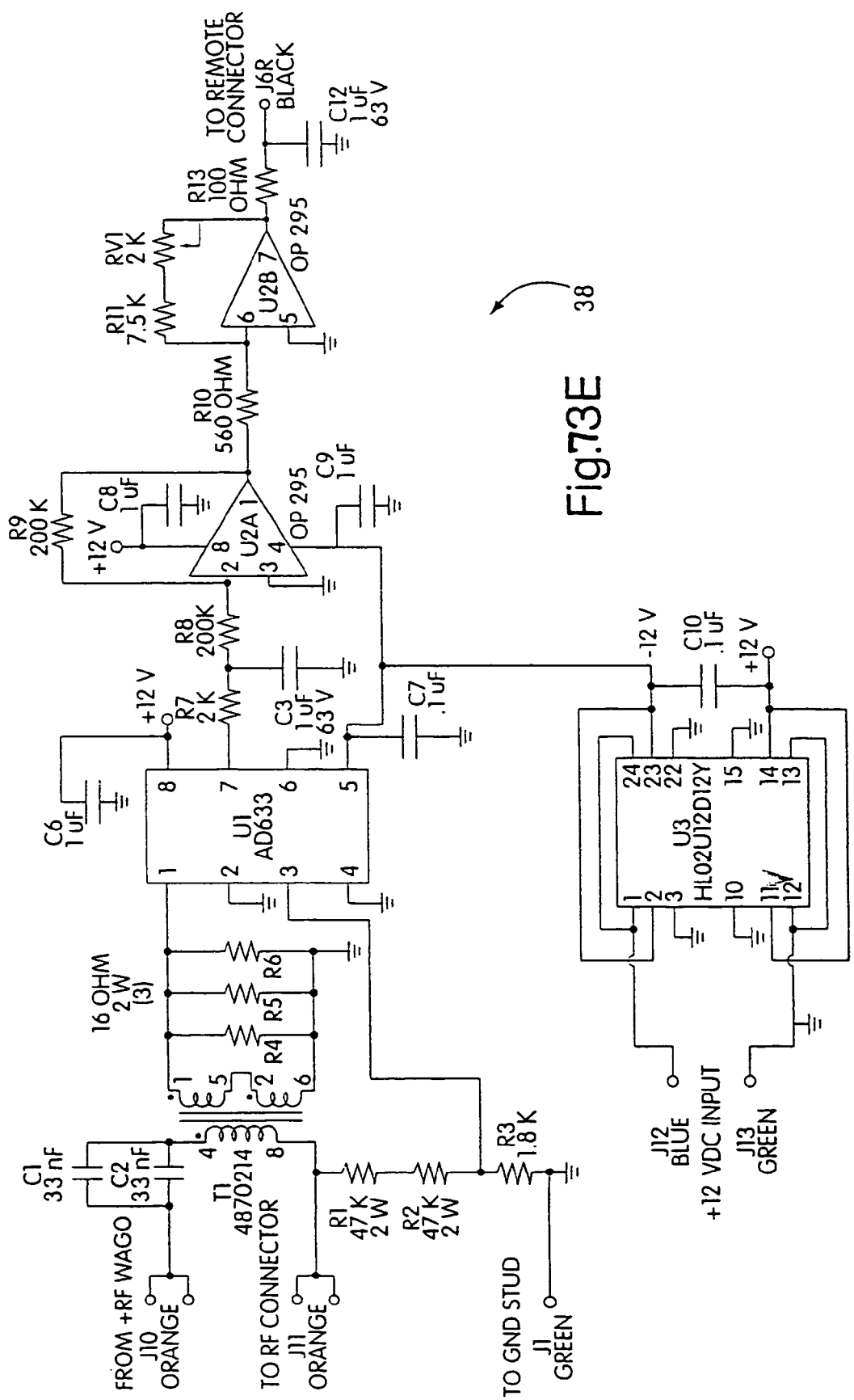
FIG. 73E shows, in schematic form, additional components of the generator of FIG. 73A.

FIG. 73E is a schematic of the circuit that measures the output power of the generator 29. This output power circuit 38 senses the time function of the generators output voltage (Vt) and senses the time function of the generators output current (It). These functions Vt and It are multiplied, averaged over time and scaled to get the output power of the generator which is supplied to J6R as a voltage signal scaled to 100 watts per volt.

Figure 73F:
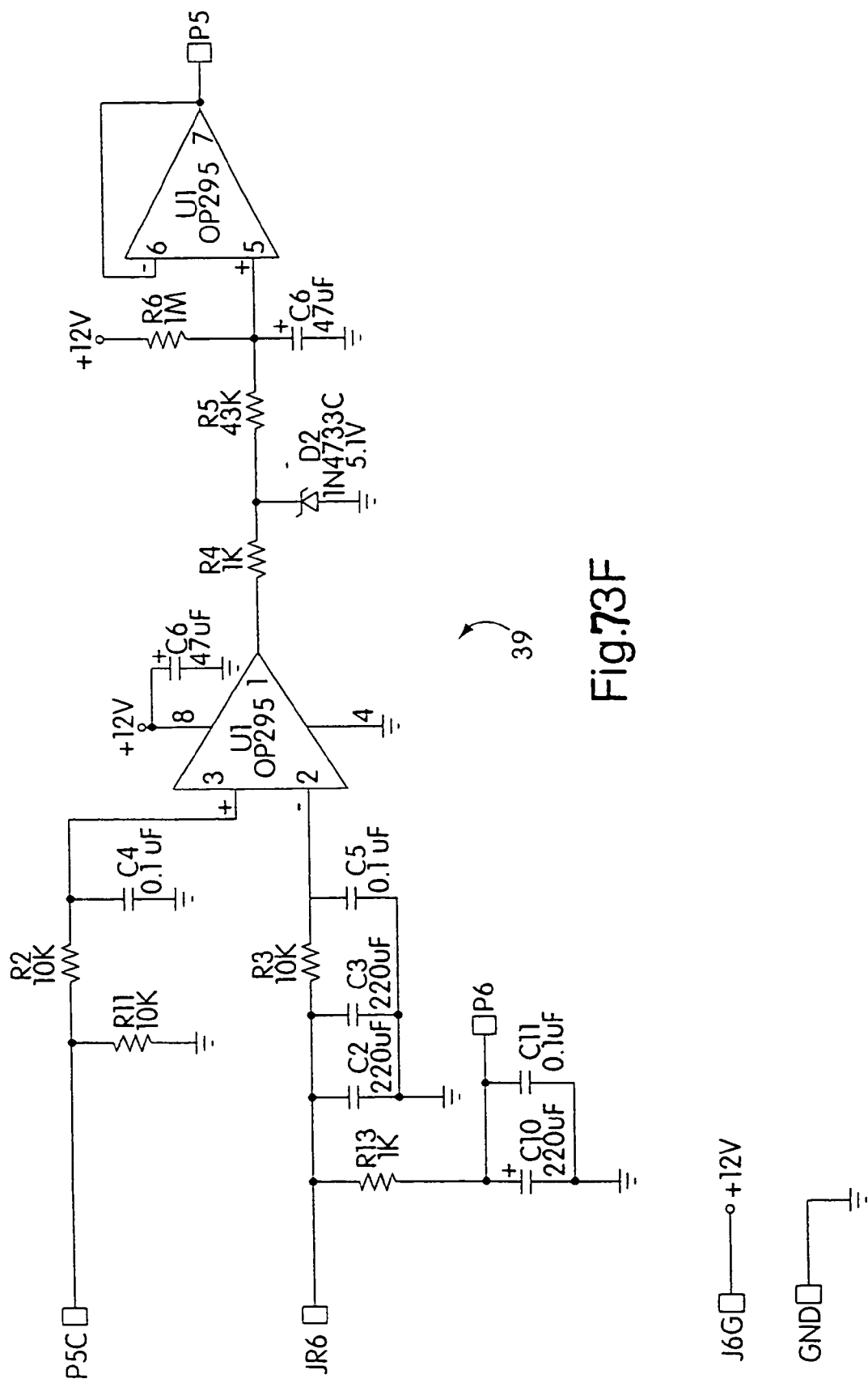
FIG. 73F shows, in schematic form, additional components of the generator of FIG. 73A.

FIG. 73F is a schematic of the output power regulator 39. A voltage (Vd) representing the desired output power is input to P5C. This is compared to the voltage (Va) representing the actual output power on JR6 (which came from the output of the output power circuit 38 as shown in FIG. 73A). If Vd is higher than Va, the voltage output on P5 increases which increases the actual output power of the generator until Va is substantially equal to Vd. If Vd is less than Va, then the output voltage on P5 is decreased until the actual output power becomes substantially equal to the desired output power.

Figure 74:
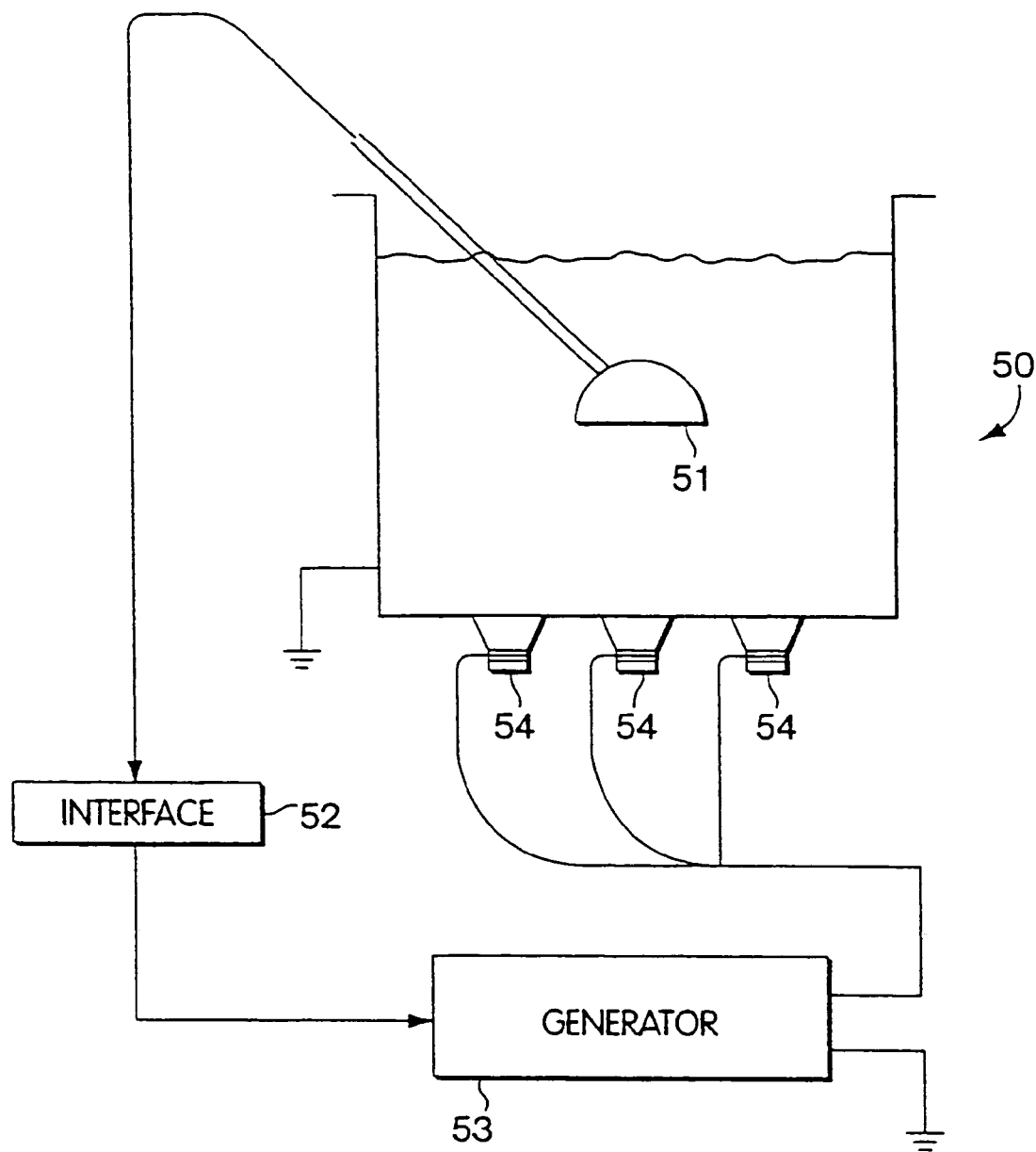
FIG. 74 shows, in diagram form, a multiple frequency system according to the present invention, controlled by a probe measuring sound characteristics in the liquid.

FIG. 74 is the system 10 in FIG. 72A with a probe 51 sensing the sound characteristics in the tank to form the feedback system 50 of FIG. 74. The probe can be of the form disclosed in U.S. application Ser. No. 09/370,302 filed Aug. 9, 1999, entitled "Probe System for Ultrasonic Processing Tank" and after proper interfacing 52 signals are sent to the remote connector on generator 53 to modify the output drive to transducer array 54. In the most sophisticated applications, the interface 52 is a PLC (programmable logic controller) or a computer that is properly programmed.

Figure 75:
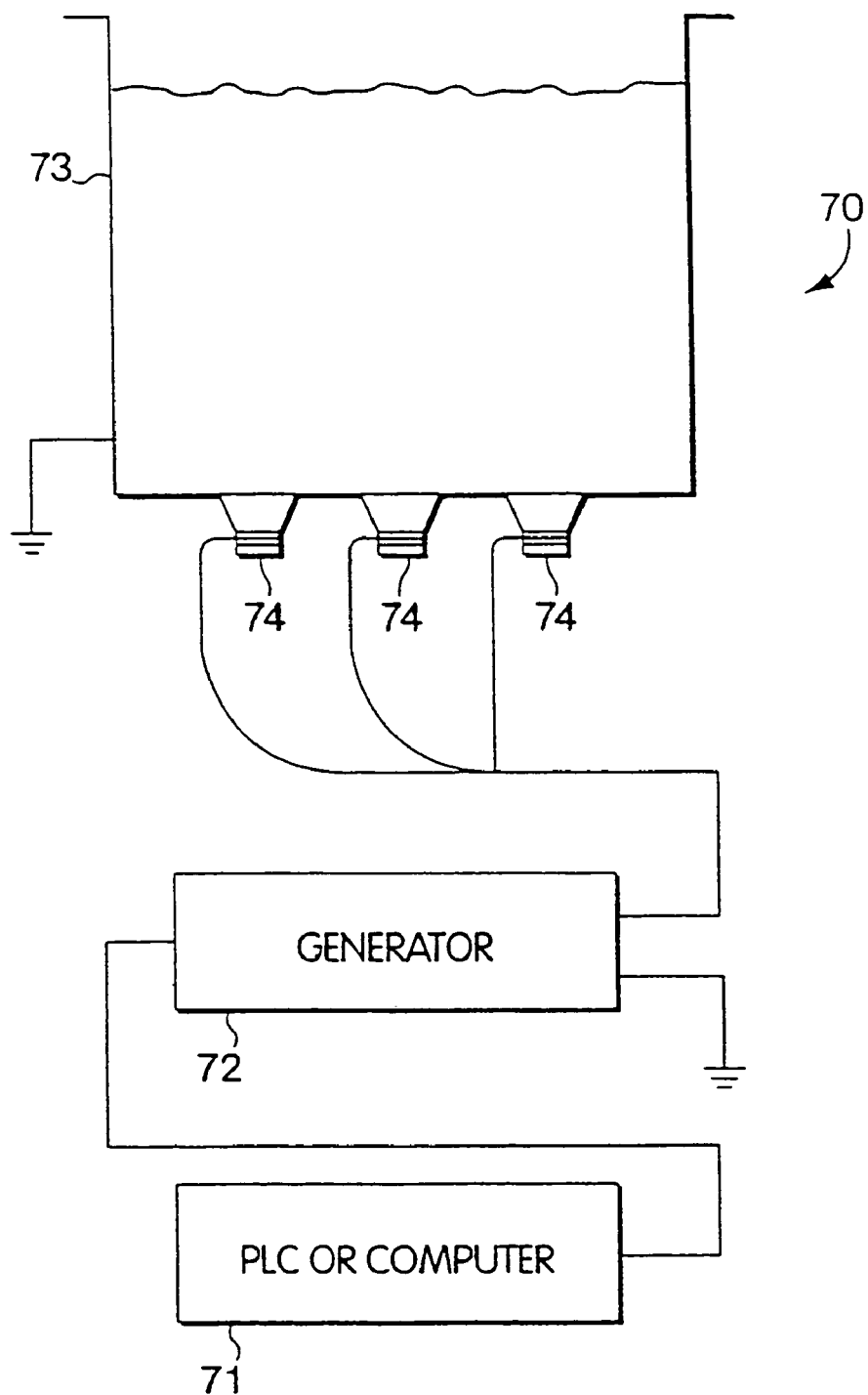
FIG. 75 shows the multiple frequency system of FIG. 74, controlled by a PLC or a computer.

The system 70 in FIG. 75 has a PLC or a computer 71 that is programmed to control and set the parameters for generator 72. The programmed parameters are output by the generator 72 to drive the transducers 74 which put sound with the programmed characteristics into tank 73.

Figure 76:
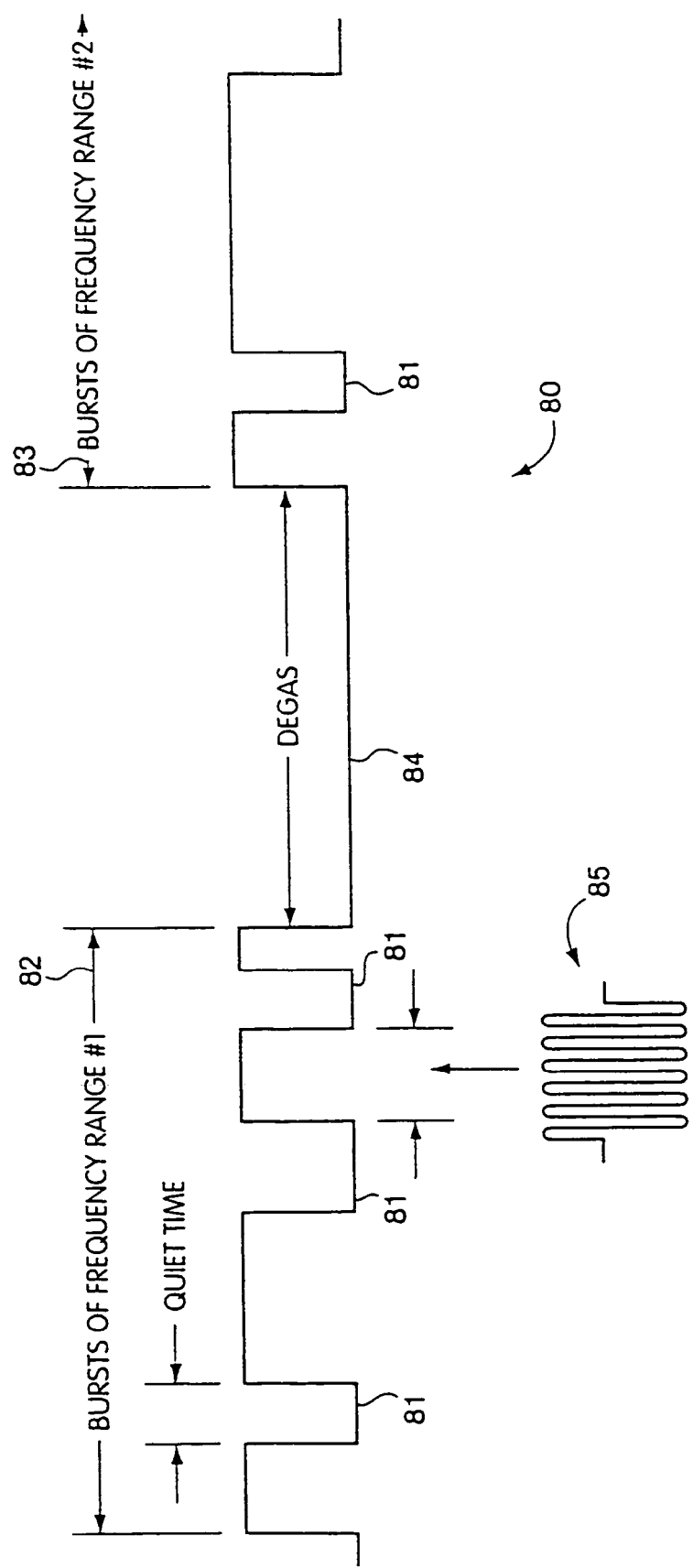
FIG. 76 shows a typical sound profile of the system of FIG. 74, where quiet times are inserted into the bursts of sound energy.

FIG. 76 shows the addition of quiet times 81 into a typical AM pattern 80 of this invention. The invention produces continuously changing sound at frequencies in a first range of frequencies 82 before jumping to frequencies in a second range of frequencies 83. Quiet times 81 are inserted into the continuously changing signal produced by the generator within a frequency range to break up the signal into smaller bursts of sound 85 for the purpose of optimizing certain processes such as the development of photosensitive polymers.

Figure 77:
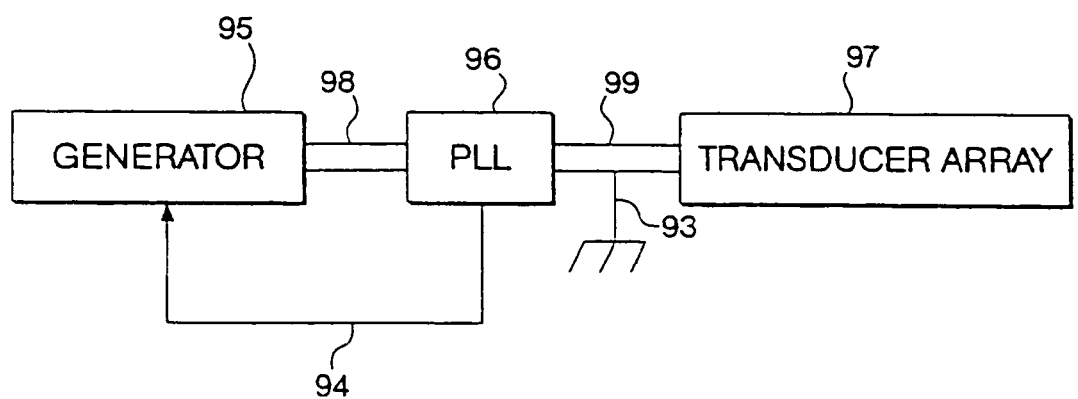
FIG. 77 shows a block diagram of the generator according to the present invention, with phase lock loop control.

FIG. 77 shows the addition of a PLL 96 (phase lock loop) to the generator 95 for the purpose of making adjustments to the center frequency of each frequency range to track changes in the resonance of the transducer array 97. The PLL 96 senses the current between line 98 and line 99 and the PLL senses the voltage between line 99 and ground 93. The PLL generates a frequency on line 94 that feeds the generator 95 VCO so that the sensed current becomes in phase with the sensed voltage at the center frequency of the range.

A further advantage of this multiple frequency system is that it can reduce the intense cavitation region that occurs just below the liquid air interface. The location of this region is frequency dependent, therefore, by jumping from one frequency range to another, the intense region changes position and is averaged over a larger area.

Figure 78A:
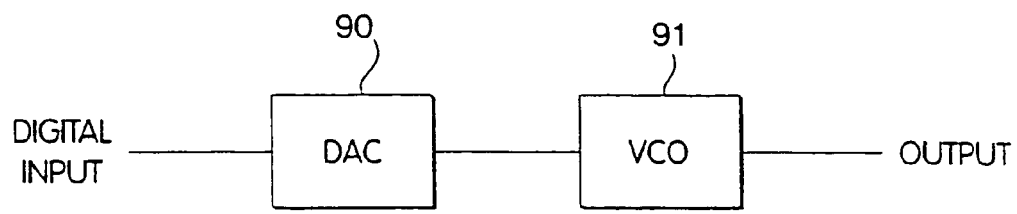
FIG. 78A shows a VCO controlled by a DAC according to the present invention, to change the frequencies of the generator.
Figure 78B:
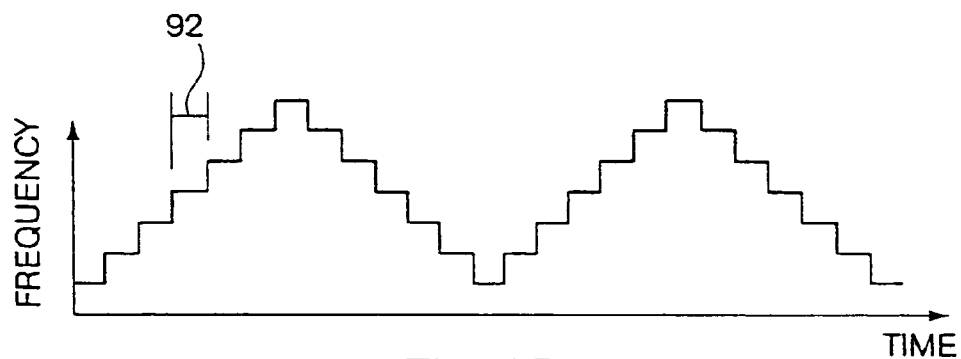
FIG. 78B shows an example of a staircase function that can result from the DAC controlled VCO of FIG. 78A.
Figure 78C:
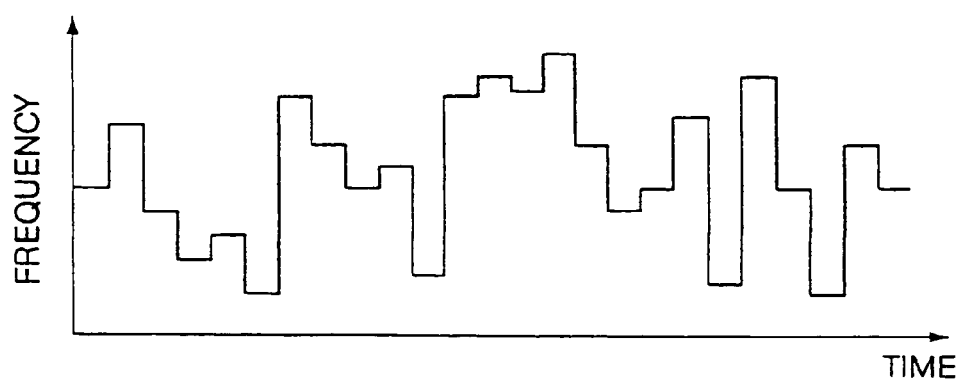
FIG. 78C shows an example of a random staircase that can be produced by the DAC controlled VCO of FIG. 78A; and, FIG. 79 shows a schematic of a modified PFC (power factor correction) circuit that adds amplitude control to the system according to the present invention.

An alternate way to control the frequency changes of this invention is shown in FIG. 78A. The method consists of specifying changing digital numbers into a DAC 90 (digital to analog converter) and then driving a VCO 91 with the output of the DAC. The VCO 91 produces the changing frequencies in response to the changing digital numbers. FIG. 78B shows a typical staircase sweeping frequency output that can result from this circuitry. If the time at each level 92 is less than the period of the frequency being produced, then the changing frequency will be a different frequency each cycle or each fraction of a cycle. If the time at each level 92 is more than the period of the frequency being produced, then there can be two or more cycles of one frequency before the frequency changes to the next frequency. FIG. 78C shows an example of a random staircase function that can be produced by the circuitry represented in FIG. 78A by inputting random or chaotic digital numbers into the DAC 90. FIGS. 78A, 78B and 78C represent the frequency changes in a single range. It is clear to someone skilled in the art that larger frequency changes are possible with this circuitry and therefore the jumping from one range to another range can also be done. It is also clear to someone skilled in the art that a separate DAC can be used for each frequency range to increase the resolution of the frequency changes. A hybrid system is also possible, i.e., using the DAC and VCO of FIG. 78A for the changes in the frequency range and using the digital number input to the series string of resistors as shown in FIG. 73B to select the specific frequency range.

It should be noted that the changing of frequency within a frequency range or amongst frequency ranges could be done with digital circuitry, analog circuitry or a hybrid combination of analog and digital circuitry. In the case of pure analog control, frequency changes within a range are normally high resolution, e.g., a different frequency every one half of a cycle, every one-quarter of a cycle or lesser fraction of a cycle. In the case of digital circuitry or hybrid analog digital circuitry, the resolution of changes depends on the speed at which the digital number is changed. This causes the staircase type of function when the resolution is low, e.g., several cycles of one frequency before several cycles of a different frequency are produced. In the purest sense, all changes can be considered a staircase function because, for example, the one half cycle changes can be considered stairs with a width equal to the time of the one half cycle.

FIG. 78B is drawn to show a constant sweep rate of the staircase function. A non constant sweep rate to eliminate resonances that can occur at a constant sweep rate or a monotonic sweep function to help remove contamination from the tank are other variations to the function shown in FIG. 78B. The non-constant sweep rate and the monotonic changing frequency are best combined to give both of the advantages. It is often most practical to simulate the monotonic function by sweeping in the high to low frequency direction for about 90% of the time and to recover from the low frequency point to the high frequency point during the remaining time. However, experimental evidence shows that any recovery time that is shorter than the time of the monotonic sweeping from high frequency to low frequency will give some benefit of moving contamination upwards in the tank.

Figure 79:
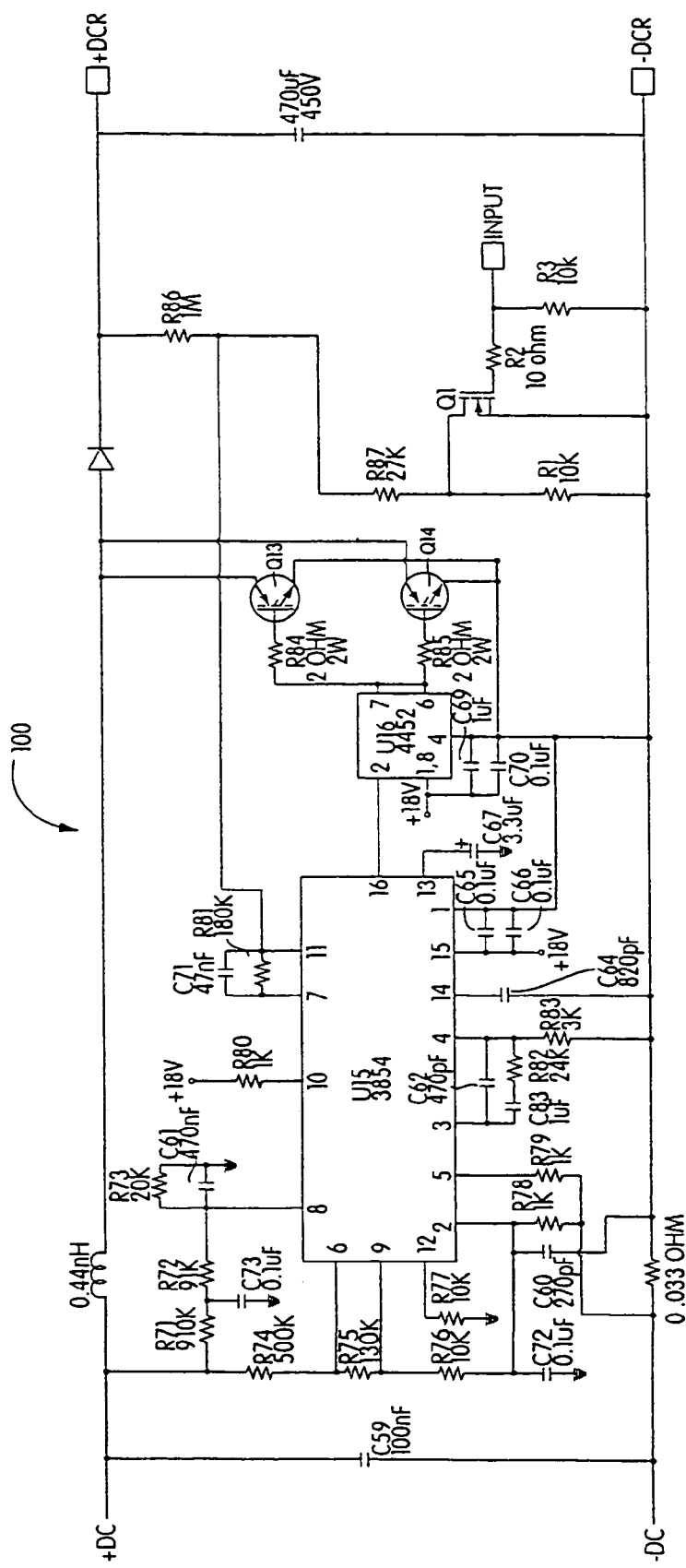

The above designs adjust the duty cycle of the generator output to regulate and/or control the output power of the system. It is sometimes advantageous to regulate and/or control the output power of the system by adjusting the amplitude of the generator's output voltage instead of the duty cycle. One way to accomplish this is by replacing the DC power supply in FIG. 73A consisting of bridge diode 33 and capacitor 34 with a modified PFC (power factor correction) circuit 100 as shown in FIG. 79. The operation of PFC circuits is well known to people skilled in the art, the modification to the PFC circuit 100 consists of the addition of R1, R2, R3 and Q1 to form an input that will allow the adjustment of the regulated output voltage of the PFC circuit 100. In operation, the control line P5 from the output power regulator 39 in FIG. 73A is connected to the input of PFC circuit 100 in FIG. 79. If more power is needed, the control line rises in voltage causing the PFC circuit 100 to regulate at a higher output voltage causing the generator 29 to increase its output power. The opposite occurs in the lower power direction. A stable condition occurs when the actual output power substantially equals the specified output power. It is clear to someone skilled in the art that both duty cycle and amplitude can be used to adjust the output power of the system. For example, the system could be set so the duty cycle stayed at maximum while the amplitude was used to do the adjusting of the output power, however, if the amplitude reached its lowest point, then the duty cycle would begin to decrease to maintain the control and/or regulation. Another configuration could use amplitude for regulation and duty cycle for control.

It is well known in the cleaning industry that each different frequency best removes a specific type and size of contamination. The inventor of this system has observed that the order in which the different frequencies are delivered to the liquid produces a new cleaning effect that best removes a specific type and size of contamination. For example, if the system produces three frequency ranges, say centered on 71.5 khz, 104 khz and 167.2 khz, then there are six different orders or permutations of the frequency ranges that can be delivered to the liquid. They are (71.5, 104, 167.2); (71.5, 167.2, 104); (104, 71.5, 167.2); (104, 167.2, 71.5); (167.2, 71.5, 104) and (167.2, 104, 71.5). Since contamination typically occurs in many different types and sizes, the more new cleaning effects that the contamination is exposed to, the more contamination that will be removed. An additional advantage is obtained by changing the order in which the different permutations of frequency ranges are delivered to the liquid. If in the example, each permutation is considered a cleaning packet, then there are six cleaning packets. There are 720 different ways these cleaning packets can be ordered, each producing a useful cleaning effect that can be supplied in a practical manner with this inventive system.

The generator detailed in FIGS. 73A to 73F is a highly integrated system. It should be noted that the function of this generator can be simulated in many ways that are more primitive by those skilled in the art and these other implementations are considered within the scope of this invention.

Figure 81:
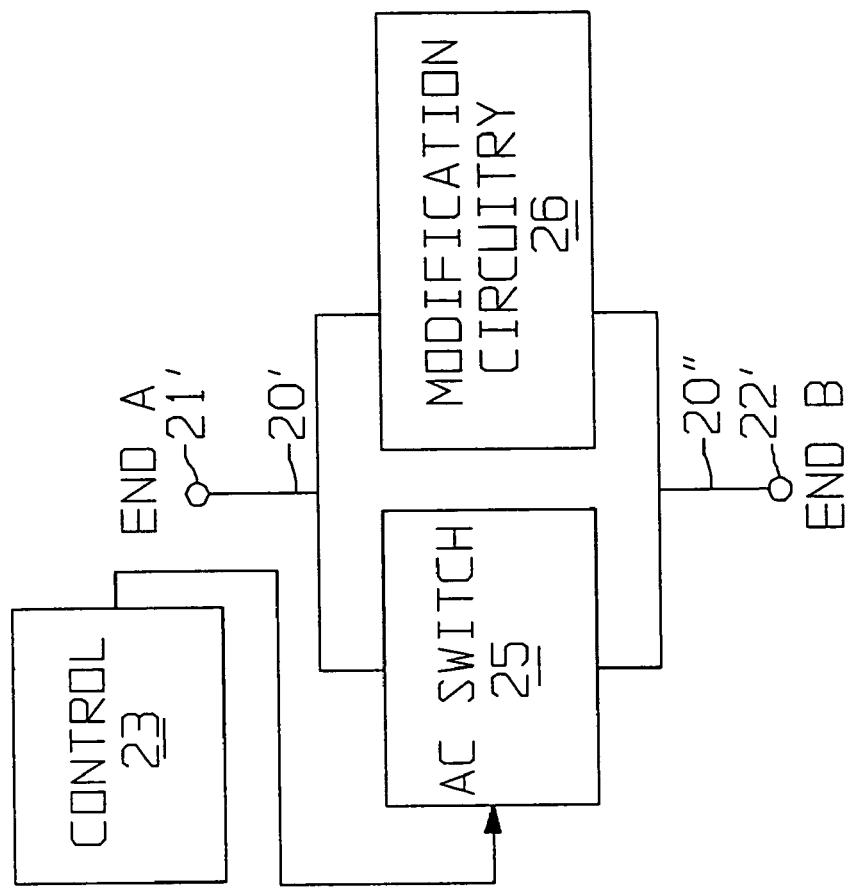
FIG. 81 shows a schematic diagram of an ultrasound generator conduction line and the AC switch and modification circuitry, in a parallel connection. The control function of the AC switch is also shown.
Figure 80:
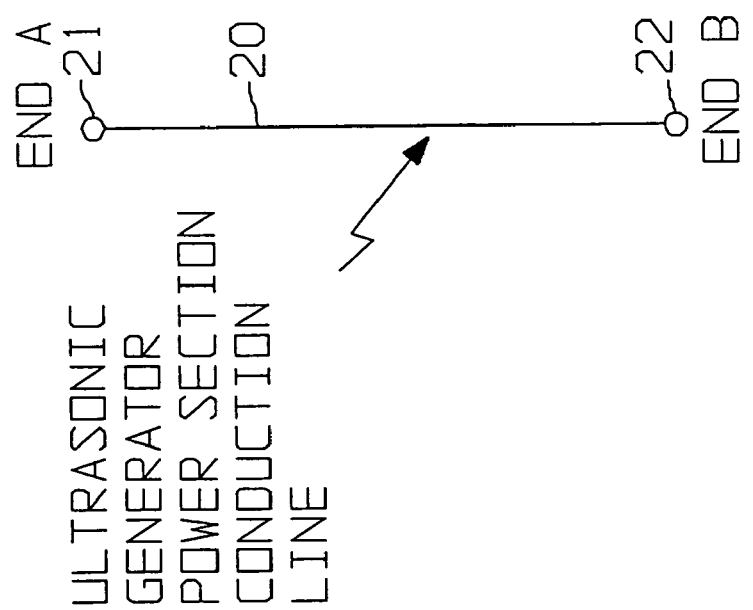
FIG. 80 shows a schematic diagram of a conduction line of an ultrasound generator.

Referring now to the drawings in detail, for the ease of the reader, like reference numerals designate identical or corresponding parts throughout the views depicted in the drawings. It should be noted that each embodiment of the present invention is not depicted by a drawing; nor are each of the notable applications of the present invention depicted by a drawing. FIG. 80 shows a schematic representation of a view of a conduction line 20 from a power section of an ultrasound generator. FIG. 81 shows a box representation of a "parallel structure". As used herein, a parallel structure refers to a modification circuitry 26 and an AC switch 25 with a control 23 where the two leads of the modification circuitry 26 are connected in parallel to the AC switch 25. The "parallel structure" is connected into the conduction line 20 of the power section of an ultrasound generator. As used herein, "power section of an ultrasound generator", "ultrasound generator power section" or "output of an ultrasound generator" is defined as that output circuitry of an ultrasound generator where the ultrasound frequency is present. Where AC switch 25 is comprised of a triac, lead number 1 of the modification circuitry 26 is connected to triac terminal MT1. Lead number 2 of the modification circuitry 26 is connected to triac terminal MT2. The triac gate is connected to the control 23. In cases where the modification circuitry 26 contains active components, the additional control leads of these active components are also connected into the control 23. In cases where the AC switch 25 is a configuration containing more than one active component, the leads of each of the active components are driven by control 23, with proper isolation between the separate control lines where necessary.

Figures 82, 83:
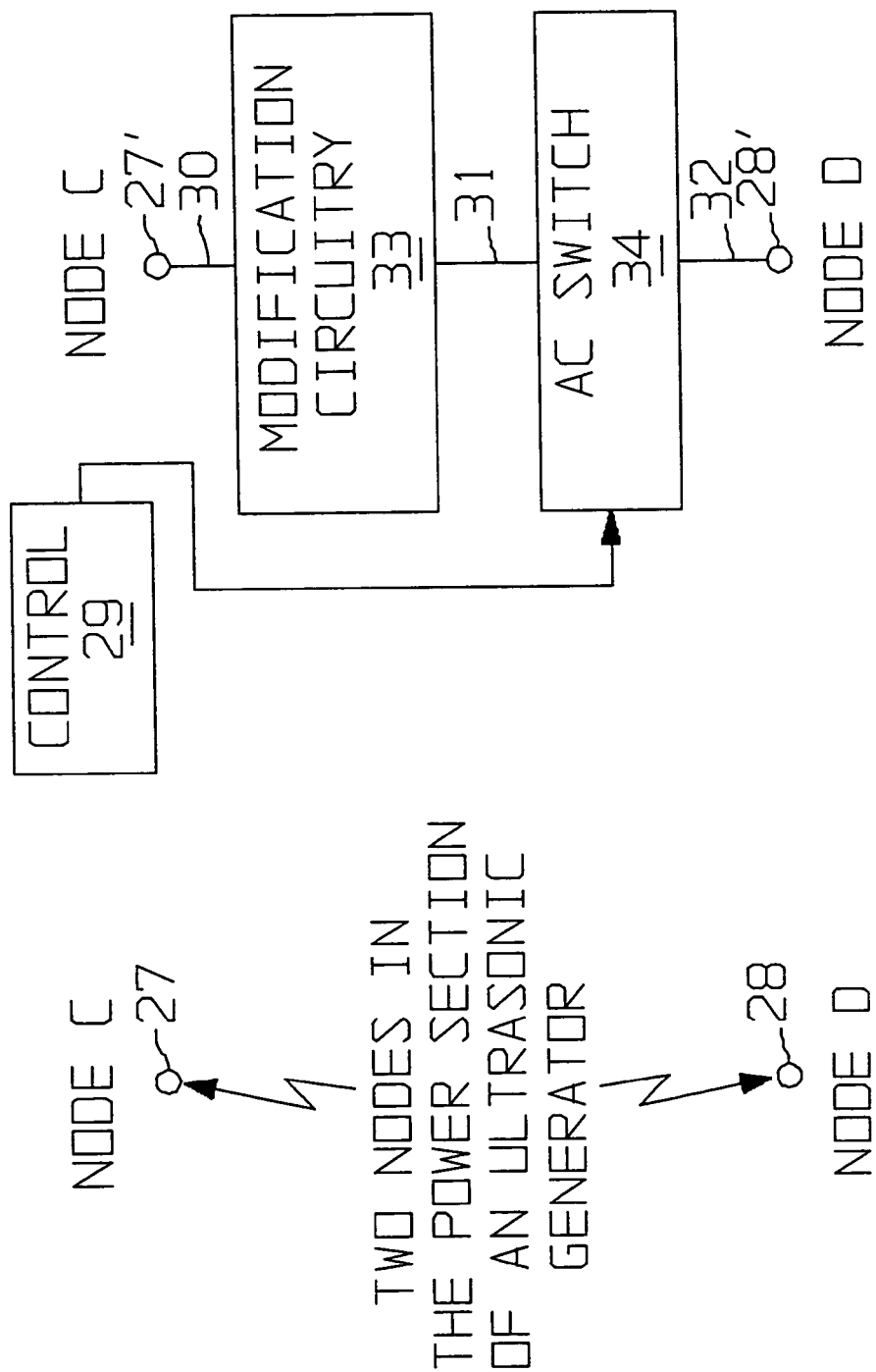
FIG. 82 shows a schematic diagram of two nodes in the power section of an ultrasound generator.
FIG. 83 shows a schematic diagram of the AC switch and modification circuitry connected in series between two nodes in the power section of an ultrasound generator. The control function of the AC switch is also shown.

FIG. 82 shows a schematic view of two nodes 27 and 28 in the power section of an ultrasound generator. FIG. 83 illustrates a "series structure". As used herein, a "series structure" refers to a modification circuitry 33 and an AC switch 34 in which the two leads of the modification circuitry 33 are connected in series with the leads of an AC switch 34. This series structure is connected between two nodes in the power section of an ultrasound generator as shown in FIG. 83. A control 29 is present to turn on and off the AC switch 34. When the AC switch 34 is comprised of a triac, the leads are the MT1 and MT2 terminals of the triac. The third lead is the gate of the triac or AC switch 34 and is connected with the control system 29. In cases where the modification circuitry 33 contains active components, the additional control leads of these active components are also connected into the control circuitry 29. In cases where the AC switch 34 is a configuration containing more than one active component, the leads of each of the active components are driven by control 29, with proper isolation between the separate control lines where necessary.

Figure 84:
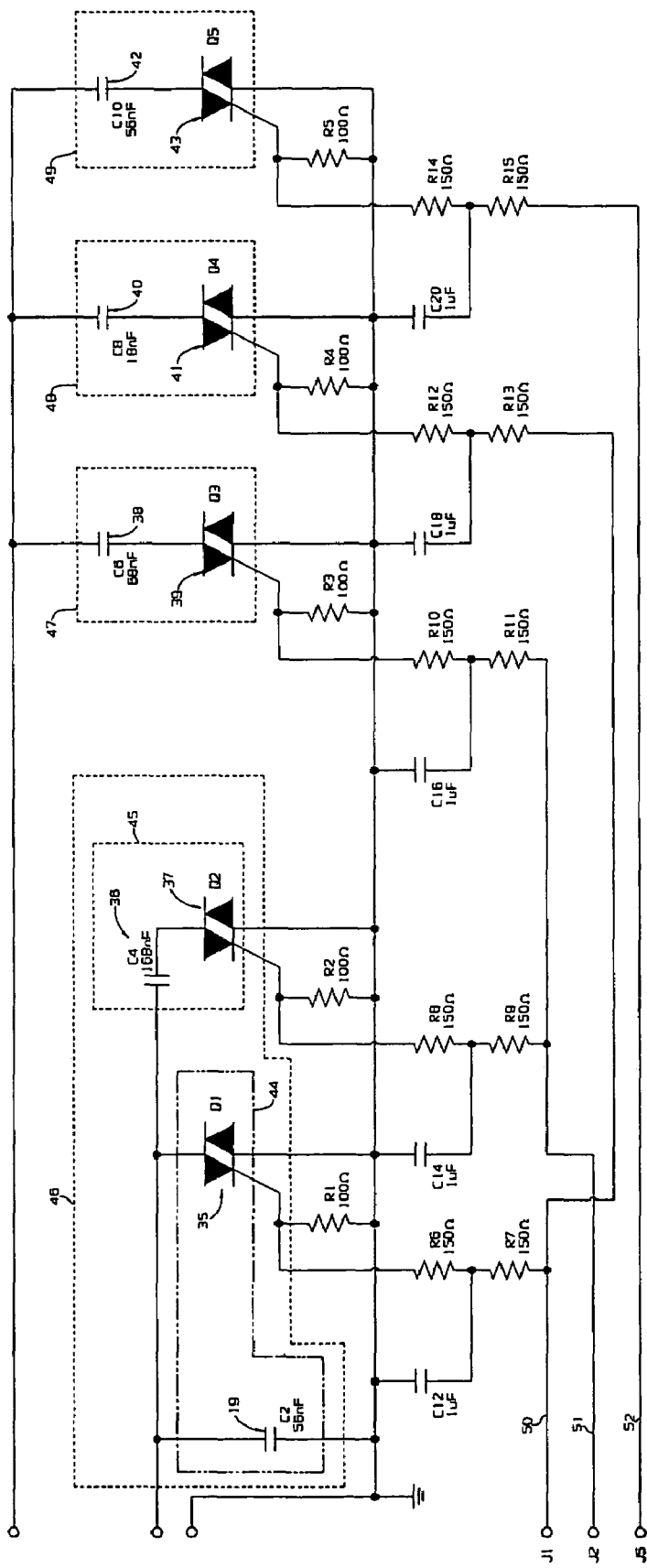
FIG. 84 shows a schematic diagram of a triac circuit employing the invention as used in the output of a multiple frequency generator.

FIG. 84 illustrates the use of a triac circuit in a preferred embodiment of the invention as depicted in FIGS. 80 and 81. The triac circuit, of FIG. 84, is used to modify the output of a multiple frequency ultrasound generator. In particular, the modification circuitry is comprised of five capacitor passive components 19, 36, 38, 40, and 42 and associated triacs 35, 37, 39, 41, and 43. The triacs switch the modification circuitry into and out of the output stage of a multiple frequency ultrasound generator. In a typical application, the output of an ultrasound generator is connected between the +RF and −RF terminals, as shown in FIG. 84. The ultrasound transducer array is connected between the +RF and GND terminals. FIG. 84 also contains a more complex parallel structure defined by the modification circuitry formed by capacitors 19 and 36 and triac 37 in parallel with the AC switch, triac 35.

The first structure 44 defined in FIG. 84 is formed by capacitor 19 and triac 35. This first structure 44 is a parallel structure and is connected in the conduction line that typically connects −RF to GND. Thus, when triac 35 is off, the capacitor 19 is inserted between −RF and GND. When triac 35 is on, capacitor 19 is shorted out which effectively connects −RF to GND. The practical effect of this first structure 44 is to place capacitor 19 in series with the transducer array when triac 35 is off and to connect the transducer array directly to the ultrasound generator when triac 35 is on. This arrangement is useful when generating the highest frequency in a multiple frequency ultrasound generator.

Capacitor 36 and triac 37 demarcate the second structure 45 in FIG. 84. This second structure 45 is a series structure and is connected between the nodes labeled −RF and GND. Thus, when triac 37 is on, capacitor 36 is inserted between −RF and GND. The reverse effect can be seen when triac 37 is off. When capacitor 36 is open circuited, capacitor 36 is effectively removed from the circuit. The practical effect of this second structure 45 is to place capacitor 36 in series with the transducer array when triac 37 is on. Assuming triac 35 is off, it will increase the capacitance, in series with the transducer array, to capacitors 19 and 36. This is useful when generating the second frequency (counting down from the highest) in a multiple frequency ultrasound generator.

The above two structures can form a more complex structure 46 which is an active/passive modification circuitry comprising capacitors 19, 36 and triac 37. This modification circuitry is in parallel with triac 35 to form the third structure 46, which is a parallel structure. The practical effect of this third structure 46 is to connect the ultrasound generator output directly to the transducer array when triac 35 is on. When triac 35 is off, it will place a capacitance in series with the transducer array (either capacitor 19 or 19 plus 36 depending on the state of triac 37) when triac 35 is off. This is useful when generating lower frequencies in a multiple frequency ultrasound generator, because when triac 35 is on, it eliminates the higher frequency structures from the system.

The fourth structure 47 present, as shown in FIG. 84, is comprised of capacitor 38 and triac 39, which form a series structure. When triac 39 is on, capacitor 38 is inserted between +RF and GND. In the case of triac 39 being off, capacitor 38 is open circuited, which effectively removes capacitor 38 from the circuit. The practical effect of this fourth structure 47 is to place capacitor 38 in parallel with the transducer array when triac 39 is on. The effect of this is to increase the capacitance in parallel with the transducer array. This is useful when generating the second frequency in a multiple frequency ultrasound generator. It allows for the addition of the appropriate capacitance, making the power delivered at the second frequency equal to the power at the first frequency.

The fifth structure 48, as shown in FIG. 84, comprises capacitor 40 and triac 41. The fifth structure 48 has the same effect as the fourth structure, (i.e., it increases or decreases the amount of capacitance in parallel with the transducer array depending on the state of triac 41). This is useful when generating the third frequency in a multiple frequency ultrasound generator. The power is kept equal to the first two frequencies by the increase or decrease of capacitance at the third frequency.

The sixth structure 49, as shown in FIG. 84, is comprised of capacitor 42 and triac 43. The sixth structure 49 is another series structure, which increases or decreases the capacitance in parallel with the transducer array depending of the state of triac 43. This is useful when generating the fourth frequency in a multiple frequency ultrasound generator. It adds sufficient capacitance to make the power at the fourth frequency equal to the first three frequencies.

Figure 85A:
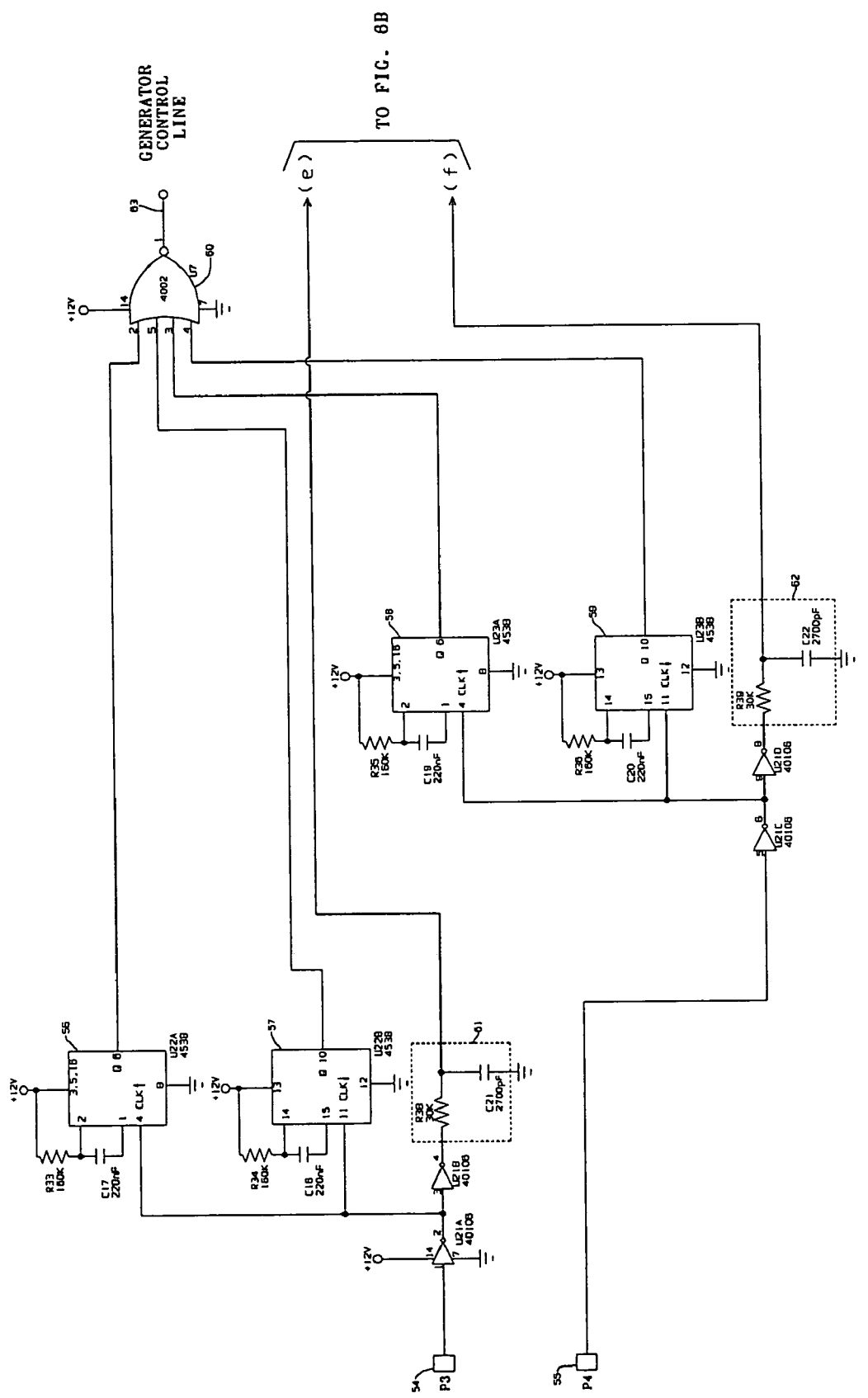
FIGS. 85A and 85B show a schematic diagram of a control circuit that produces on and off signals for the gates of the triacs in FIG. 84 and on and off signals for the frequency generation of the ultrasound generator.
Figure 85B:
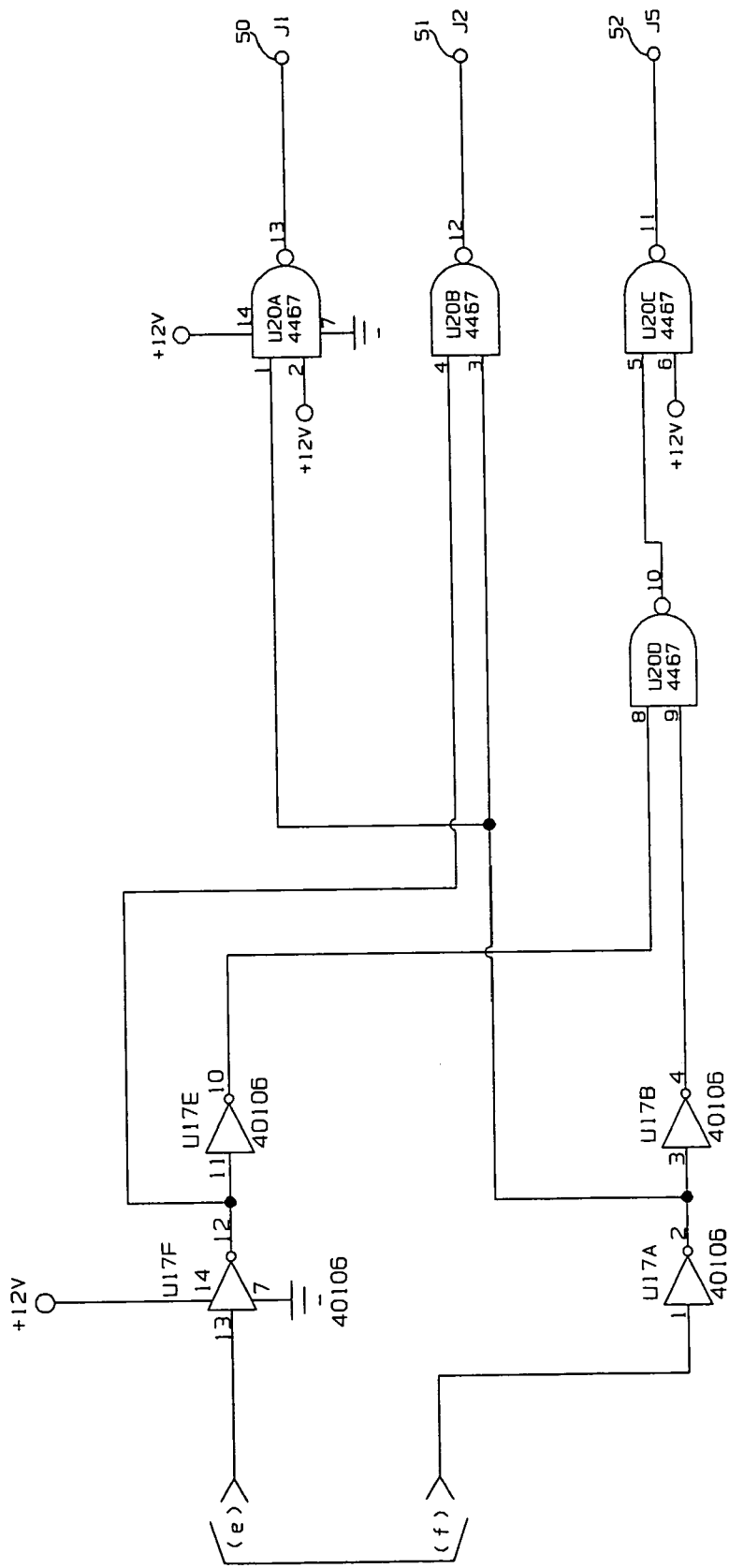
Figure 86:
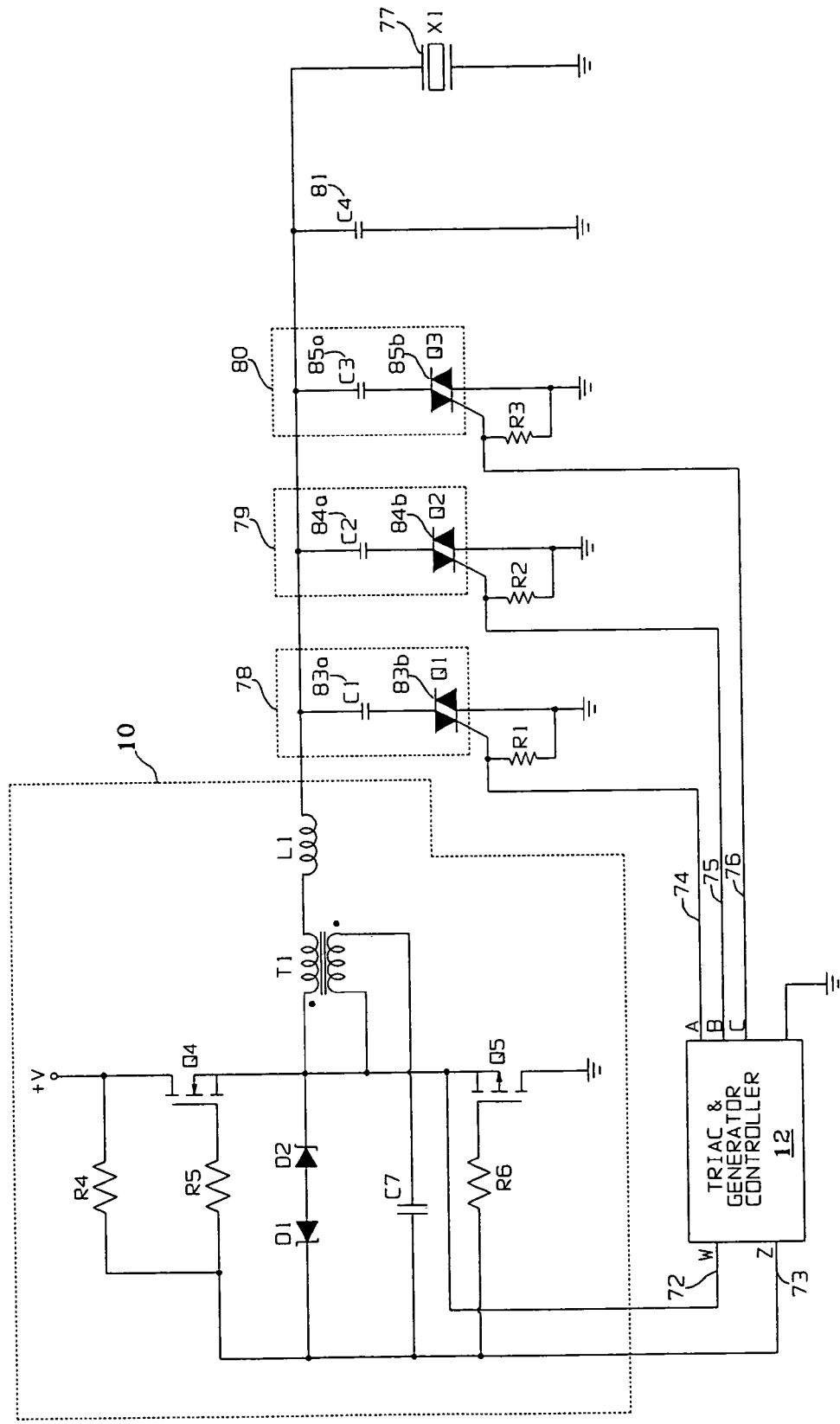
FIG. 86 shows a schematic diagram of an ultrasound frequency oscillator with a triac network in the output to step sweep the frequency output of the oscillator.

The five gates of triacs 35 to 43 can be controlled individually, as are the gates as depicted in FIG. 86. However, as shown in FIG. 84, the gates for triacs 35 and 41 are controlled by the same signal 50. Similarly, the gates for triacs 37 and 39 are controlled by the same signal 51. Finally, the gate for triac 43 is controlled independently by signal 52. The reason for the mixture of dependent and independent control of the various gates is that, in the logic design of this particular circuit, the truth table for the gates of triacs 35 and 41 are identical. The same is true for the gates of triacs 37 and 39. The signals from 50, 51 and 52 come from the control circuitry as depicted in FIGS. 85A and 85B.

The FIGS. 85A and 85B illustrate a control circuit for the circuits in FIG. 84. In FIG. 85A, the inputs 54 and 55 accept a binary code to determine the state of the triacs in FIG. 84. The logic in FIG. 85B decodes the binary code to generate the gate drive signals for the triacs in FIG. 84. The drive signal can be a positive voltage to the gate that will turn on the triac allowing the triac to conduct. The turn off signal is more complicated. To keep a triac conducting or in the on state, a current above a minimum current or the threshold current is sufficient. Therefore, to turn off a triac, the current flow has to be zero or less than the threshold current. The gates of the triac also need an off signal, usually zero volts. The "triac turn off time" as used herein is defined as the time required to accomplish the turn off of the triac with the gate at zero and with no current flow in the triac. The generator control line 63 in FIG. 85A goes low when the generator must be turned off to allow a triac to turn off (that is, when the generator is turned off, the output current decays to zero which lowers the current through the triac to below its threshold current, thus allowing the triac to turn off). The controller functions as follows. When the signal to inputs 54 or 55 is changed, one or more of the monostable multivibrators 56, 57, 58 or 59 triggers a high level output for approximately 37 milliseconds. These outputs proceed into NOR gate 60 and lower the voltage to the generator control line 63 for 37 milliseconds. The time the generator control line 63 is lowered depends on the time required for the energy stored in reactive components to decay, as well as on the application energy feedback. For example, in the case of a cleaning tank, the sound energy in the tank feeds back into the transducer, which will generate an AC ultrasound voltage on the output stage of the generator. This feedback will typically take about 20 milliseconds to decay below the threshold of the triac. It is for this reason than the monostable multivibrators 56, 57, 58, or 59 will output a signal for approximately 37 milliseconds, allowing for the above-mentioned conditions to be met. This 37 millisecond signal has the effect of turning the generator off and therefore stops the ultrasound current from flowing through the "on" triacs. The signal change representing the new binary code is delayed about 50 microseconds. This delay is accomplished by either a resistor and capacitor combination 61 or by resistor and capacitor combination 62 or by both. The purpose of this delay is to make sure that the generator has accomplished its turn off sequence before the binary code is decoded into the new set of triac gate signals. It is acceptable to have the zero gate signal to the triac applied at any time with respect to the generator off signal. The only mandatory condition for the generator off signal is that the triac current be below the threshold (referred to herein as D2) and that it and the triac zero gate signal (referred to herein as D1) be concurrent for a time equal to or greater than the triac turn off time. The logic in FIG. 85B decodes the signals in a way that is well known to those familiars with NAND and invert logic. The gate signals are output onto 50, 51 and 52, as shown in FIG. 84. The high level outputs provide the on signal for the respective triacs, which will be turned on, and a low level output on the gates of the other triacs.

The binary code for the logic in FIGS. 85A and 85B is (P1, P2)=(0,0) for the highest frequency, (P1, P2)=(1,0) for the second frequency, (P1, P2)=(0, 1) for the third frequency, and (P1, P2)=(1,1) for the fourth frequency.

Figure 87:
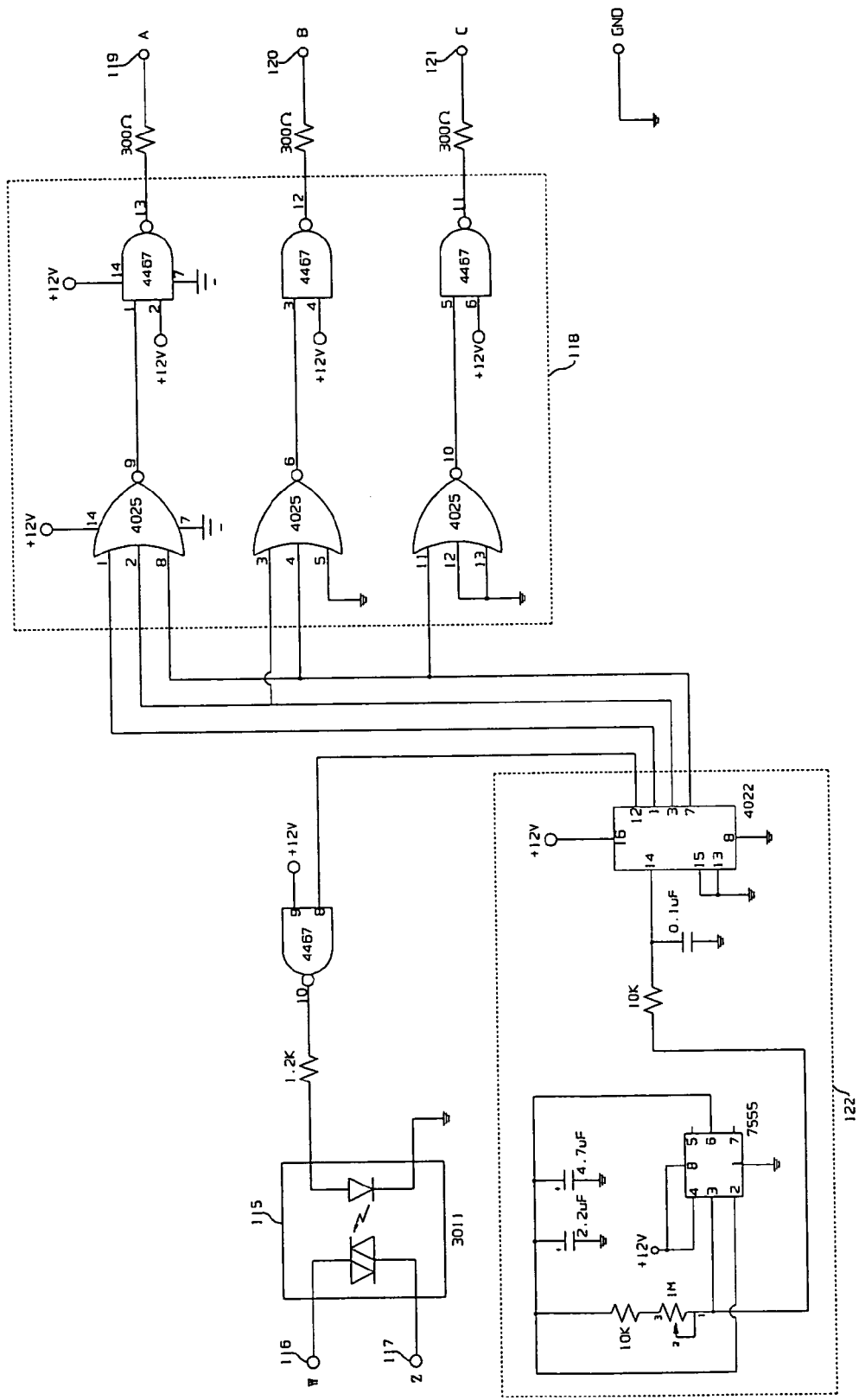
FIG. 87 shows a schematic diagram of a control circuit that produces on and off signals for the gates of the triacs in FIG. 86 and on and off signals for the oscillator in FIG. 86.

FIG. 86 depicts another preferred embodiment of this invention. The output frequency of an ultrasound oscillator 10 is changed by the addition of three series structures (78, 79, and 80) to the output of the oscillator. The first series structure 78 consists of capacitor 83a and triac 83b. The second series structure 79 consists of capacitor 84a and triac 84b. Finally, the third series structure 80 consists of capacitor 85a and triac 85b. A controller 12 turns the oscillator 10 on and off by way of isolated lines 72 and 73. The turn off and turn on signals are applied according to the circuit being a short circuit or an open circuit. The short circuit turns the oscillator off and the open circuit turns the oscillator on. The controller 12 also turns the triacs, 83b, 84b and 85b, on and off by way of lines 74, 75 and 76. Lines 74, 75, 76 are functionally similar to 50, 51 and 52 from FIG. 85B of this application. The controller 12 can contain circuitry similar to FIGS. 85A and 85B, so as to provide the turn off and on signal to the triacs, as shown in FIG. 86. An alternative to control function 12 of FIG. 86 is depicted in FIG. 87.

When the capacitance of the transducer 77 is defined to be a capacitance value 77, then with all the triacs in their off state, oscillator 10 produces a frequency approximately equal to f1 where $$f1 = \frac{1}{2\pi\sqrt{(L1(81+77))}}$$

When triac 83b is turned on by the controller 12, thereby putting a high level on line 74 during operation of the oscillator (while maintaining the high level on line 74 or while maintaining the current flow through triac 83b or maintaining both of these conditions, i.e., maintaining the on state of triac 83b), the oscillator changes frequency from the above value to approximately f2, where $$f2 = \frac{1}{2\pi\sqrt{(L1(83a+81+77))}}$$

Therefore, the oscillator frequency made a step change from frequency f1 to a lower frequency f2.

In a similar fashion, when triac 84*b* is then turned on by the controller 12, thereby putting a high level on line 75 during operation of the oscillator (while maintaining the on state of triacs 83*b* and 84*b*), the oscillator changes frequency from the above value to approximately f3, where $$f3 = \frac{1}{2\pi\sqrt{(L1(83a+84a+81+77))}}$$

Therefore, the oscillator frequency made a step change from frequency f2 to a lower frequency f3.

In a similar fashion, when triac 85*b* is then turned on by the controller 12, thereby putting a high level on line 76 during operation of the oscillator, the oscillator changes frequency from the above value to approximately f4, where $$f4 = \frac{1}{2\pi\sqrt{(L1(83a+84a+85a+81+77))}}$$

Therefore, the oscillator frequency made a step change from frequency f3 to a lower frequency f4.

The above examples show a method to step sweep the output frequency of an oscillator from a high frequency to a lower frequency by successively turning on additional series structures comprising a capacitor modification circuitry and a triac. According to the invention, it is then necessary for the controller 12 to output a short circuit between lines 72 and 73 to turn the oscillator 10 off before the triacs 83*b*, 84*b* and 85*b* can be turned off. In a preferred embodiment, the controller 12 turns off all the triacs during this generator off time. The generator off time is timed to be at least as long as the triac turn off time plus the decay time of the sound field. Then the cycle of turning on the triacs one at a time to step sweep from the highest frequency f1 to the lowest frequency f4 can occur again. The controller then starts another oscillator off time where all the triacs are turned off and the cycle repeats. This step swinging operation can be accomplished with the control circuit, as shown in FIG. 87.

It is clear to those skilled in the art that the circuit in FIG. 86 can produce other frequency cycles. With three series structures (78, 79, 80) having unequal values for capacitors 83*a*, 84*a* and 85*a*, a total of eight different frequencies are possible. The four listed above and $$f5 = \frac{1}{2\pi\sqrt{(L1(84a+81+77))}}$$
$$f6 = \frac{1}{2\pi\sqrt{(L1(83a+85a+81+77))}}$$
$$f7 = \frac{1}{2\pi\sqrt{(L1(84a+85a+81+77))}}$$
$$f8 = \frac{1}{2\pi\sqrt{(L1(85a+81+77))}}$$

Any permutation of these eight frequencies (8! or 40,320 permutations) can be organized into a cycle by the controller 12 and supplied to the transducer. It should be noted that for any frequency change that does not require a triac to be turned off, the frequency change can be accomplished without the controller 12 turning off the oscillator. However, if any frequency change occurs where one or more triacs have to be turned off, then the controller 12 concurrently turns off the oscillator for a time at least as long as the turn off time of the triacs plus the decay time of the sound field.

FIG. 87 shows a schematic diagram of a control circuit representing the controller 12 of FIG. 86. Since in the discussion of FIG. 86 above the main functional characteristics of FIG. 87 were mentioned, only a brief description of the main elements will be discussed herein below. The controller 12 (or 101 from FIG. 88) produces on/off signals for the gates of the triacs and on/off signals for the oscillator. The signal to turn on/off the oscillator 10 is sent by way of lines 116 and 117 (these lines are equivalent to lines 72 and 73 in FIG. 86). This on/off signal is generated by element 115 when the output is a short circuit, thereby turning off oscillator 10. The component 118 decodes the signal to be output onto 119, 120 and 121 (these lines are equivalent to lines 74, 75 and 76 of FIG. 86) which is the signal sent into the triacs (83*b*, 84*b*, and 85*b*). The element 122 is in charge of sending the signals to be interpreted by 118 and 115.

Figure 88:
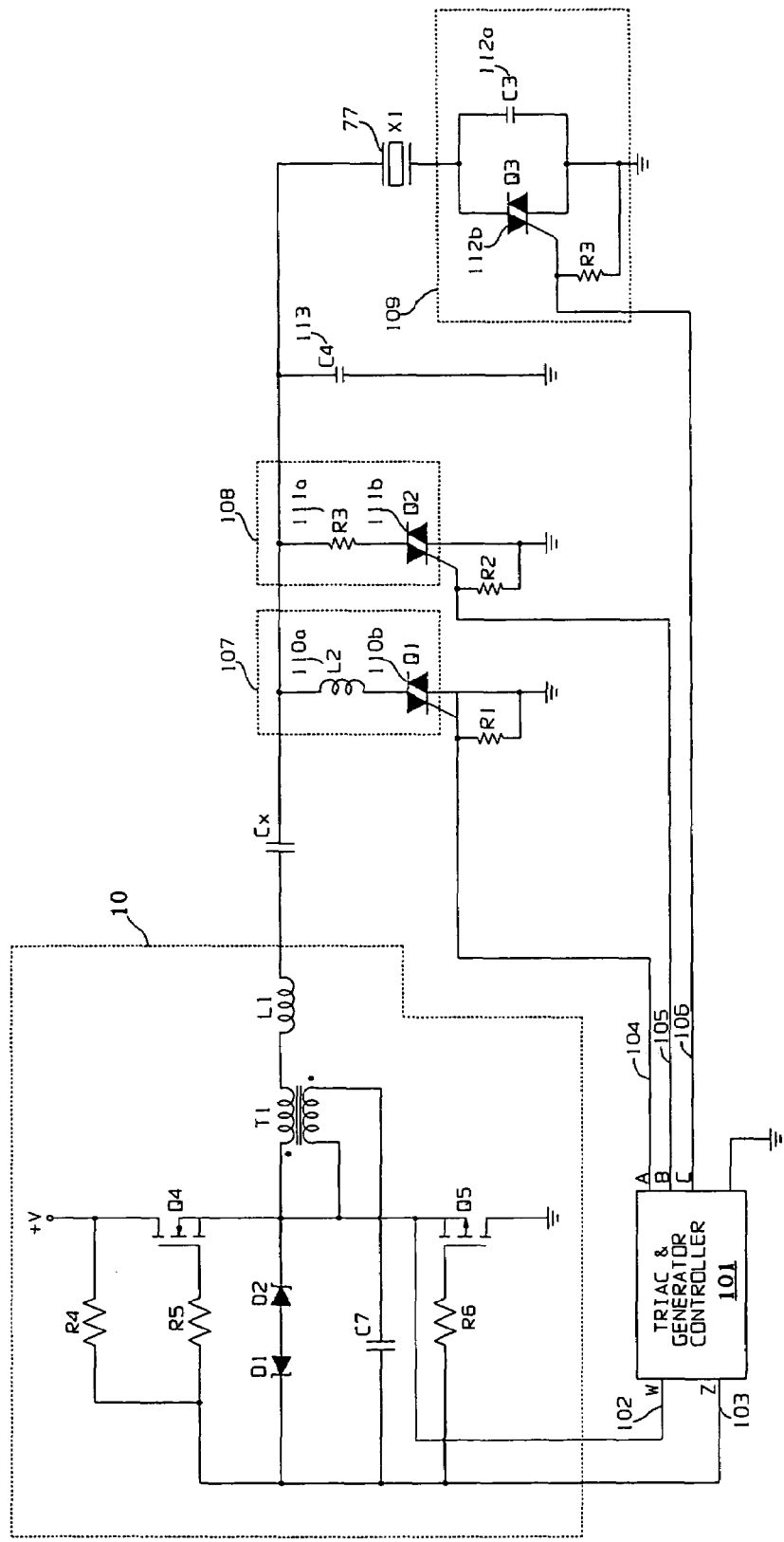
FIG. 88 shows a schematic diagram of an ultrasound frequency oscillator with a triac network in the output using inductive, capacitive and resistive modification circuits.

FIG. 88 shows that an inductive modification circuit, a resistive modification circuit and a parallel structure can also modify an oscillator 10. The operation of FIG. 88 is similar to that described for FIG. 86. The control 101 for FIG. 88 can be similar to the control shown in FIG. 87.

With reference to FIG. 88, the series structure 107, comprising inductor 110*a* and triac 110*b*, will increase the frequency of the oscillator when triac 110*b* is turned on. The series structure 108 comprising resistor 111*a* and triac 111*b* will decrease the output amplitude and power when triac 111*b* is turned on. The parallel structure 109 comprising capacitor 112*a* and triac 112*b* will increase the frequency when triac 112*b* is turned on.

Another application of the present invention is to change the output power and amplitude of an ultrasound generator. With some ultrasound generators that are not of the self-oscillating type (FIG. 86 is an example of a self-oscillating type, U.S. Pat. No. 4,743,789 is an example of a non self-oscillating type) their output power and amplitude are dependent on the total amount of capacitance connected to their outputs. Connecting series structures, comprising a capacitor and a triac, as shown, for example, in FIG. 86, to the output of these non self-oscillating generators allows the power and amplitude to be changed by controlling the state of the triacs. With n series structures, 2 raised to the power n power levels and amplitude levels can be programmed into the controller.

FIGS. 84 through 88 illustrate triacs utilized as the AC switch. However, as one skilled in the are will readily appreciate, any AC switch can be used (not just triacs). There are many ways to build AC switches, such as from transistors, including bipolar junction transistors (BJTs), metal oxide semiconductor field effect transistors (MOSFETs), and insulated gate bipolar transistors (IGBTs). Additionally, suitable AC switches can be constructed from thyristors, such as gate turn-off thyristors (GTOs), silicon controlled rectifiers (SCRs), MOS controlled thyristors (MCTs), and asymmetrical silicon controlled rectifiers (AS-CRs). Other AC switches or devices with forced turn off and turn on capability, such as a bi-directional lateral insulated gate bipolar transistor or a relay, can be used. Such a transistor is described in U.S. Pat. No. 5,977,569. Triacs are preferred because they are inexpensive and have only one gate lead. As is well know in the art, most of the other AC switches, including transistors and thyristors, require more than one control lead to be driven. Often these multiple drives have to be isolated from one another. Gate turn off thyristors (GTOs) can make suitable AC switch, particularly if the cost of two control leads can be justified, because GTOs can be forced off by their gate leads.

Figure 89B:
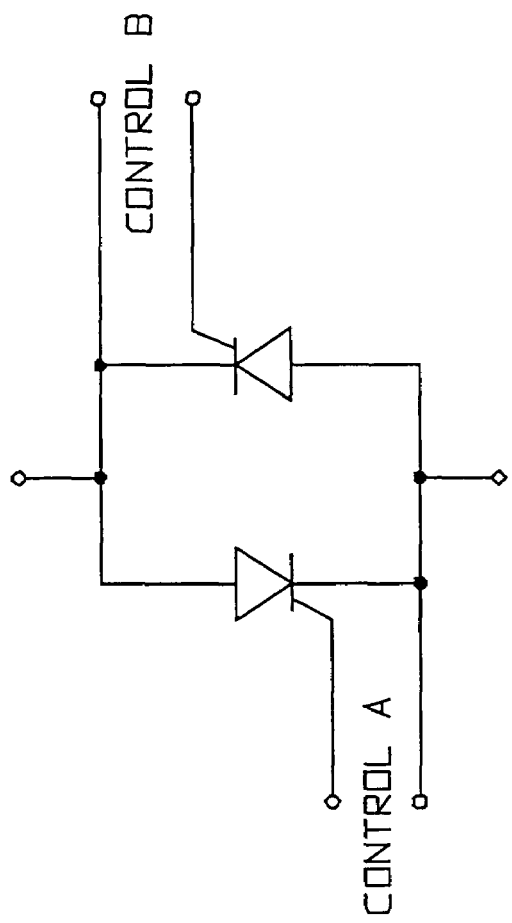
FIGS. 89A, 89B and 89C show schematic diagrams of AC switches formed from various active components.
Figure 89A:
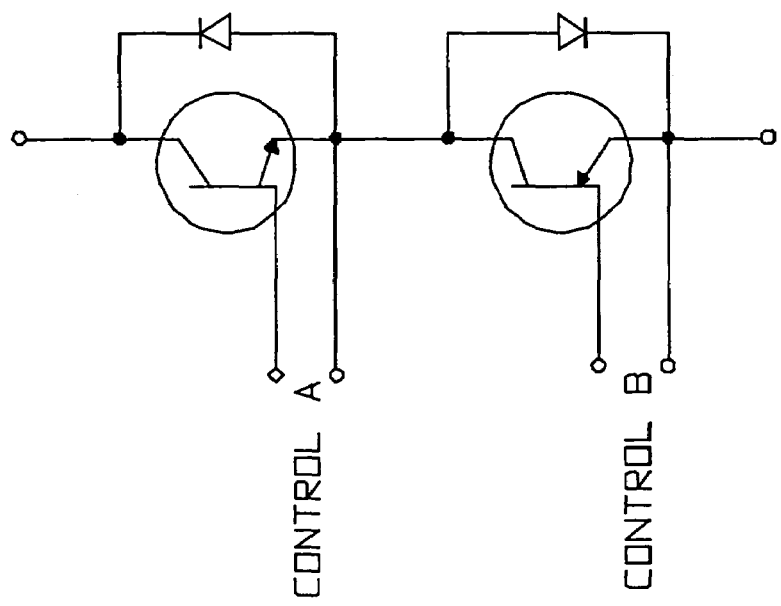
Figure 89C:
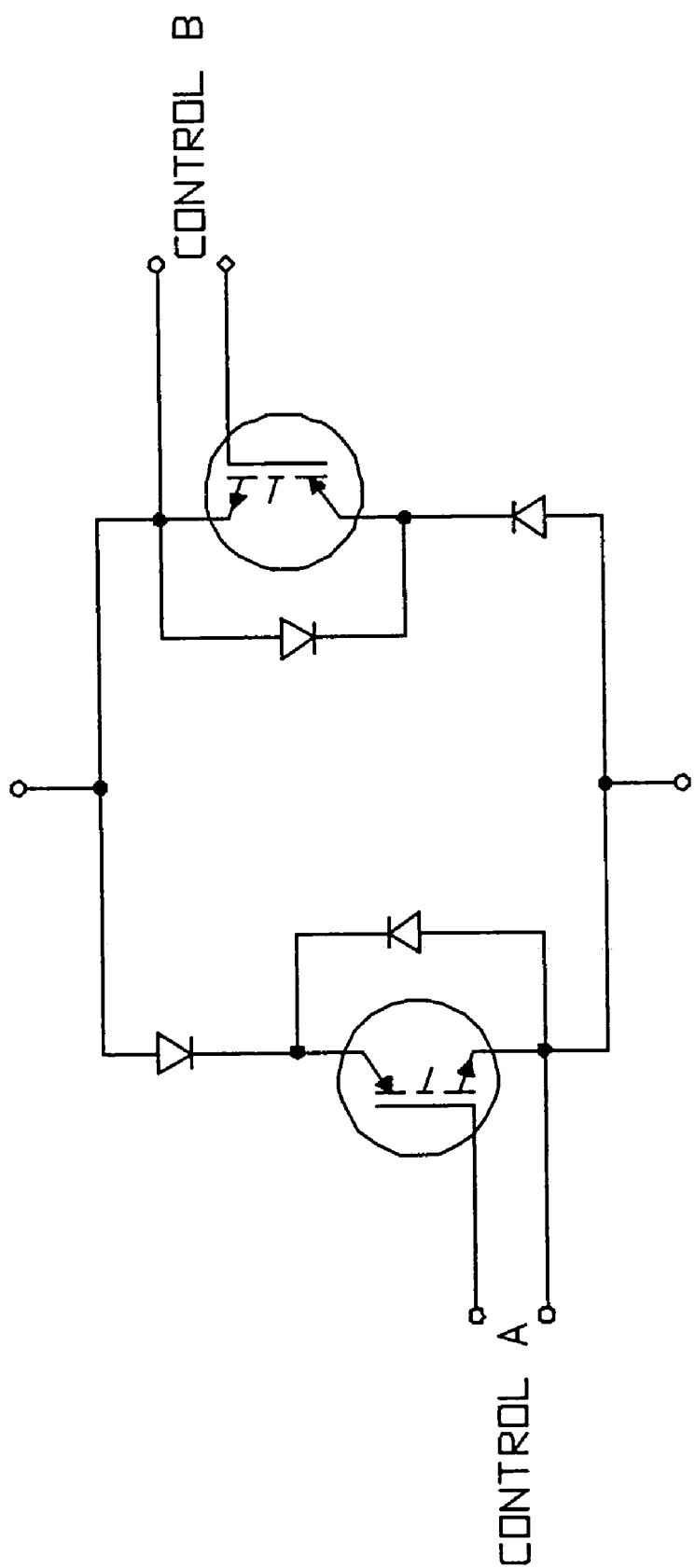

FIG. 89A shows an AC switch in a series transistor configuration where BJTs (one N channel BJT and one P channel BJT) are used. FIG. 89B shows an AC switch made in a parallel thyristor configuration where SCRs are used. This FIG. 89B circuit is commonly known as back to back SCRs. Those skilled in the art can readily appreciate the use any active components (i.e., active components that can function as a switch) either in a parallel configuration or in a series configuration to form an AC switch. Typically, diodes are needed in the series or parallel configuration to pass current or to protect the active device. FIG. 89C shows a transistor parallel configuration using IGBTs where the AC switch comprises four diodes. As used herein, the phrase "series/parallel active device configuration" mean active components either in series or in parallel. The active components can be a transistor configuration or a thyristor configuration or a combination of active devices and zero or more diodes. The active devices in series or parallel configuration will form an AC switch where one active device conducts current during one half of an AC cycle and the other active device conducts current during the other half of the AC cycle.

In an ultrasonic or microsonic cleaning or processing liquid, it is known that a particular frequency or a set of closely spaced frequencies will resonate a certain size population of bubbles or voids within the liquid. A conventional sweeping frequency ultrasonic or microsonic cleaning or processing signal produces a particular frequency or a set of closely spaced frequencies followed by the next particular frequency or set of closely spaced frequencies adjacent to the first particular frequency or set of closely spaced frequencies.

Unfortunately, cavitation efficiency suffers with this type of conventional sweeping frequency ultrasonic or microsonic cleaning or processing signal because the first particular frequency or set of closely spaced frequencies depletes members of that certain size population of bubbles or voids within the liquid leaving a smaller population for the second adjacent particular frequency or set of closely spaced frequencies to resonate.

Figure 90:
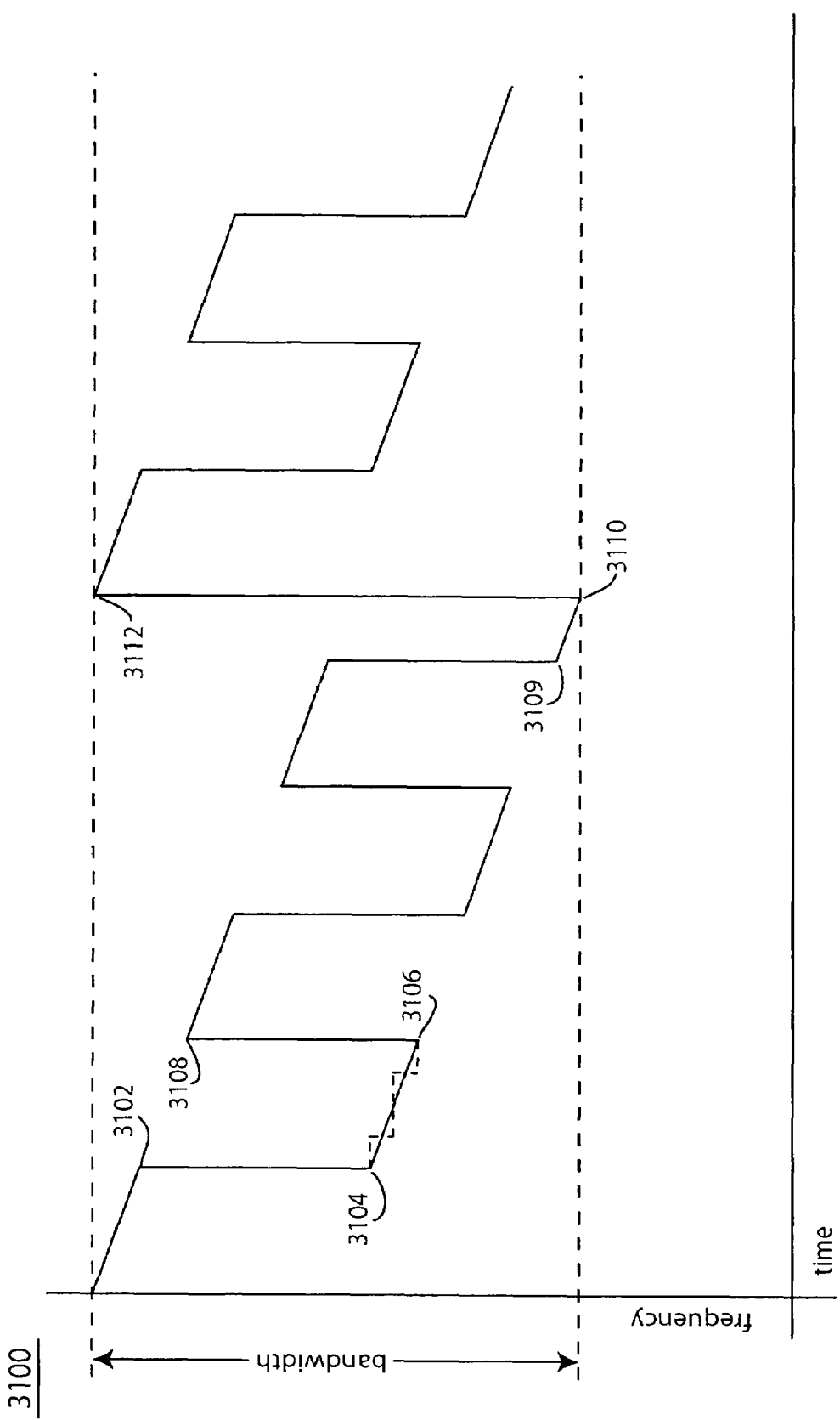
FIG. 90 shows a waveform of a sweeping frequency signal according to the invention.

There is shown in FIG. 90, a sweeping frequency drive signal 3100 that overcomes the above-described cavitation efficiency limitation of the prior art. When a certain size population of bubbles or voids within the liquid begins to be depleted causing a loss in cavitation efficiency, drive signal 3100 jumps, changes or rapidly sweeps to a non adjacent frequency within the bandwidth of the transducer array, such that the process continues with improved cavitation allowed by the new bubble population associated with this new non adjacent particular frequency or set of closely spaced frequencies.

In a preferred embodiment, drive signal 3100 can be maintained in the upper half of a bandwidth. The bandwidth is typically 10% of the center frequency (unless the system employs a special design/procedure, e.g., overlapping transducers frequency ranges). Therefore, for a center frequency at the high end of the microsonic frequency range (350 khz), the bandwidth is typically 35 khz. For 40 khz ultrasonic transducers, the bandwidth is typically about 4 khz. After a defined period of time (i.e., before cavitation efficiency suffers) at point 3102, the frequency is changed to a new frequency that is typically one half bandwidth lower than the current frequency. This change in frequency may occur by sweeping the frequency to the new lower frequency (not shown; wherein the sweep time is typically less than 25% of the defined period of time), or stepping the frequency to the new lower frequency, as shown in FIG. 90. The length of this "defined period of time" is dependent on the frequency, power density, sweep rate, type of chemistry and chemistry conditions such as temperature. "Defined periods of time" vary inversely with respect to frequency and span the range from ten microseconds to two milliseconds. At point 3104, this sweeping frequency continues from this new lower frequency. After the defined period of time (described above) at point 3106, the frequency jumps to a new higher frequency (point 3108) that is typically one half bandwidth higher than the current frequency.

While a one half bandwidth frequency jump is typical, other amounts are possible. For example, the frequency may be jumped by a much larger percentage of the bandwidth, e.g., from a frequency proximate the lower limit of the bandwidth to a frequency proximate the upper limit of the bandwidth, such as from point 3110 to point 3112. Less than one-half bandwidth changes can also be used and are an improvement over the prior art; however, they are not as optimum an improvement as the preferred embodiment described herein.

Further, while the system is described above as sweeping the frequency between points 3104 and 3106, other configurations are possible. For example, the frequency may be maintained constant (not shown) during the defined period of time. Alternatively, the frequency may be changed (between points 3104 and 3106) via one or more frequency steps (shown in phantom); or the set of closely spaced frequencies between points 3104 and 3106 may be random frequencies (not shown).

This frequency sweeping and frequency jumping continues until striking the lowest frequency in the bandwidth (at point 3110). At this point, the frequency jumps to the highest frequency in the bandwidth (to point 3112), and the sweeping and jumping process is repeated until the lowest frequency in the bandwidth is reached again (not shown). This high cavitation efficiency process is repeated and continued for the time needed in that particular bandwidth.

If a multiple frequency generator is driving a multiple frequency transducer array with a set of defined bandwidths (e.g., multiple harmonic or overtone bandwidths), then after the time needed in a particular bandwidth has elapsed, the drive signal may change to a different bandwidth and may produce a similar high cavitation efficiency signal in that different bandwidth. Also, in the case of a multiple frequency generator driving a multiple frequency transducer array with a set of defined bandwidths, the change or jump (upon the depletion of a certain size population of bubbles or voids within the liquid) can be to a frequency in another bandwidth. This has the added advantage that besides a new bubble population for increased cavitation efficiency, the cavitation in the prior bandwidth typically produced bubbles that are resonant in the new bandwidth to which the signal changed or jumped.

In the prior art generator and transducer array systems, it is typical to have amplitude modulation of a frequency modulated waveform as the output signal from the generator and driving the transducer array. A typical amplitude modulation pattern is full wave modulation and a typical frequency modulation pattern is a triangular sweeping frequency waveform. The inventor has found that the cleaning or processing efficiency when using this type of waveform drops off as the process continues because the single form of cavitation produced by the given waveform can not do all aspects of the process efficiently. The inventor has found that using two forms of cavitation, where the first form is predominantly stable cavitation and the second form is predominantly transient cavitation, allows the process to proceed to a more complete level, for example, in the case of a cleaning process, the two forms of cavitation applied in succession over a given time span result is a lower percentage of particles left on the part being cleaned than will occur with one form of cavitation being applied over the same time span.

Figure 91:
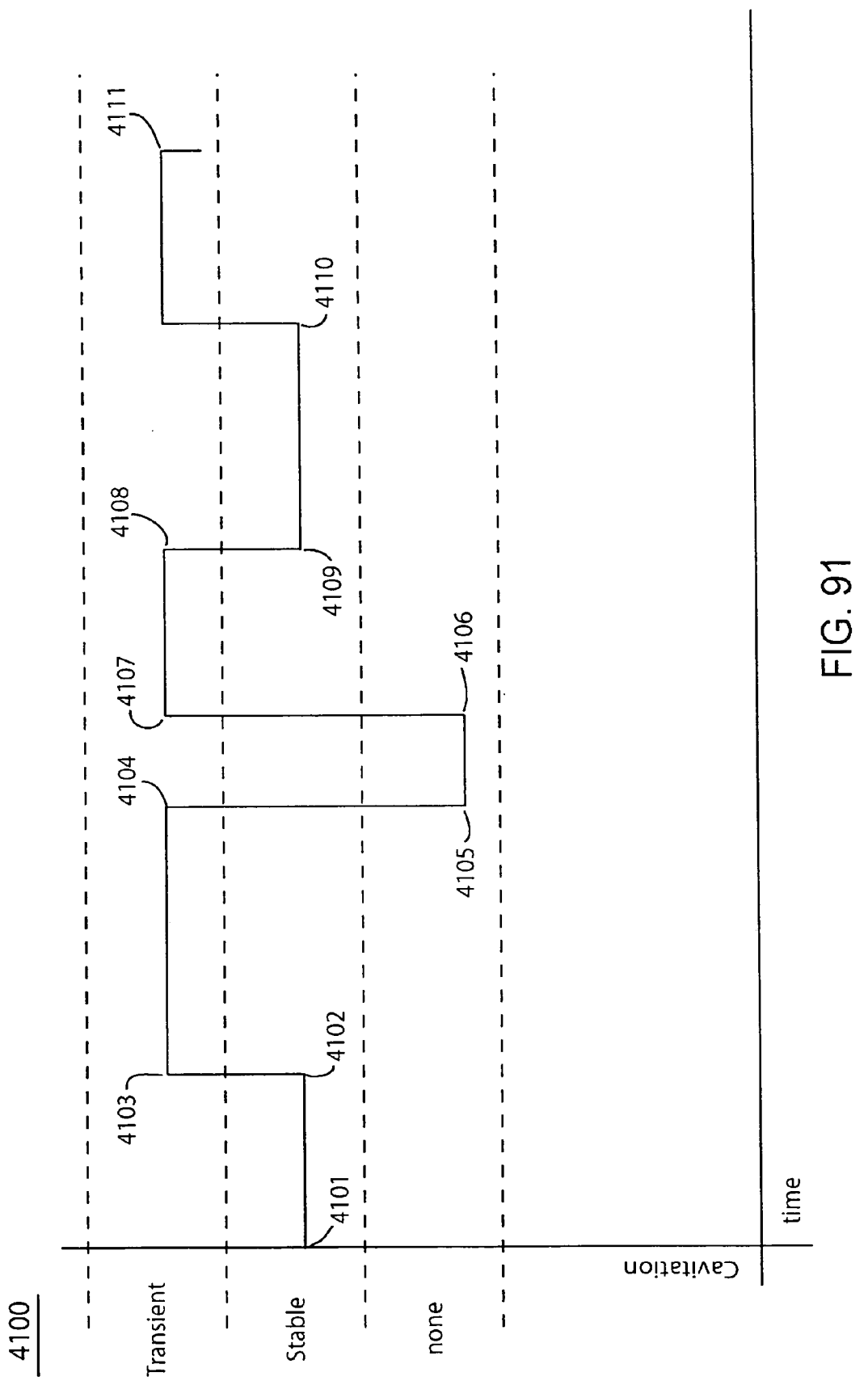
FIG. 91 shows a time sequence of different forms of cavitation according to the invention.

There is shown in FIG. 91, a diagram 4100 that shows a succession of time periods with different forms of cavitation in successive time periods. In the first time period shown between points 4101 and 4102, there exists a first form of cavitation where the cavitation is predominantly stable cavitation. The predominantly stable cavitation can be produced by one or more of the techniques described below. In the second time period shown between points 4103 and 4104, there exists a second form of cavitation where the cavitation is predominantly transient cavitation. The transient cavitation can be produced as described below. In the third time period shown between points 4105 and 4106, there exists a cavitation region called "none". This is typically an off period of the generator, where no acoustic energy is delivered to the transducer array. The term "none" will also mean a condition where there is acoustic energy in the liquid but that acoustic energy is below the threshold of cavitation or so low that the cavitation produced is below that which is practical to accomplish the cleaning or processing. This "none" condition can also be achieved by excess gas in the liquid, absorption of acoustic energy by the part being cleaned or by contamination in the liquid. In FIG. 91 point 4107 to point 4108 is a time period of predominantly transient cavitation followed by a successive time period of predominantly stable cavitation from points 4109 to 4110, demonstrating that different order to the forms of cavitation will have a beneficial effect on the process. FIG. 91 ends showing between points 4110 and 4111a time period of predominantly transient cavitation, but it is clear to one skilled in the art that any succession of time periods where at least one time period has predominantly stable cavitation and at least one of the successive time periods has predominantly transient cavitation, or the reverse order of this, will produce the increased cleaning or processing efficiency described herein.

The following waveforms and systems are used to produce predominantly stable cavitation and the existence of any one or combination at the output of a generator or system supplements the classical definition of stable cavitation for the purposes of this invention. (1)

Rapidly changing frequencies (sweep rates) where the frequency change (df/dt) is greater than $(0.106)*(fc)$ Mhz per second, where fc is the average of the highest frequency in khz and the lowest frequency in khz in the set of rapidly changing frequencies (typically, this set of frequencies is within a bandwidth of operation of the transducer array) and the delivered power is in the range of 25 to 60 watts per transducer. (2) Narrow rectangular pulse width amplitude modulation where the pulse width is less than 24/Pp milliseconds, where Pp is the peak power of the pulse in watts and the frequency change (df/dt) ranges from zero to less than $(0.106)*(fc)$ Mhz per second. (3) Irregular shaped amplitude modulation where the area under the power versus time curve for each pulse is less than 24 milliwatt-seconds per transducer in the array. (4)

Changing to a new frequency set or bandwidth before the onset of imploding cavitations, this is typically before 24 milliwatt-seconds per transducer of acoustic power is delivered at the current frequency set or bandwidth. (5) Sweeping a full wave modulated waveform at a rate below $(0.106)*(fc)$ Mhz per second while chopping the amplitude into pulses that change in width to maintain an area under each pulse curve that is less than 24 milliwatt-seconds per transducer. (6)

Applying conventional normal power operation to a concurrent multiple ultrasound frequency system where the growth and decay of bubbles simulates the effects of stable cavitation.

Figure 94:
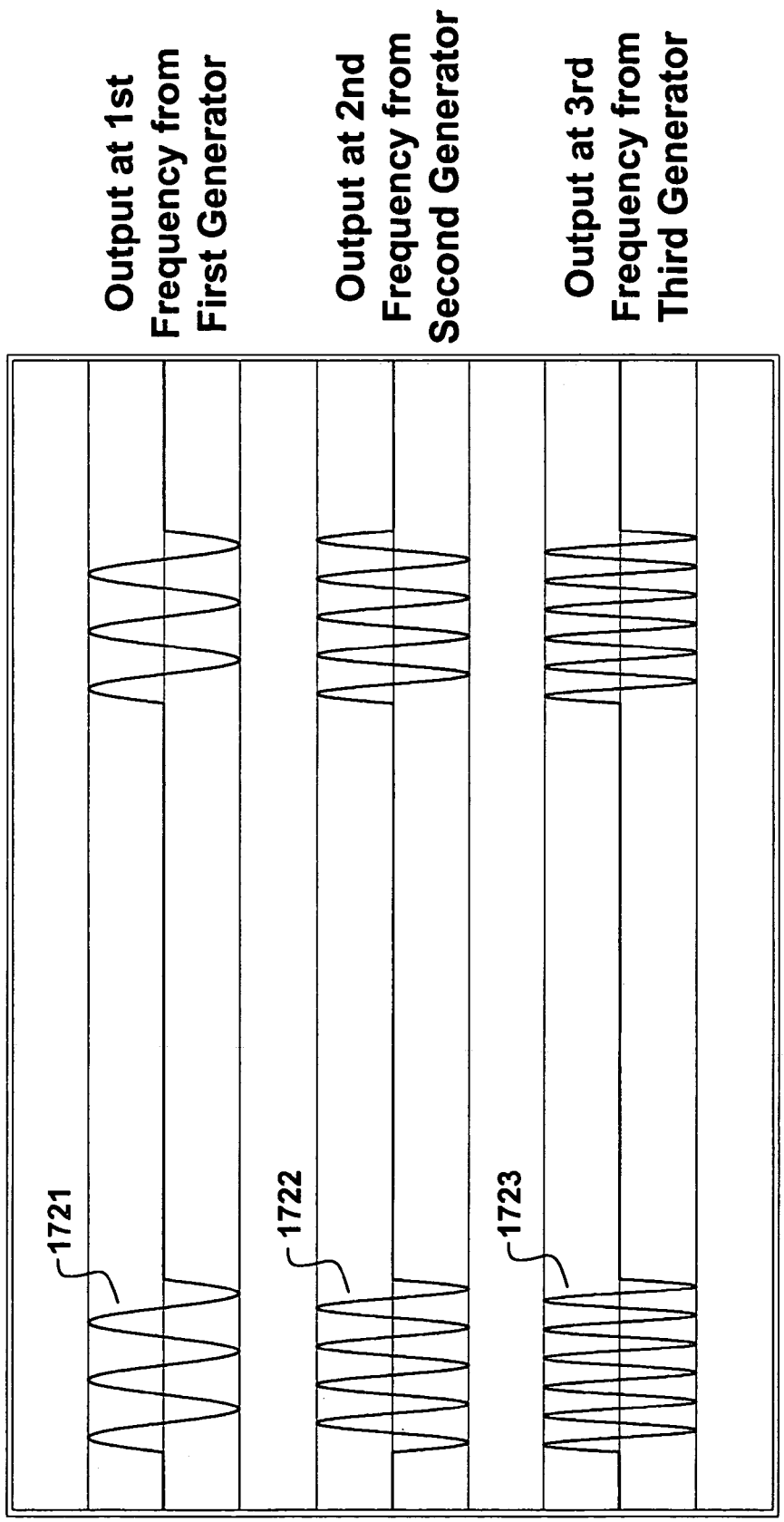
FIG. 94 shows an example of synchronized high peak power different frequency ultrasound bursts.

Waveforms to produce transient cavitation are well known to those skilled in the art of ultrasonic cleaning. Optimum sweep rates, typically in the range of 120 to 550 hz combined with wide pulses or full wave modulation (typically repetitive every 8.33 milliseconds or every 10 milliseconds) produce the best state of the art cavitation. Improved transient cavitation efficiency as described above and shown in FIG. 90 is a preferred embodiment for use in the time periods where transient cavitation is employed. For concurrent multiple ultrasound frequency systems, the teachings as shown in FIG. 94 are a preferred method to produce transient cavitation.

The teachings above and as shown in FIG. 91 have wide application for improving the inactivation of organisms (the word "organisms" will be used herein to mean microorganisms, spores, viruses and small lifeforms such as parasites) for processes such as disinfection, sterilization and pasteurization. The predominantly transient cavitation time periods are effective at breaking up clumps of organisms and removing organisms from instruments and other objects. The predominantly stable cavitation time periods maximize the production of active media in the liquid such as hydrogen peroxide, ozone, super oxygen, ions and other radicals which have a chemical inactivation effect on the organisms. During a follow on predominantly transient cavitation time period there is a synergistic effect between this chemical inactivation effect and the high localized temperatures associated with the transient cavitation implosions. This process as shown in FIG. 91 will be referred to herein as "a succession of predominantly stable and predominantly transient cavitation".

It has long been known that the microbiological action of certain microbiologically active chemicals such as glutaraldehyde or IPA is improved by the application of ultrasound to the microbiologically active chemicals. A review of the literature shows that this ultrasound was the type that has predominantly transient cavitation or was generated by equipment known to produce predominantly transient cavitation. The use of ultrasound with predominantly stable cavitation as described herein gives additional improvement in the speed of the microbiological effect of the microbiologically active chemicals. This microbiological effect is further improved by a succession of predominantly stable and predominantly transient cavitation.

The inventor has found that the addition of an electrolyte, for example, NaCl, to an aqueous solution, the application of UV light and/or the application of an electric current have a significant microbiological effect toward improving the speed of organism inactivation. Consider these organism inactivation processes along with the cavitation processes described herein, i.e., predominantly stable cavitation, a succession of predominantly stable and predominantly transient cavitation, predominantly transient cavitation and multiple frequency processes, and many improved (improvement is defined as achieving inactivation or reducing the process time needed to achieve a specified inactivation) organism inactivation processes result. Some of the most effective ones showing the greatest improvement over prior art are listed below.

Microbiologically active chemicals with a succession of predominantly stable and predominantly transient cavitation produced within this chemistry.

Aqueous chemistries with an electrolyte added, and electric current flowing through the chemistry.

Clear liquids such as water with UV light applied and a succession of predominantly stable and predominantly transient cavitation applied.

Microbiologically active chemicals with multiple frequencies applied to this chemistry.

Applying a succession of different frequencies (multiple frequencies) to the liquid.

Simulating the effects of stable cavitation with normal power operation of a concurrent multiple ultrasound frequency system by the growth and decay of bubbles to enhance the production of active media in the liquid such as hydrogen peroxide, ozone, super oxygen, ions and other radicals which have a chemical inactivation effect on the organisms It is understood by one skilled in the art that many other combinations of the eight stated process parameters, i.e., multiple frequencies, predominantly stable cavitation, predominantly transient cavitation, a succession of predominantly stable and predominantly transient cavitation, UV light, electric current, an electrolyte and microbiologically active chemicals, give improved ways to inactivate organisms.

Figure 92:
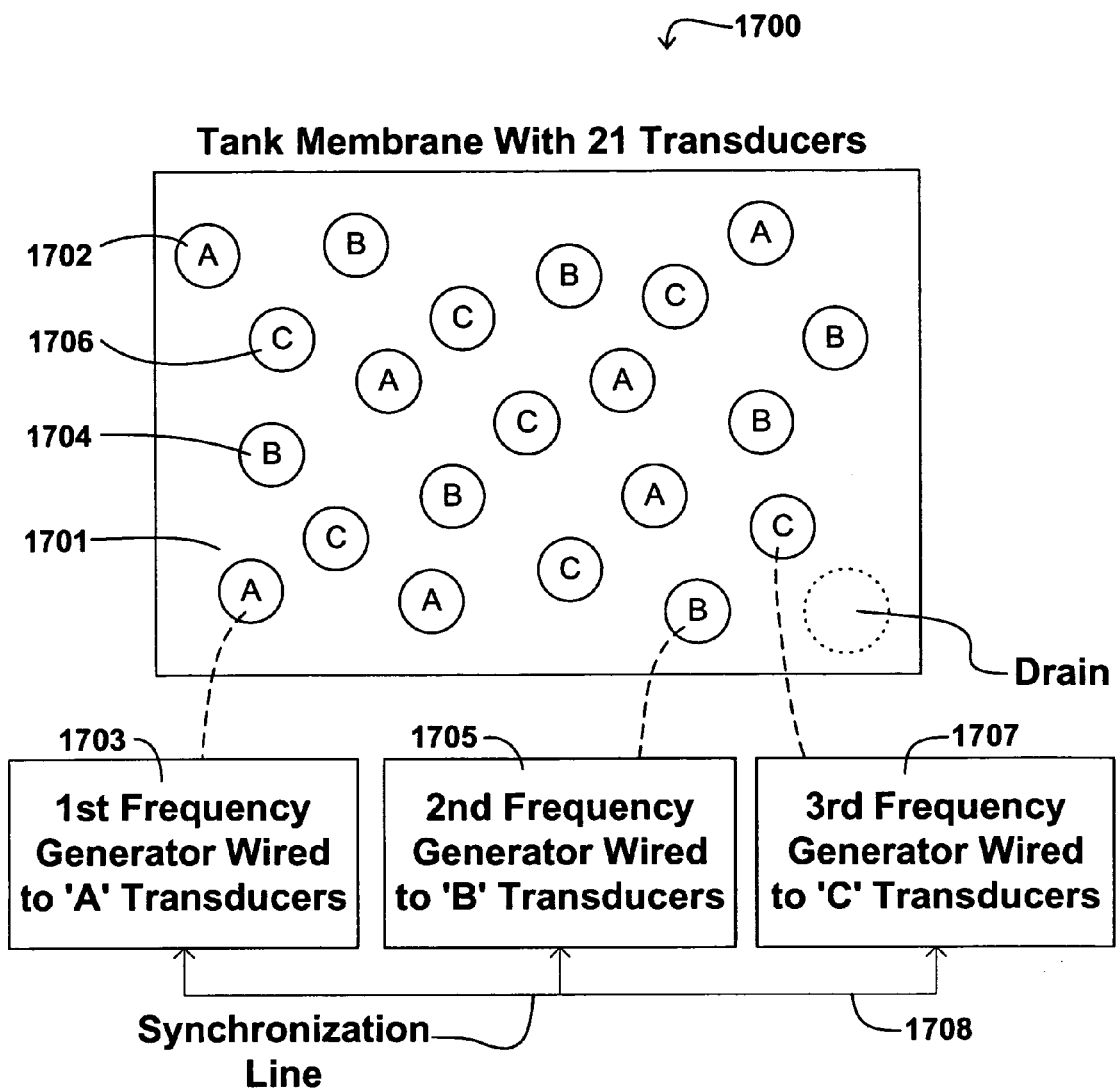
FIG. 92 shows a diagrammatic pictorial of a concurrent multiple frequency ultrasound system constructed according to the invention.

FIG. 92 illustrates an embodiment of the invention with a diagrammatic pictorial of a concurrent multiple frequency ultrasound system 1700 constructed according to the invention. A ultrasound tank bottom 1701 contains twenty-one randomly spaced transducers of three types, type A 1702 operate in a first frequency range and are wired to the first generator 1703, type B 1704 operate in a second frequency range and are wired to the second generator 1705, and type C 1706 operate in a third frequency range and are wired to the third generator 1707. The first generator 1703, second generator 1705 and third generator 1707 are synchronized by line 1708. This synchronization line 1708 functions to time output bursts of the different frequency ultrasound from each generator such that the bursts occur at the same time.

Figure 93:
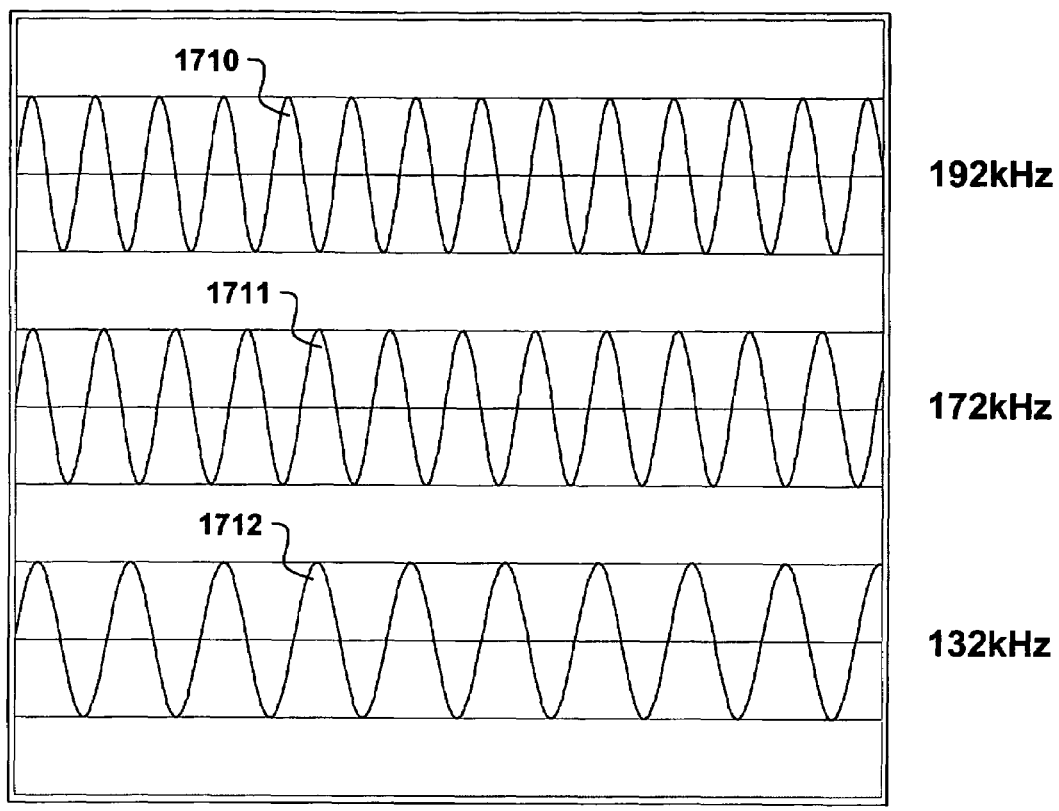
FIG. 93 shows three different frequencies that are applied concurrently to a tank.

FIG. 93 shows three different frequencies, 192 khz 1710, 172 khz 1711 and 132 khz 1712 that are examples of possible outputs from generators 1707, 1705 and 1703 respectively of FIG. 92.

Figure 93A:
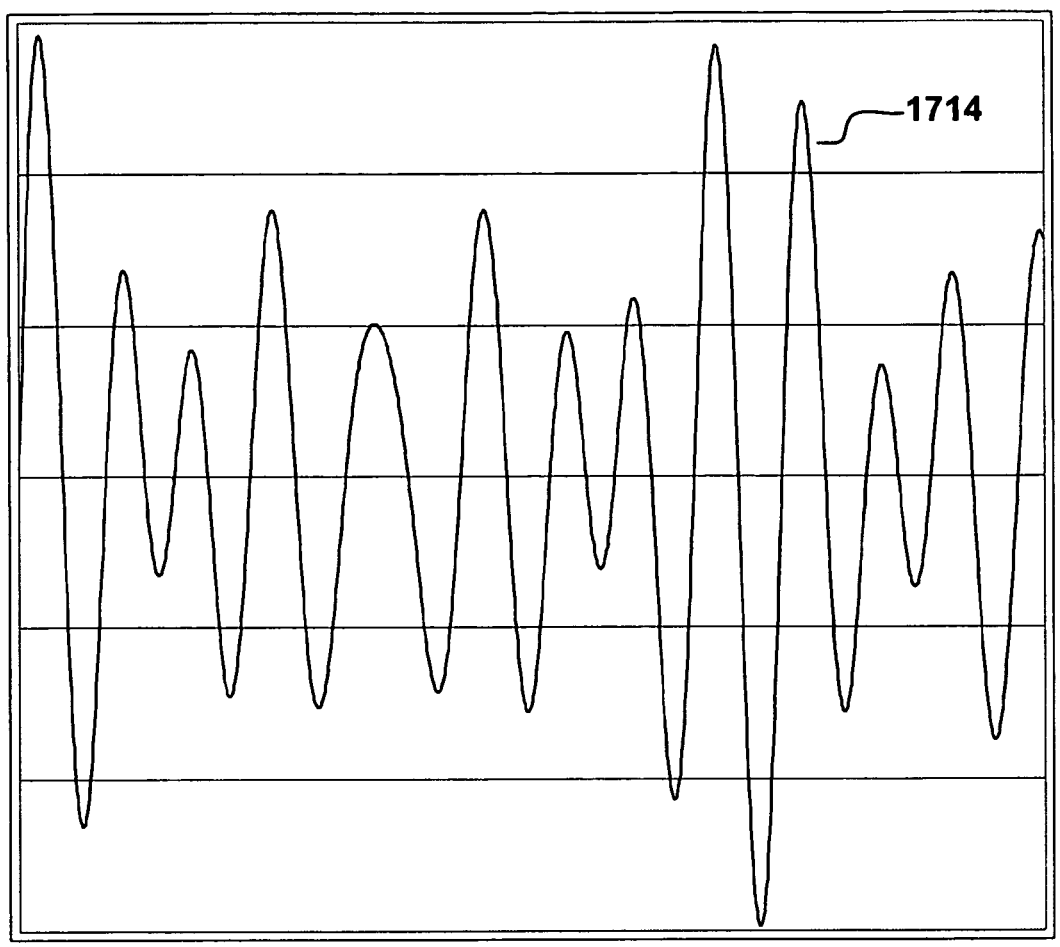
FIG. 93A shows the resultant sound wave pattern in the tank when the three frequencies in FIG. 93 are applied.

FIG. 93A shows the resultant sound wave pattern 1714 in a tank when the three frequencies 1710, 1711 and 1712 in FIG. 93 are applied concurrently.

FIG. 94 shows an example of synchronized high peak power different frequency ultrasound bursts which is the preferred embodiment of the invention. The first burst pattern 1721 represents an output from the first generator 1703 in FIG. 92. The second burst pattern 1722 represents an output from the second generator 1705 in FIG. 92. The third burst pattern 1723 represents an output from the third generator 1707 in FIG. 92. Each of these bursts 1721, 1722 and 1723 is sized and timed such that a minimum of 84 percent of the energy available in a cycle is delivered in a maximum of 27 percent of the cycle time.

In another preferred embodiment, a method for cleaning and processing is provided by supplying both concurrent multiple ultrasound frequencies and successive multiple ultrasound frequencies in series to a liquid to improve the efficiency of the cleaning or processing.

In another embodiment of the invention a method for cleaning or processing an object in a liquid medium comprises the steps of driving two or more first transducer arrays coupled to the liquid medium for a first time period, each of the first transducer arrays being driven at an associated drive frequency, the above frequencies being different from each other, driving one or more second transducer arrays coupled to the liquid medium for a second time period, the second time period being different from the first time period, each of the second transducer arrays being driven at an associated drive frequency. This embodiment also includes the method where the first time period precedes the second time period. This embodiment also includes the method where the first and second time periods are contiguous. This embodiment also includes the method where the first and second time periods are non-contiguous. This embodiment also includes the method where the drive frequency of at least one of the second transducer arrays is the same as the drive frequencies of one of the first transducer arrays. This embodiment also includes the method where the drive frequencies of the second transducer arrays are different from the drive frequencies of the first transducer arrays. This embodiment also includes the method where at least one of the first transducer arrays includes only a single transducer. This embodiment also includes the method where at least one of the first transducer arrays includes two or more transducers. This embodiment also includes the method where at least one of the second arrays includes only a single transducer. This embodiment also includes the method where at least one of the second transducer arrays includes two or more transducers.

In another embodiment of the invention a method for cleaning or processing an object in a liquid medium comprises the steps of driving two or more first transducer arrays coupled to the liquid medium for a first time period, each of the first transducer arrays being driven at an associated drive frequency, the above frequencies being different from each other, driving one or more second transducer arrays coupled to the liquid medium for a second time period, the second time period being different from the first time period, each of the second transducer arrays being driven at an associated drive frequency and where the second time period precedes the first time period. This embodiment also includes the method where the first and second time periods are contiguous. This embodiment also includes the method where one of the transducers of the first transducer array is one of the transducers of the second transducer array.

Figures 95A, 95B:
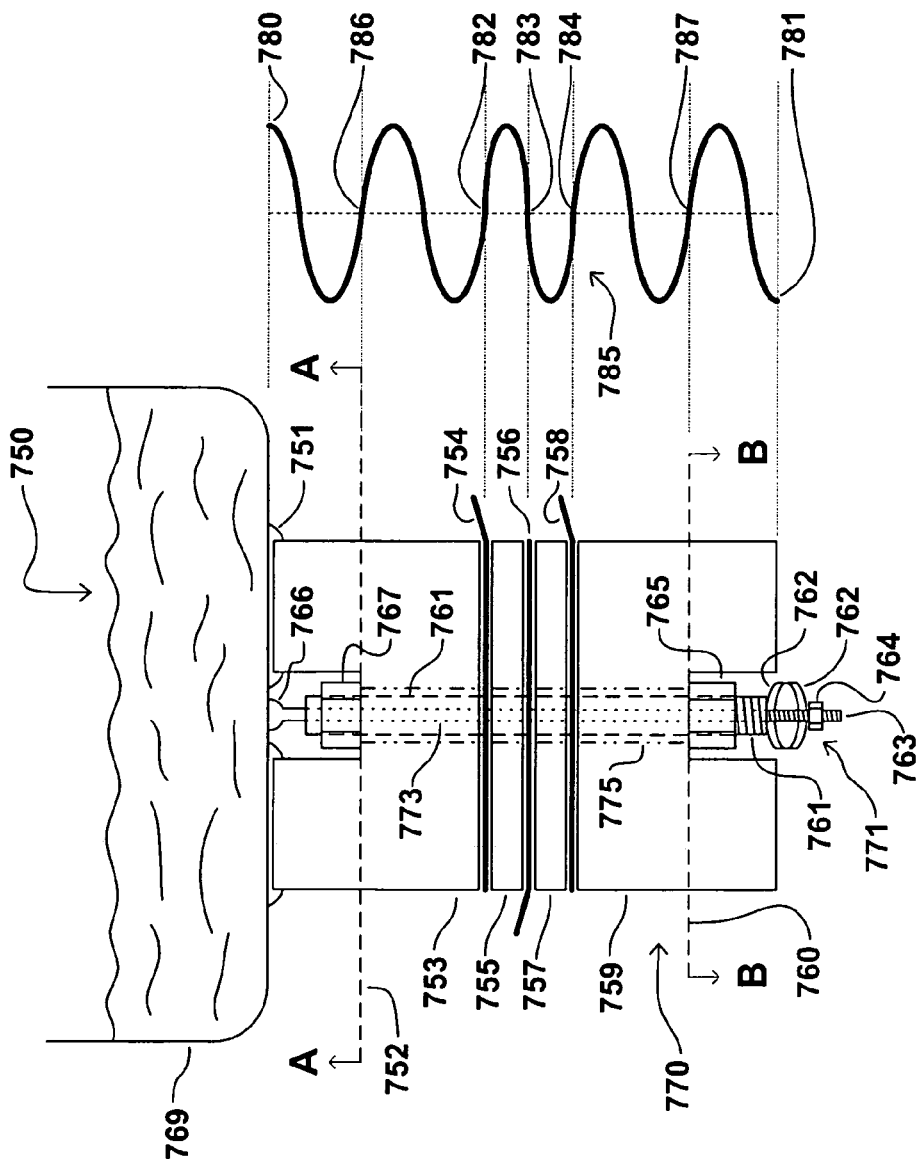
FIG. 95A shows one embodiment of the multiple frequency transducer assembly constructed according to one embodiment of the invention.
FIG. 95B shows a sinusoid of a standing resonant wave within the transducer assembly of FIG. 95A, characterizing the displacement nodes and antinodes of the transducer assembly in FIG. 95A.

FIG. 95A illustrates one embodiment of transducer assembly 770 constructed according to the invention and attached to processing tank 769 using epoxy layer 751 to form system 750. In this embodiment, transducer assembly 770 is comprised of front mass 753, two polarized piezoelectric ceramic drive elements 755 and 757, back mass 759, and a double compression clamping assembly 771 consisting of 761, 762, 763, 764, 765, 766, 767 and 773 inserted into center bore 775 with construction and operational properties as previously described in connection with FIG. 60. Transducer assembly 770 has electrodes 754, 756 and 758 that for this embodiment are considered to be sufficiently thin such that they define interfaces rather than significantly add to the acoustic length of transducer assembly 770. These interfaces within the transducer assembly 770 have corresponding points in FIG. 95B, that is, the interface defined by electrode 754 in FIG. 95A corresponds to point 782 in FIG. 95B, the interface defined by electrode 756 in FIG. 95A corresponds to point 783 in FIG. 95B and the interface defined by electrode 758 in FIG. 95A corresponds to point 784 in FIG. 95B. A fourth interface for system 750 occurs near the epoxy bond line 751 and usually within the thickness of the tank 769 bottom material. This interface is precisely defined in FIG. 95B by point 780, but will be referred to herein as the epoxy bond line 751. Therefore, transducer assembly 770 has four interfaces approximately defined by 751, 754, 756 and 758, i.e., the point or points of contact between the various layers of transducer assembly 770. In the embodiment shown in FIG. 95A, these four interfaces associated with transducer assembly 770 are located as follows, first interface 754 between front mass 753 and first polarized piezoelectric ceramic element 755, second interface 756 between first polarized piezoelectric ceramic element 755 and second polarized piezoelectric ceramic element 757, third interface 758 between polarized piezoelectric ceramic element 757 and back mass 759 and fourth interface 751 between front mass 753 and processing tank 769. As shown, ultrasonic transducer 770 is mounted to the outside surface of processing tank 30.

A resonant standing wave of the particular frequency being employed can be formed within transducer assembly 770 in which transducer assembly 770 experiences maximum molecular displacement at the antinodes of the resonant standing wave within it and no molecular displacement at the nodes of the resonant standing wave. While heat generation at the interfaces is not generally a limitation at frequencies in the lower microsonic and ultrasonic ranges, ultrasonic transducers cannot generally be operated off resonance in the upper microsonic and megasonic ranges and cannot therefore be swept off of their center frequencies at frequencies in the upper microsonic and megasonic ranges because polarized piezoelectric ceramic elements 755 and 757 over-heat due to the friction at the interfaces between one another and between them and front mass 753 and back mass 759, making high amplitude resonance within the processing tank impossible with previous constructions.

In the embodiment shown in FIG. 95A, according to the invention, transducer assembly 770 is constructed such that polarized piezoelectric ceramic elements 755 and 757 are each of a thickness equal to an integer number of half wavelengths of a particular sound wave within the upper microsonic or megasonic frequency range. As a result, when operated at the particular frequency, a resonant standing wave of this highest fundamental frequency is formed within ultrasonic transducer 770. According to the invention, transducer assembly 770 is constructed such that the nodes of the resonant standing sound wave exist at interfaces 754, 756 and 758, i.e., between front mass 753 and polarized piezoelectric ceramic element 755, between polarized piezoelectric ceramic elements 755 and 757, and between polarized piezoelectric ceramic element 757 and back mass 759.

By constructing transducer assembly 770 with each layer of a particular thickness, transducer assembly 770 can be operated at a frequency within the upper microsonic and megasonic ranges and sweep within the lower microsonic and ultrasonic frequency ranges because at the highest frequency, the nodes of the high frequency wave exist at the interfaces and there is no agitation (positive or negative displacement) of the molecules at the nodes, reducing energy losses due to friction between the components and allowing transducer assembly 770 to become under damped when operated at the upper microsonic or megasonic frequency, resulting in resonance within transducer assembly 770 and the ability of transducer assembly to create cavitating power at the higher frequencies. By constructing transducer assembly 770 such that the nodes of the fundamental frequency exist at the interfaces, coupled with the cooling effect of back mass 759 and front mass 753, megasonic and upper microsonic sweeping is possible. Thus, transducer assembly 770 of the present invention can be operated throughout the lower microsonic and ultrasonic ranges, and at a specific frequency in the upper microsonic and megasonic ranges, as well as at sweeping frequencies as much +/−5% of the center frequency in the upper microsonic and megasonic ranges. The inventor has experimentally found unique advantages over the single frequency prior art megasonics equipment by sweeping frequency at megasonic frequencies. The collimated megasonic characteristic of the prior art is reduced by sweeping megasonics and the process efficiency is improved because there is less absorption of sound energy when sweeping compared to prior art single frequency megasonics.

The same transducer assembly 770 can also be operated throughout the ultrasonic and low microsonic frequency ranges because, even though the nodes and antinodes may not exist at the interfaces, the friction and heat generated at these relatively low frequencies is not significant enough to damage the piezoelectric ceramics. Transducer assembly 10 operates in the low ultrasonic and/or low microsonic frequencies in the same fashion as a Langevin transducer with harmonics, i.e., the lowest frequency is the half wavelength resonance of the complete stack, and higher frequencies are harmonics or overtones of this selected or fundamental resonance.

The thickness of transducer assembly 770 determines the "fundamental resonant frequency." The fundamental resonant frequency of a transducer is that specific frequency or bandwidth in the ultrasonic frequency range at which the transducer can be operated. "Bandwidth" is the range of frequencies in a resonant or harmonic region of a transducer over which the acoustic power output of a transducer remains at least 50% of the maximum output value. Typically, this bandwidth is approximately plus or minus as much as 5% of the center frequency. For example, a 40 khz transducer can be used at approximately 40 khz+/−2 khz, or between 38 and 42 khz; and at 700 khz the transducer can be used at approximately 700 khz plus or minus as much as 35 khz, or at an off-center frequency range with a minimum value of 665 khz and a maximum value of 735 khz.

In addition, according to the embodiment of transducer assembly 770 shown in FIG. 95A, front mass 753 plus epoxy bond 751 and part of tank material 769 is an integer number of half wavelengths of the highest center frequency plus one quarter wavelength thick so that an antinode of the resonant standing wave exists near fourth interface 751 between front mass 753 and processing tank 769, i.e., the radiating surface. If, instead, a node were at the interface between front mass 753 and processing tank 769, there would be no alternating positive and negative displacement at that surface and no sonic energy would be transmitted into processing tank 769. However, because epoxy layer 751 and the tank thickness 769 become part of the resonant structure during bonding, the antinode is only approximately at the interface between front mass 753 and processing tank 769, i.e., the antinode is positioned within epoxy layer 751 or the tank material 769.

Furthermore, back mass 759 is also an integer number of half wavelengths of the fundamental frequency plus one quarter wavelength thick. As with front mass 753, this thickness places an antinode of the resonant standing wave at the back most surface of transducer assembly 770, i.e., back surface 772 of back mass 759. Having an antinode at back surface 772 of back mass 759 allows for positive and negative displacement at that point of back mass 759 which supplies and equal and opposite reaction to the positive and negative displacement of front mass 753 at the interface with processing tank 769 so that transducer assembly 770 can exert a high force on tank 769. That is, front mass 753 exerts a pulse against processing tank 769 and back mass flexes in an opposite direction. Without this extra quarter wavelength thickness, there would be no displacement at back surface 772 of back mass 759 and no way to have an opposite reaction to the displacement force of the front surface of front mass 753 towards processing tank 769. It is important to note that while the most efficient operation results if every interface is at a node, it is not necessary that every node be at an interface. That is, additional nodes can exist within front mass 753, polarized piezoelectric ceramic elements 755 and 757, and back mass 759.

Back mass 759 and front mass 753 can be made of steel, aluminum, aluminum alloys, titanium, titanium alloys, ceramic, quartz, or most any other material that is able to conduct sound (i.e., does not absorb sound waves). Examples of materials which absorb sound, and are therefore not useful materials for constructing back mass 759 and front mass 753, include Teflon, sponge, rubber, and polypropylene. Furthermore, if transducer assembly 770 is mounted within processing tank 769, the material(s) chosen must be able to resist any corrosive characteristics of the cleaning solution. Still further, front mass 753 and back mass 759 can be made of different materials for the same transducer assembly 770. For example, transducer assembly 770 can be constructed with back mass 759 being made of silicon and front mass 753 made of aluminum.

Because sound travels at different speeds in various materials, the exact thickness of both front mass 753 and back mass 759 depend on the material chosen and the speed of sound in that particular material. If sound moves through a material relatively fast, a thicker amount of the material would be needed to be as thick as the same integer number of half wavelengths as compared to a material in which sound moves slower.

Polarized piezoelectric ceramic materials are generally very strong when compressed, but weak when under tension, i.e. pulled apart. Polarized piezoelectric drive elements 755 and 757 rapidly expand and contract when subject to an electric current. As they expand, without clamping assembly 771, they would go into tension and consequently have short life spans. By using clamping assembly 771, polarized piezoelectric ceramic elements 755 and 757 of transducer assembly 770 remain under constant pressure throughout the entire cycle of expansion and contraction.

The double bolt construction of transducer assembly 770 is only used for illustrative purposes. It is the location of the nodes at interfaces 754, 756 and 758 of transducer assembly 770 along with the antinodal points of the resonant standing wave approximately at the junction surface between front mass 753 and processing tank 769 and at the back surface of back mass 759 that allows it to operate at both one frequency or a bandwidth of frequencies at the highest frequency (megasonic and upper microsonic) and an additional set of frequency bandwidths throughout the lower frequencies (low microsonic and low ultrasonic). However, one of ordinary skill in the art will recognize that other clamping assemblies known in the art which keep ultrasonic transducer 770 under pressure may also be employed.

Transducer assembly 770 depicted in FIG. 95A has two polarized piezoelectric ceramic elements 755 and 757 which should also not be considered a limitation. Transducer assembly 770 could be constructed with a single polarized piezoelectric ceramic element. In the case of a transducer constructed with only a single polarized piezoelectric ceramic element, an insulation mechanism is necessary. Two examples of an insulation mechanism are constructing the transducer assembly with a back mass 759 and front mass 753 made of a non-conductive material, or adding insulators between the single polarized piezoelectric ceramic element and front mass and/or between the single polarized piezoelectric ceramic element and back mass 759. If non-conductive materials for back mass 759 and/or front mass 753, or if an insulation mechanism were not used, bias bolt 761 and/or clamping assembly 771 would short the single polarized piezoelectric ceramic. Examples of non-conductive materials that could be used for front mass 753 and back mass 759 are quartz, silicon carbide, and aluminum oxide. If an insulator is added between the single polarized piezoelectric ceramic element and front mass 753 and/or between the single polarized piezoelectric ceramic element and back mass 759, then the thickness of the insulator must be taken into account if its thickness is significant. Each interface between the layers would thus still have a nodal point.

FIG. 95B shows a sinusoid 785 of a the specific nodal pattern for a high operating frequency resonant standing wave for operation within transducer assembly 770 in FIG. 95A when operating in the megasonic or upper microsonic frequency range. Nodes 782, 783 and 784 correspond to the three critical interfaces within the embodiment of transducer assembly 770 shown in FIG. 95A. Nodal points 786 and 787 in FIG. 95B correspond to secondary interfaces that are located at load-bearing surfaces AA 752 and BB 760 of the clamping assembly 771 in FIG. 95A. Although nodes at these load bearing surfaces are not required, it is a good engineering practice and further reduces the frictional loss. Antinodes 780 and 781 of the resonant standing wave are also shown in FIG. 95B. As described, transducer assembly 770 is constructed such that antinodes 781 and 780 occur at back surface 772 of back mass 759 and at the surface at which transducer assembly 770 abuts processing tank 769, respectively.

The specific nodal pattern exists for only one frequency or bandwidth around a center frequency in the megasonic or upper microsonic range, and operation of transducer assembly 770 of the present invention is, in some cases, limited to this one selected frequency, as is common with megasonic equipment. This transducer assembly 770, however, is also capable of operating throughout the low microsonic and low ultrasonic ranges. In a more general case, frequency changes (for example, sweep frequency) around this specific center frequency with nodes 754, 756 and 758 being slightly displaced from the interface at the frequencies off of a center frequency result in six distinct ways transducer assembly 770 of FIG. 95A can be operated:

as a single frequency megasonic transducer;

as a sweeping frequency transducer in the megasonic frequency range, capable of reliably producing high intensity sweeping frequency sound at these high frequencies;

as a sweeping frequency transducer in the upper microsonic frequency range, capable of reliably producing high intensity sweeping frequency sound at these high frequencies;

in multiple frequency systems where there is single frequency drive at a megasonic frequency and sweeping frequency drive at one or more frequencies in the low ultrasonic and/or low microsonic frequency ranges;

in a multiple frequency system where there is sweeping frequency drive at a megasonic frequency and sweeping frequency drive at one or more frequencies in the low ultrasonic and/or microsonic frequency ranges; and in a multiple frequency system where there is sweeping frequency drive at an upper microsonic frequency and sweeping frequency drive at one or more frequencies in the low ultrasonic and/or microsonic frequency ranges.

The ultrasonic generator drives the transducers at frequencies within a bandwidth to obtain broadband acoustical disturbances within the liquid. In one embodiment, the ultrasonic generator sweeps at frequencies through the overall bandwidth and simultaneously varies the rate at which those frequencies are changed. That is, the ultrasonic generator has a "sweep rate," the rate at which the ultrasonic generator changes from one frequency within the bandwidth to the next, which varies as a function of time (a phenomenon denoted herein as "sweeping the sweep rate"). The sweep rate could also be varied linearly, randomly, or as some other function of time to optimize the process conditions within the cleaning tank. In an alternate embodiment, the ultrasonic generator produces a "random sweep rate," as defined supra.

FIG. 96A shows graphs of single frequency particle removal for process time x and for process time 20x demonstrate the difficulty of removing particles that are outside the optimum size range for the particular single frequency.

FIG. 96B shows graphs of particle removal for seven successive multiple ultrasound frequencies each with a process time of x for a total process time of 7x and the combined effect graph. This demonstrates the improvement provided by the successive multiple ultrasound frequency aspects of this invention. That is, when the combined effect graph of FIG. 96B is compared to the process time Y graph of FIG. 96A, it is seen that more particles are removed in less time by using the successive multiple ultrasound frequency aspects of this invention.

The invention thus attains the objects set forth above, among those apparent in the preceding description. Since certain changes may be made in the above description without departing from the scope of the invention, it is intended that all matter contained in the above description or shown in the accompanying drawings be interpreted as illustrative and not in a limiting sense. It is also to be understood that the following claims are to cover all generic and specific features of the invention described herein, and all statements of the scope of the invention which, as a matter of language, might be said.

What is claimed is:

1. A method for cleaning or processing an object in a liquid medium comprising the steps of:
    driving two or more first transducer arrays coupled to said liquid medium for a first time period, each of said first transducer arrays being driven at an associated drive frequency said above frequencies being different from each other,
    driving one or more second transducer arrays coupled to said liquid medium for a second time period, said second time period being of different duration than said first time period, each of said second transducer arrays being driven at an associated drive frequency.

2. The method of claim 1 wherein said first time period precedes said second time period.

3. The method of claim 2 wherein said first and second time periods are contiguous.

4. The method of claim 2 wherein said first and second time periods are non-contiguous.

5. The method of claim 1 wherein said second time period precedes said first time period.

6. The method of claim 5 wherein said first and second time periods are contiguous.

7. The method of claim 5 wherein said first and second time periods are non-contiguous.

8. The method of claim 1 wherein said drive frequency of at least one of said second transducer arrays is the same as the drive frequencies of one of said first transducer arrays.

9. The method of claim 1 wherein said drive frequencies of said second transducer arrays are different from said drive frequencies of said first transducer arrays.

10. The method of claim 1 wherein at least one of said first transducer arrays includes only a single transducer.

11. The method of claim 1 wherein at least one of said first transducer arrays includes two or more transducers.

12. The method of claim 1 wherein at least one of said second arrays includes only a single transducer.

13. The method of claim 1, wherein at least one of said second transducer arrays includes two or more transducers.

14. The method of claim 10 wherein one of said transducers of said first transducer array is one of said transducers of said second transducer array.

15. The method of claim 11 wherein one of said transducers of said first transducer array is one of said transducers of said second transducer array.

16. The method of claim 12 wherein one of said transducers of said first transducer array is one of said transducers of said second transducer array.

17. The method of claim 13 wherein one of said transducers of said first transducer array is one of said transducers of said second transducer array.

18. The method of claim 1 wherein said associated drive frequencies are ultrasound frequencies in the range between 18 Khz to 5 Mhz.

19. The method of claim 1 comprising the further steps of:
    providing as a transducer of one of said first transducer arrays and said second transducer arrays, a transducer assembly extending along the transducer axis of said transducer assembly including:
        vi. a piezoelectric assembly including a stack of p polarized piezoelectric ceramic elements extending along said transducer axis between a piezoelectric assembly top surface and a piezoelectric assembly bottom surface, each of said polarized piezoelectric ceramic elements having an element top surface and an element bottom surface, and being characterized by a thickness Pi along said transducer axis, where i is an integer 1, 2, . . . , p, each of said element top surfaces and said element bottom surfaces having an electrically conductive layer disposed thereon, and including means for coupling a drive signal to said electrically conductive layers,
        vii. a tank wall extending between a tank wall top surface and a tank wall bottom surface, said tank wall having a thickness T in the direction of said transducer axis, said thickness T being small relative to other thicknesses in said transducer assembly, said tank wall top surface forming said drive surface, and said tank wall bottom surface bonded to a front mass effectively adding a thickness T/2 to said front mass;
        viii. said front mass extending between said tank wall bottom surface and said piezoelectric assembly top surface, said front mass having a thickness D in the direction of said transducer axis;

ix. a back mass extending between a bottom transducer surface and said bottom piezoelectric assembly surface, said back mass having a thickness B in the direction of said transducer axis;

x. a compression assembly including means for applying a compressive force F across said front mass and said back mass;

whereby said front mass, said piezoelectric assembly, said back mass and said tank wall are dimensioned so that in response to said compressive force F:

$P_i$ is equal to $n_i \lambda_p/2$ $D+T/2$ is equal to $m_1 \lambda_D/2 + \lambda_D/4$ B is equal to $m_2 \lambda_B/2 + \lambda_B/4$ where $n_i$, $m_1$ and $m_2$ are integers and $\lambda_p$ is the characteristic acoustic wavelength of said polarized piezoelectric ceramic elements, and $\lambda_B$ and $\lambda_D$, are the characteristic acoustic wavelengths of said back mass and said front mass, respectively [where $\lambda = v/f$]

wherein said transducer is characterized by a vibratory fundamental first frequency having wavelength $\lambda_{f1}$ equal to $2 (\Sigma_i P_i + D + T/2 + B)$ and a vibratory second frequency having wavelength $\lambda_{f2}$ equal to $2\lambda_P$, and coupling a drive surface of said transducer assembly to said liquid medium.

20. The method of claim 1 comprising the further steps of: providing as a transducer of one of said first transducer arrays and said second transducer arrays a transducer assembly for operation at a first frequency within a megasonic range and at sweeping frequencies within a set of bandwidths which are within the frequency spectrum lower than said first frequency, comprising:

a front mass with a front surface and a back surface;

a bonded structure consisting of a radiating diaphragm and a bonding material, said radiating diaphragm having a front surface and a back surface with said bonding material adhering said back surface of said radiating diaphragm to said front surface of said front mass;

a first polarized piezoelectric ceramic element with a front surface and a back surface, with said front surface of said first polarized piezoelectric ceramic element positioned adjacent to said front mass at said back surface of said front mass and forming a first interface there between;

a second polarized piezoelectric ceramic element with a front surface and a back surface, with said front surface of said second polarized piezoelectric ceramic element positioned adjacent to said first polarized piezoelectric ceramic element at said back surface of said first polarized piezoelectric ceramic element and forming a second interface there between;

a back mass with a front surface and a back surface, with said front surface of said back mass positioned adjacent to said second polarized piezoelectric ceramic element at said back surface of said second polarized piezoelectric ceramic element, forming a third interface there between; and a clamping assembly for compressing said first polarized piezoelectric ceramic element and said second polarized piezoelectric ceramic element between said front mass and said back mass;

wherein said first polarized piezoelectric ceramic element and said second polarized piezoelectric ceramic element produce a resonant standing wave within said transducer assembly when driven by an electric signal at said first frequency;

wherein said front mass, said first polarized piezoelectric ceramic element, said second polarized piezoelectric ceramic element, and said back mass are each of a thickness such that when said transducer assembly is operated at said first frequency within said megasonic range, a first node of said resonant standing wave within said transducer assembly is positioned at said first interface, a second node of said resonant standing wave is positioned at said second interface, a third node of said resonant standing wave is positioned at said third interface, a first antinode of said resonant standing wave is positioned near said front surface of said front mass and within said bonded structure, and a second antinode of said resonant standing wave is positioned at said back surface of said back mass, and coupling a drive surface of said transducer assembly to said liquid medium.

21. The method of claim 1 comprising the further steps of: providing as a transducer of one of said first transducer arrays and said second transducer arrays, a Langevin structure bonded transducer assembly for producing a sound wave at a high frequency within the megasonic range comprised of:

a front mass having a bonded front surface and a back surface and of a thickness equal to an integer number of half wavelengths plus one quarter wavelength of a high frequency resonant standing wave within said megasonic range such that an antinode of said high frequency resonant standing wave exists at said bonded front surface and a node of said high frequency resonant standing wave exists at said back surface;

a plurality of polarized piezoelectric ceramic elements arranged in a stack said stack having a front surface and a back surface, said front surface of said stack positioned adjacent to said front mass at said back surface of said front mass, at least one interface between each of said plurality of polarized piezoelectric ceramic elements within said stack, each of said plurality of polarized piezoelectric ceramic elements of said stack of a thickness equal to an integer number of half wavelengths of said high frequency resonant standing wave within said megasonic range such that a node of said high frequency resonant standing wave within said megasonic range exists at each of said at least one interface within said stack;

a back mass with a front surface and a back surface, the said front surface of said back mass positioned adjacent to said back surface of said stack and of a thickness equal to an integer number of half wavelengths plus one quarter wavelength of said high frequency resonant standing wave within said megasonic range such that an antinode of said high frequency resonant standing wave exists at said back surface of said back mass and a node of said high frequency resonant standing wave exists at said front surface; and a clamping assembly for compressing said plurality of polarized piezoelectric ceramic elements of said stack between said front mass and said back mass, and coupling a drive surface of said transducer assembly to said liquid medium.

\* \* \* \* \*